(12) United States Patent
Hatakeyama et al.

(10) Patent No.: US 10,759,938 B2
(45) Date of Patent: *Sep. 1, 2020

(54) BIO-ELECTRODE COMPOSITION, BIO-ELECTRODE, AND METHOD FOR MANUFACTURING A BIO-ELECTRODE

(71) Applicant: SHIN-ETSU CHEMICAL CO., LTD., Tokyo (JP)

(72) Inventors: Jun Hatakeyama, Joetsu (JP); Osamu Watanabe, Joetsu (JP); Motoaki Iwabuchi, Joetsu (JP); Shiori Nonaka, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 75 days.

This patent is subject to a terminal disclaimer.

(21) Appl. No.: 16/130,184

(22) Filed: Sep. 13, 2018

(65) Prior Publication Data
US 2019/0127578 A1 May 2, 2019

(30) Foreign Application Priority Data

Oct. 26, 2017 (JP) .................................. 2017-207629

(51) Int. Cl.
| | | |
|---|---|---|
| C08L 75/04 | (2006.01) | |
| C08L 33/16 | (2006.01) | |
| C08L 33/14 | (2006.01) | |
| A61B 5/053 | (2006.01) | |
| C08G 18/66 | (2006.01) | |
| C08G 18/48 | (2006.01) | |
| C08G 18/32 | (2006.01) | |
| C08G 18/67 | (2006.01) | |
| C08G 18/38 | (2006.01) | |
| C08G 18/79 | (2006.01) | |
| C08G 18/34 | (2006.01) | |
| C08G 18/78 | (2006.01) | |
| C08G 18/75 | (2006.01) | |
| C08G 18/73 | (2006.01) | |
| A61B 5/024 | (2006.01) | |
| C08F 220/24 | (2006.01) | |
| C08F 230/08 | (2006.01) | |
| C08F 220/38 | (2006.01) | |
| C08K 3/04 | (2006.01) | |

(52) U.S. Cl.
CPC .............. *C08L 75/04* (2013.01); *A61B 5/024* (2013.01); *A61B 5/053* (2013.01); *C08F 220/24* (2013.01); *C08F 220/38* (2013.01); *C08F 230/08* (2013.01); *C08G 18/3206* (2013.01); *C08G 18/329* (2013.01); *C08G 18/3212* (2013.01); *C08G 18/348* (2013.01); *C08G 18/3893* (2013.01); *C08G 18/4825* (2013.01); *C08G 18/4833* (2013.01); *C08G 18/4854* (2013.01); *C08G 18/6666* (2013.01); *C08G 18/6674* (2013.01); *C08G 18/6677* (2013.01); *C08G 18/679* (2013.01); *C08G 18/73* (2013.01); *C08G 18/755* (2013.01); *C08G 18/758* (2013.01); *C08G 18/7831* (2013.01); *C08G 18/792* (2013.01); *C08K 3/04* (2013.01); *C08K 3/041* (2017.05); *C08L 33/16* (2013.01); *A61B 2562/0215* (2017.08); *C08F 2500/00* (2013.01); *C08K 2201/00* (2013.01); *C08L 2203/02* (2013.01); *C08L 2203/20* (2013.01)

(58) Field of Classification Search
CPC ... C08L 33/14; C08G 18/61; C08F 2220/382; C08F 2220/385
See application file for complete search history.

(56) References Cited

U.S. PATENT DOCUMENTS

| | | | | |
|---|---|---|---|---|
| 4,839,443 A | * | 6/1989 | Akutsu | ............... C08G 18/3893 525/474 |
| 5,475,127 A | * | 12/1995 | Klein | .................. B01F 17/0071 556/445 |
| 2002/0009650 A1 | | 1/2002 | Michot et al. | |

(Continued)

FOREIGN PATENT DOCUMENTS

| | | |
|---|---|---|
| JP | H05-095924 A | 4/1993 |
| JP | 2002-075443 A | 3/2002 |

(Continued)

OTHER PUBLICATIONS

Jun. 24, 2019 Taiwanese Office Action and Search Report in Taiwanese Application No. 107137271.

*Primary Examiner* — Marc S Zimmer
(74) *Attorney, Agent, or Firm* — Oliff PLC

(57) ABSTRACT

The present invention provides a bio-electrode composition including: a resin containing a main chain having a urethane bond and two side chains each having a silicon-containing group; and an electro-conductive material, wherein the electro-conductive material is a polymer compound having one or more repeating units selected from fluorosulfonic acid salts shown by the following formulae (1)-1 and (1)-2, sulfonimide salts shown by the following formula (1)-3, and sulfonamide salts shown by the following formula (1)-4. This can form a living body contact layer for a bio-electrode that is excellent in electric conductivity and biocompatibility, light in weight, manufacturable at low cost, and free from large lowering of the electric conductivity even when it is wetted with water or dried. The present invention also provides a bio-electrode in which the living body contact layer is formed from the bio-electrode composition, and a method for manufacturing the bio-electrode.

17 Claims, 2 Drawing Sheets

(56) References Cited

U.S. PATENT DOCUMENTS

| | | |
|---|---|---|
| 2010/0119970 A1 | 5/2010 | Ohsawa et al. |
| 2016/0155530 A1 | 6/2016 | Someya et al. |
| 2017/0251941 A1 | 9/2017 | Hatakeyama et al. |
| 2018/0020936 A1 | 1/2018 | Kwon et al. |

FOREIGN PATENT DOCUMENTS

| | | |
|---|---|---|
| JP | 2003-225217 A | 8/2003 |
| JP | 2004-033468 A | 2/2004 |
| JP | 2005-320418 A | 11/2005 |
| JP | 2010-113209 A | 5/2010 |
| JP | 2011-201955 A | 10/2011 |
| JP | 2012-152725 A | 8/2012 |
| JP | 2015-019806 A | 2/2015 |
| JP | 2015-100673 A | 6/2015 |
| TW | 201527413 A | 7/2015 |
| WO | 2013/039151 A1 | 3/2013 |
| WO | 2016/114298 A1 | 7/2016 |

\* cited by examiner

Connected to a sensor device

To an impedance measurement apparatus

1'  Distance of 15 cm  1'

BIO-ELECTRODE COMPOSITION, BIO-ELECTRODE, AND METHOD FOR MANUFACTURING A BIO-ELECTRODE

TECHNICAL FIELD

The present invention relates to a bio-electrode, which is in contact with living skin and can detect physical conditions such as a heart rate on the basis of electric signals from the skin, and a method for manufacturing the same, as well as a bio-electrode composition that is usable for a bio-electrode suitably.

BACKGROUND ART

In recent years, wearable devices have been developed progressively with the spread of Internet of Things (IoT). Representative examples thereof include a watch and glasses that can be connected with internet. Wearable devices that can always monitor physical conditions are also necessary in a medical field and a sports field, and are expected to be a growth field in the future.

In the medical field, wearable devices have been investigated to monitor organic conditions such as an electrocardiogram measurement, which detects heart beats by concentration change of ions released from skin linked to the heart beats. The electrocardiogram is measured by fitting a body with electrodes on which electro-conductive paste is applied, and this measurement is performed only once in a short period of time. On the other hand, the aim of development of the foregoing medical wearable device is to develop devices that monitor health conditions continuously for several weeks. Accordingly, bio-electrodes used for a medical wearable device have to keep the electric conductivity unchanged and not to cause skin allergies even when being used for a long time. In addition to these, it is desirable that the bio-electrode is light in weight and can be manufactured at low cost.

Medical wearable devices include a type in which the device is attached to a body and a type in which the device is incorporated into clothes. As the type in which the device is attached to a body, it has been proposed a bio-electrode using water soluble gel containing water and electrolyte, which are materials of the foregoing electro-conductive paste (Patent Literature 1). On the other hand, as the type in which the device is incorporated into clothes, it has been proposed a means to use cloth in which an electro-conductive polymer such as poly-3,4-ethylenedioxythiophene-polystyrenesulfonate (PEDOT-PSS) or silver paste is incorporated into the fibers for electrodes (Patent Literature 2).

When using the foregoing water soluble gel containing water and electrolyte, however, the electric conductivity is lost as the water is lost due to drying. On the other hand, some people can cause skin allergies by the use of metal with high ionization tendency such as copper. The use of an electro-conductive polymer such as PEDOT-PSS also has a higher risk of skin allergies due to the strong acidity of the electro-conductive polymer.

One of the role of bio-electrodes include conversion of concentration change of ions released from skin to electric signals. Accordingly, they have to have higher ionic conductivity. The bio-electrode of water-soluble gel electrolyte has higher ionic conductivity. On the other hand, the use of metal having higher electron conductivity such as silver or gold as a bio-electrode causes inferior electric conductance and higher resistance between the bio-electrode and skin. It has been investigated to use metal nanowire, carbon black, carbon nanotube, etc., which have excellent electron conductivity, as an electrode material (Patent Literatures 3, 4, and 5). These bio-electrodes, however, fails to exhibit high performance by the reason described above.

To improve the ionic conductivity of solid-state batteries, it has been investigated to combine ionic electrolyte and polyethylene glycol. The ionic conduction is brought by ions hopping on the polyethylene glycol chain.

It has started to use silicone for use such as medical tubes and so on since silicone is excellent in biocompatibility and repels water such as perspiration. However, it is difficult to use silicone for bio-electrodes since silicone is an insulating material.

Urethane may be usable for bio-electrodes since urethane is also excellent in biocompatibility, and the electric insulation property is not so high as that of silicone. Urethane, however, has higher hydrophilicity and is hydrolysable, thereby being unsuitable for uses that involve contact with skin for a long time.

In order to prevent the hydrolysis of polyurethane, polyurethane having a silicone main chain has been investigated (Patent Literature 6).

When the bio-electrode is away from skin, it becomes impossible to obtain information from the body. Just the change of contact area fluctuates the quantity of electricity to be conducted, thereby fluctuating the baseline of an electrocardiogram (electric signals). Accordingly, the bio-electrode have to be in contact with skin continually without changing the contact area in order to obtain stable electric signals from a body. For that purpose, the bio-electrode preferably has tackiness. It also needs stretchability and flexibility to cope with expansion and contraction as well as change of bending of skin.

Urethane is processible to a soft gel state after curing. Water-containing bio-electrodes based on urethane gel have been proposed for the bio-electrode use described above (Patent Literature 7).

CITATION LIST

Patent Literature

Patent Literature 1: International Patent Laid-Open Publication No. WO 2013/039151
Patent Literature 2: Japanese Unexamined Patent Application Publication No. 2015-100673
Patent Literature 3: Japanese Unexamined Patent Application Publication No. H5-095924
Patent Literature 4: Japanese Unexamined Patent Application Publication No. 2003-225217
Patent Literature 5: Japanese Unexamined Patent Application Publication No. 2015-019806
Patent Literature 6: Japanese Unexamined Patent Application Publication No. 2005-320418
Patent Literature 7: Japanese Unexamined Patent Application Publication No. 2011-201955

SUMMARY OF THE INVENTION

Technical Problem

The present invention has been accomplished to solve the foregoing problems, and an object thereof is to provide a bio-electrode composition capable of forming a living body contact layer for a bio-electrode that is excellent in electric conductivity and biocompatibility, light in weight, manufacturable at low cost, and free from large lowering of the electric conductivity even when it is wetted with water or dried; a bio-electrode in which the living body contact layer is formed from the bio-electrode composition; and a method for manufacturing the bio-electrode.

Solution to Problem

To solve the above problems, the present invention provides a bio-electrode composition comprising:

a resin containing a main chain having a urethane bond and two side chains each having a silicon-containing group; and an electro-conductive material, wherein the electro-conductive material is a polymer compound having one or more repeating units selected from the group consisting of fluorosulfonic acid salts shown by the following formulae (1)-1 and (1)-2, sulfonimide salts shown by the following formula (1)-3, and sulfonamide salts shown by the following formula (1)-4,

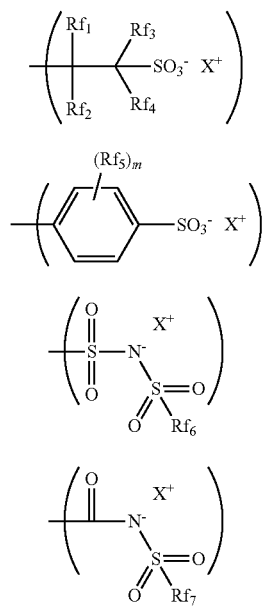

wherein $Rf_1$ and $Rf_2$ each represent a hydrogen atom, a fluorine atom, a trifluoromethyl group, or an oxygen atom, provided that when $Rf_1$ represents an oxygen atom, $Rf_2$ also represents an oxygen atom to form a carbonyl group together with a carbon atom bonded therewith; $Rf_3$ and $Rf_4$ each represent a hydrogen atom, a fluorine atom, or a trifluoromethyl group; provided that one or more fluorine atoms are contained in $Rf_1$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; $X^+$ represents a sodium ion, a potassium ion, or a cation having an ammonium ion structure shown by the following formula (1)-5; and "m" is an integer of 1 to 4,

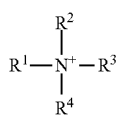

wherein $R^1$ to $R^4$ each represent a hydrogen atom, a linear, branched, or cyclic alkyl group having 1 to 20 carbon atoms, an alkenyl group having 2 to 14 carbon atoms, or an alkynyl group having 2 to 5 carbon atoms, optionally having an ether group, an ester group, a carbonyl group, a sulfonyl group, a cyano group, an amino group, a nitro group, hydroxy group, a sulfur atom except in the sulfonyl group, or a halogen atom, and optionally bonded to each other to form a ring.

The inventive bio-electrode composition is capable of forming a living body contact layer for a bio-electrode that is excellent in electric conductivity and biocompatibility, light in weight, manufacturable at low cost, and free from large lowering of the electric conductivity even when it is wetted with water or dried.

It is preferable that the one or more repeating units selected from the group consisting of fluorosulfonic acid salts shown by the formulae (1)-1 and (1)-2, sulfonimide salts shown by the formula (1)-3, and sulfonamide salts shown by the formula (1)-4 be one or more repeating units selected from repeating units a1 to a7 shown by the following formulae (2),

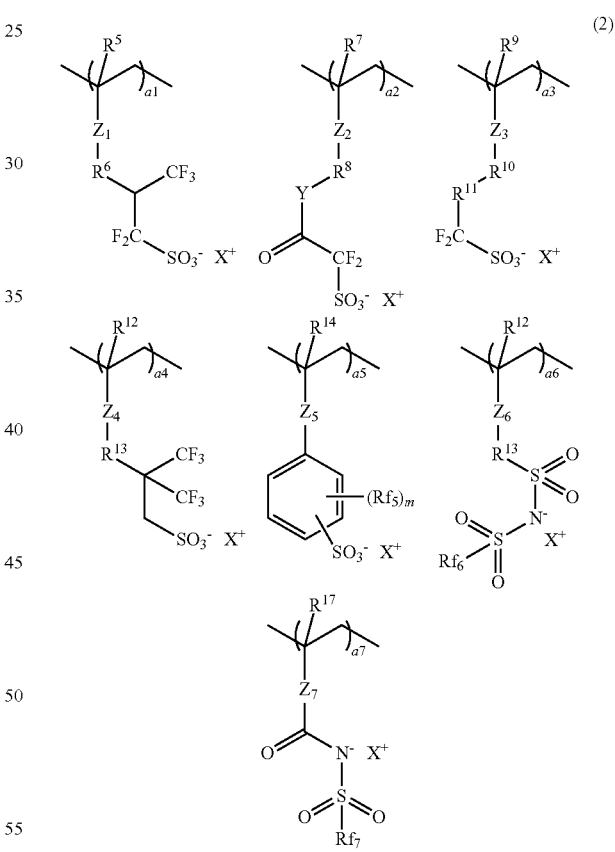

wherein $R^5$, $R^7$, $R^9$, $R^{12}$, $R^{14}$, $R^{15}$, and $R^{17}$ each independently represent a hydrogen atom or a methyl group; $R^6$, $R^8$, $R^{10}$, $R^{13}$, and $R^{16}$ each independently represent any of a single bond, an ester group, or a linear, branched, or cyclic hydrocarbon group having 1 to 13 carbon atoms optionally having either or both of an ether group and an ester group; $R^{11}$ represents a linear or branched alkylene group having 1 to 4 carbon atoms, and one or two of the hydrogen atoms in $R^{1'}$ are optionally substituted with a fluorine atom; $Z_1$, $Z_2$, $Z_3$, $Z_4$, and $Z_6$ each independently represent any of a single bond, a phenylene group, a naphthylene group, an ether group, an ester group, or an amide group; $Z_5$ represents any of a single bond, an ether group, or an ester group; $Z_7$ represents a single bond, an arylene group having 6 to 12 carbon atoms, or —C(=O)—O—$Z^8$—; and $Z^8$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $Z^8$; Y represents an oxygen atom or an —$NR^{18}$— group; $R^{18}$ represents a hydrogen atom, or a linear or branched alkyl group having 1 to 4 carbon atoms, optionally bonded to $R^8$ to form a ring; "m" is an integer of 1 to 4; a1, a2, a3, a4, a5, a6, and a7 satisfy $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 \leq a1+a2+a3+a4+a5+a6+a7 \leq 1.0$; and $Rf_5$, $Rf_6$, $Rf_7$, and $X^+$ have the same meanings as defined above.

With the bio-electrode composition using an electro-conductive material that has the repeating unit like this, the effect of the present invention can be more improved.

The electro-conductive material is preferably a polymer compound having a repeating unit of a sulfonamide salt shown by the formula (1)-4.

The bio-electrode composition using an electro-conductive material that has the repeating unit like this is favorably used for a bio-electrode with lower irritant to skin.

It is preferable that the resin containing a main chain having a urethane bond and two side chains each having a silicon-containing group has a structure shown by the following formula (3),

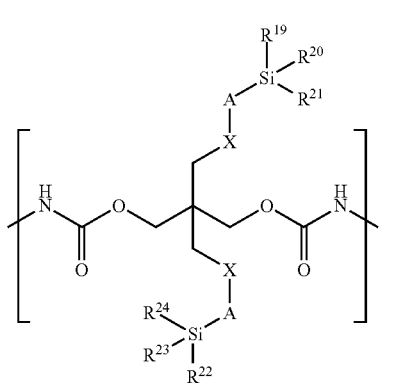

(3)

wherein $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —$(OSiR^{25}R^{26})_n$—$OSiR^{27}R^{28}R^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; and X represents a methylene group or an ether group.

The bio-electrode composition that contains a resin containing a main chain having a urethane bond and two side chains each having a silicon-containing group like this is favorably used for a bio-electrode with really excellent repellency.

It is preferable that the resin containing a main chain having a urethane bond and two side chains each having a silicon-containing group has a structure containing a polyether main chain shown by the following formula (4),

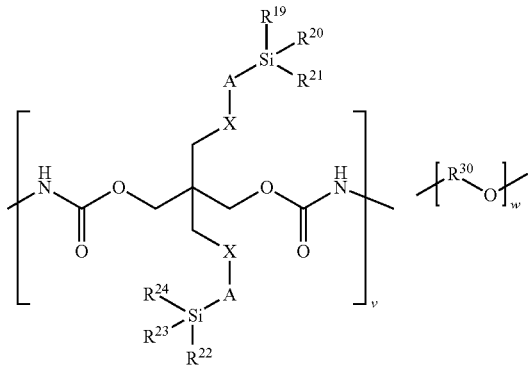

(4)

wherein $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —$(OSiR^{25}R^{26})_n$—$OSiR^{27}R^{28}R^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; X represents a methylene group or an ether group; $R^{30}$ represent a linear, branched, or cyclic alkylene group having 2 to 12 carbon atoms; and "v" and "w" satisfy $0<v<1.0$, $0<w<1.0$, and $0<v+w \leq 1.0$.

The bio-electrode composition that contains a resin containing a main chain having a urethane bond and two side chains each having a silicon-containing group like this is favorably used for a bio-electrode that is more flexible and excellent in ionic conductivity.

It is preferable that the resin containing a main chain having a urethane bond and two side chains each having a silicon-containing group is a reaction product of a diol compound shown by the following formula (5), a polyether compound having a hydroxy group at the terminal, and a compound having an isocyanate group,

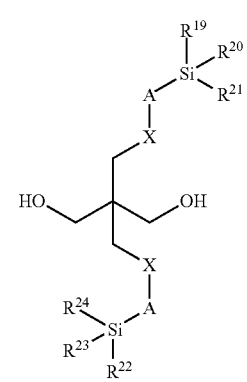

(5)

wherein $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —$(OSiR^{25}R^{25})_n$—$OSiR^{27}R^{28}R^{29}$; $R^{25}$, $R^{26}$, $R^{27}$, $R^{28}$, and $R^{25}$ have the same meanings as $R^{19}$ to $R^{24}$; "n" is a number in a range of 0 to 100; "A" represents a linear or branched alkylene group having 1 to 4 carbon atoms; and X represents a methylene group or an ether group.

The bio-electrode composition that contains a resin containing a main chain having a urethane bond and two side chains each having a silicon-containing group like this facilitates to form a living body contact layer for a bio-electrode that is excellent in electric conductivity and biocompatibility, light in weight, manufacturable at low cost, and free from large lowering of the electric conductivity even when it is wetted with water or dried.

It is preferable that the bio-electrode composition further comprises an organic solvent.

This further improve the coating properties of the bio-electrode composition.

It is preferable that the bio-electrode composition further comprises a carbon material.

The bio-electrode composition like this is capable of forming a living body contact layer with more improved electric conductivity.

It is preferable that the carbon material be either or both of carbon black and carbon nanotube.

In the bio-electrode composition of the present invention, it is possible to use these carbon materials particularly favorably.

The present invention also provides a bio-electrode comprising an electro-conductive base material and a living body contact layer formed on the electro-conductive base material;

wherein the living body contact layer is a cured material of the bio-electrode composition described above.

The inventive bio-electrode is excellent in electric conductivity and biocompatibility, light in weight, manufacturable at low cost, and free from large lowering of the electric conductivity even when it is wetted with water or dried.

It is preferable that the electro-conductive base material comprises one or more species selected from gold, silver, silver chloride, platinum, aluminum, magnesium, tin, tungsten, iron, copper, nickel, stainless steel, chromium, titanium, and carbon.

In the bio-electrode of the present invention, it is possible to use electro-conductive base material like this particularly favorably.

The present invention also provides a method for manufacturing a bio-electrode having an electro-conductive base material and a living body contact layer formed on the electro-conductive base material, comprising:

applying the bio-electrode composition described above onto the electro-conductive base material; and curing the bio-electrode composition; thereby forming the living body contact layer.

The inventive method for manufacturing a bio-electrode makes it possible to easily manufacture a bio-electrode that is excellent in electric conductivity and biocompatibility, light in weight, manufacturable at low cost, and free from large lowering of the electric conductivity even when it is wetted with water or dried.

It is preferable that the electro-conductive base material comprises one or more species selected from gold, silver, silver chloride, platinum, aluminum, magnesium, tin, tungsten, iron, copper, nickel, stainless steel, chromium, titanium, and carbon.

The electro-conductive base material like this is usable for the inventive method for manufacturing a bio-electrode particularly favorably.

Advantageous Effects of Invention

As described above, the inventive bio-electrode composition makes it possible to form a living body contact layer for a bio-electrode that is capable of conducting electric signals efficiently from skin to a device (i.e., excellent in electric conductivity), free from the risk of causing allergies even when it is worn on skin for a long time (i.e., excellent in biocompatibility), light in weight, manufacturable at low cost, and free from large lowering of the electric conductivity even when it is wetted with water or dried. The electric conductivity can be more improved by adding a carbon material. It is possible to manufacture a bio-electrode with high flexibility and stretchability to be always in contact with skin by combining flexible urethane gel. Accordingly, the inventive bio-electrode, with the living body contact layer being formed by using the inventive bio-electrode composition like this, is particularly suitable as a bio-electrode used for a medical wearable device. Moreover, the inventive method for manufacturing a bio-electrode makes it possible to manufacture such a bio-electrode easily at low cost.

DESCRIPTION OF EMBODIMENTS

Figure 1:
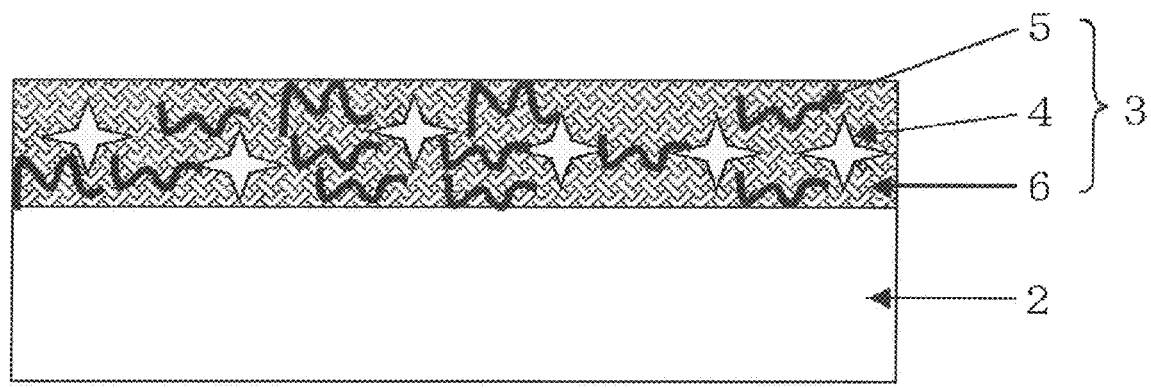
FIG. 1 is a schematic sectional view showing an example of the inventive bio-electrode.

As described above, it has been desired to develop a bio-electrode composition capable of forming a living body contact layer for a bio-electrode that is excellent in electric conductivity and biocompatibility, light in weight, manufacturable at low cost, and free from large lowering of the electric conductivity even when it is wetted with water or dried; a bio-electrode in which the living body contact layer is formed from the bio-electrode composition; and a method for manufacturing the same.

The bio-electrode has a function to convert concentration change of ions released from skin to electric signals. Accordingly, it is necessary to increase the ionic conductivity in the film. Metal films have very high electron conductivity, but have lower performance as a bio-electrode. This is due to lower ionic conductivity of metal films. Water or polar solvent that contains ions has higher ionic conductivity, and bio-electrodes of water-soluble gel that contain hydrated water-soluble polymers and ions have been used widely. However, it has a drawback of lowering the ionic conductivity when the water is dried as described above. It has been required for a dry bio-electrode with high ionic conductivity without containing water or organic solvent.

The method for improving the ionic conductivity other than the addition of a salt of ionic electrolyte include combination of polyether or polycarbonate and a salt. The ions move on the oxygen functional groups of these polymers such that they are hopping. In comparison between polyether and polycarbonate, polyether has stretchability, but polycarbonate does not have stretchability. Since the bio-electrode adhered on skin have to stretch along with the expansion and contraction of skin, polyether is more preferable.

The bio-electrode film composed of a bio-electrode composition is required to be always in contact with skin without fluctuating the area. Fluctuation of contact area is not preferable since it changes the electric conductivity. Accordingly, the bio-electrode film has to be a soft film. As long as it is a soft film, the tackiness is inessential. A soft bio-electrode in a gel state can be always in contact with skin to give stable biological signals. Polyurethane in which a polyether group is introduced is excellent in flexibility. In this case, the urethane resin is formed by the reaction of an isocyanate compound and polyether having hydroxy groups at the terminals. A soft urethane resin with tackiness in a gel state can be produced by reducing the crosslinking density.

Illustrative examples of the salt of ionic electrolyte include ionic liquid. Ionic liquids are characterized by high thermal and chemical stability as well as excellent electric conductivity, thereby having been widely used for battery uses. Illustrative examples of known ionic liquid include hydrochloric acid salt, hydrobromic acid salt, hydroiodic acid salt, trifluoromethanesulfonic acid salt, nonafluorobutanesulfonic acid salt, bis(trifluoromethanesulfonyl)imidic acid salt, hexafluorophosphate salt, and tetrafluoroborate salt of sulfonium, phosphonium, ammonium, morpholinium, pyridinium, pyrrolidinium, and imidazolium. However, these salts (particularly, the ones with low molecular weight) are generally liable to hydrate, thereby causing a bio-electrode to lower the electric conductivity due to extraction of the salt with perspiration or by washing when these salts are added to a self-adhesive composition to form the living body contact layer. The tetrafluoroborate salt is highly toxic, and the other salts have high solubility in water to easily permeate into skin, each of which causes rough dry skin (i.e., highly irritative to skin).

Additionally, urethane resins have higher hydrophilicity and are degraded by gradual hydrolysis of the urethane bonds. To decrease the hydrolysis, it is efficient to increase the hydrophobicity. Accordingly, silicone-urethanes having a silicone bond have been investigated. A urethane resin in which silicone is introduced into the main chain has both of a silicone moiety and a urethane moiety in the main chain. In this case, introduction of silicone lowers the stretchability and the strength. This is because silicone has lower strength compared to urethane. When silicone with shorter chain length is introduced into the side chain, the strength is rather improved far from being lowered. This is probably due to increased hydrogen bonding of the urethane bond caused by introduction of a silicone side chain with shorter chain length. The silicone side chain is capable of increasing the repellency more efficiently.

For highly-sensitive bio-electrodes, which can detect weak biological signals, higher ionic conductivity is necessary. Silicones are insulators, but urethanes are allowed to have improved ionic conductivity by introducing polyether into the chain extending moiety. From this viewpoint, urethanes that have polyethers introduced into the main chain are preferable rather than urethanes that have polysiloxanes introduced into the main chain. Among the polyethers, polyethylene glycol chains have highest electric conductivity and are preferable.

Accordingly, the inventors have diligently investigated the above problems to find that bio-electrode compositions that contain a resin containing a main chain having a urethane bond and two side chains each having a silicon-containing group excels in repellency and electric conductivity, and to find that bio-electrode compositions with the electro-conductive material being a polymeric salt do not cause lowering of electric conductivity due to water extraction or irritating the skin due to passing through skin; thereby bringing the present invention to completion.

That is, the present invention is a bio-electrode composition comprising:

a resin containing a main chain having a urethane bond and two side chains each having a silicon-containing group; and an electro-conductive material, wherein the electro-conductive material is a polymer compound having one or more repeating units selected from the group consisting of fluorosulfonic acid salts shown by the following formulae (1)-1 and (1)-2, sulfonimide salts shown by the following formula (1)-3, and sulfonamide salts shown by the following formula (1)-4,

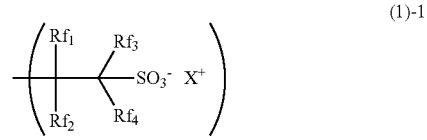
(1)-1

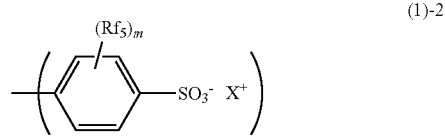
(1)-2

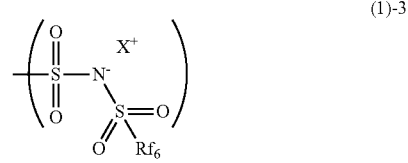
(1)-3

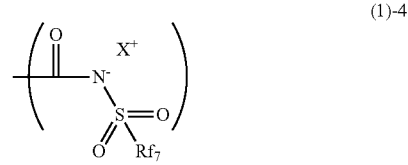
(1)-4 wherein $Rf_1$ and $Rf_2$ each represent a hydrogen atom, a fluorine atom, a trifluoromethyl group, or an oxygen atom, provided that when $Rf_1$ represents an oxygen atom, $Rf_2$ also represents an oxygen atom to form a carbonyl group together with a carbon atom bonded therewith; $Rf_3$ and $Rf_4$ each represent a hydrogen atom, a fluorine atom, or a trifluoromethyl group; provided that one or more fluorine atoms are contained in $Rf_1$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; $X^+$ represents a sodium ion, a potassium ion, or a cation having an ammonium ion structure shown by the following formula (1)-5; and "m" is an integer of 1 to 4,

(1)-5 wherein $R^1$ to $R^4$ each represent a hydrogen atom, a linear, branched, or cyclic alkyl group having 1 to 20 carbon atoms, an alkenyl group having 2 to 14 carbon atoms, or an alkynyl group having 2 to 5 carbon atoms, optionally having an ether group, an ester group, a carbonyl group, a sulfonyl group, a cyano group, an amino group, a nitro group, hydroxy group, a sulfur atom except in the sulfonyl group, or a halogen atom, and optionally bonded to each other to form a ring.

Hereinafter, the present invention will be described specifically, but the present invention is not limited thereto.

<Bio-Electrode Composition>

The inventive bio-electrode composition contains an electro-conductive material (polymeric ionic material) and a resin containing a main chain having a urethane bond and two side chains each having a silicon-containing group (urethane resin having two pendant silicon-containing group in the side chains branched from a carbon atom of the main chain). Hereinafter, each component will be described more specifically.

[Electro-Conductive Material (Salt)]

The salt to be added to the inventive bio-electrode composition as an electro-conductive material is a polymer compound having one or more repeating units selected from the group consisting of fluorosulfonic acid salts shown by any of the following formulae (1)-1 and (1)-2, sulfonimide salts shown by the following formula (1)-3, and sulfonamide salts shown by the following formula (1)-4,

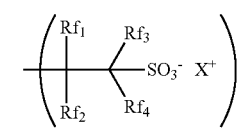

(1)-1

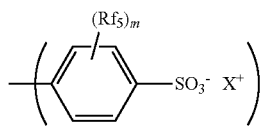

(1)-2

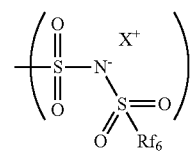

(1)-3

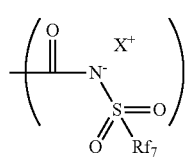

(1)-4 wherein $Rf_1$ and $Rf_2$ each represent a hydrogen atom, a fluorine atom, a trifluoromethyl group, or an oxygen atom, provided that when $Rf_1$ represents an oxygen atom, $Pf_2$ also represents an oxygen atom to form a carbonyl group together with a carbon atom bonded therewith; $Rf_3$ and $Rf_4$ each represent a hydrogen atom, a fluorine atom, or a trifluoromethyl group; provided that one or more fluorine atoms are contained in $Rf_1$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; $X^+$ represents a sodium ion, a potassium ion, or a cation having an ammonium ion structure shown by the following formula (1)-5; and "m" is an integer of 1 to 4,

(1)-5 wherein $R^1$ to $R^4$ each represent a hydrogen atom, a linear, branched, or cyclic alkyl group having 1 to 20 carbon atoms, an alkenyl group having 2 to 14 carbon atoms, or an alkynyl group having 2 to 5 carbon atoms, optionally having an ether group, an ester group, a carbonyl group, a sulfonyl group, a cyano group, an amino group, a nitro group, hydroxy group, a sulfur atom except in the sulfonyl group, or a halogen atom, and optionally bonded to each other to form a ring.

The electro-conductive material used for the inventive bio-electrode composition, being the salt as described above, is excellent in electric conductivity, and being a polymeric salt (ionic polymer), has extremely low water solubility and does not pass through skin.

The irritation to skin is higher as the polymeric acid is stronger before neutralization with sodium, potassium, ammonium, etc. Among the electro-conductive materials described above, the sulfonamide shown by the formula (1)-4 has lowest acidity and lowest irritation to skin thereby, and is preferably used.

It is preferable that the one or more repeating units selected from the group consisting of fluorosulfonic acid salts shown by the formulae (1)-1 and (1)-2, sulfonimide salts shown by the formula (1)-3, and sulfonamide salts shown by the formula (1)-4 be one or more repeating units selected from repeating units a1 to a7 shown by the following formulae (2),

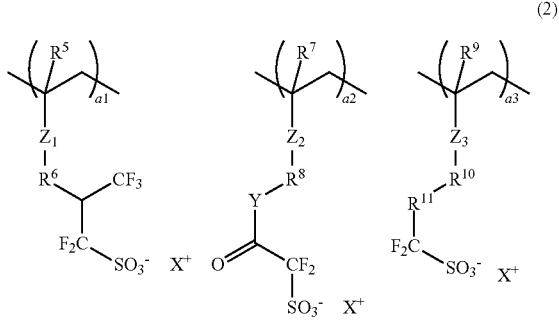

(2)

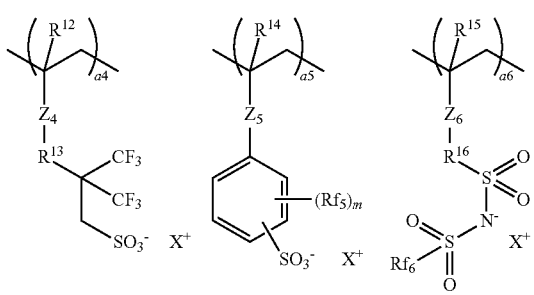

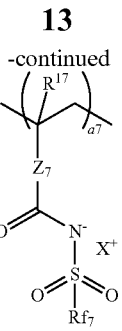

wherein $R^5$, $R^7$, $R^9$, $R^{12}$, $R^{14}$, $R^{15}$, and $R^{17}$ each independently represent a hydrogen atom or a methyl group; $R^6$, $R^8$, $R^{10}$, $R^{13}$, and $R^{16}$ each independently represent any of a single bond, an ester group, or a linear, branched, or cyclic hydrocarbon group having 1 to 13 carbon atoms optionally having either or both of an ether group and an ester group; $R^{11}$ represents a linear or branched alkylene group having 1 to 4 carbon atoms, and one or two of the hydrogen atoms in $R^{11}$ are optionally substituted with a fluorine atom; $Z_1$, $Z_2$, $Z_3$, $Z_4$, and $Z_5$ each independently represent any of a single bond, a phenylene group, a naphthylene group, an ether group, an ester group, or an amide group; $Z_5$ represents any of a single bond, an ether group, or an ester group; $Z_7$ represents a single bond, an arylene group having 6 to 12 carbon atoms, or —C(=O)—O—$Z^8$—; and $Z^8$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $Z^8$; Y represents an oxygen atom or an —$NR^{18}$— group; $R^{18}$ represents a hydrogen atom, or a linear or branched alkyl group having 1 to 4 carbon atoms, optionally bonded to $R^8$ to form a ring; "m" is an integer of 1 to 4; a1, a2, a3, a4, a5, a6, and a7 satisfy $0 \le a1 \le 1.0$, $0 \le a2 \le 1.0$, $0 \le a3 \le 1.0$, $0 \le a4 \le 1.0$, $0 \le a5 \le 1.0$, $0 \le a6 \le 1.0$, $0 \le a7 \le 1.0$, and $0 \le a1+a2+a3+a4+a5+a6+a7 \le 1.0$; and $Rf_5$, $Rf_6$, $Rf_7$, and $X^+$ have the same meanings as defined above.

The fluorosulfonic acid salt monomer to obtain the repeating unit a1 in the formulae (2) is not particularly limited, and illustrative examples thereof include the following.

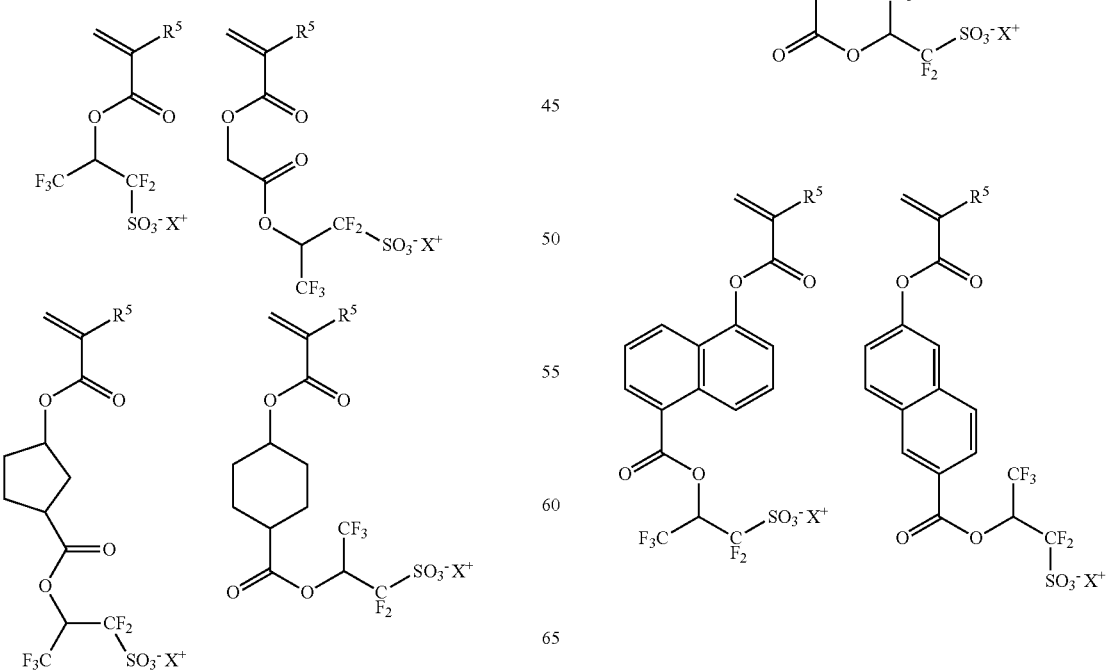

-continued
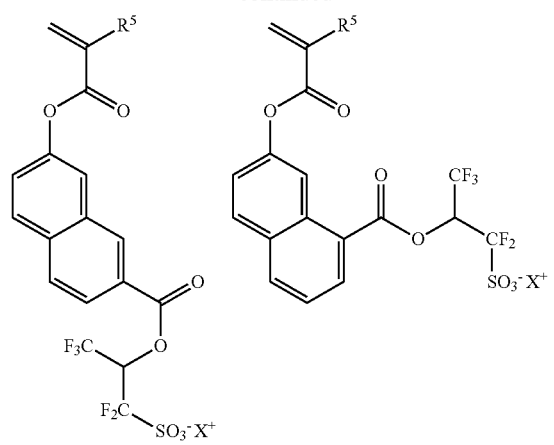
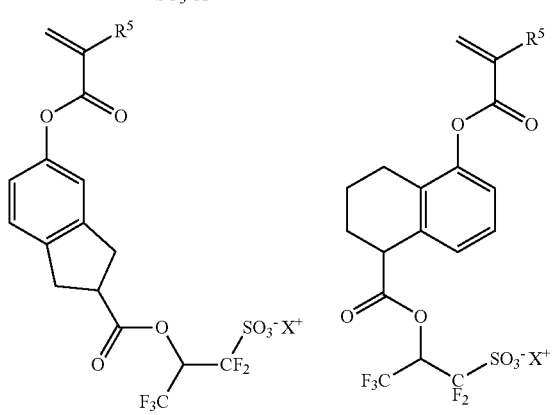
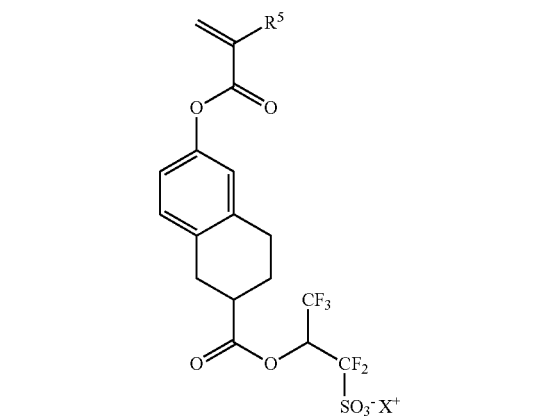
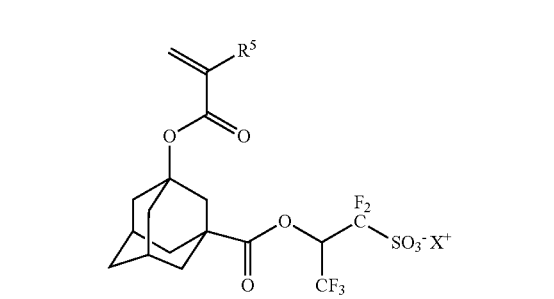
-continued
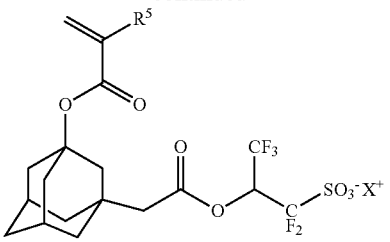
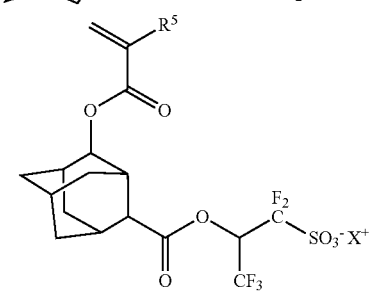
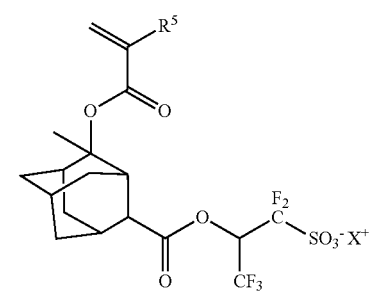
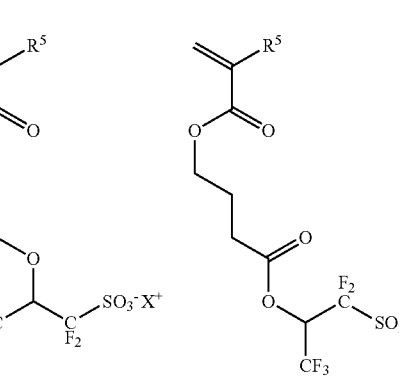
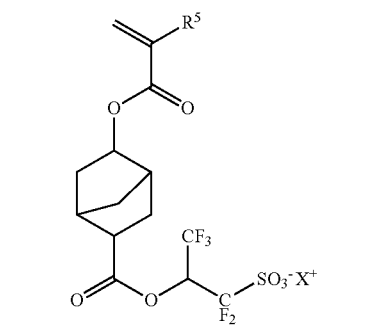

-continued
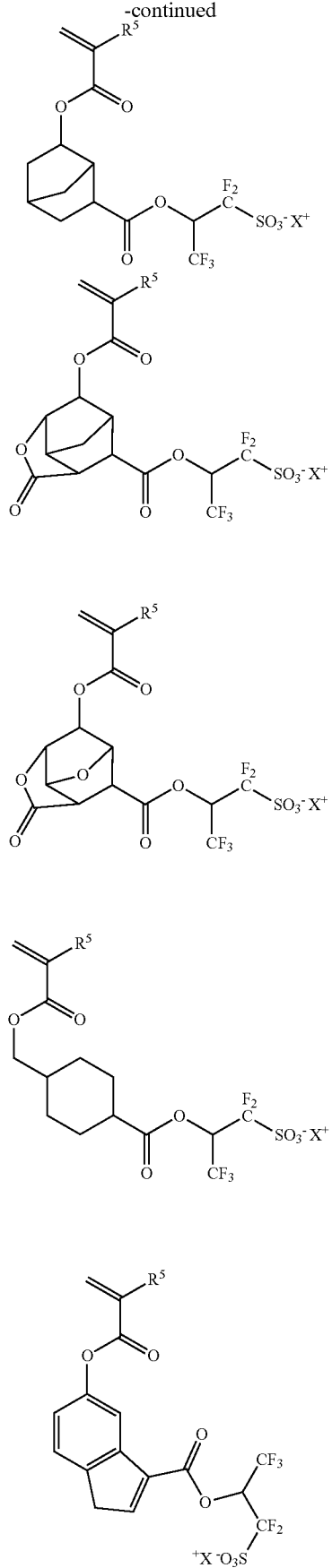
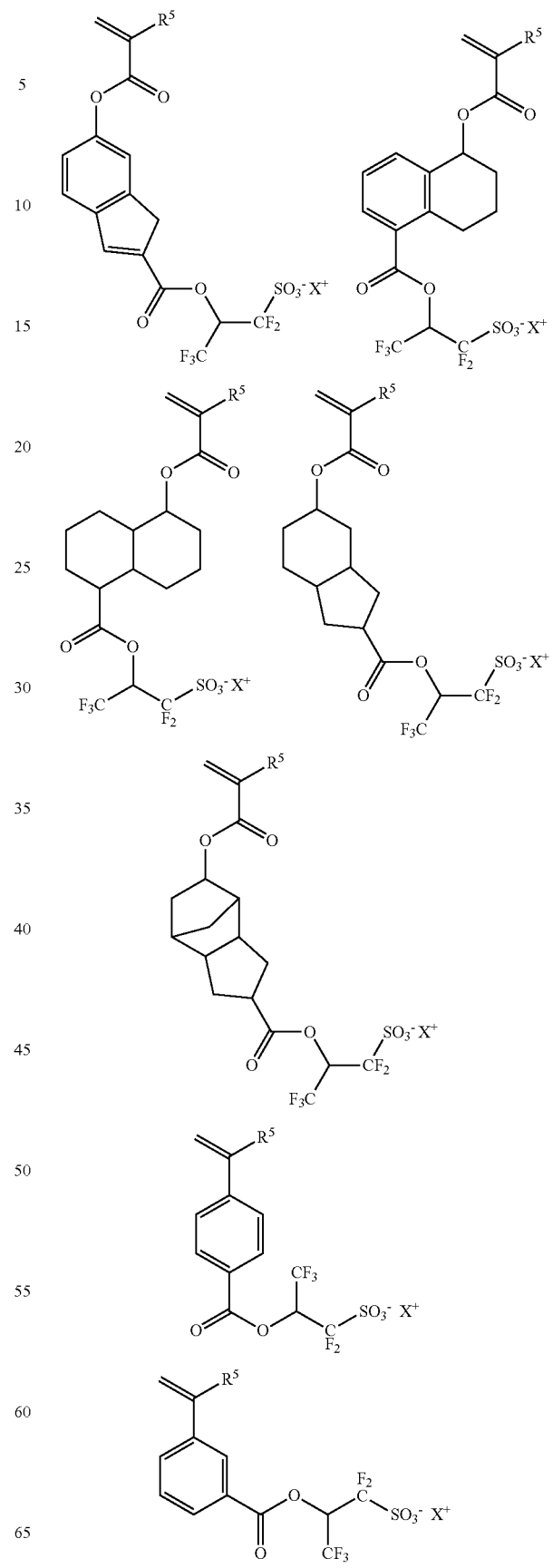

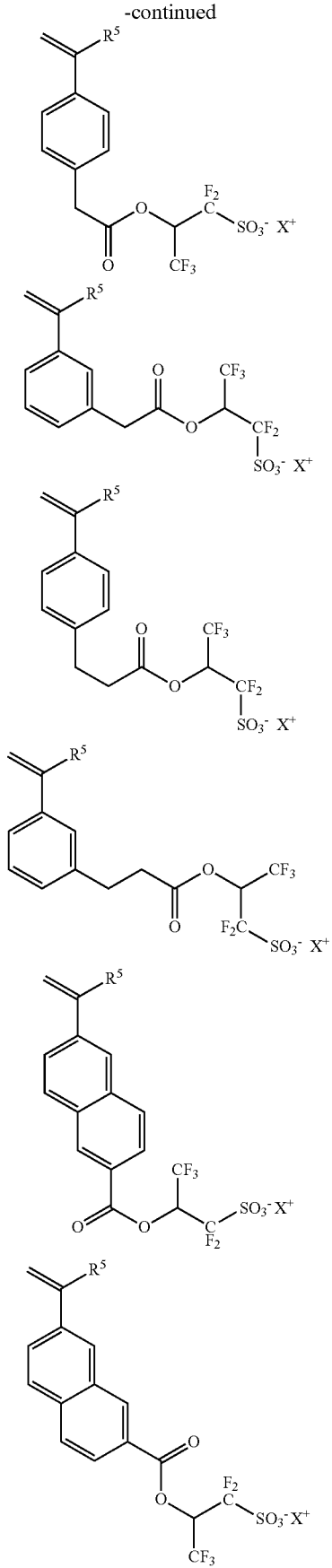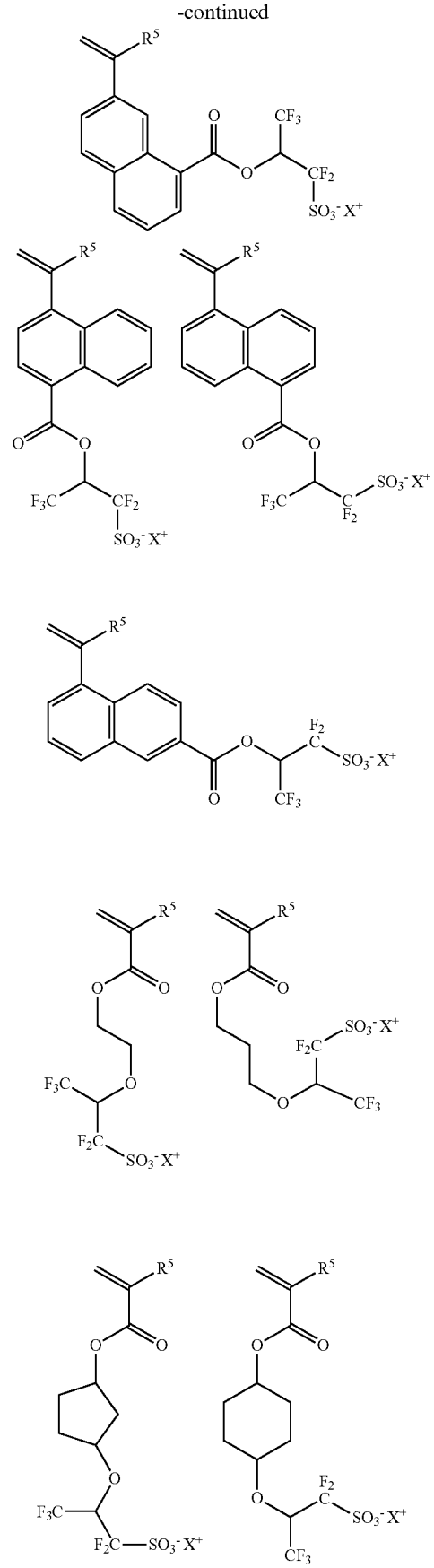

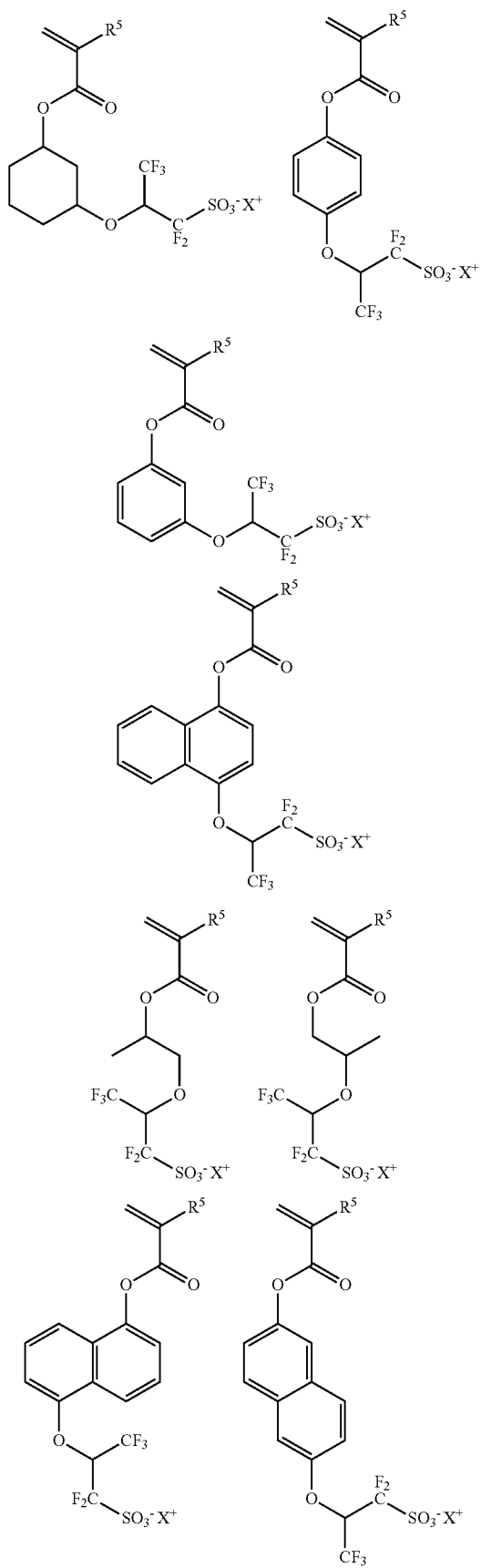
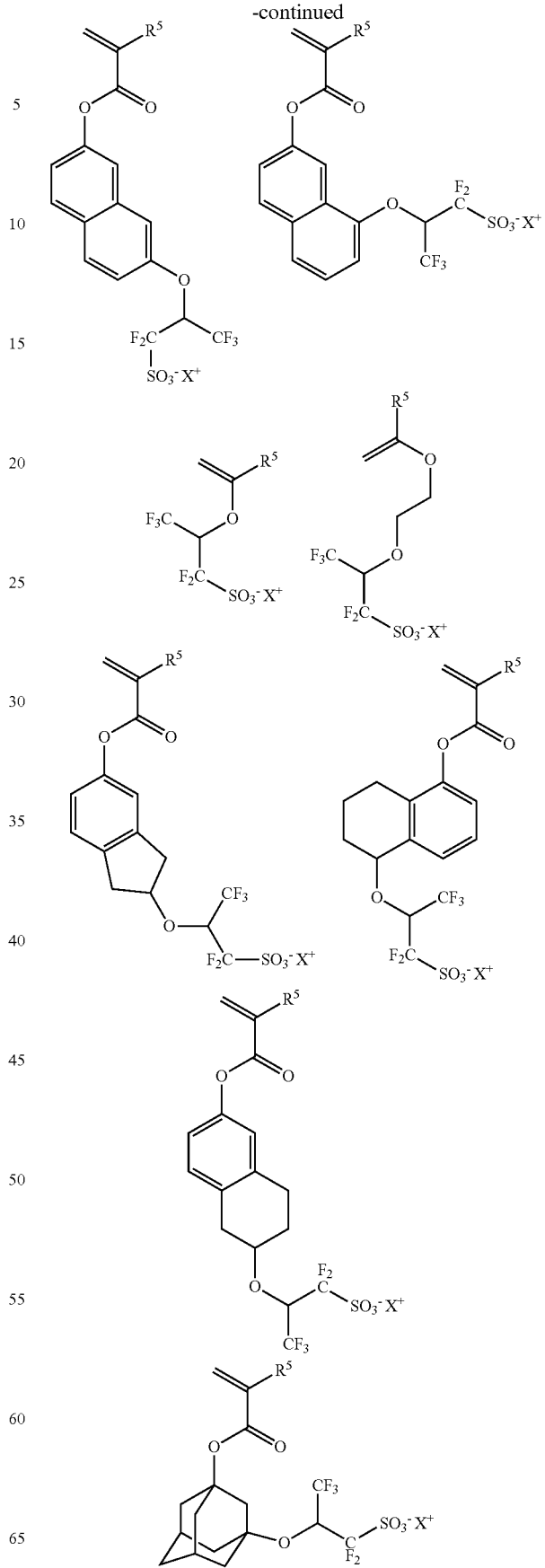

-continued
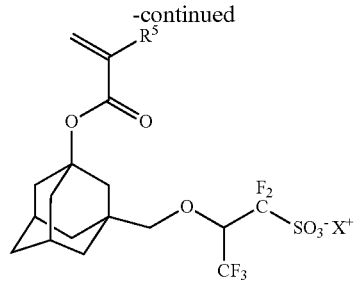
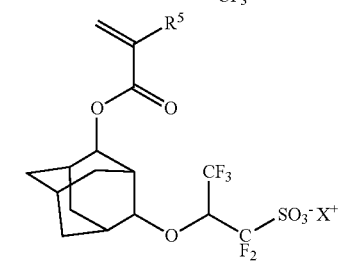
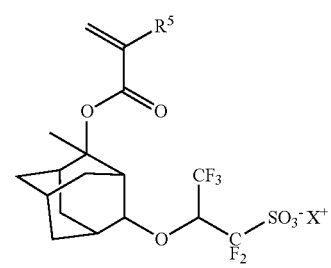
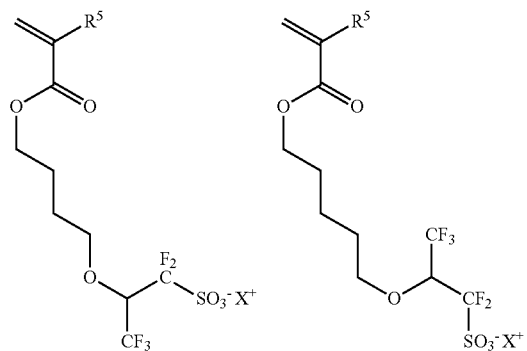
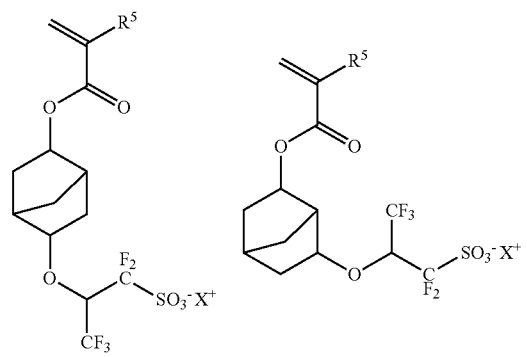
-continued
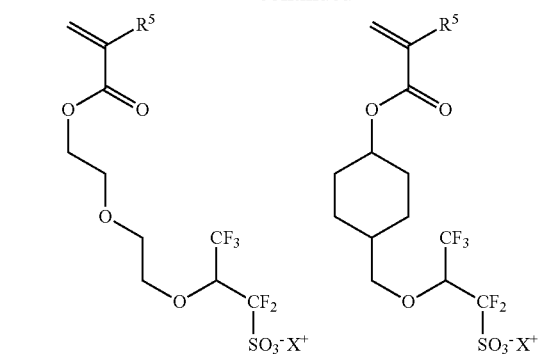
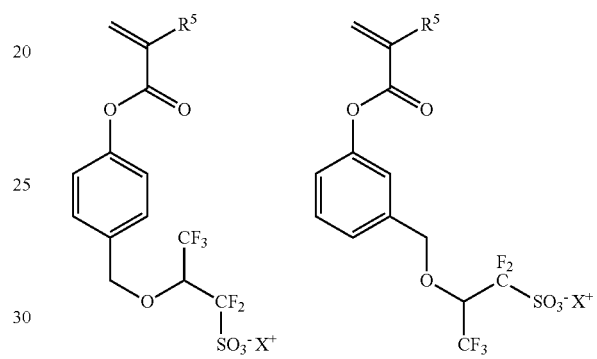
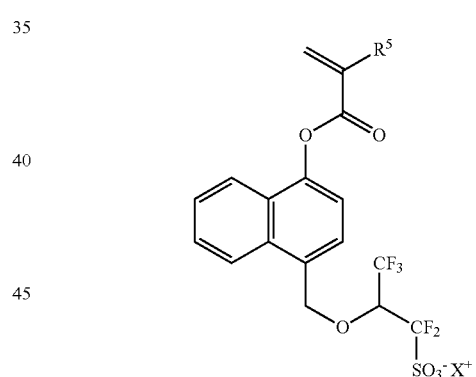
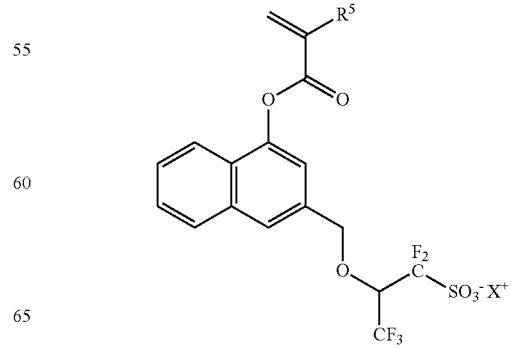

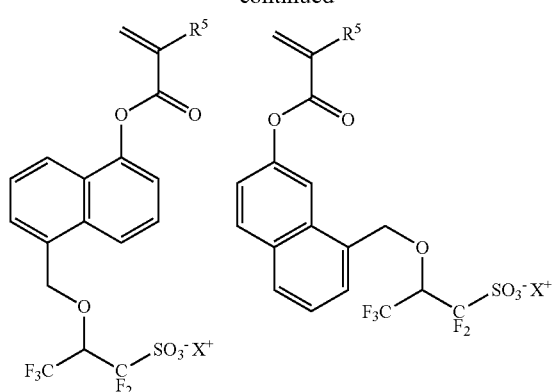
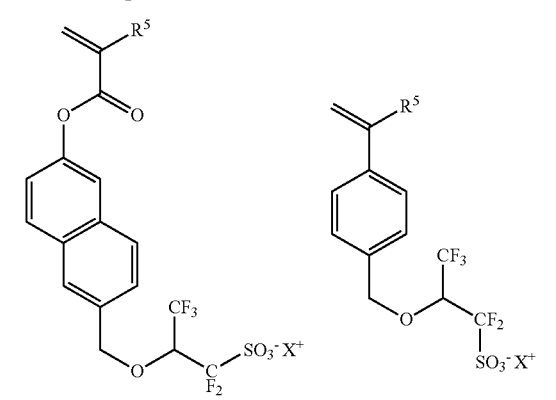
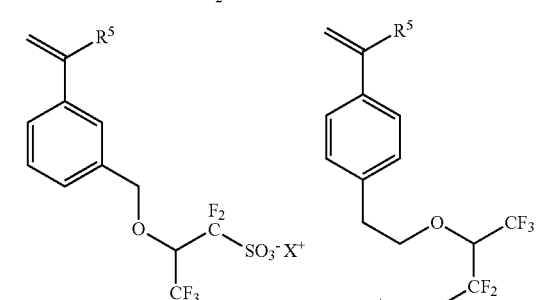
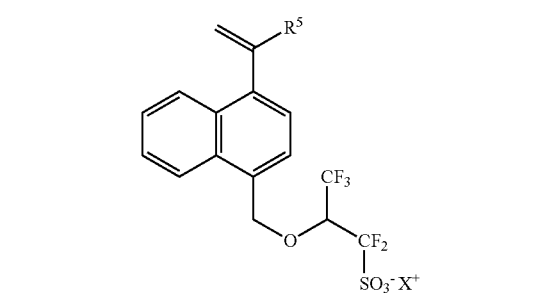
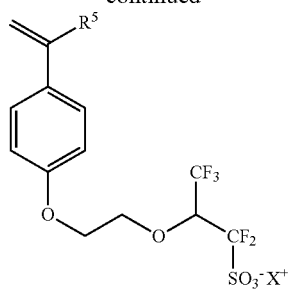
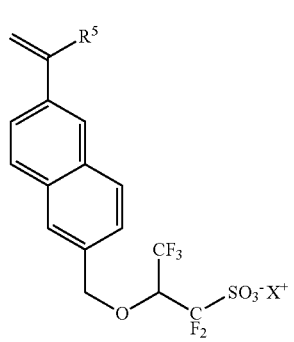
In the formulae, $R^5$ and X have the same meanings as defined above.
The fluorosulfonic acid salt monomer to obtain the repeating unit a2 in the formulae (2) is not particularly limited, and illustrative examples thereof include the following.
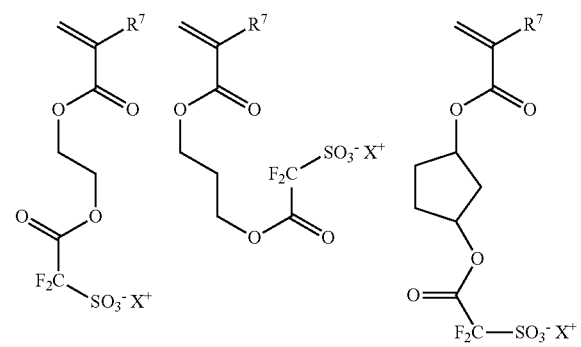
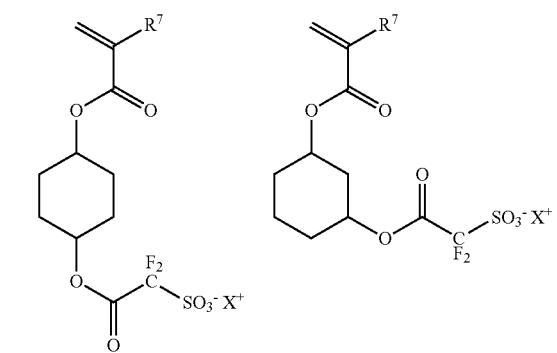

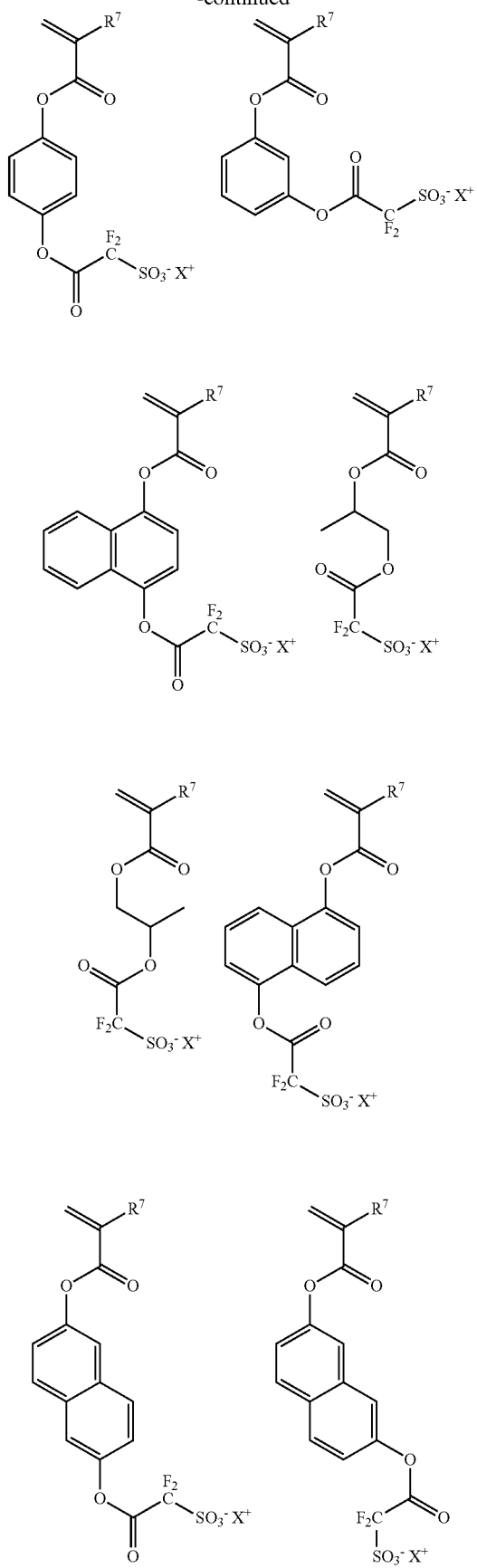
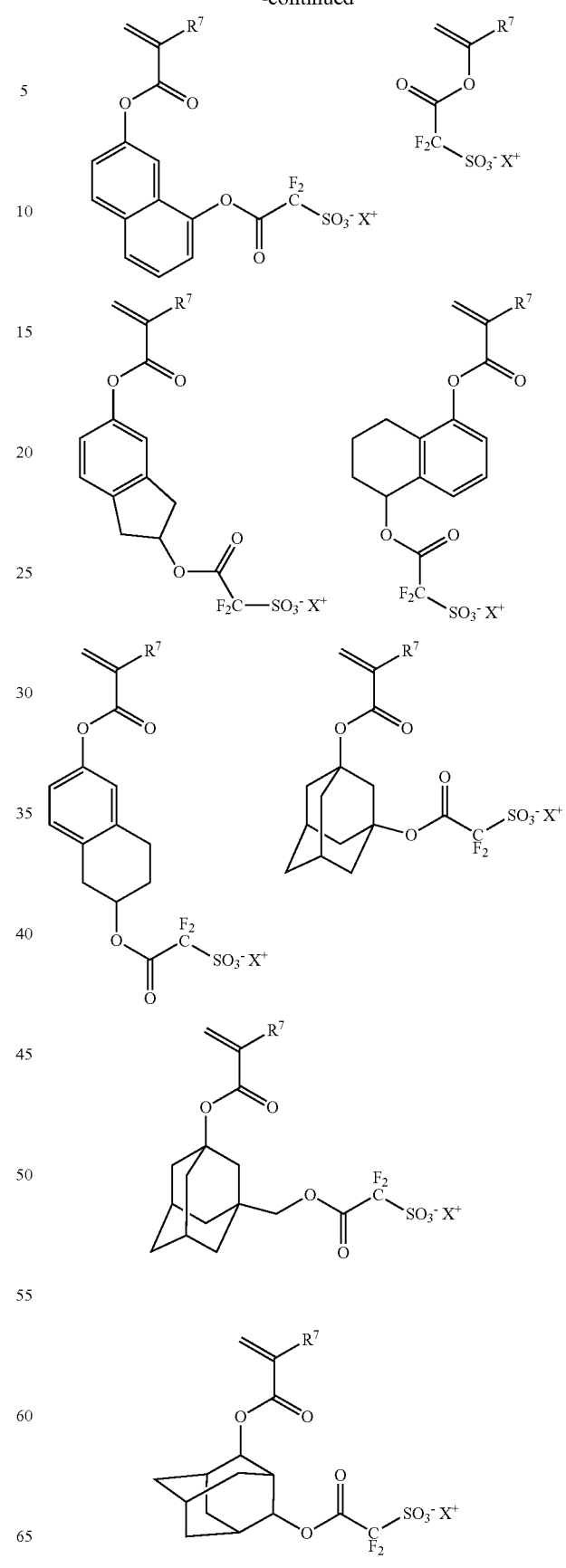

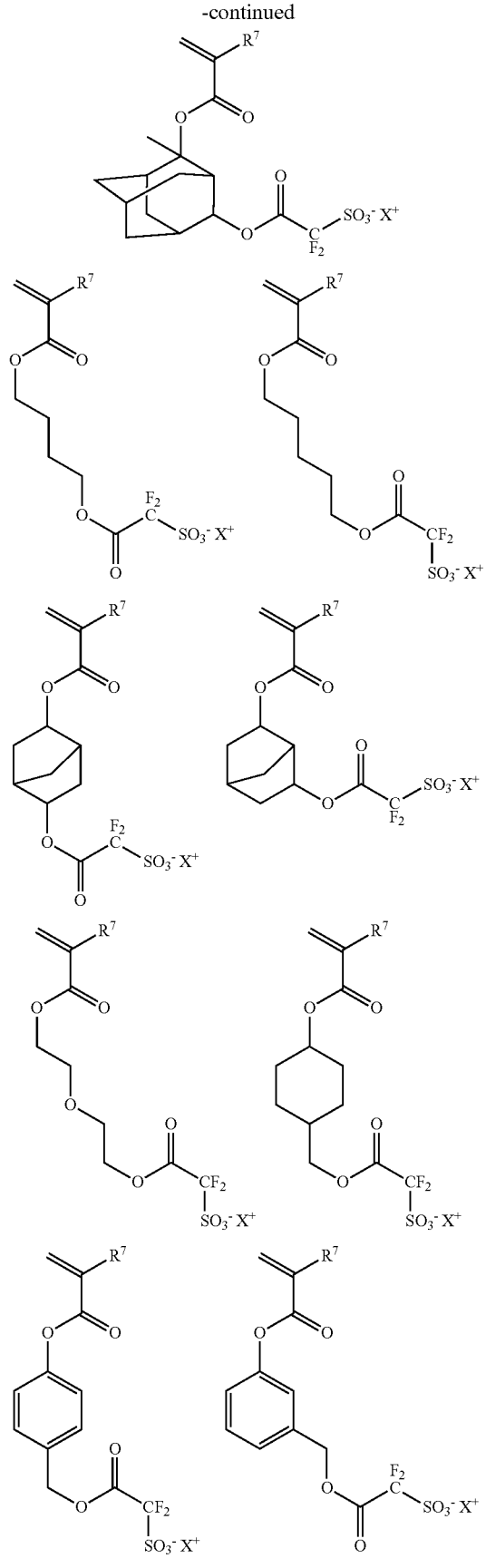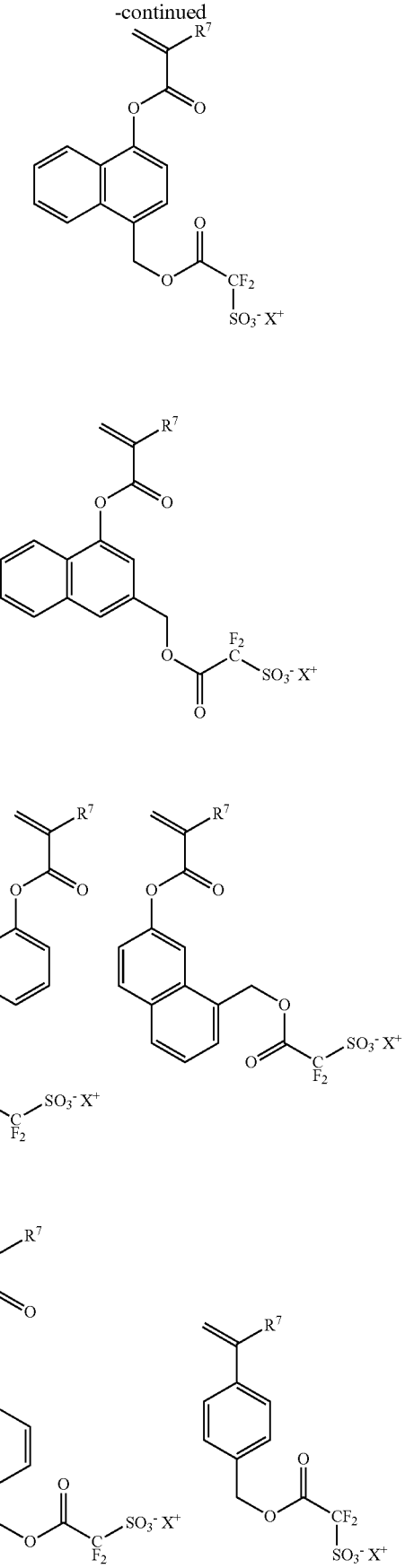

-continued
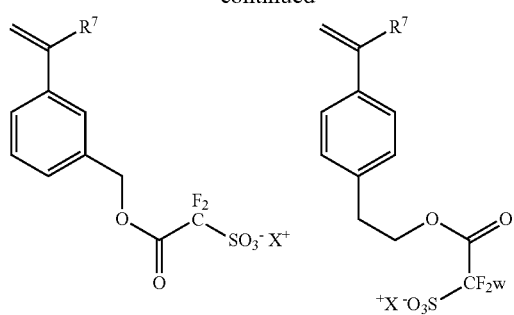
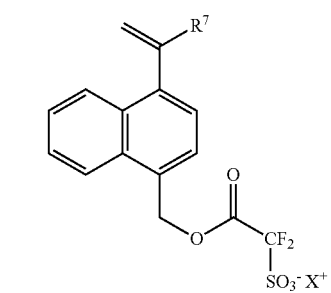
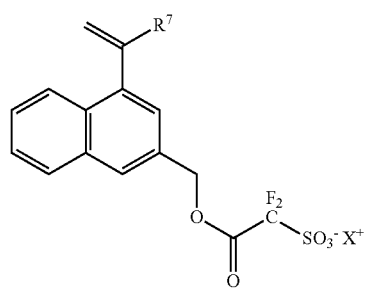
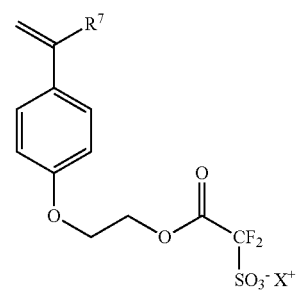
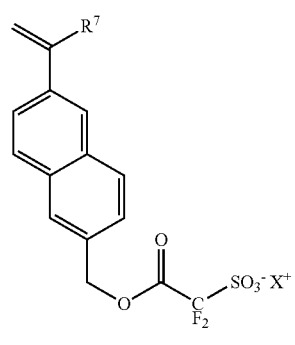
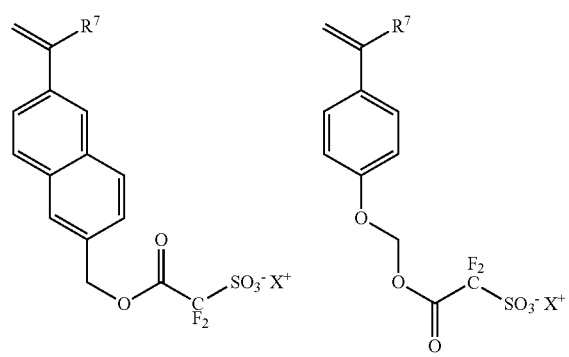
-continued
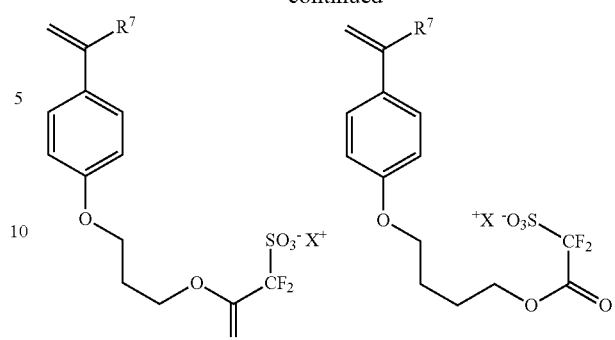
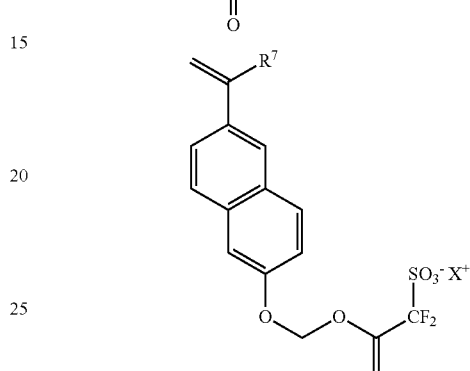
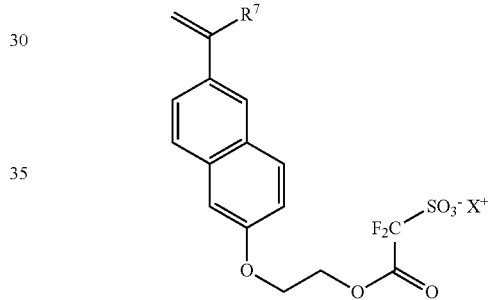
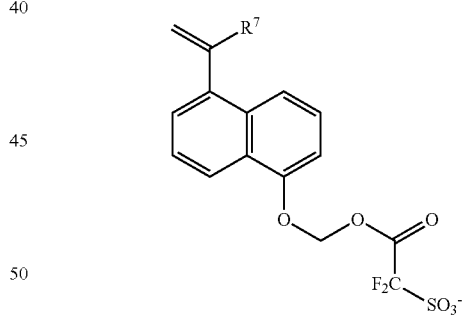
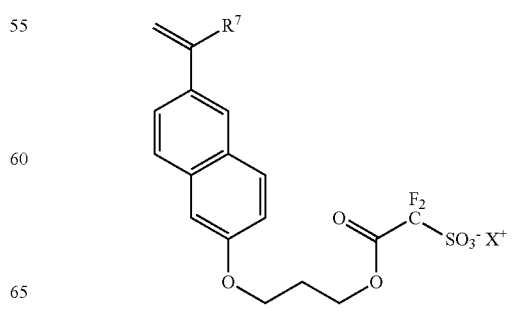

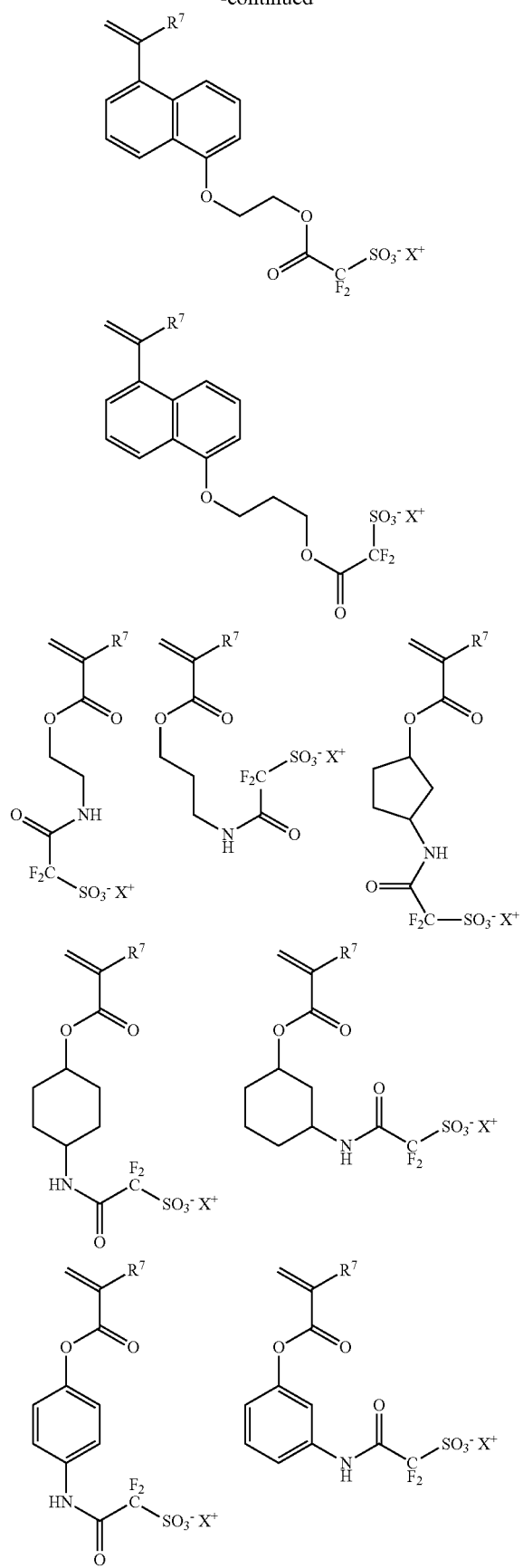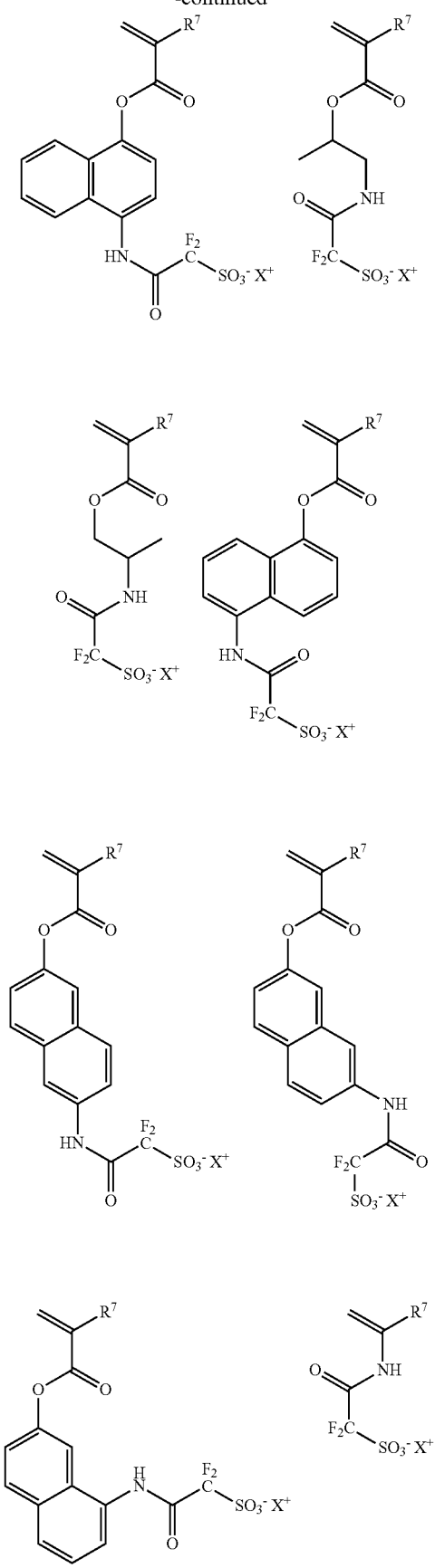

-continued
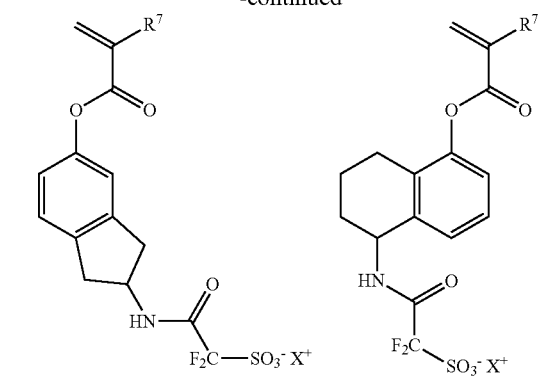
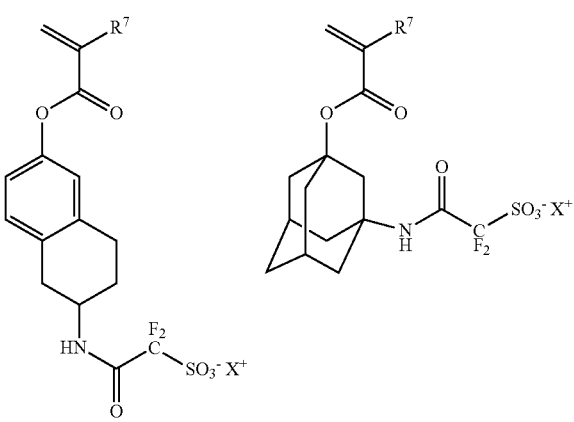
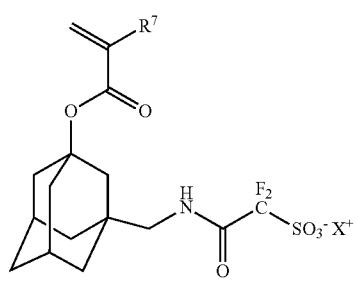
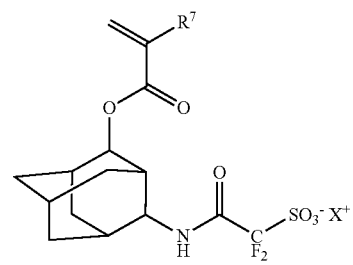
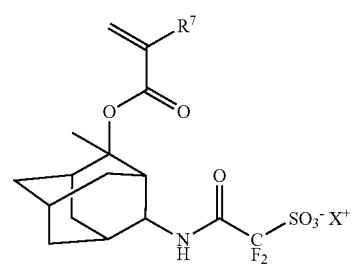
-continued
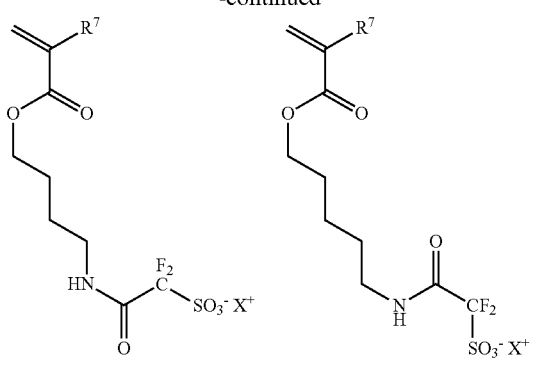
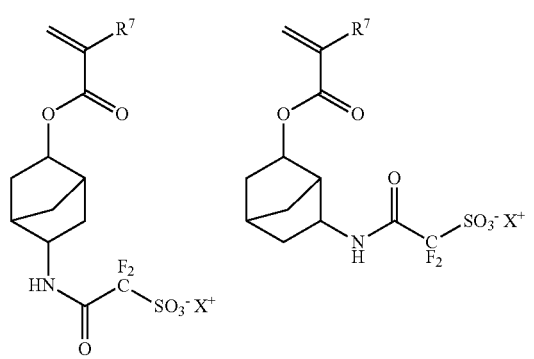
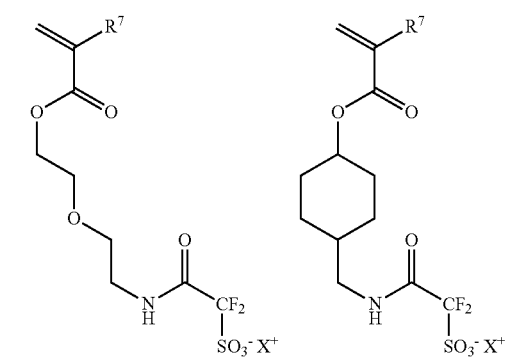
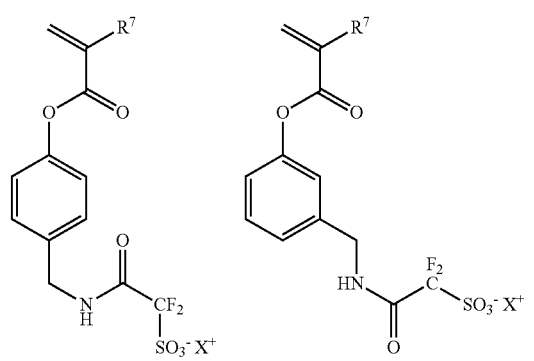

-continued
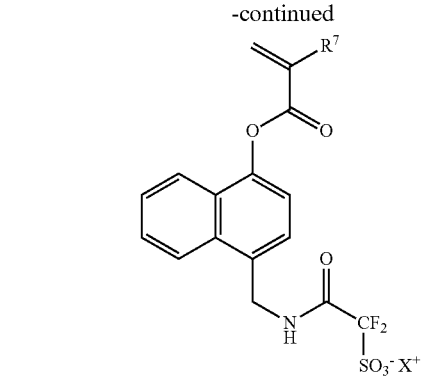
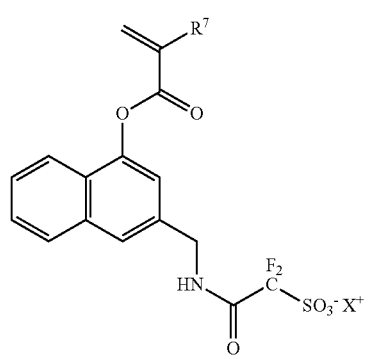
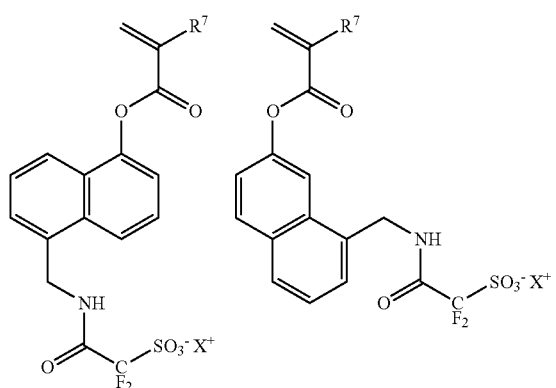
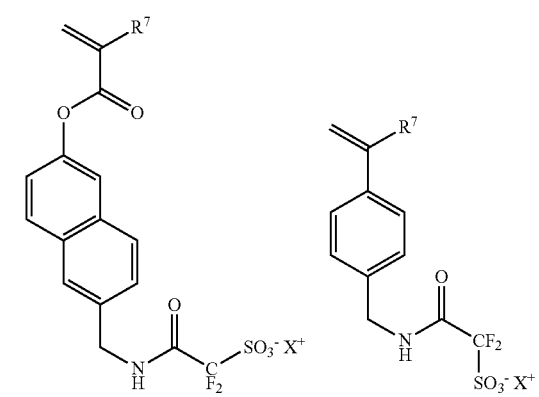
-continued
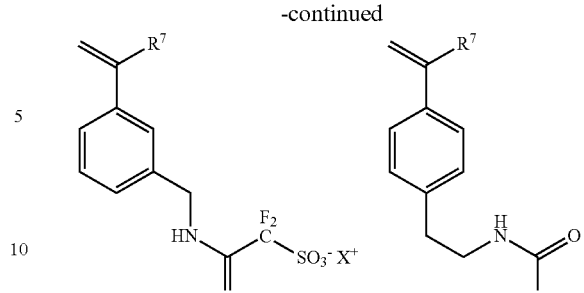
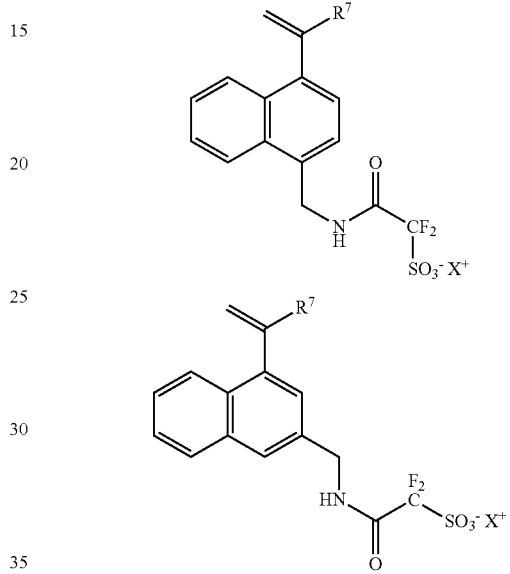
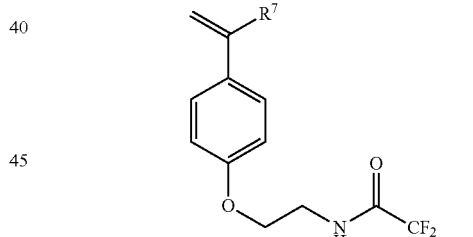
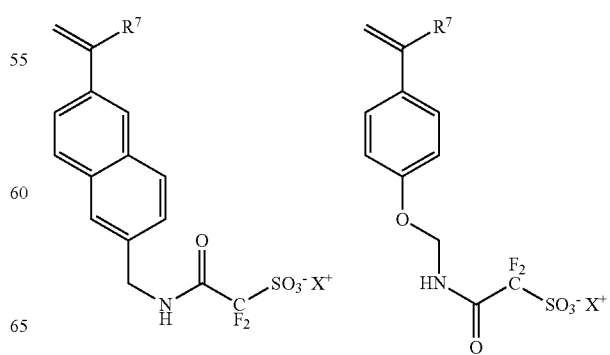

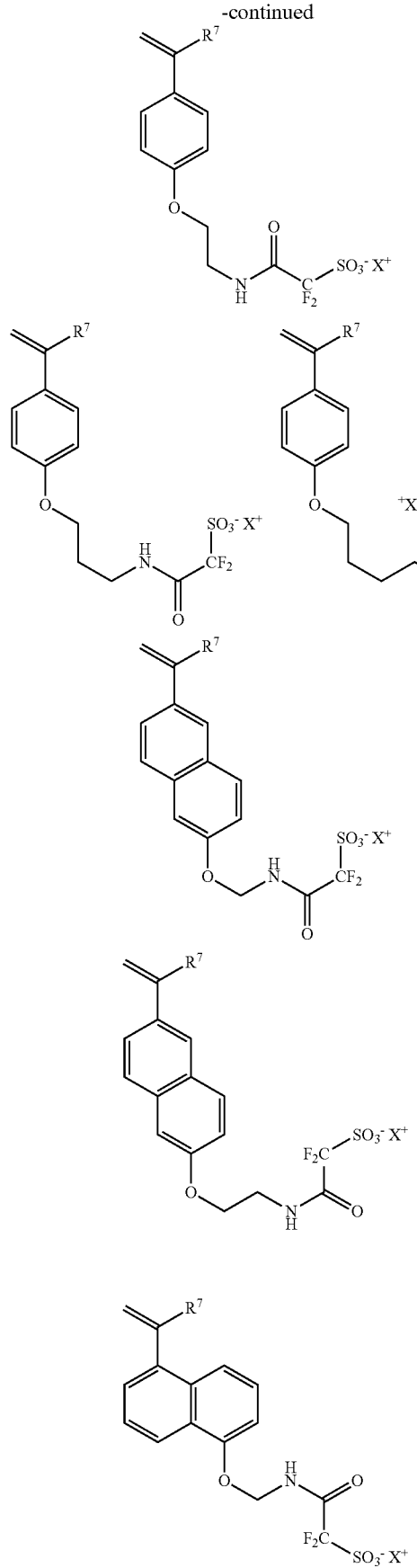
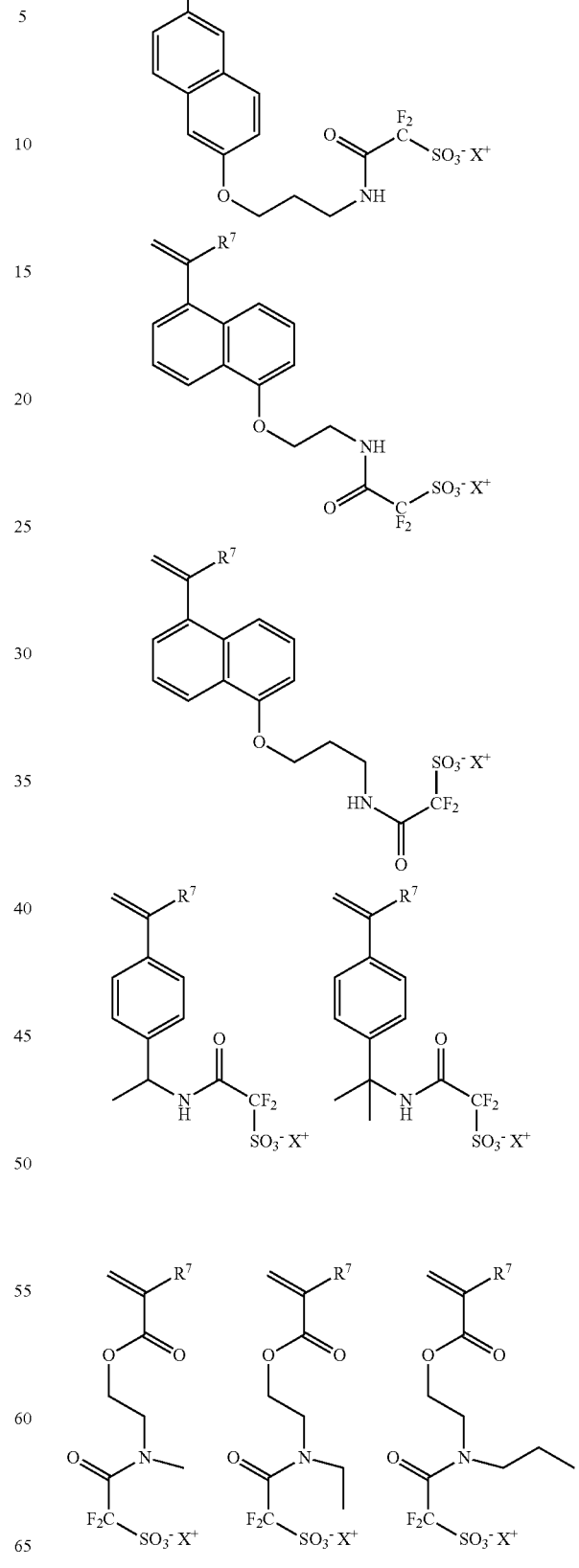

41
-continued
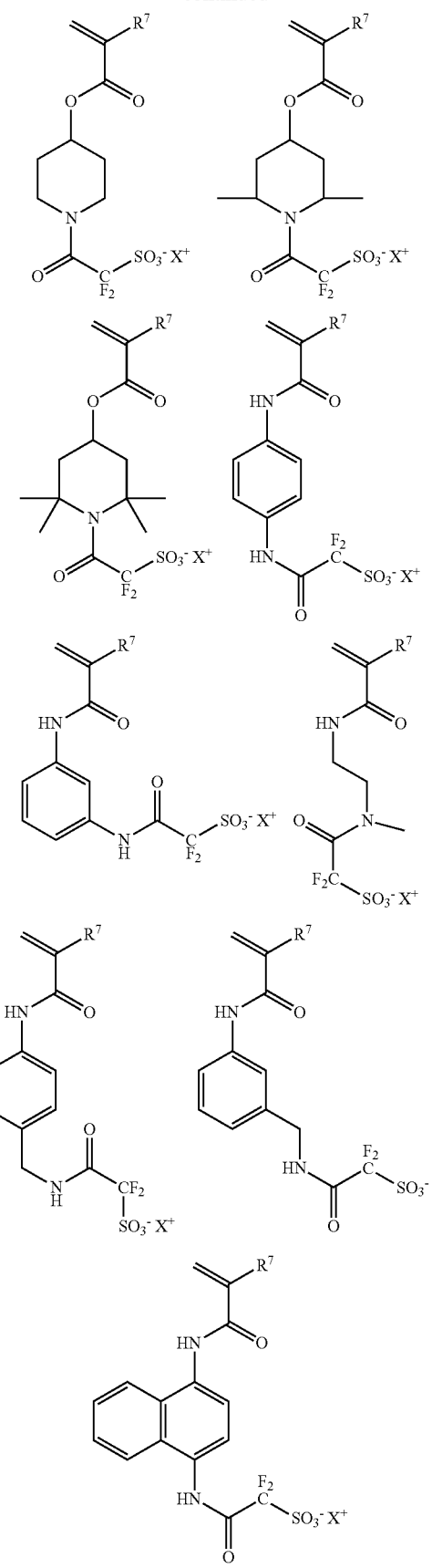
42
-continued
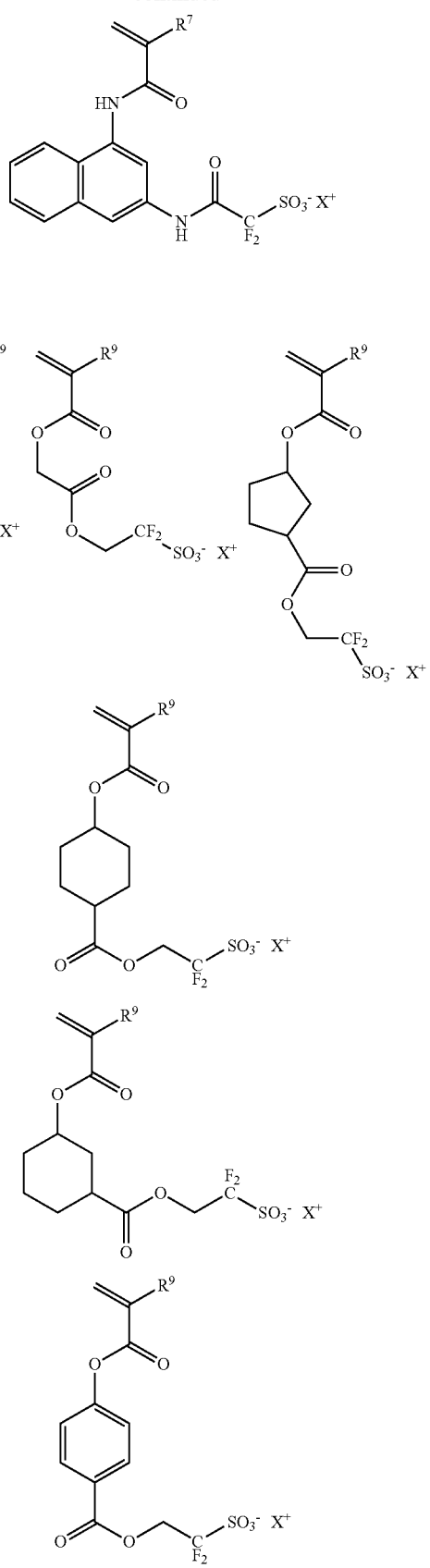

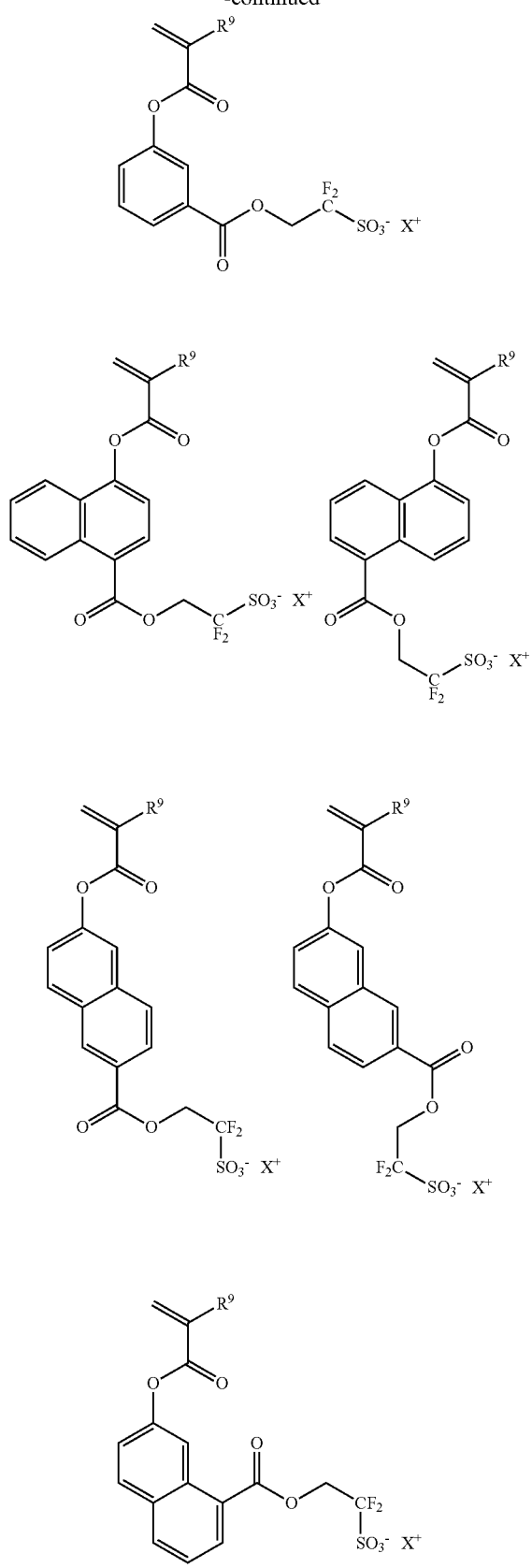
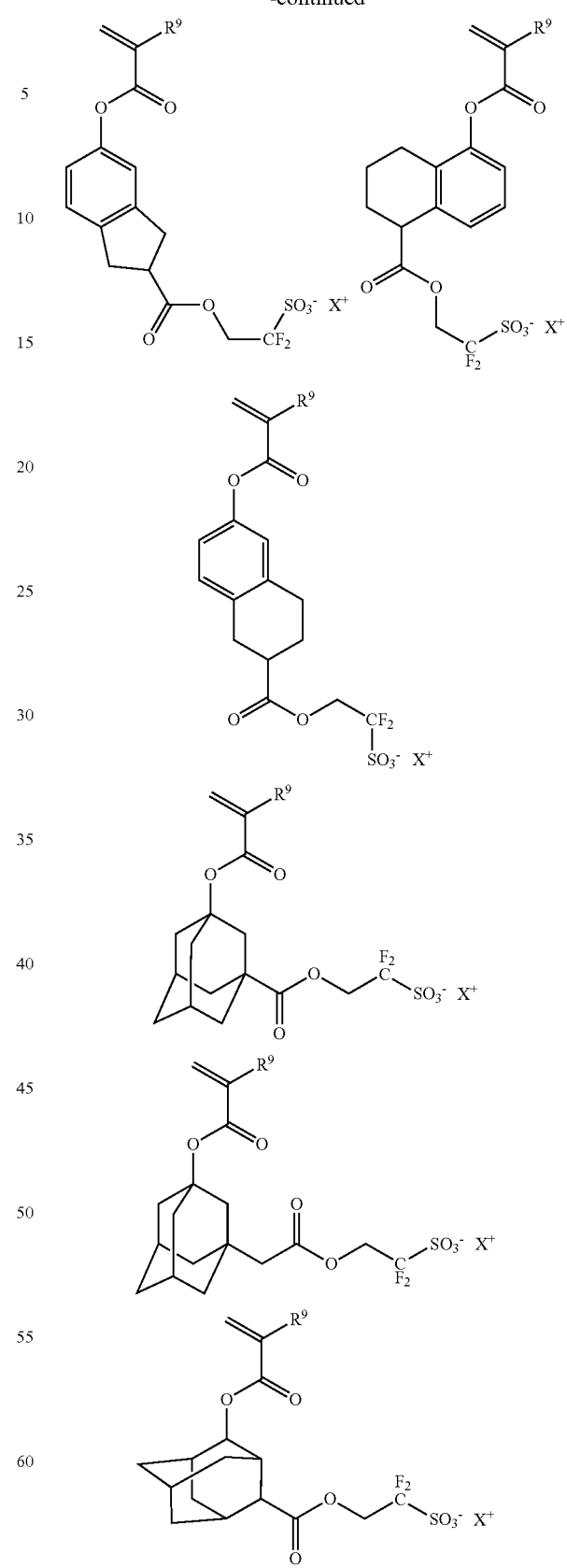

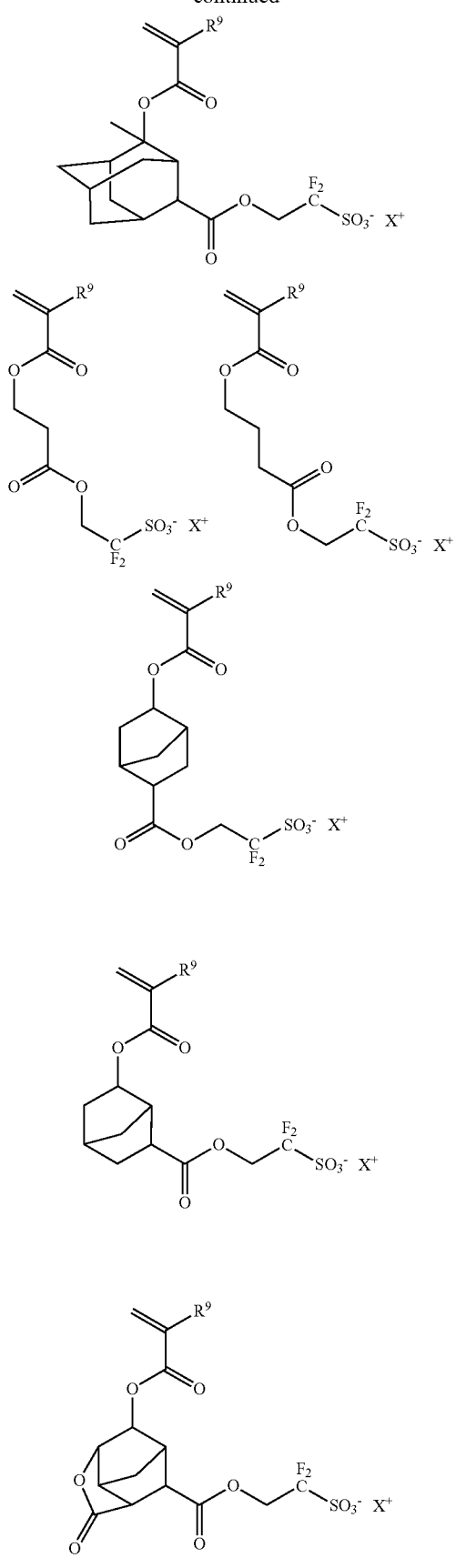

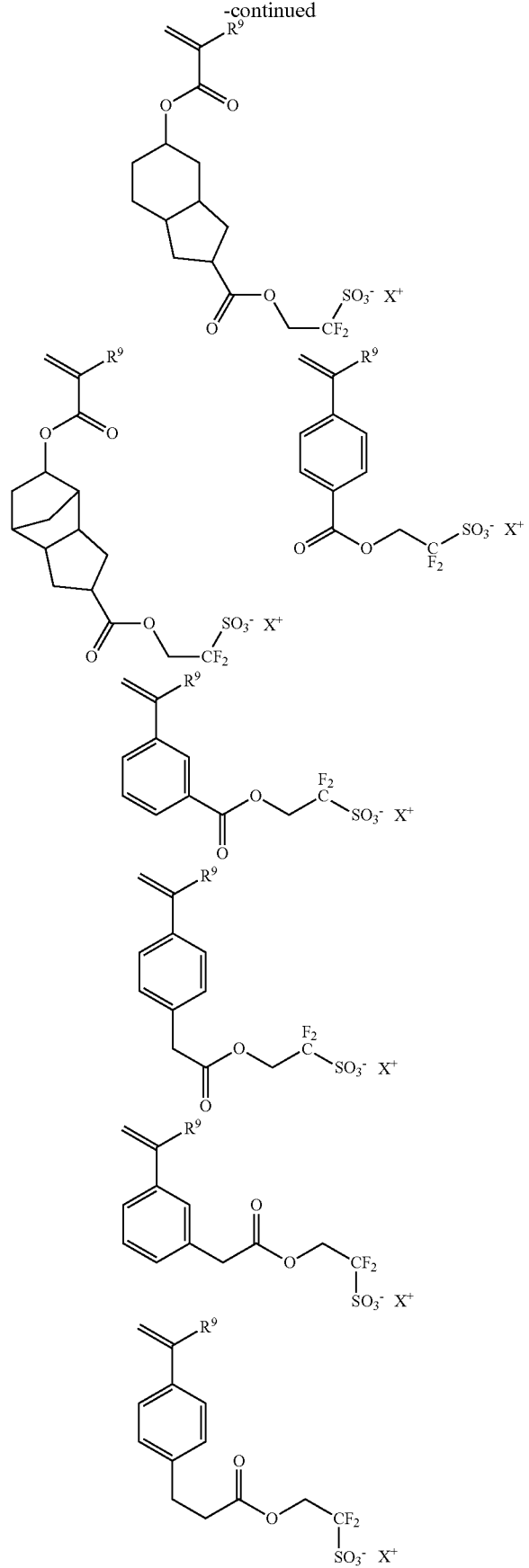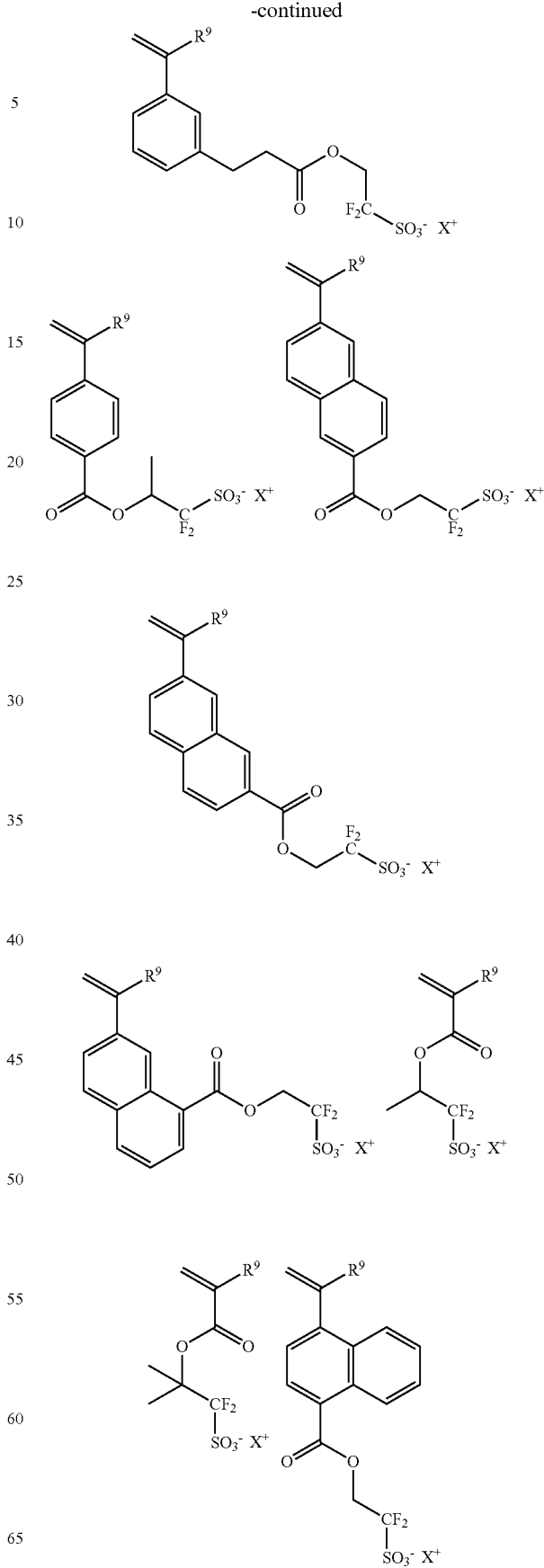

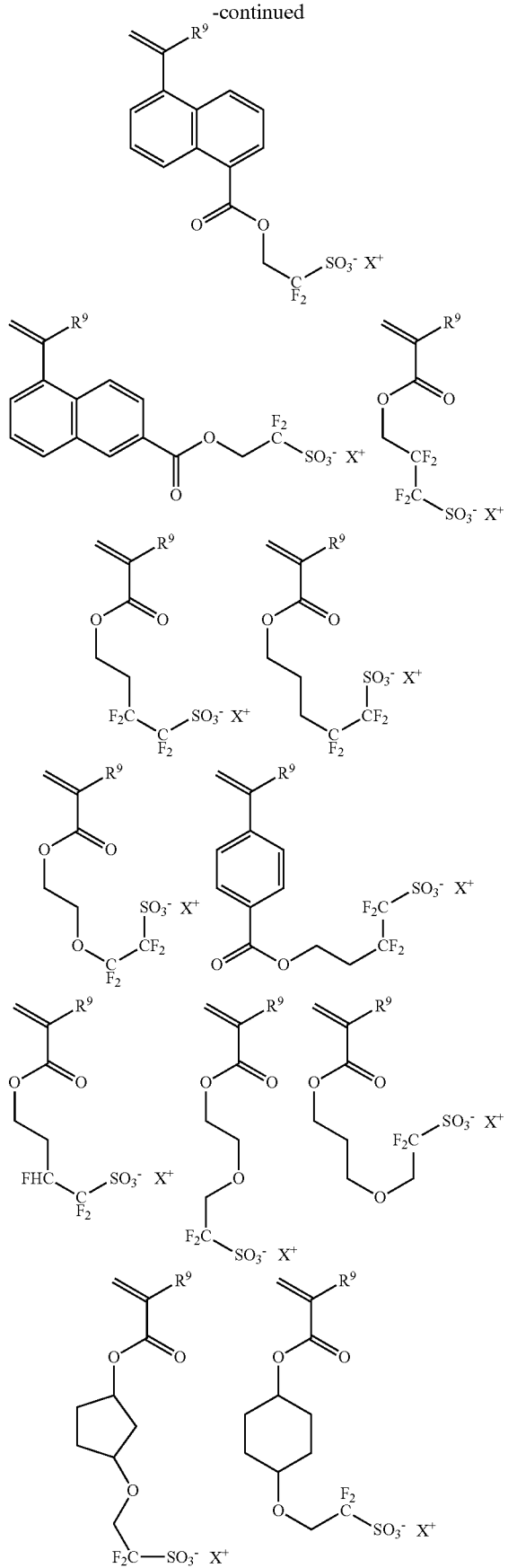
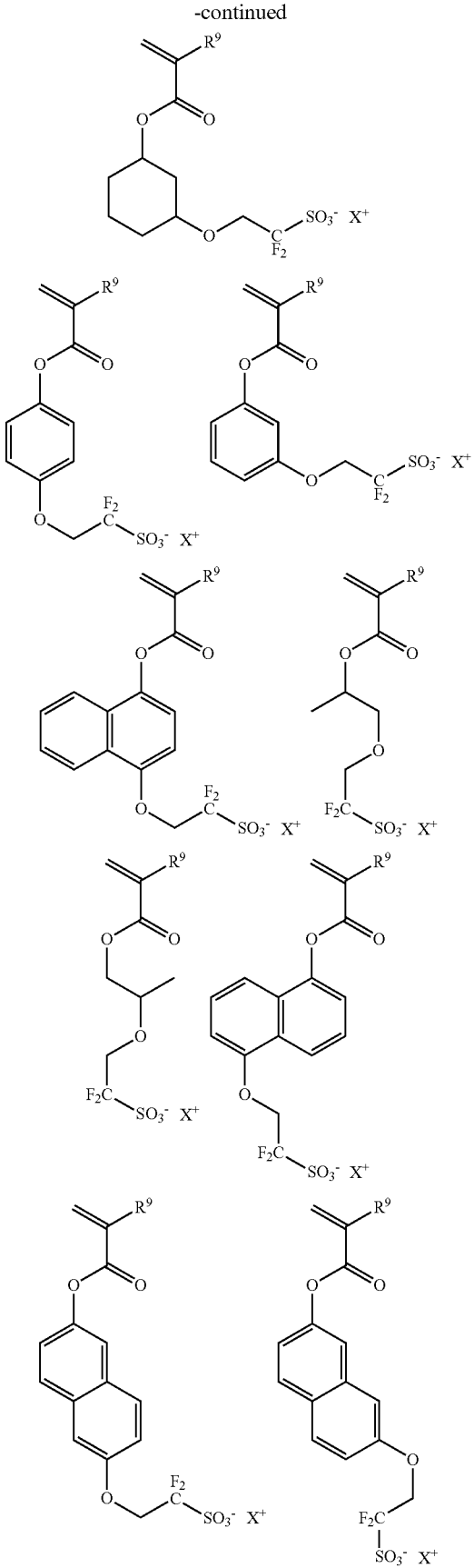

-continued
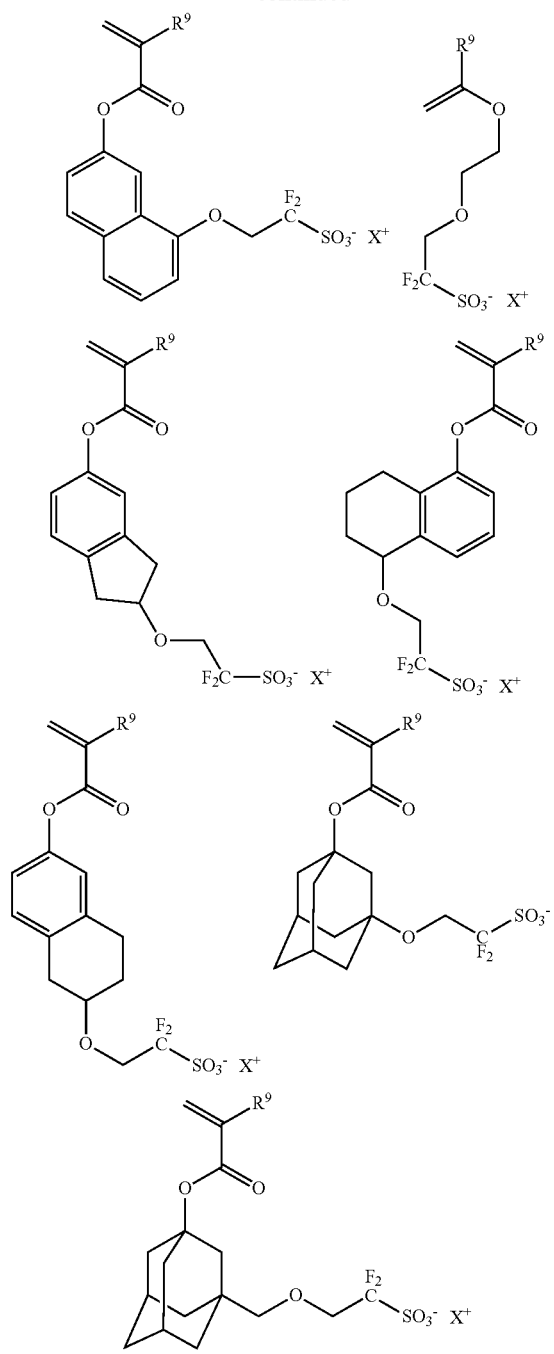
-continued
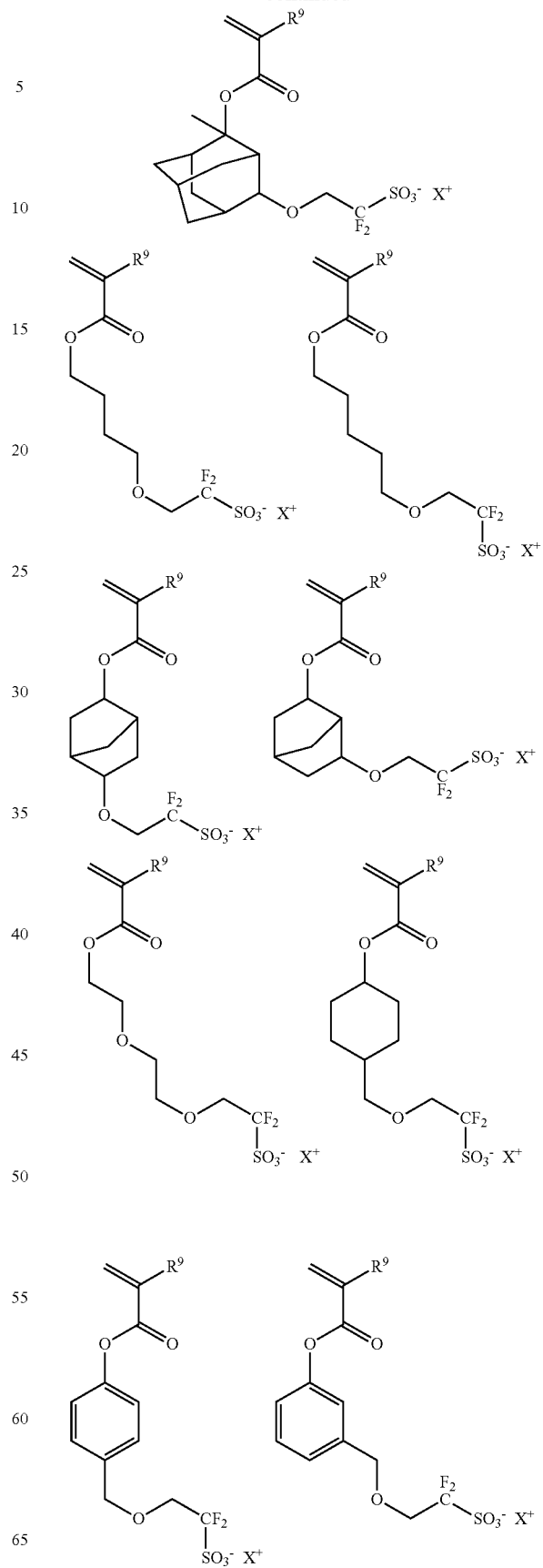

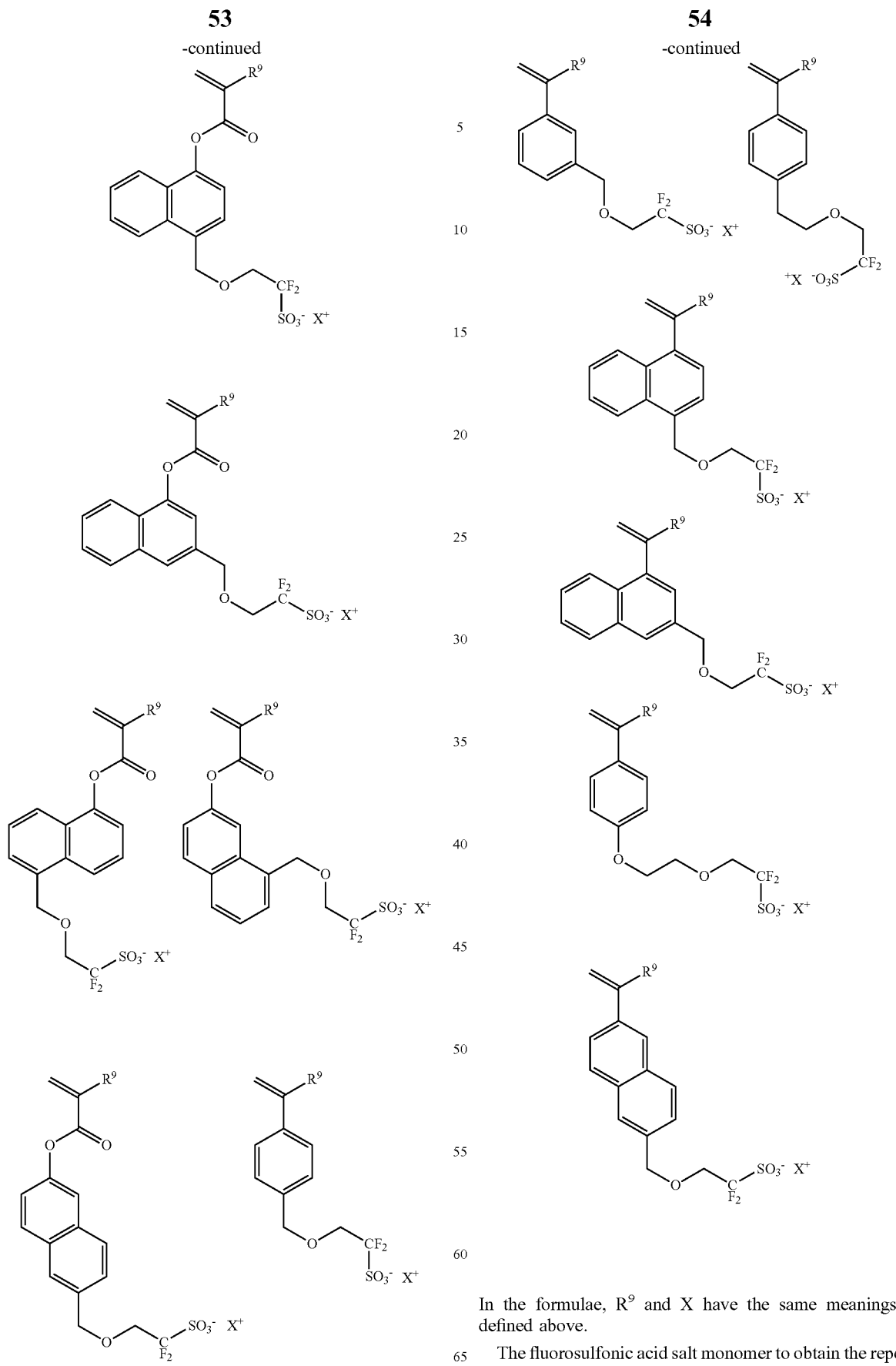
In the formulae, $R^9$ and X have the same meanings as defined above.
The fluorosulfonic acid salt monomer to obtain the repeating unit a4 in the formulae (2) is not particularly limited, and illustrative examples thereof include the following.

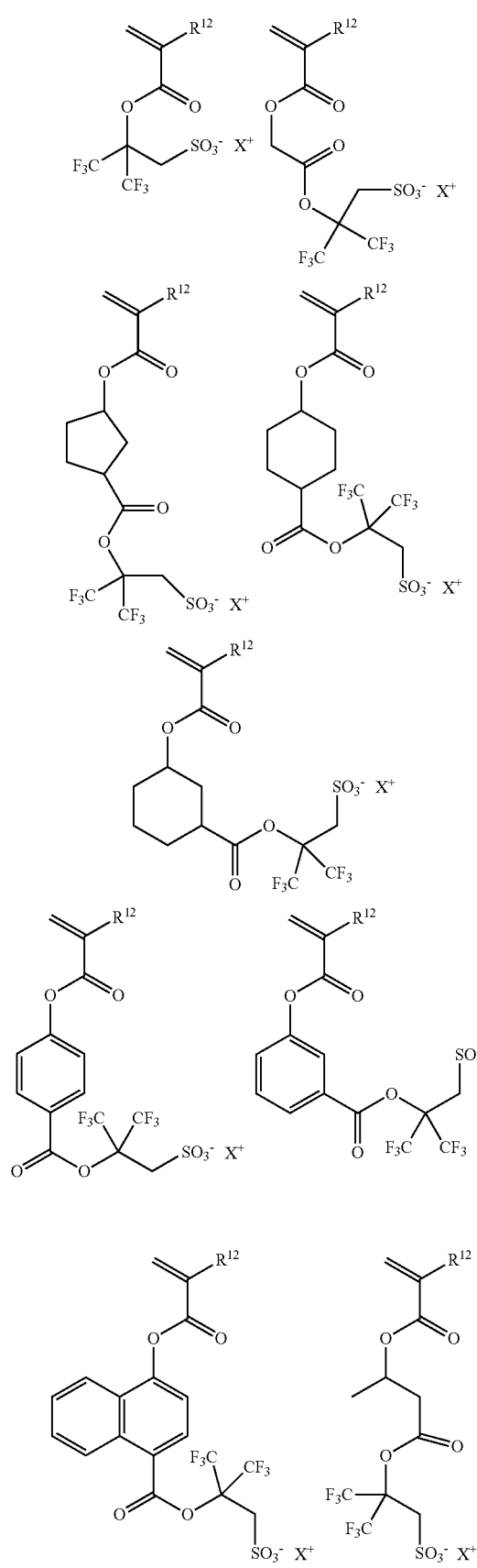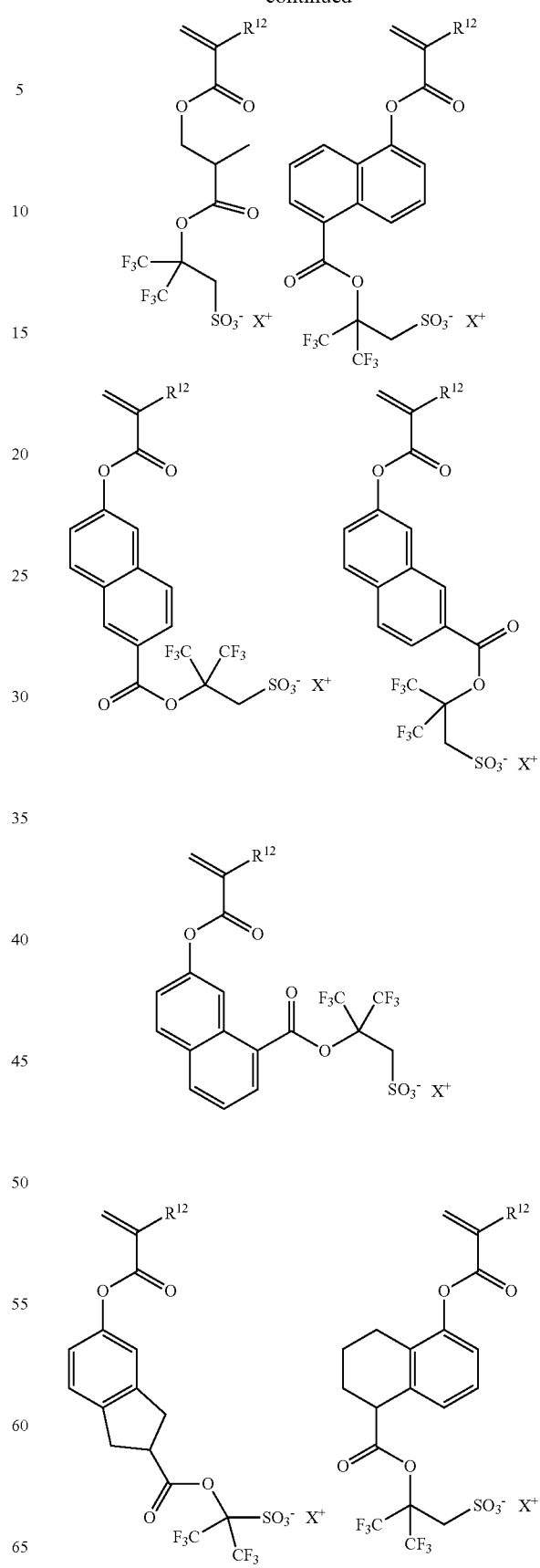

57
-continued
58
-continued
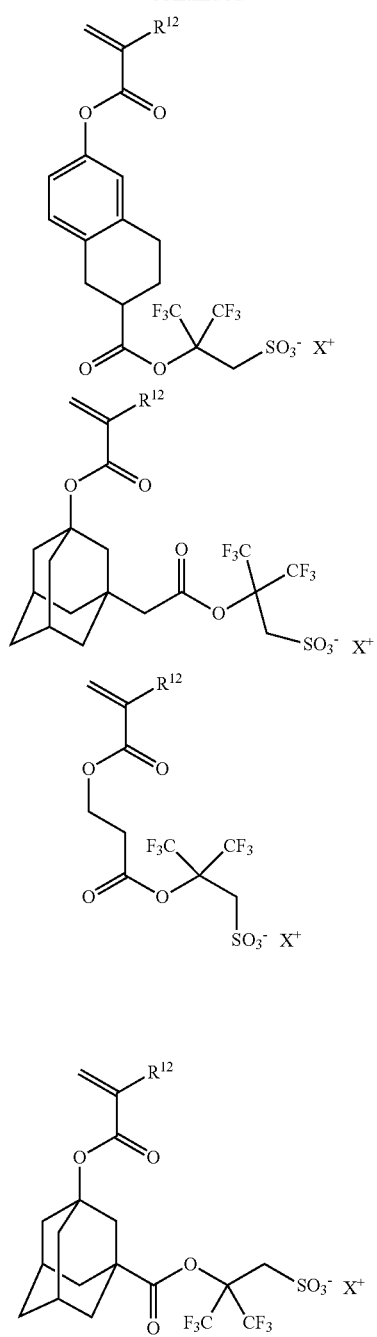
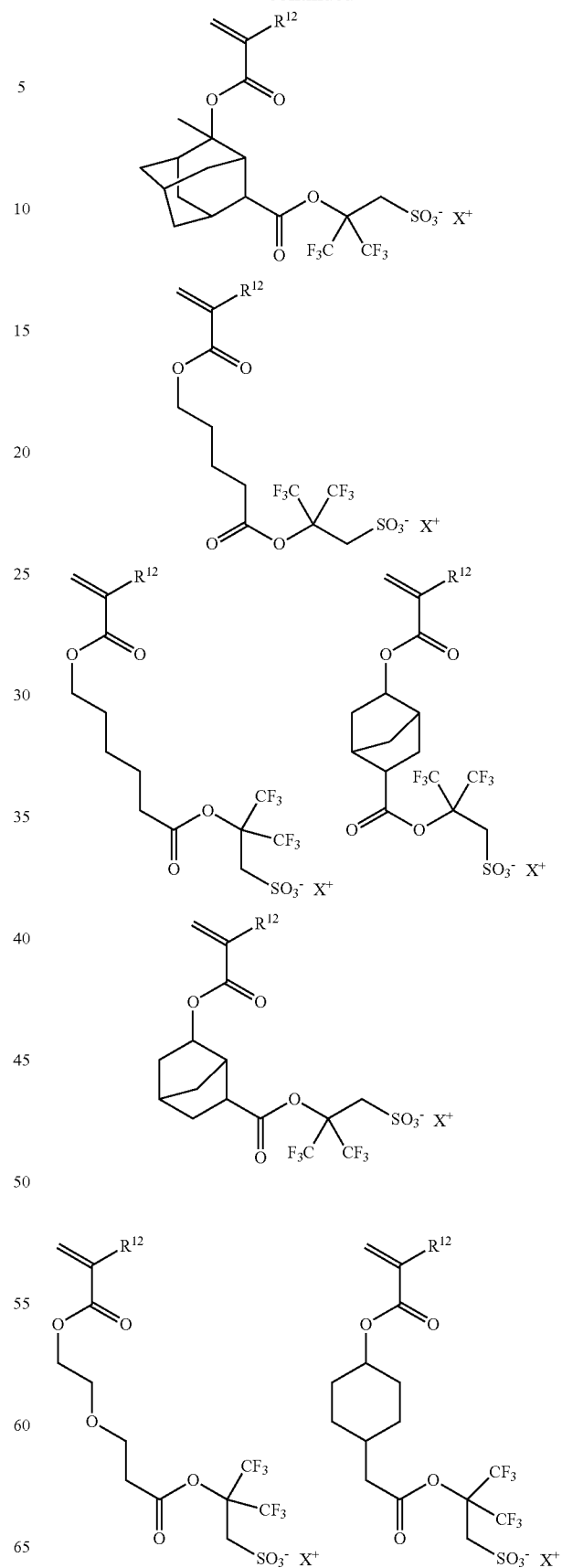

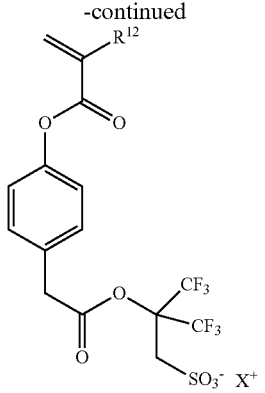
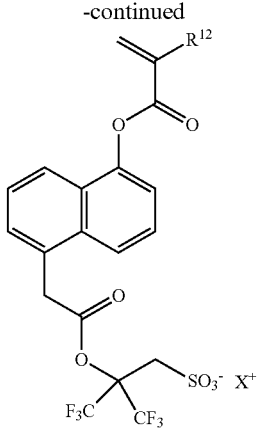
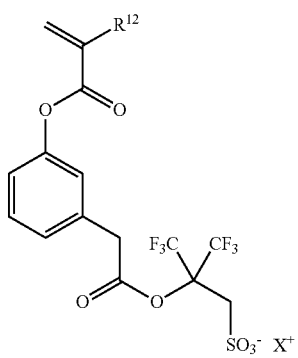
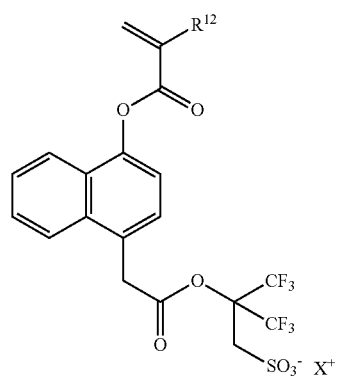
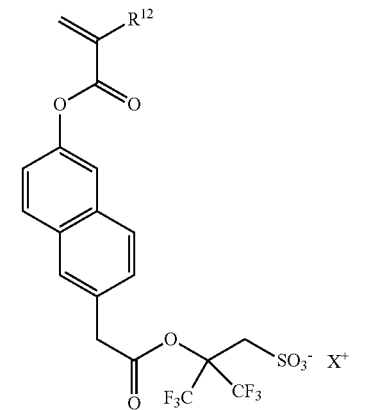
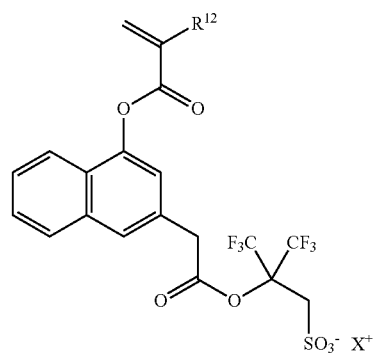

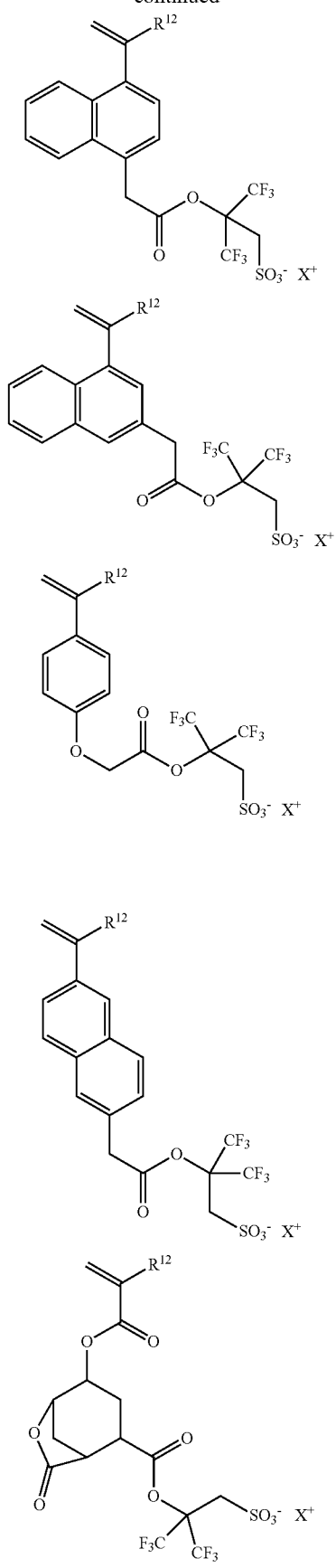
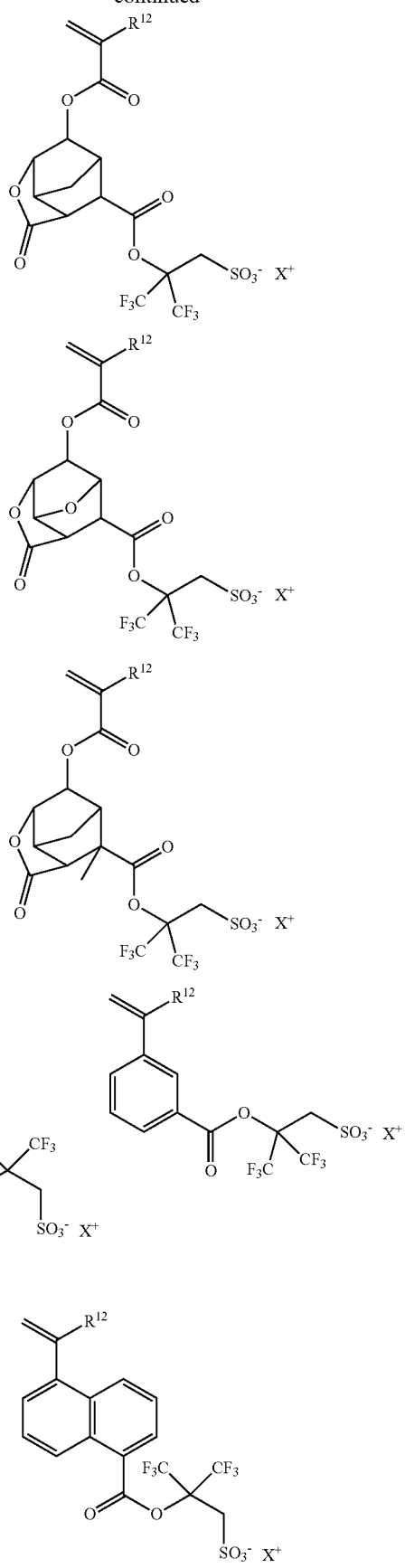

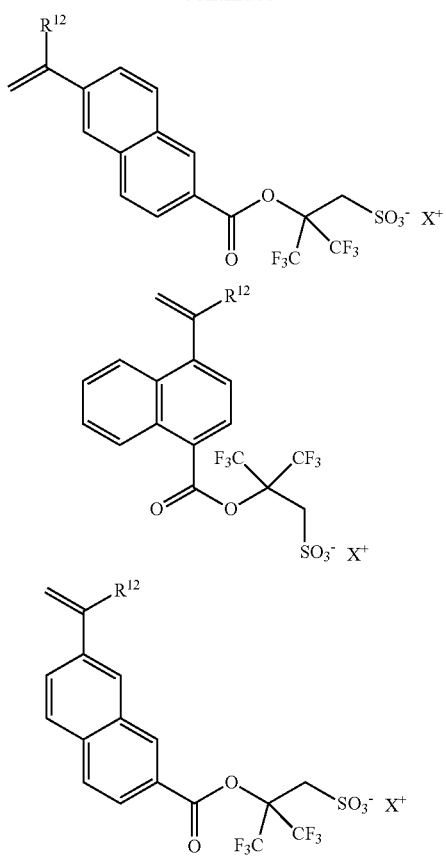

In the formulae, $R^{12}$ and X have the same meanings as defined above.

The fluorosulfonic acid salt monomer to obtain the repeating unit a5 in the formulae (2) is not particularly limited, and illustrative examples thereof include the following.

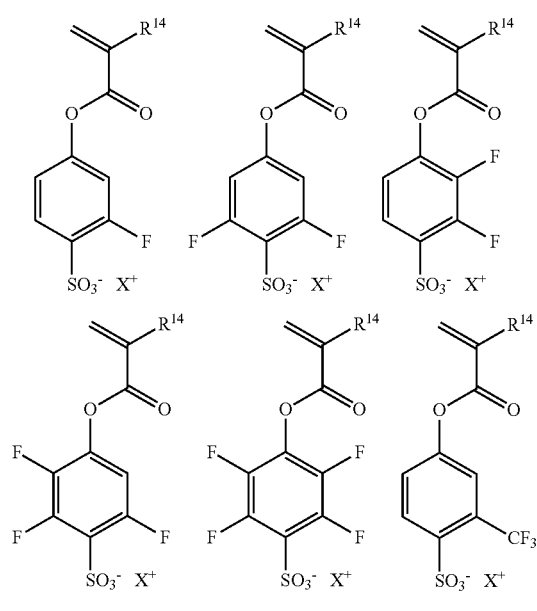

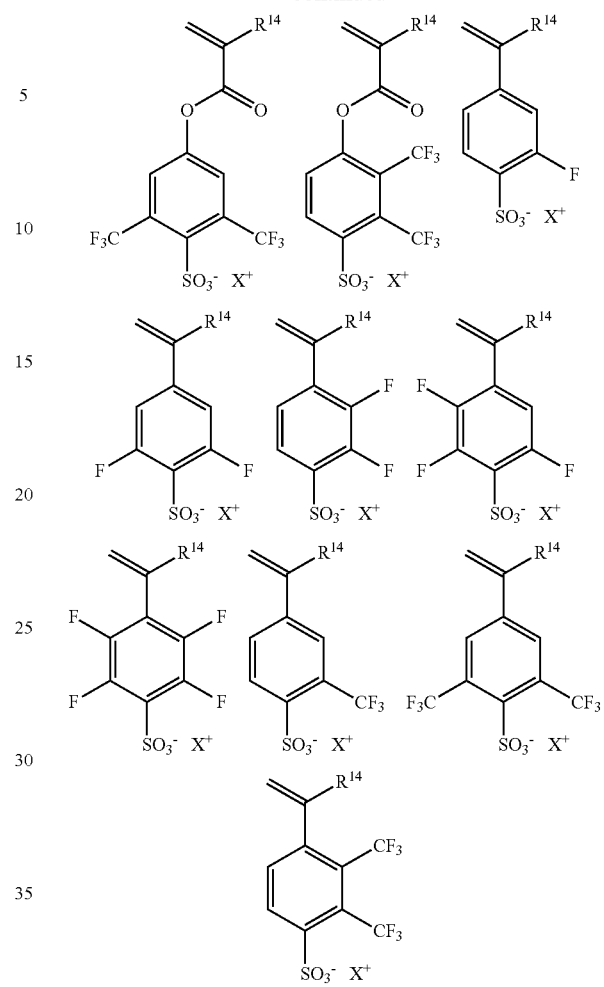

In the formulae, $R^{14}$ and X have the same meanings as defined above.

The sulfonimide salt monomer to obtain the repeating unit a6 in the formulae (2) is not particularly limited, and illustrative examples thereof include the following.

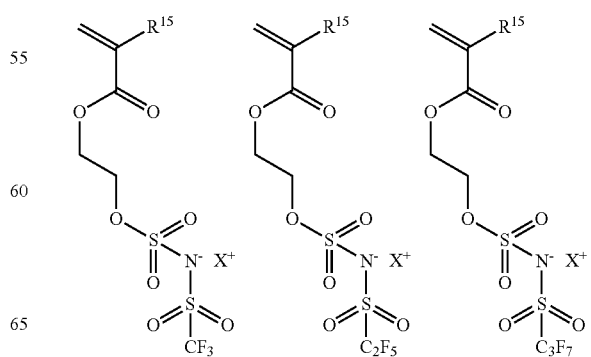

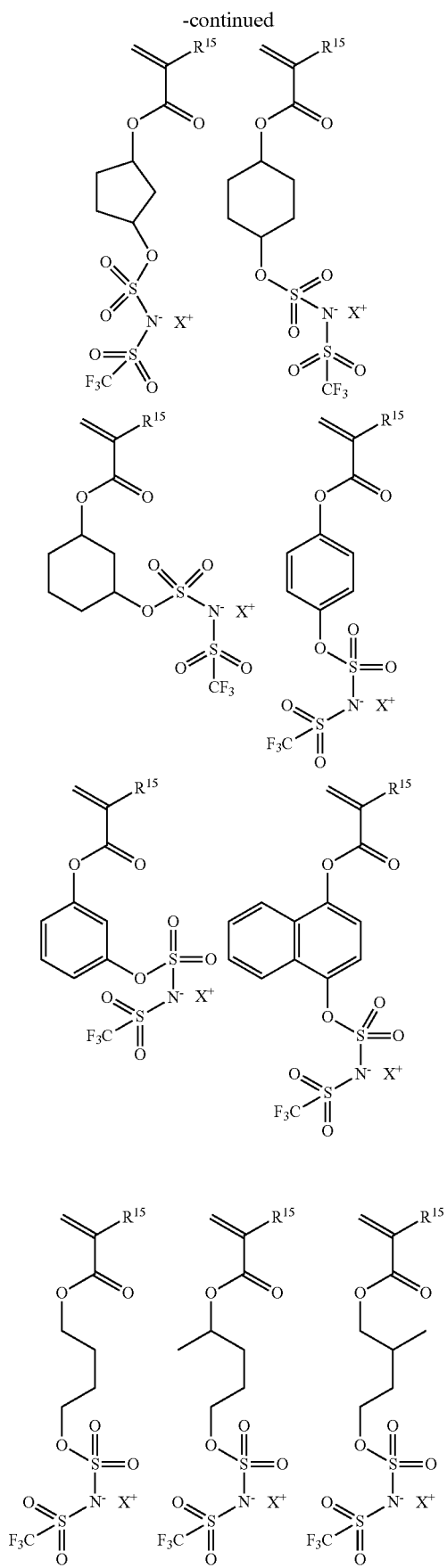
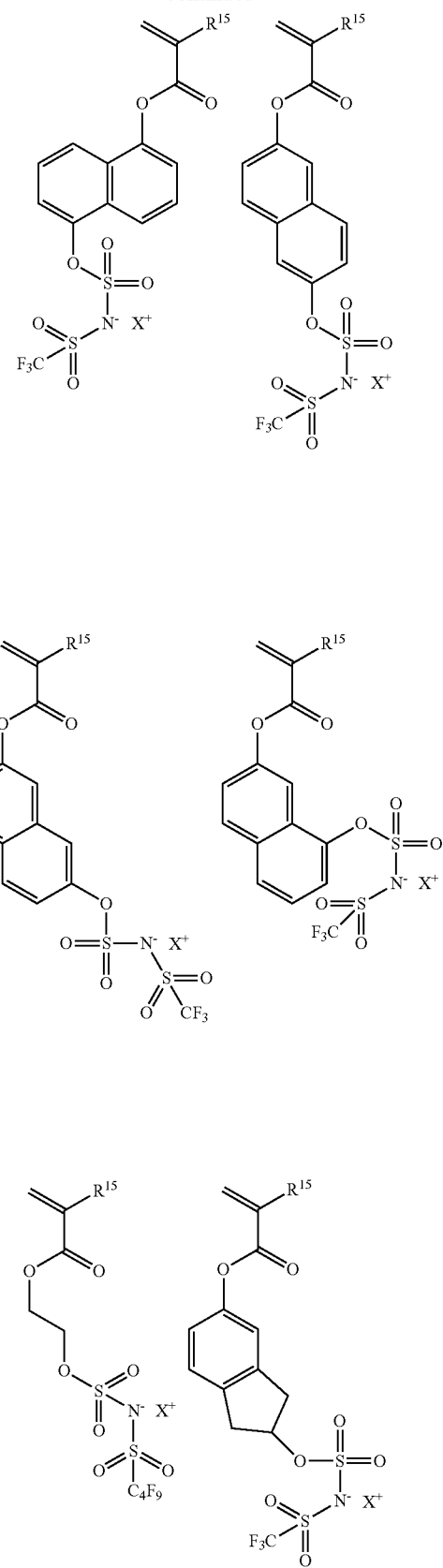

67
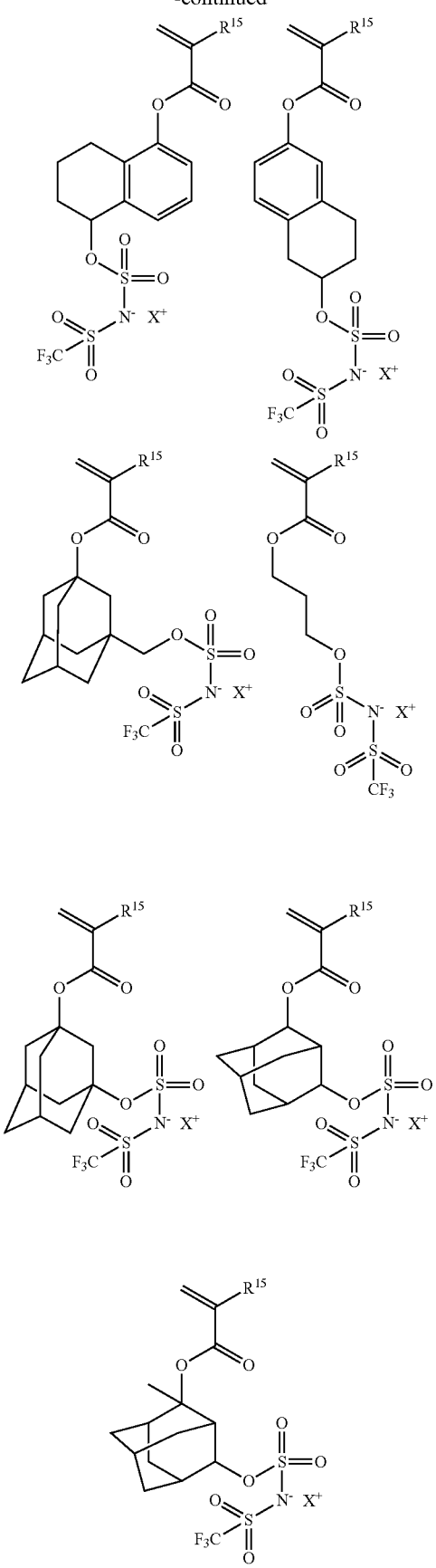
68
-continued
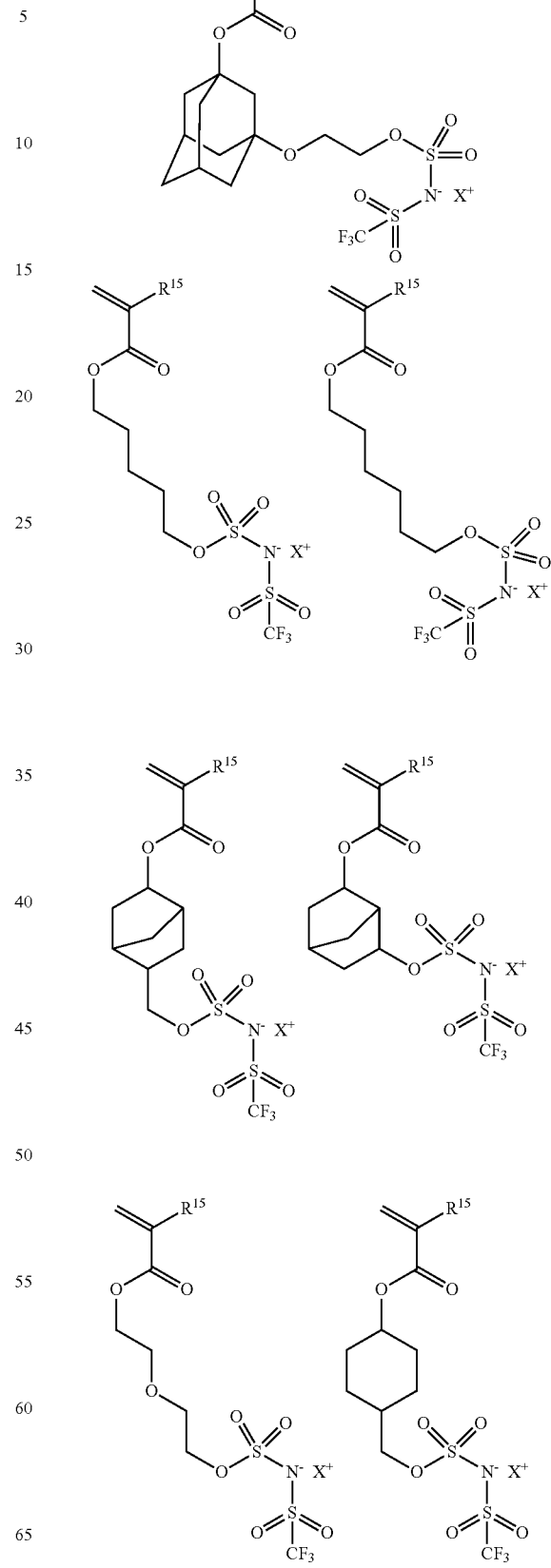

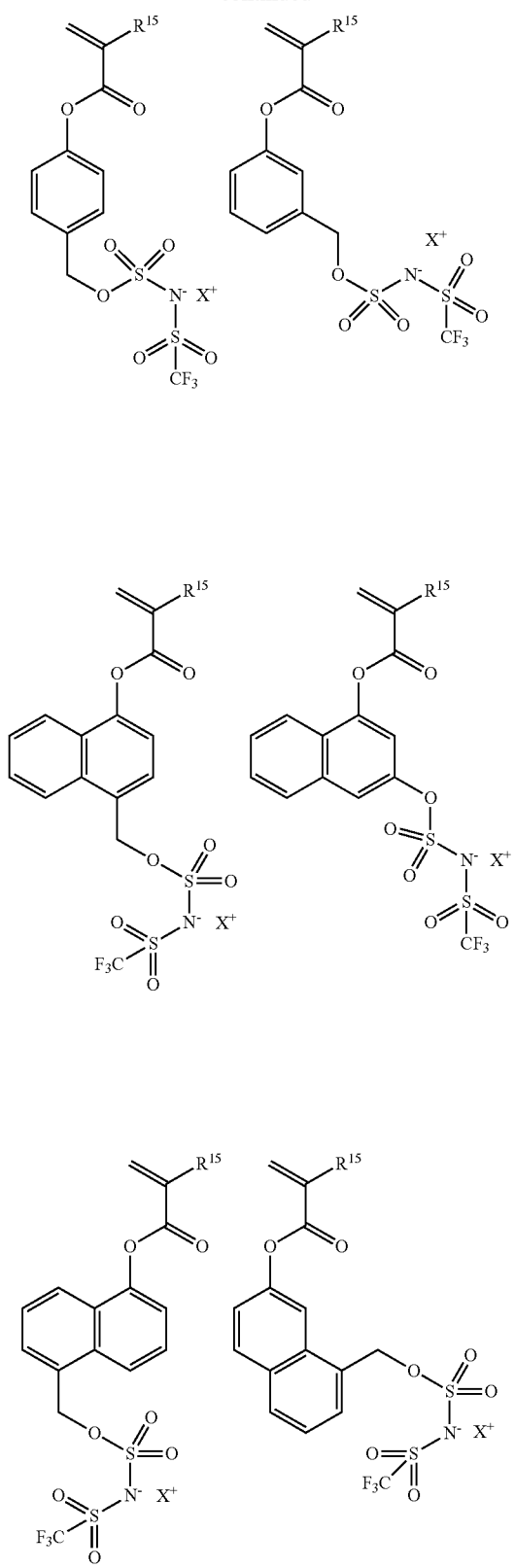
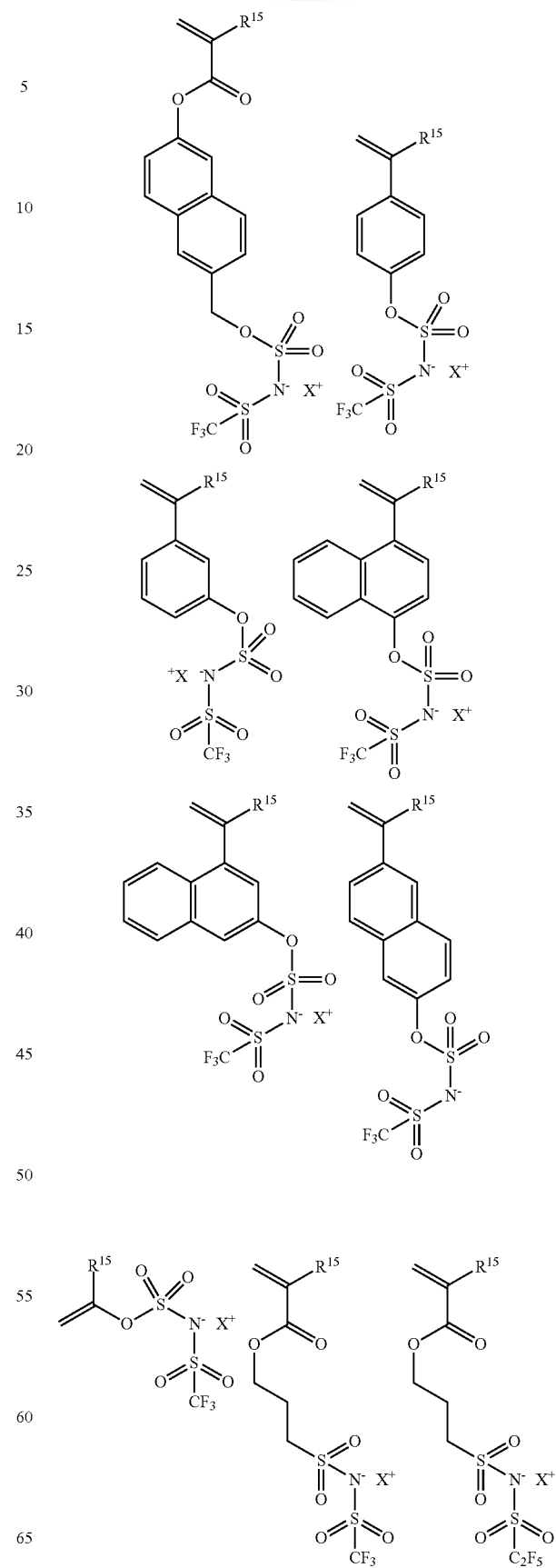

71
-continued
72
-continued
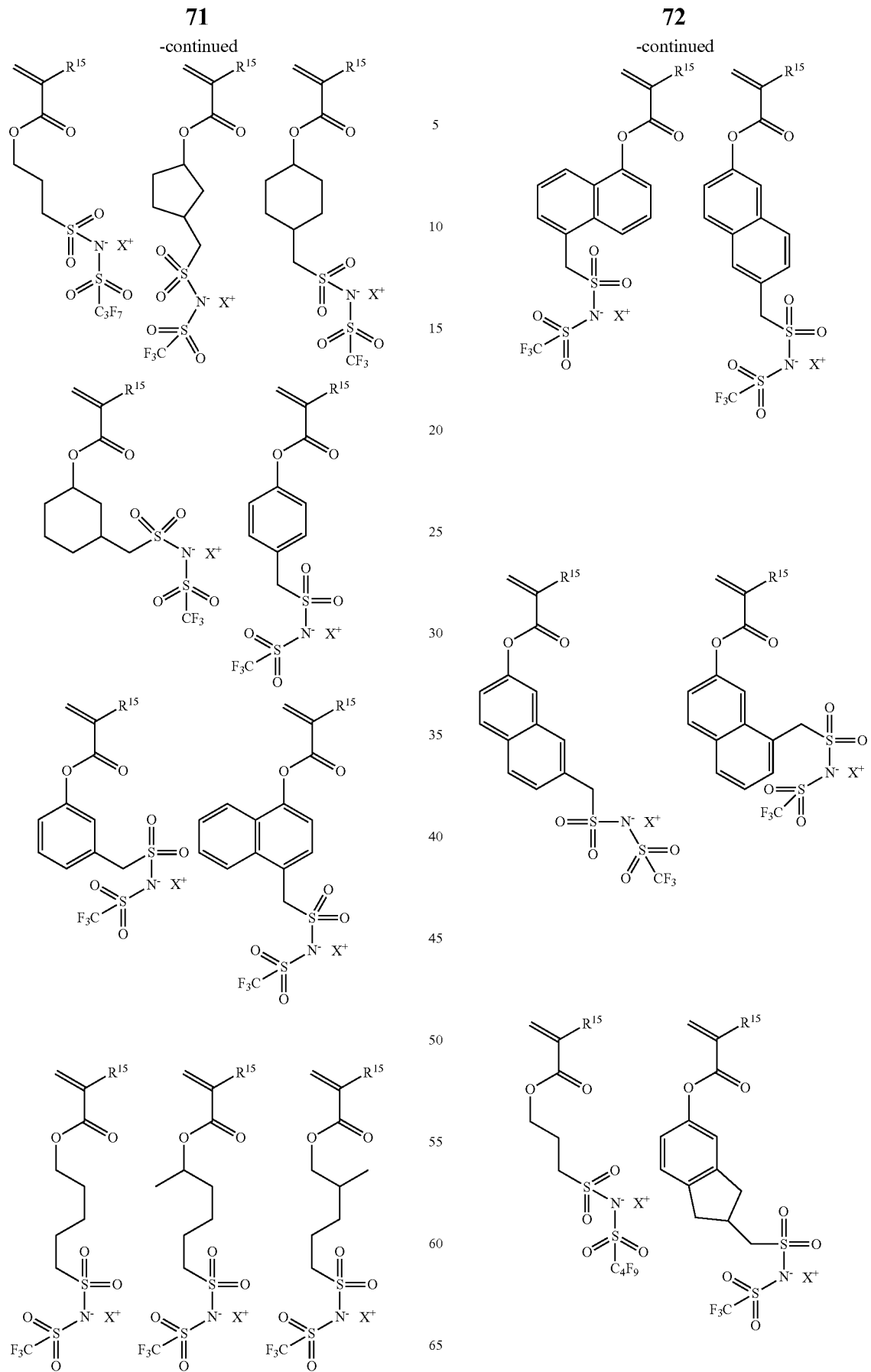

73
-continued
74
-continued
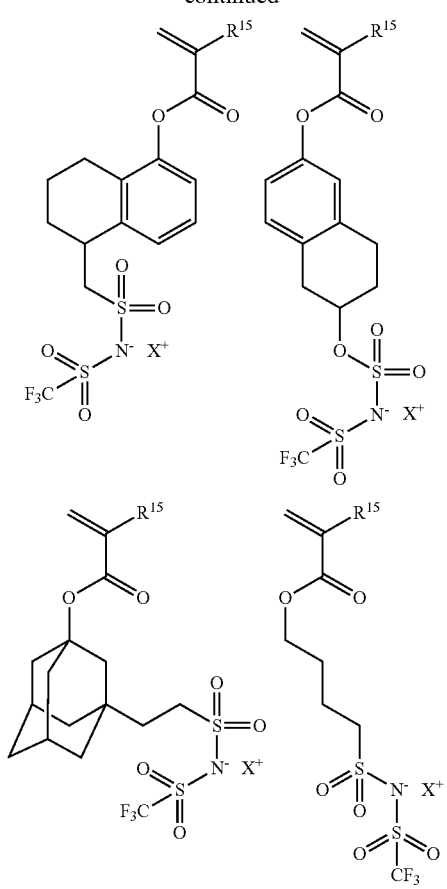
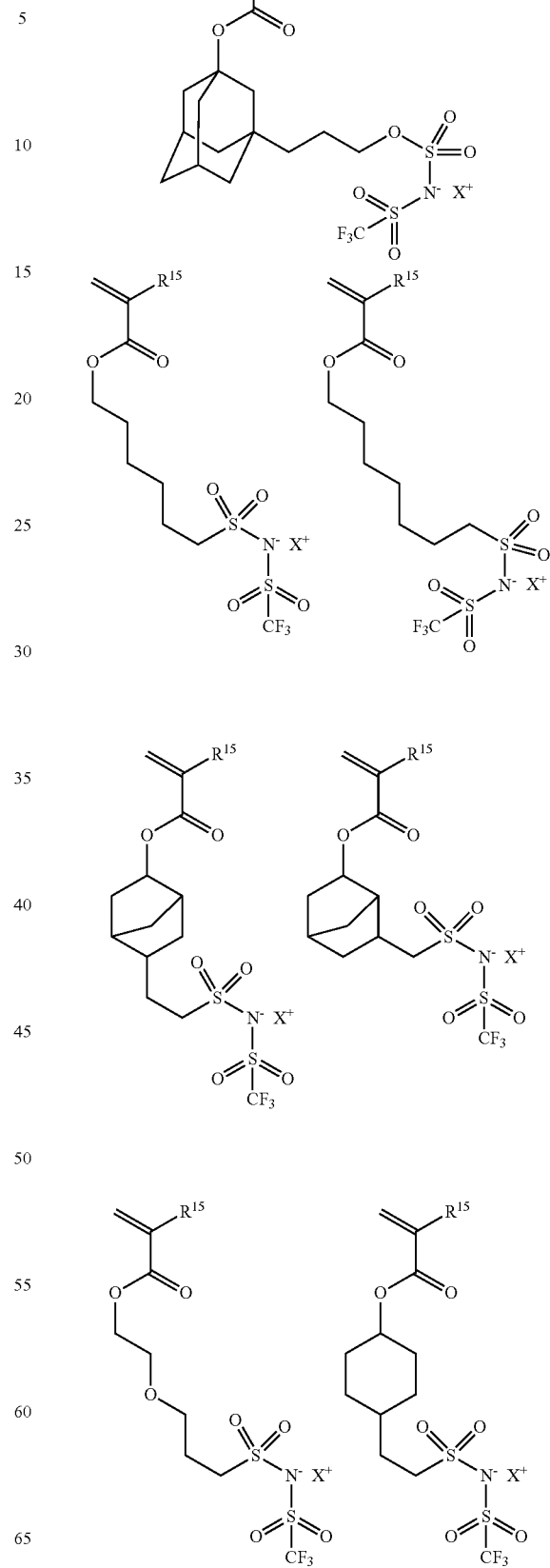

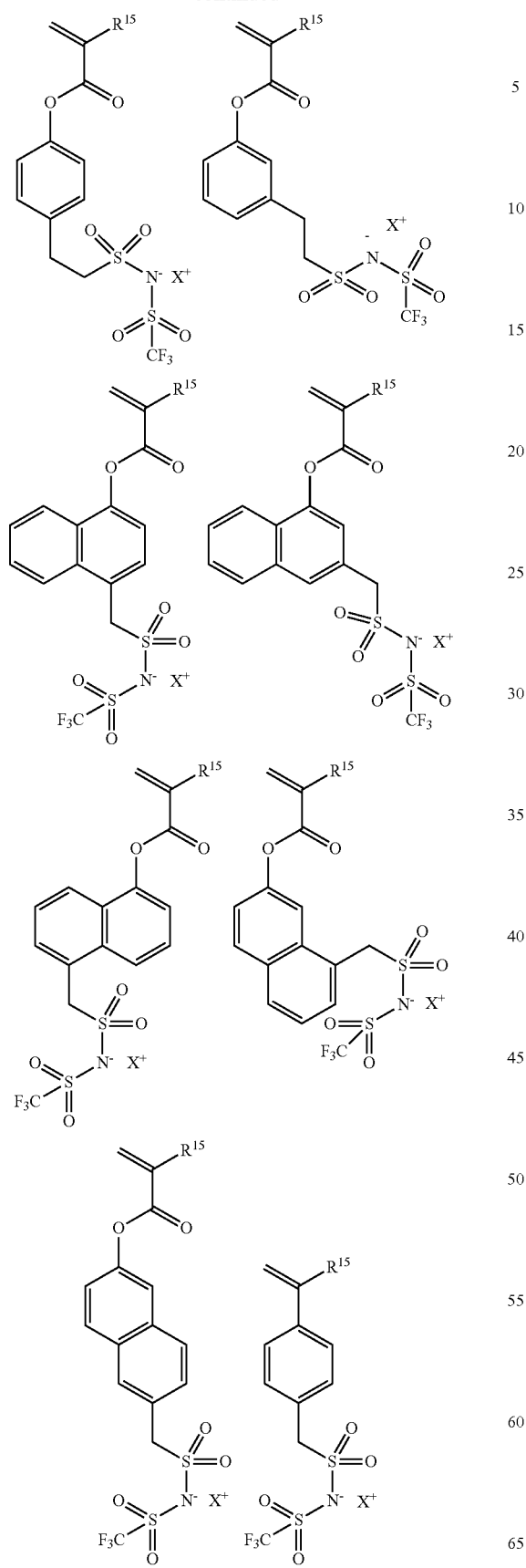
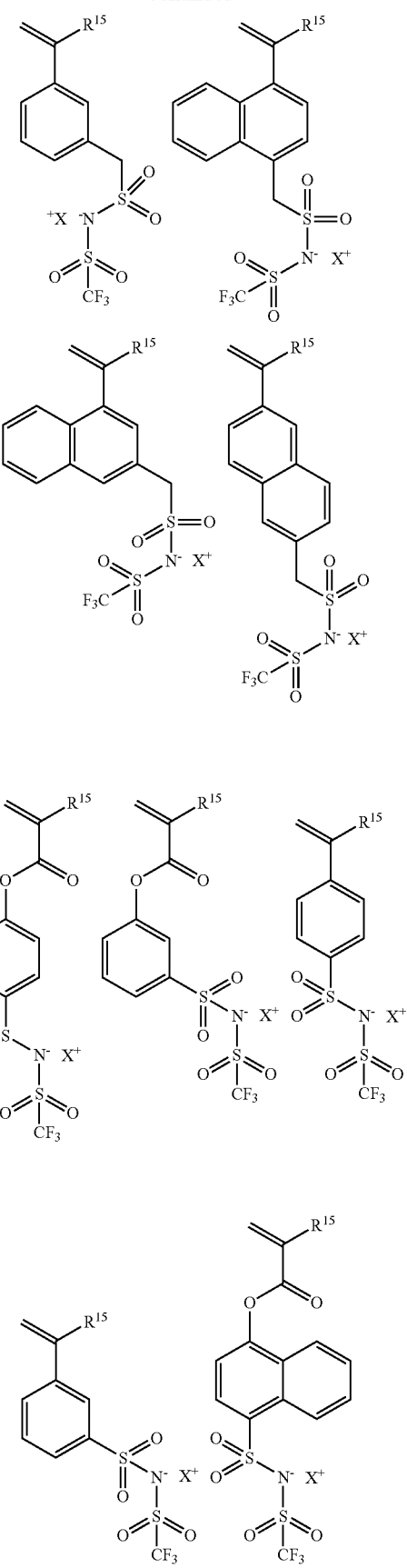

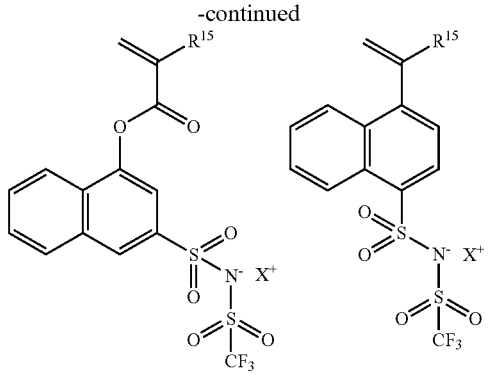
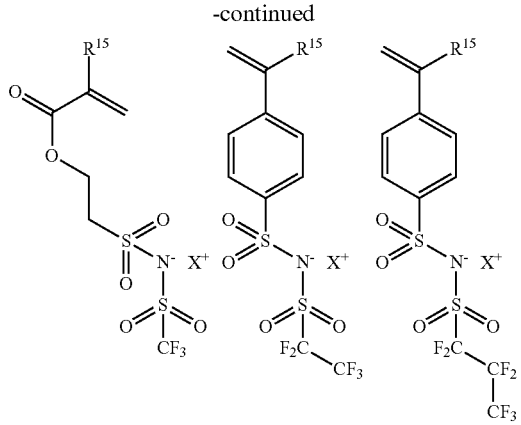
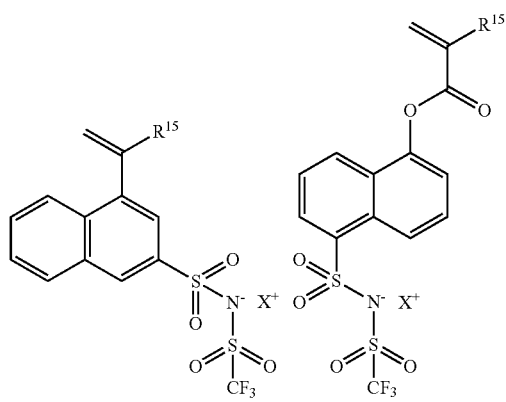
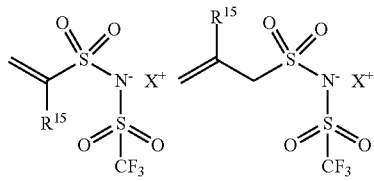
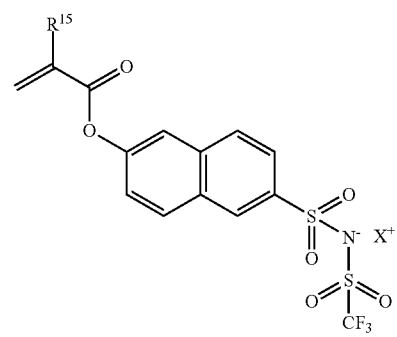
In the formulae, $R^{15}$ and X have the same meanings as defined above.
The sulfonamide salt monomer to obtain the repeating unit a7 in the formulae (2) is not particularly limited, and illustrative examples thereof include the following.
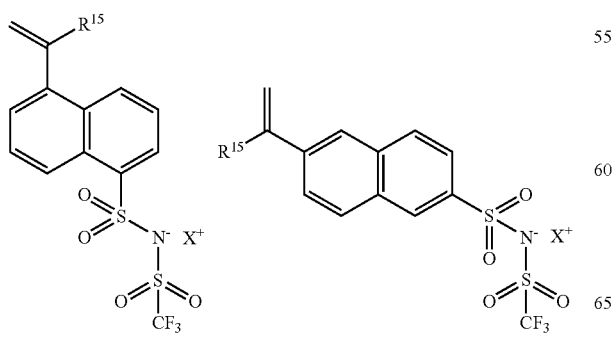
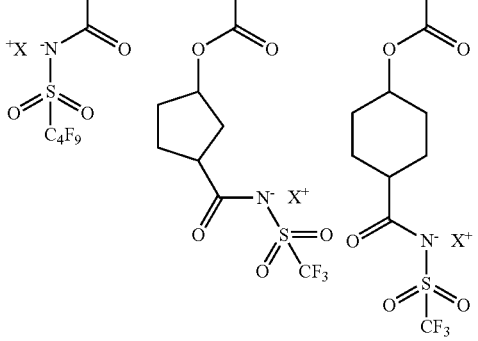

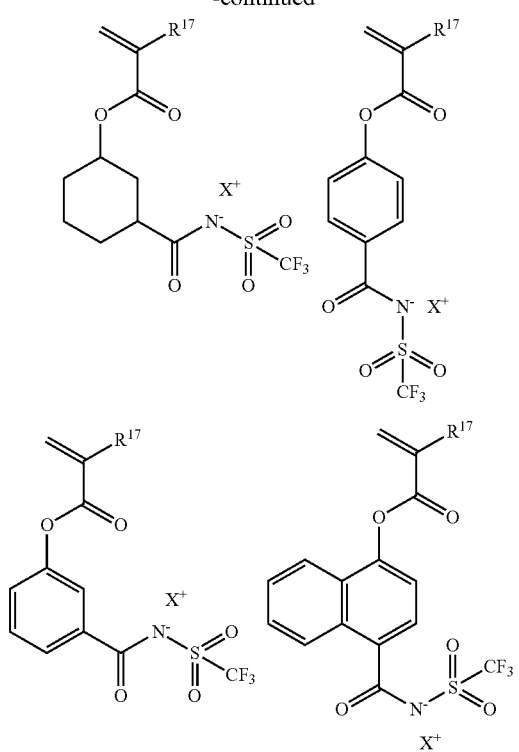
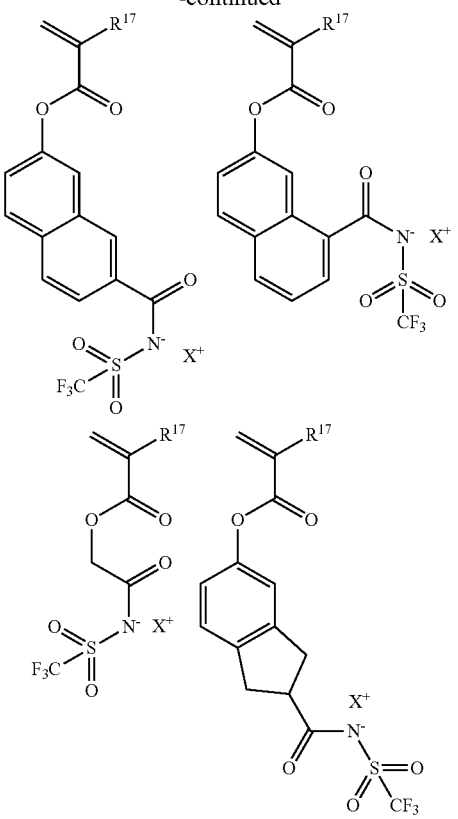
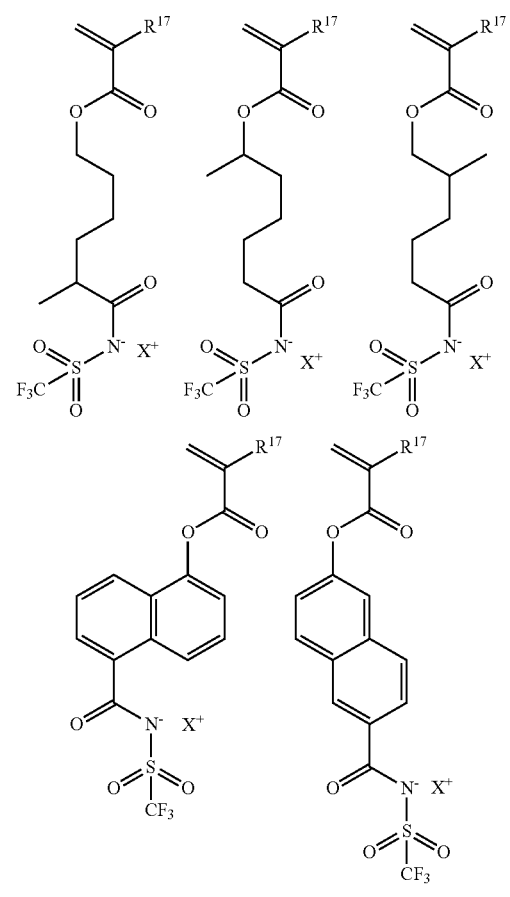
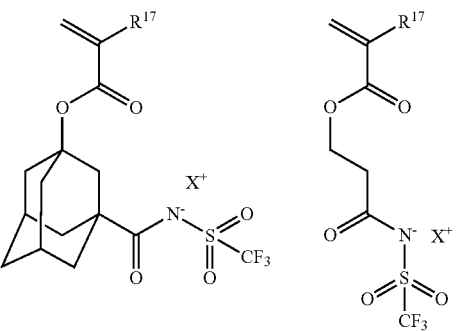

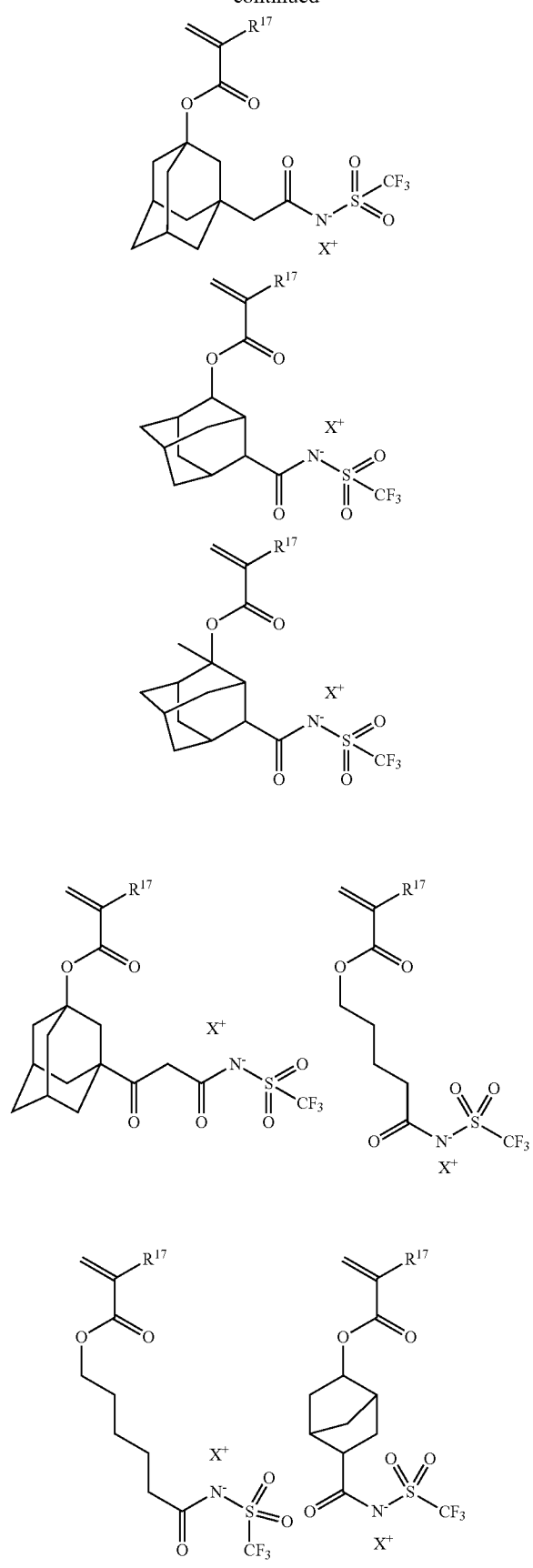
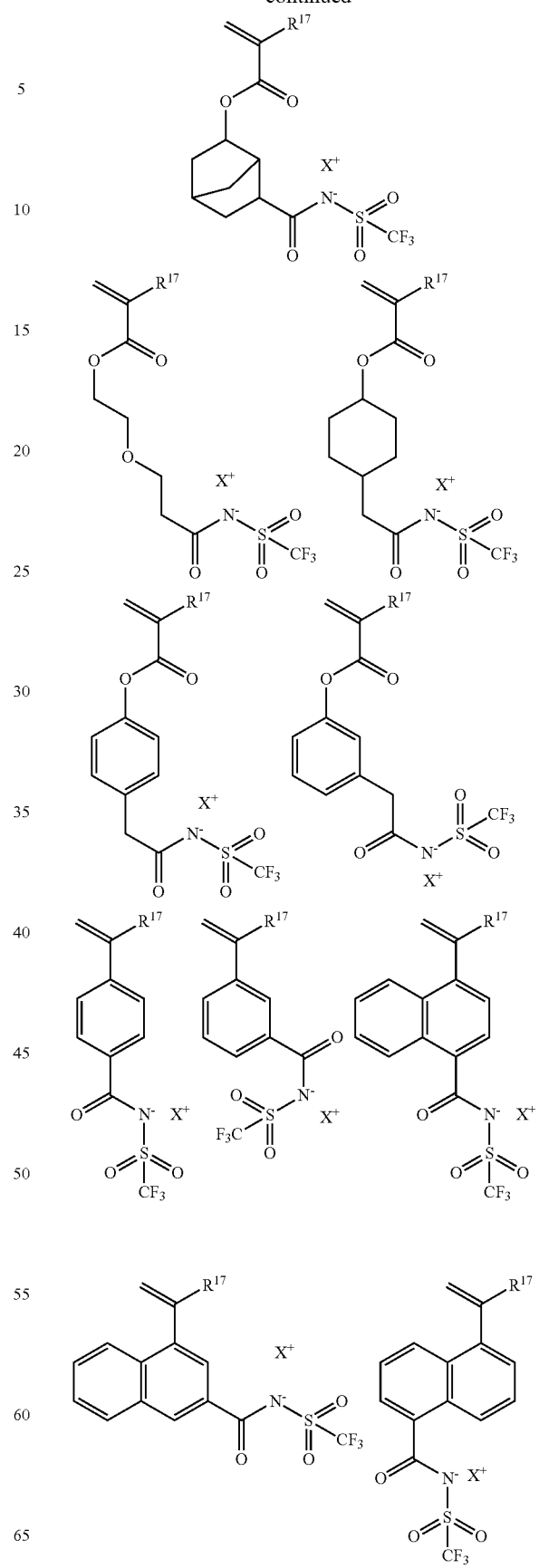

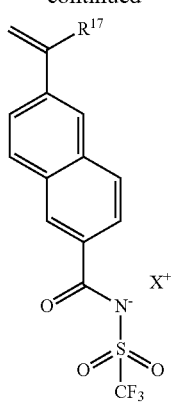
In the formulae, $R^{17}$ and X have the same meanings as defined above.
The ammonium cation structure shown by the formula (1)-5 is not particularly limited, and illustrative examples thereof include the following.
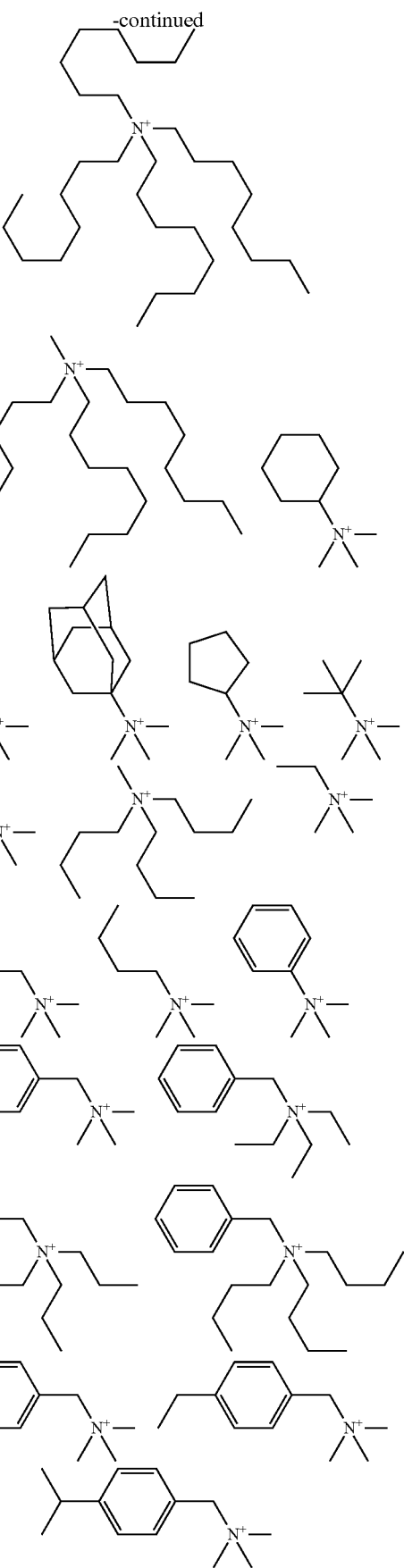

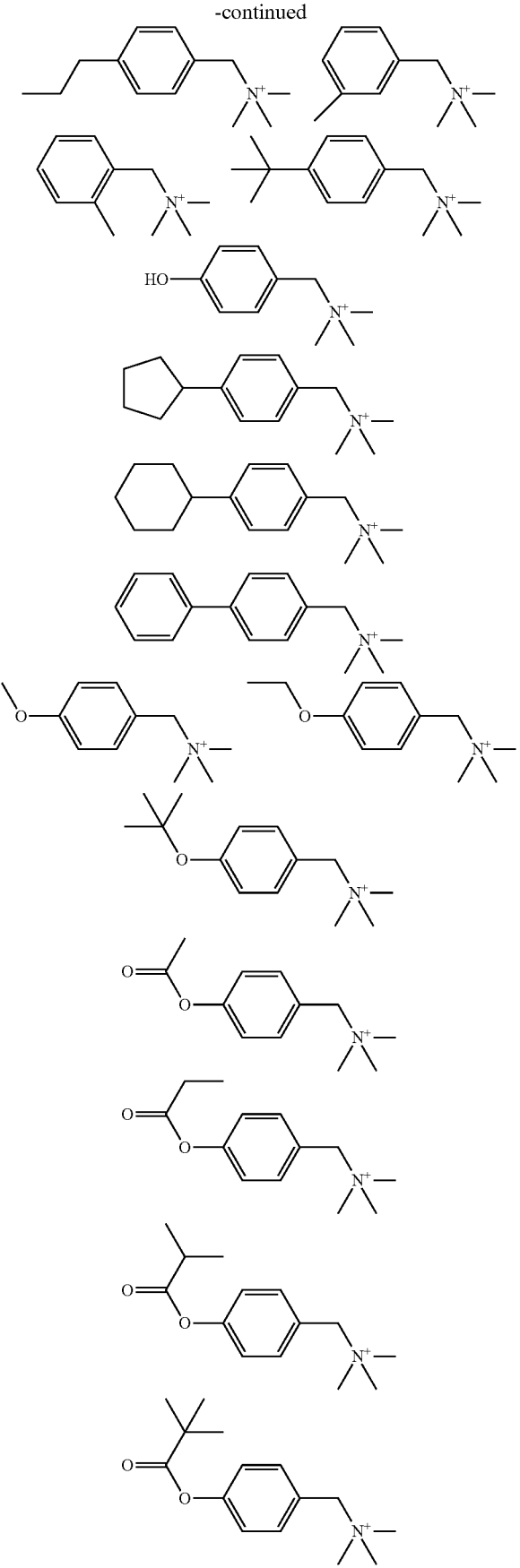
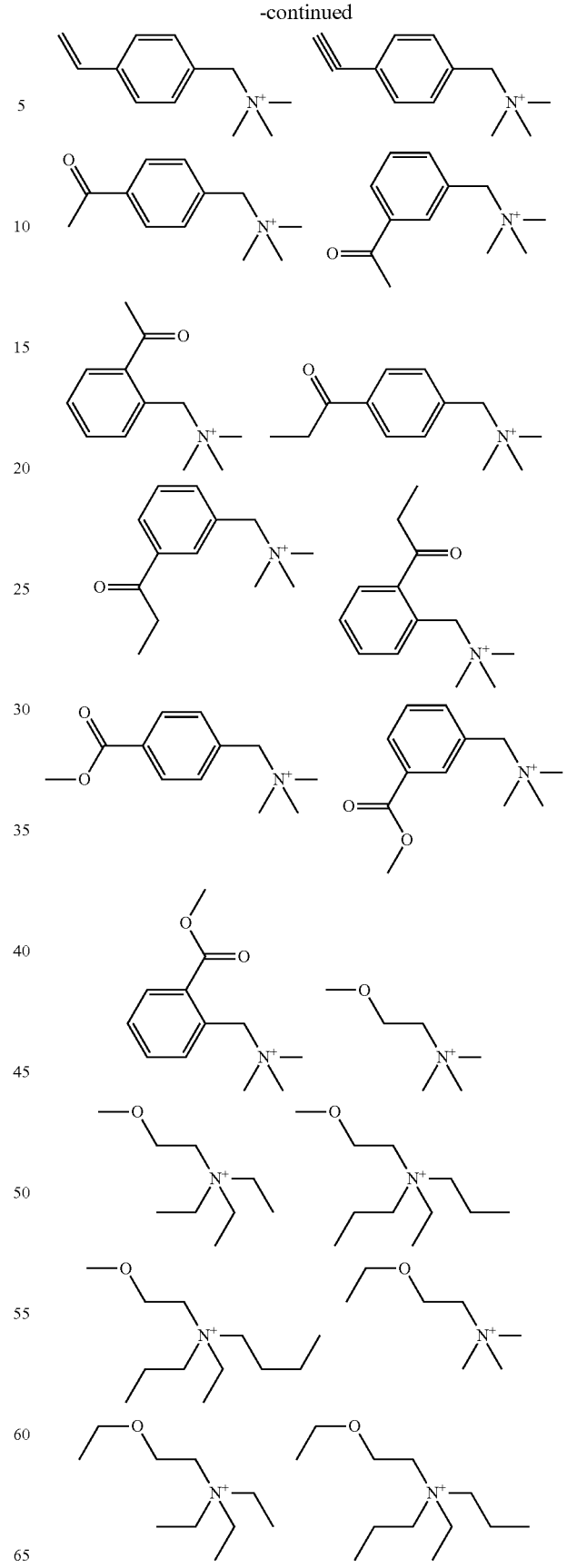

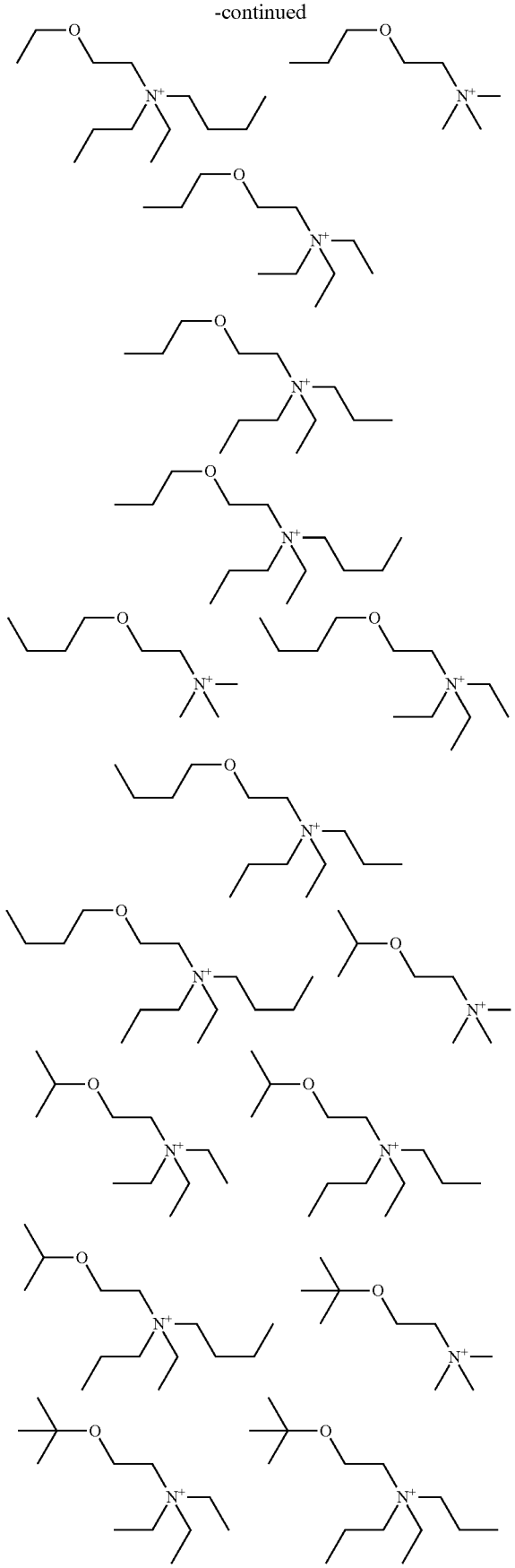
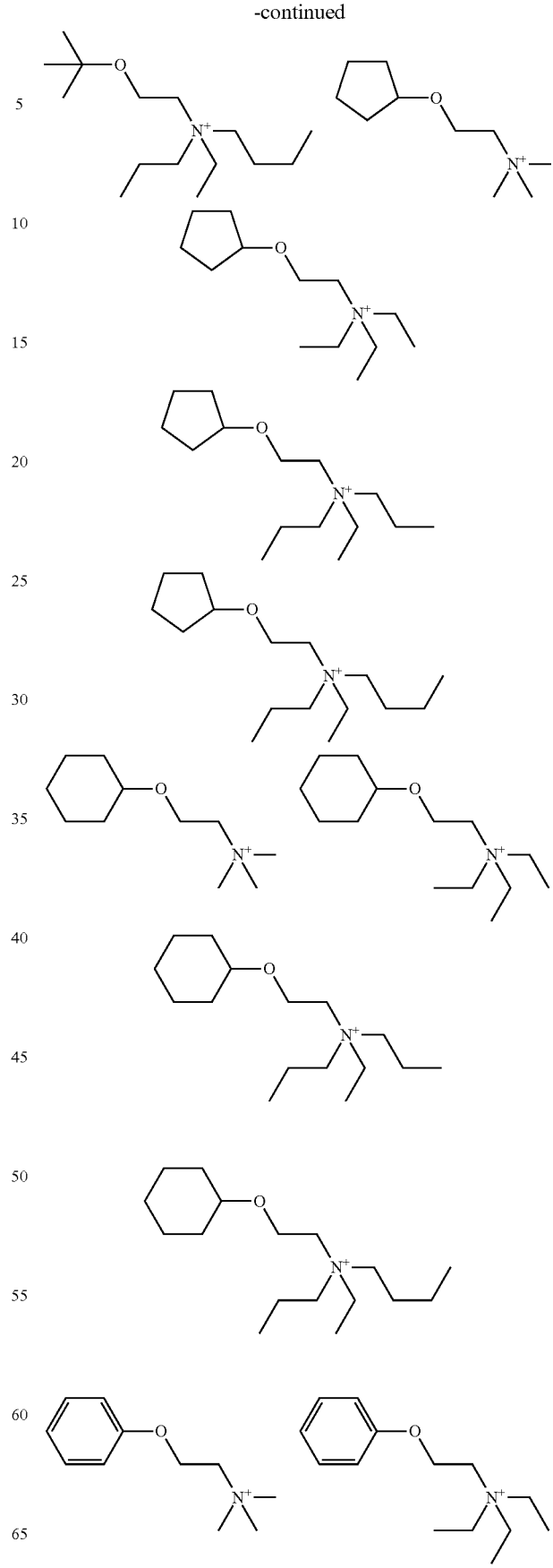

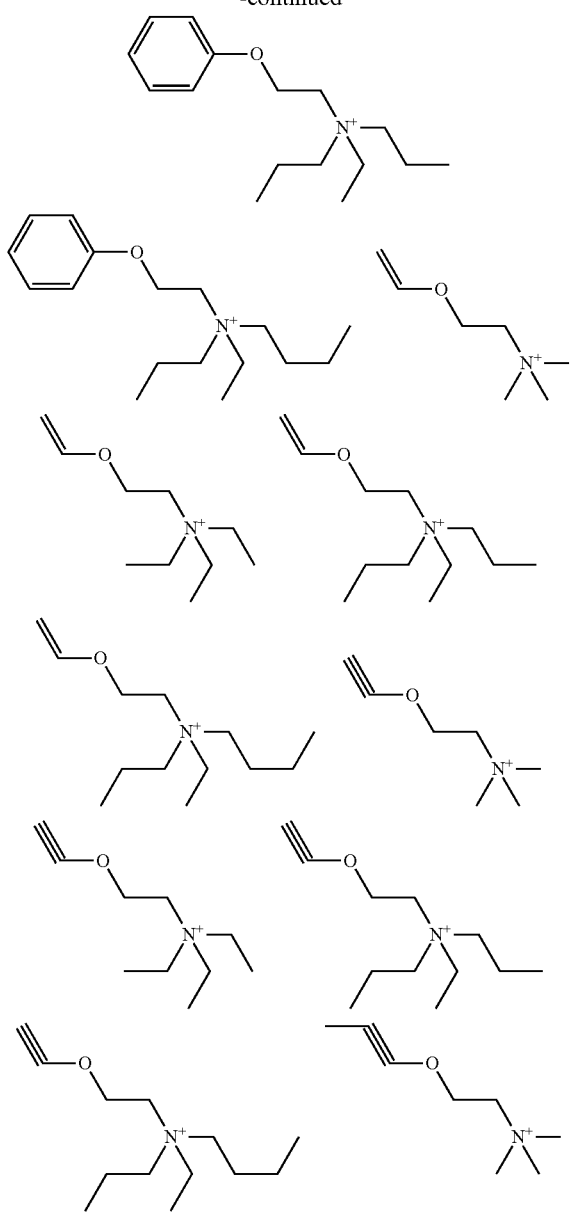
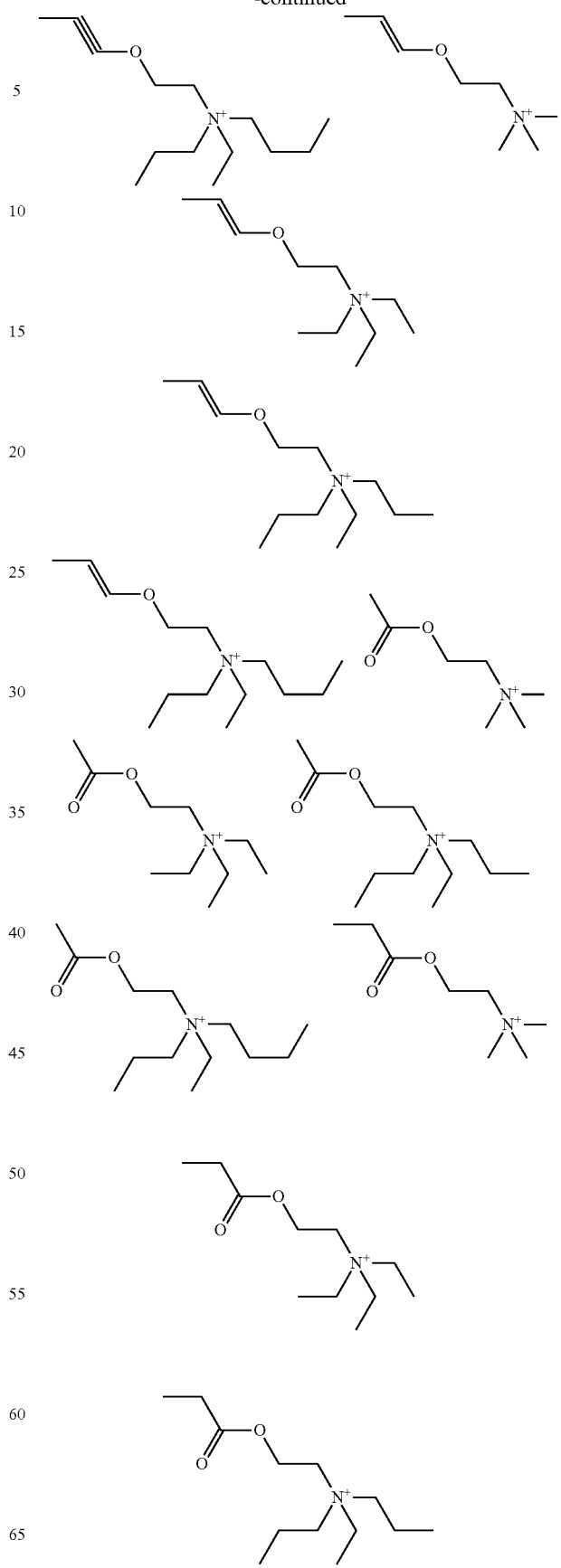

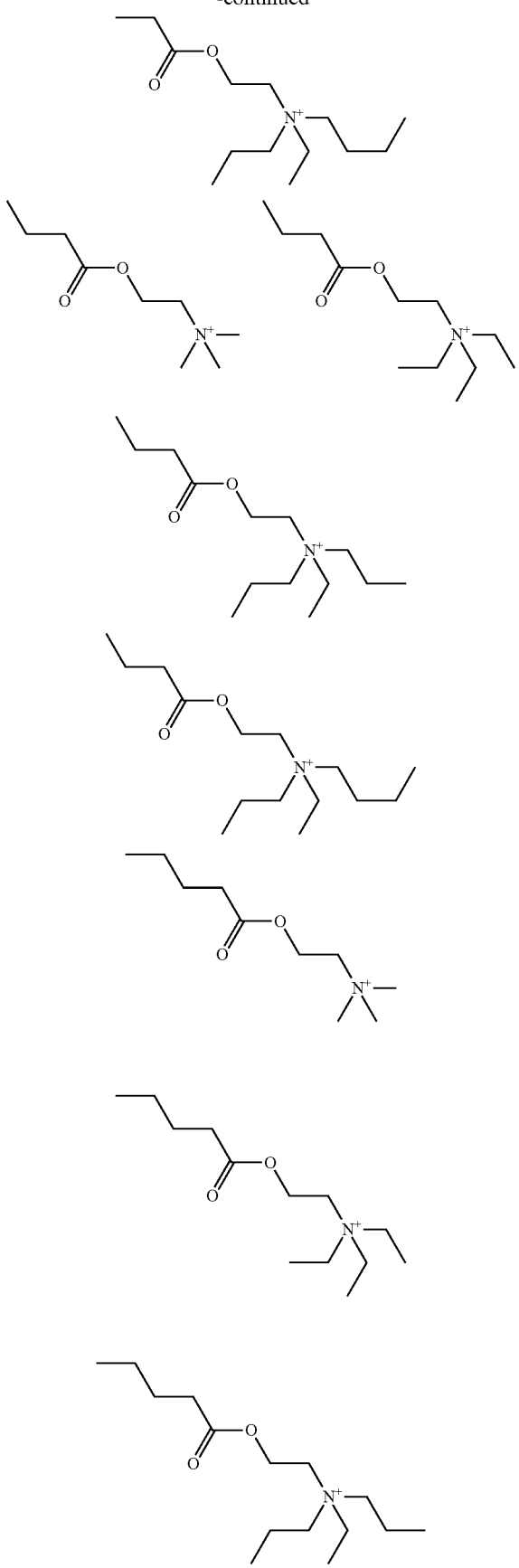
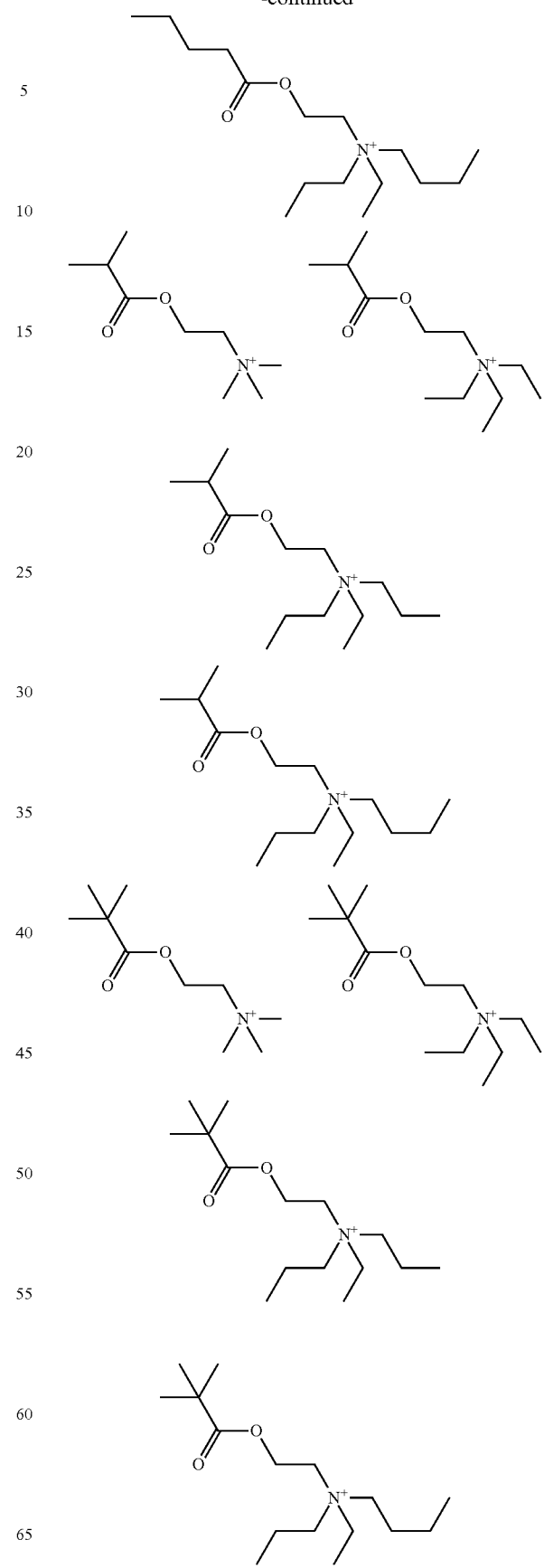

93
-continued
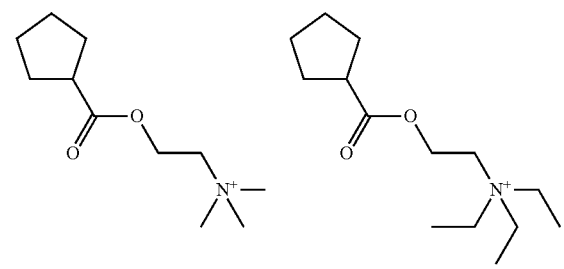
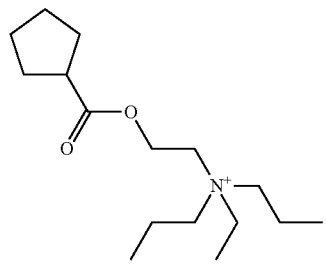
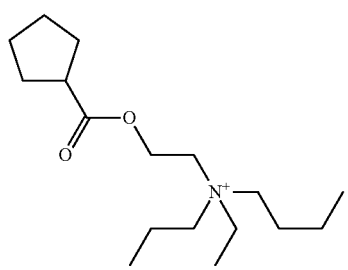
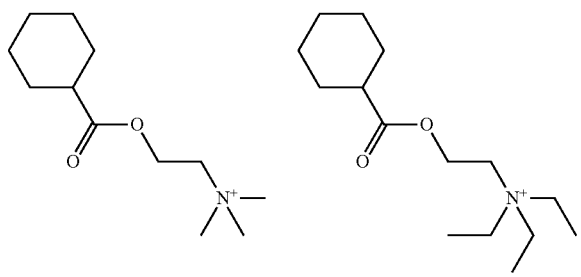
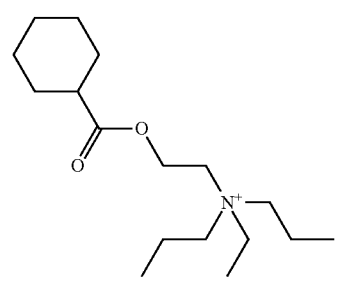
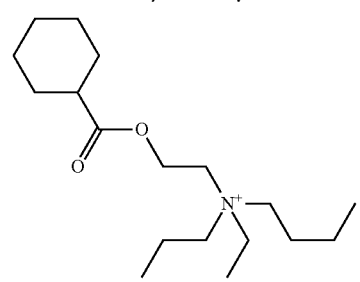
94
-continued
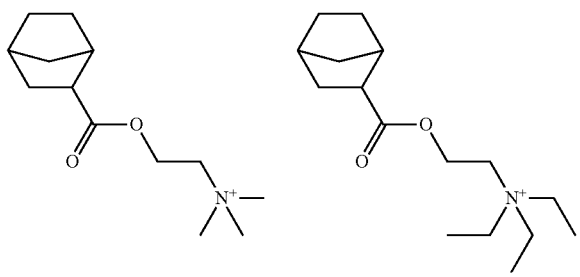
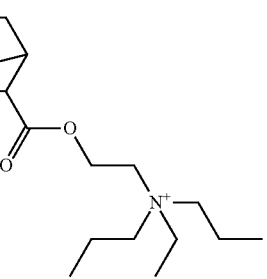
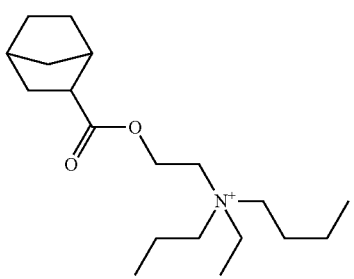
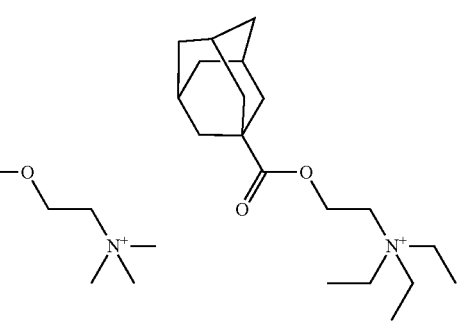
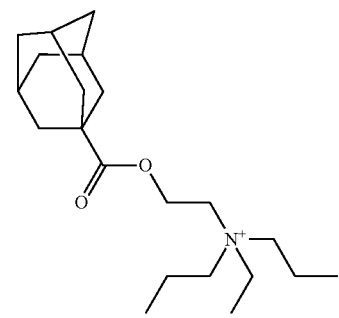

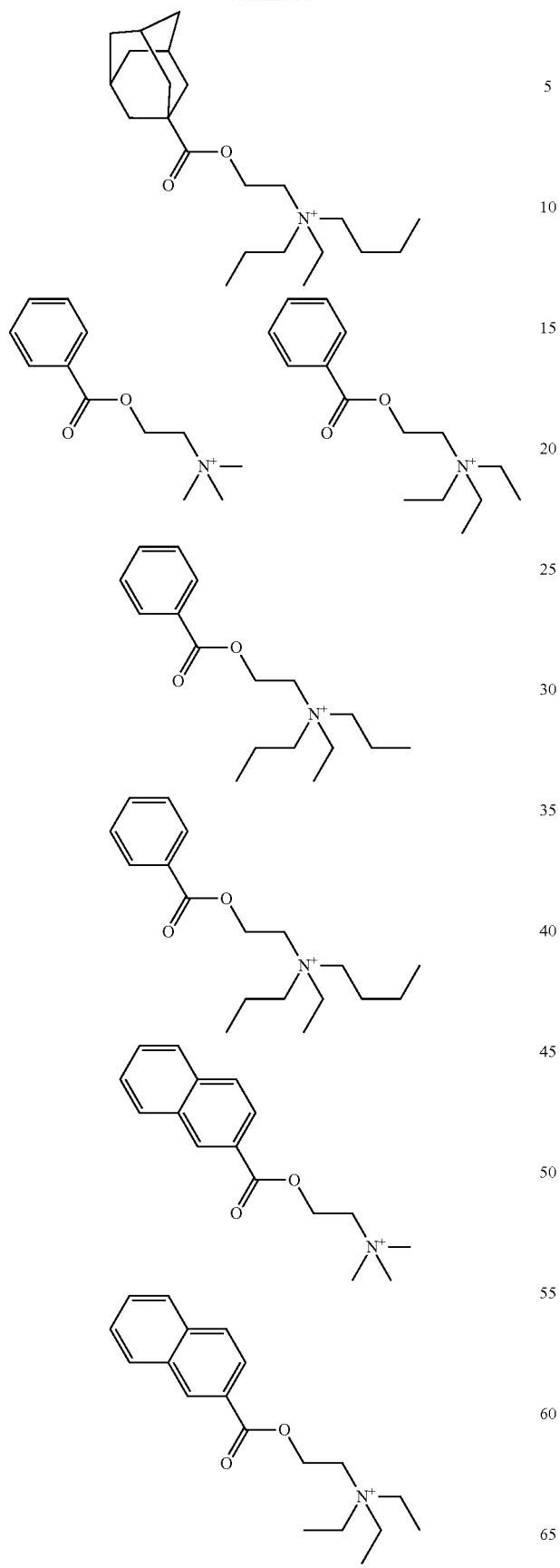

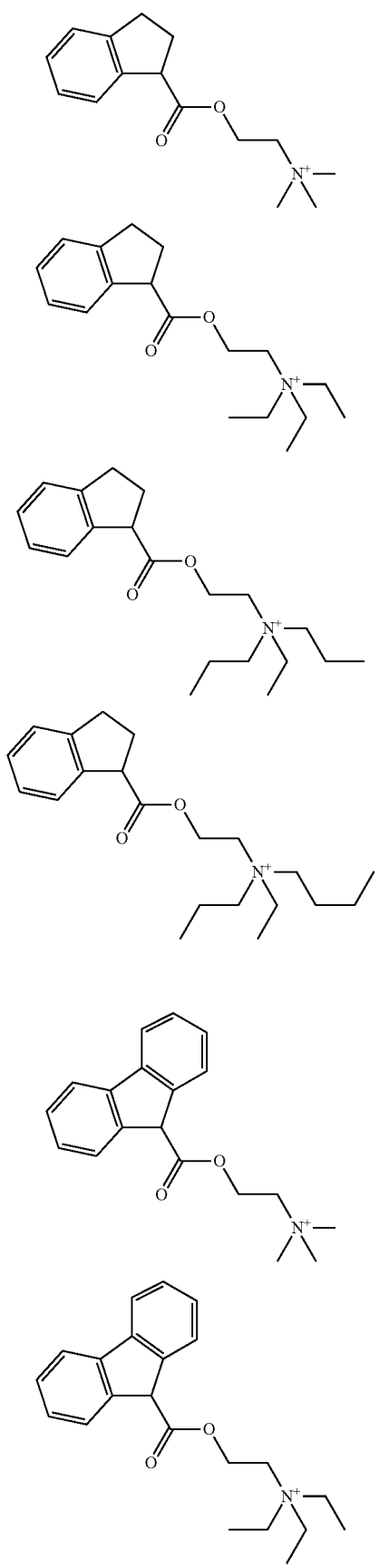
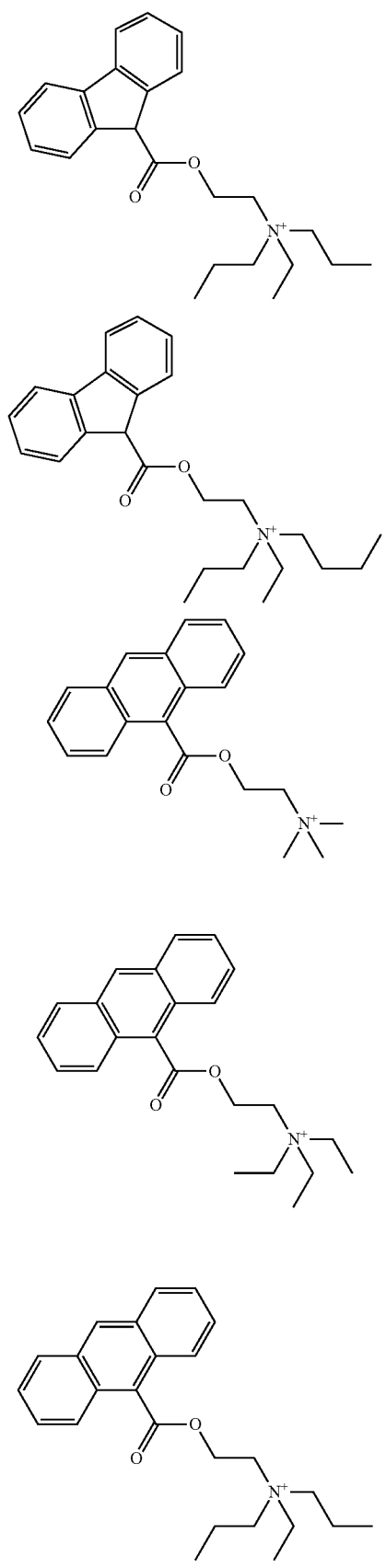

99
-continued
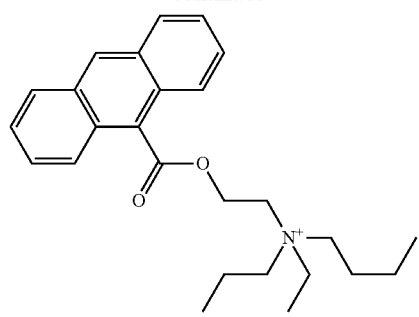
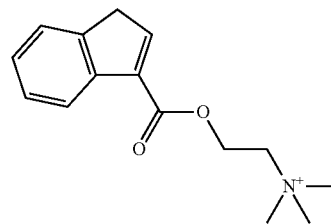
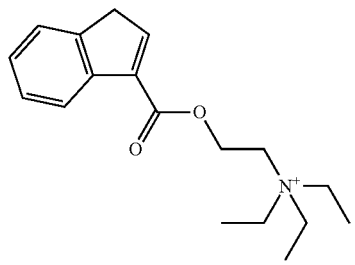
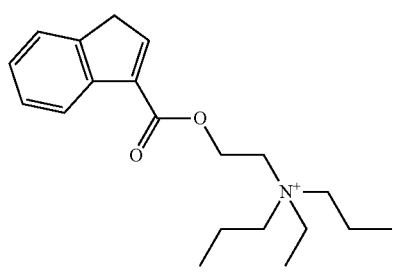
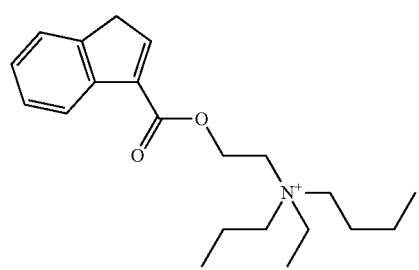
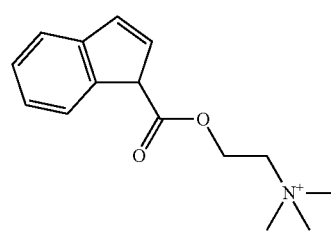
100
-continued
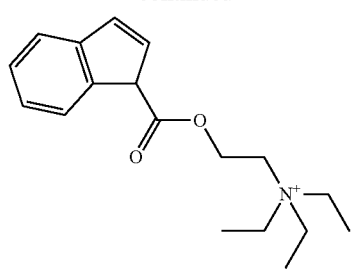
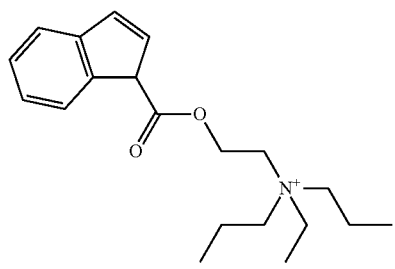
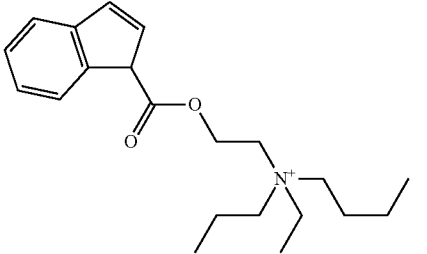
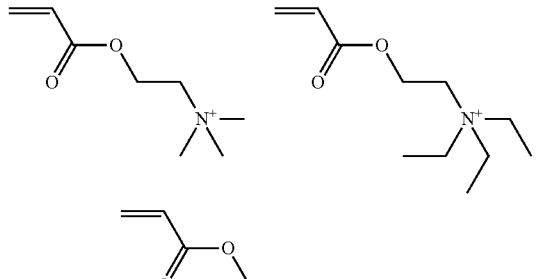
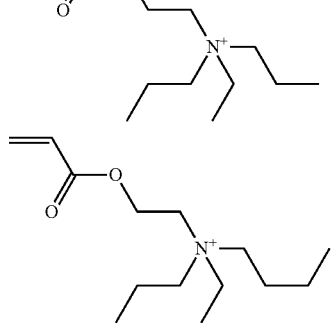
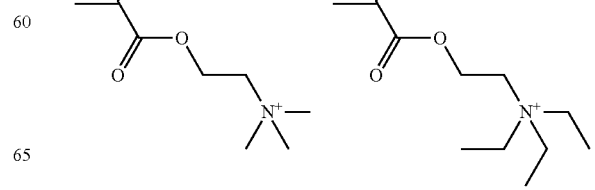

101
-continued
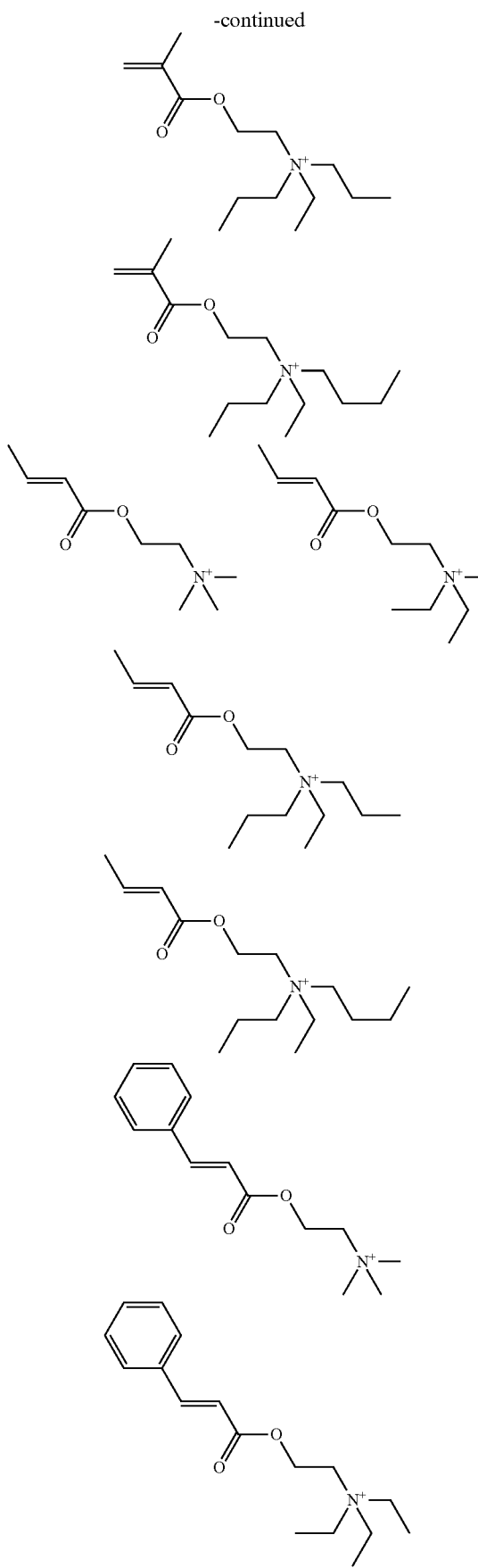
102
-continued
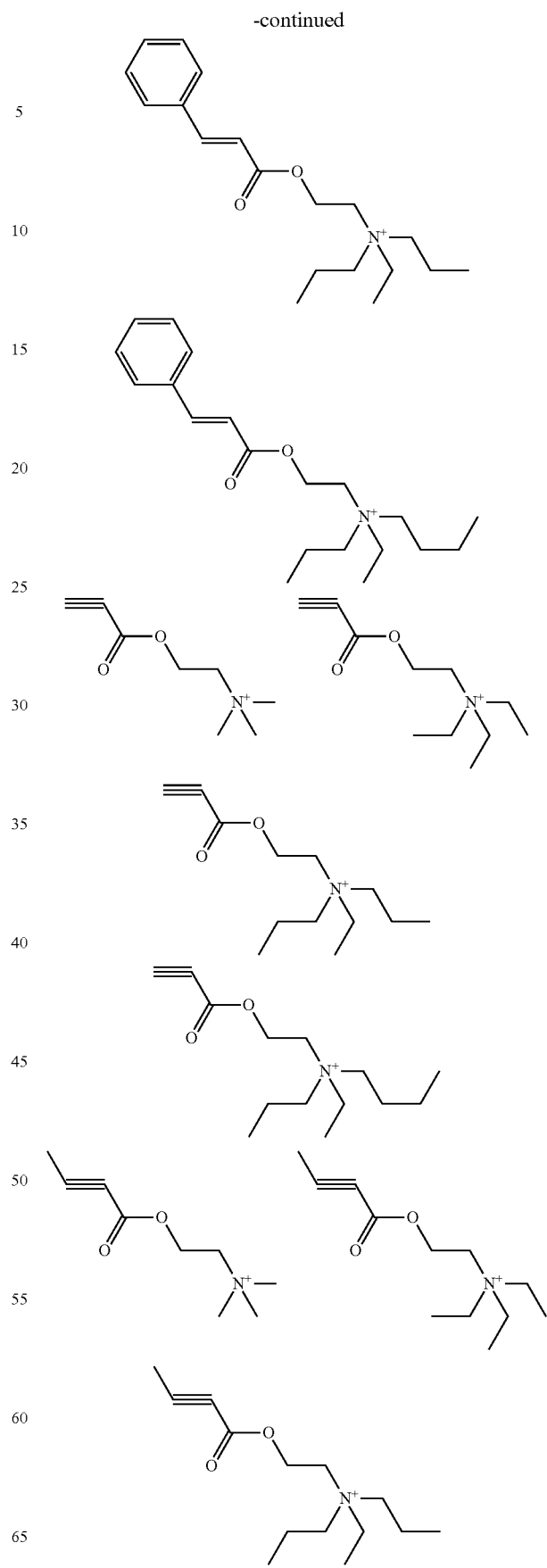

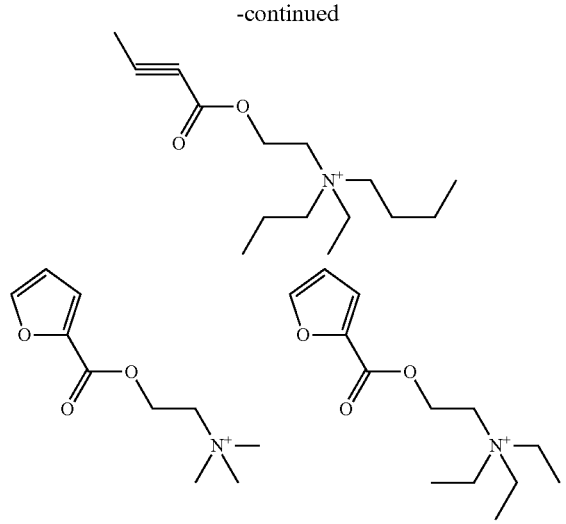
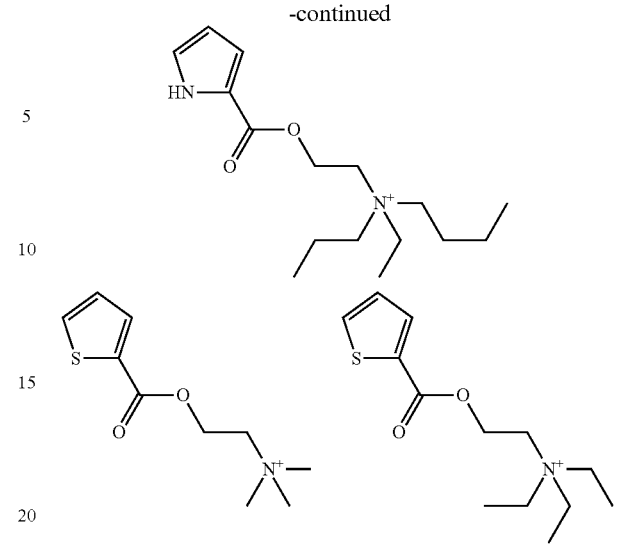
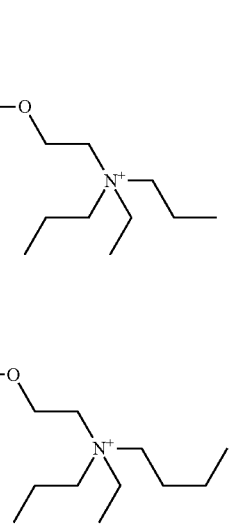
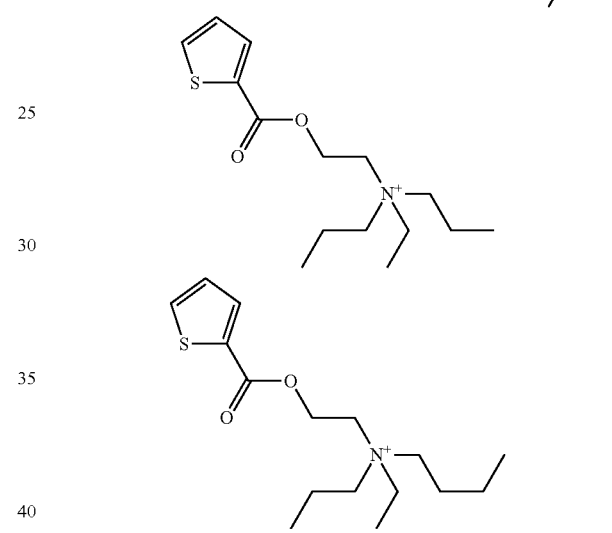
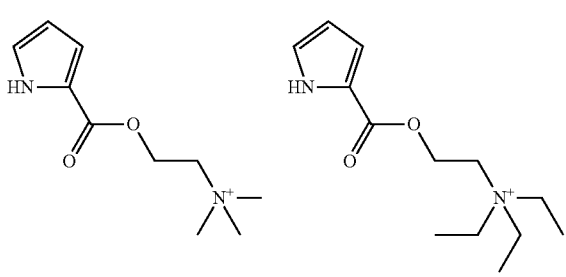
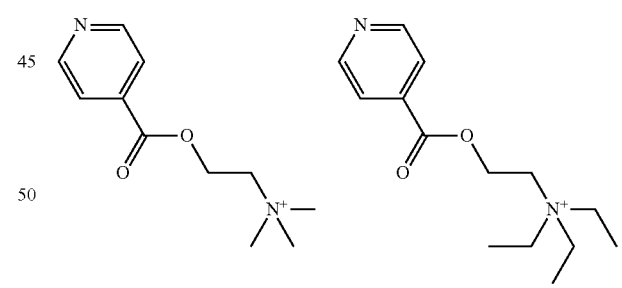
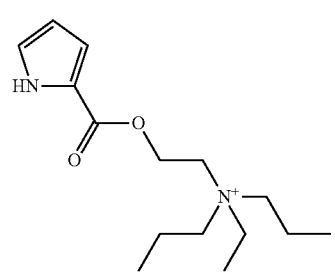
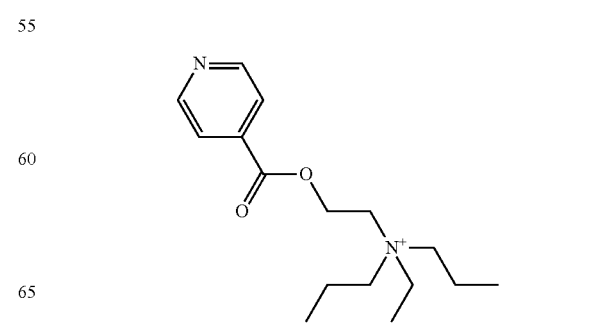

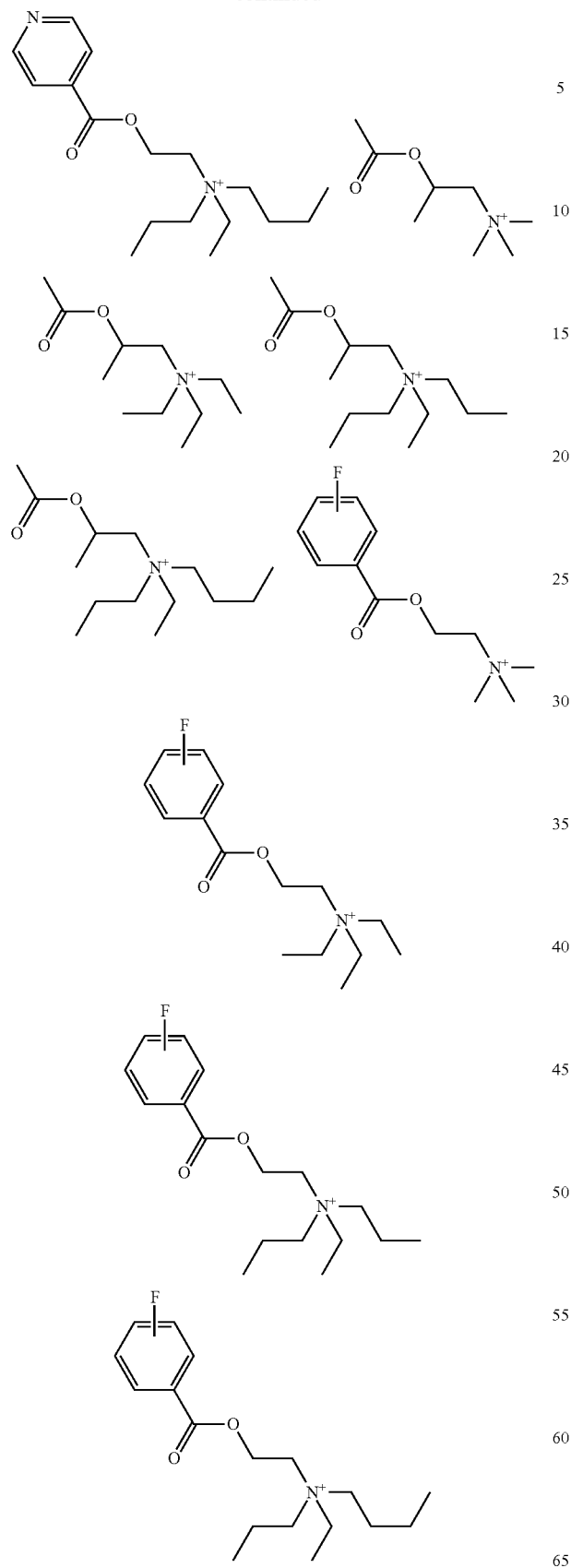
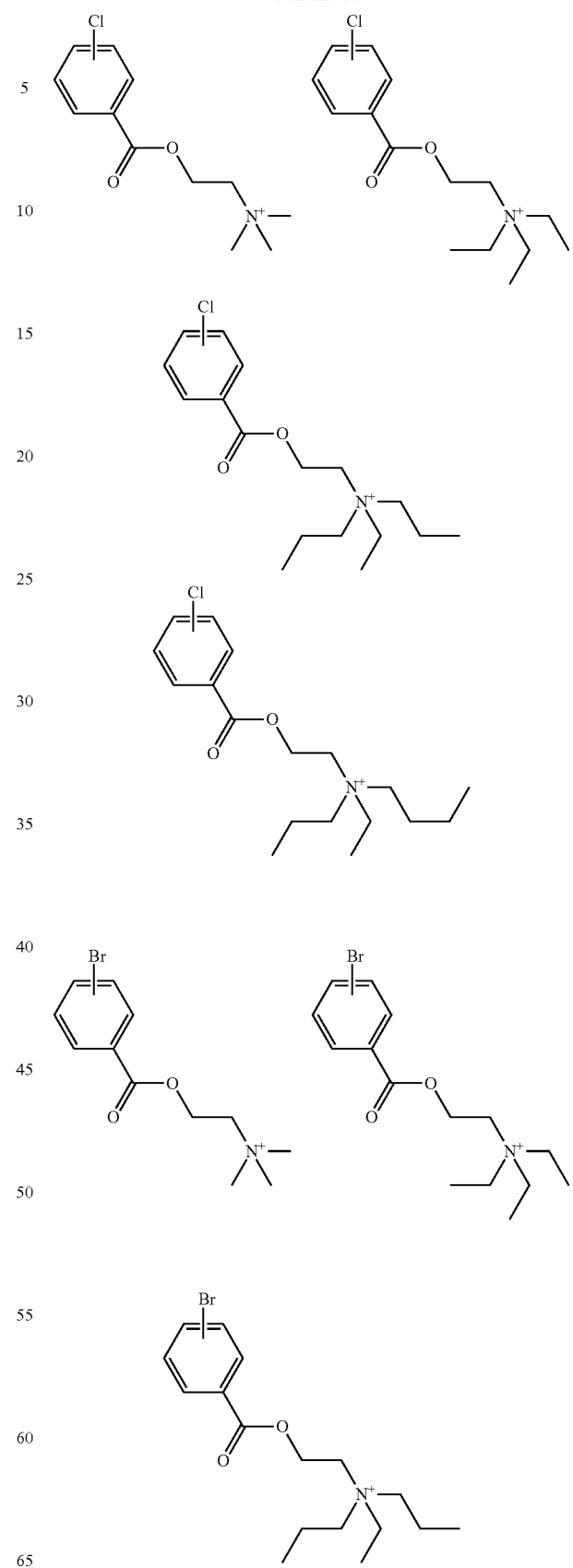

107
-continued
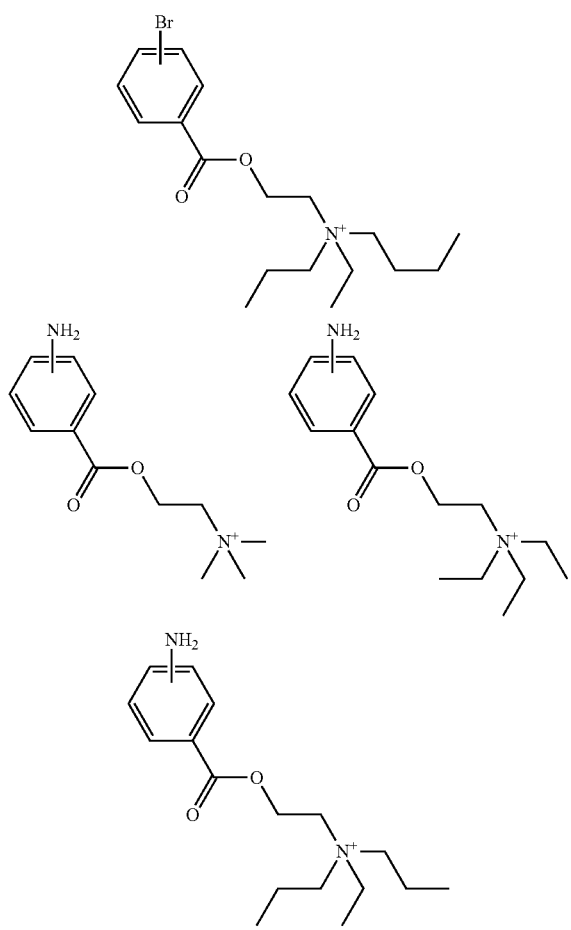
108
-continued
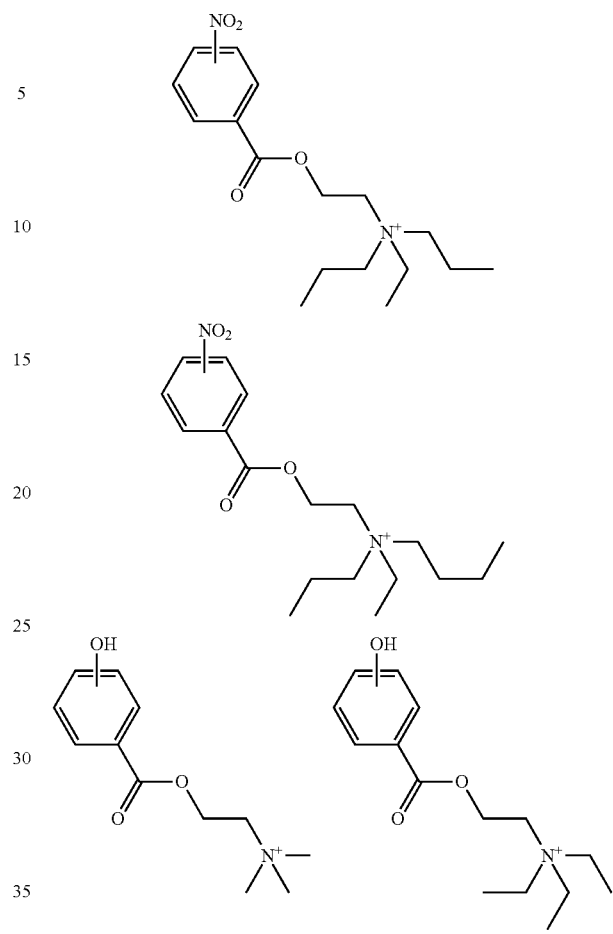
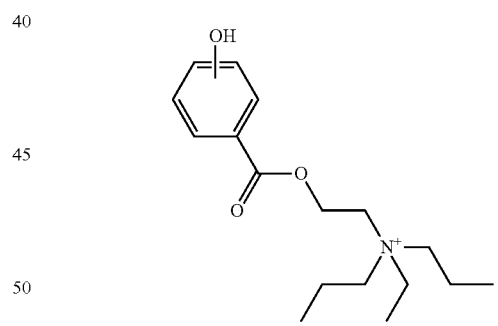
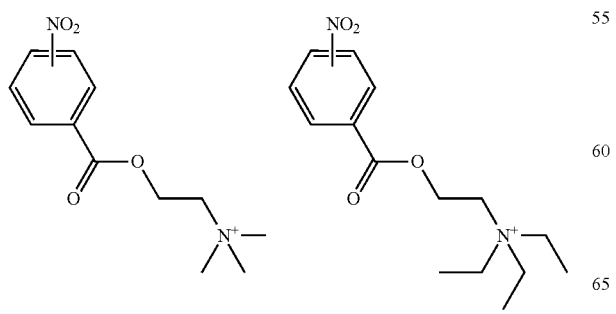
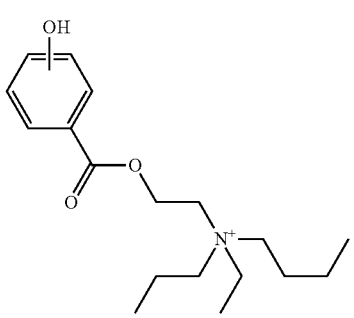

-continued
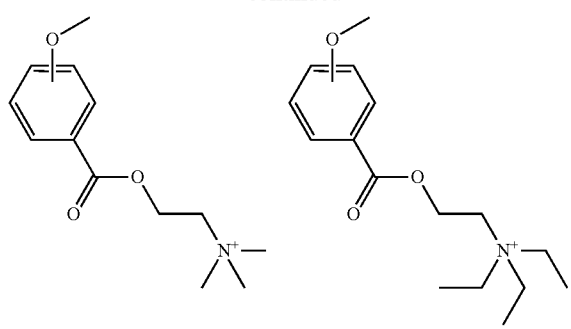
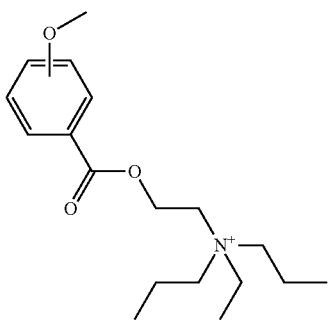
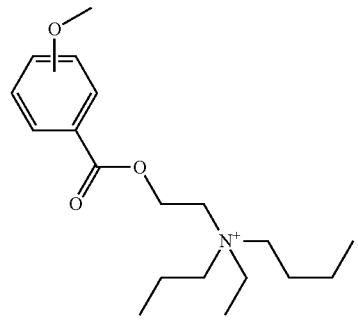
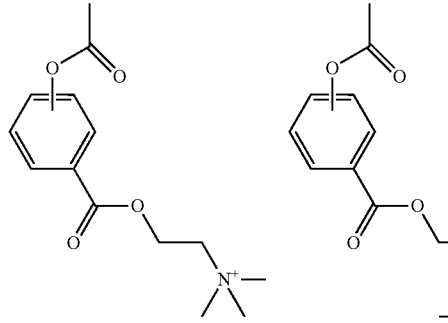
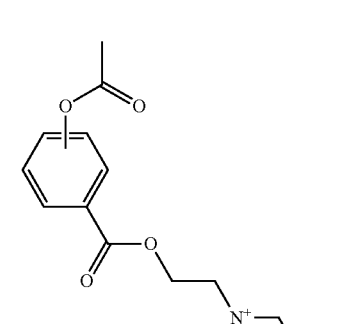
-continued
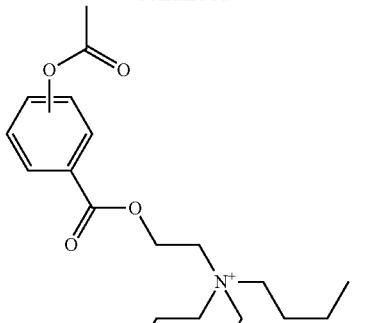
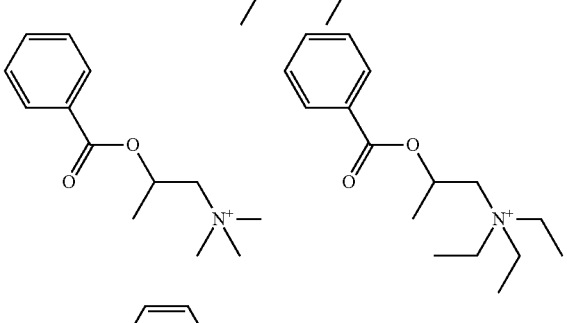
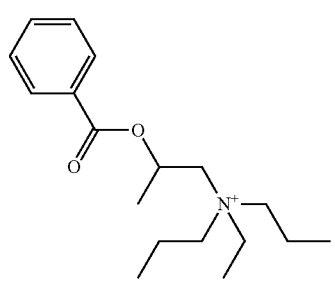
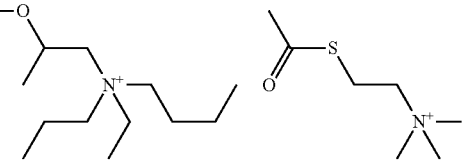
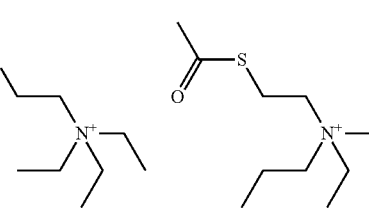
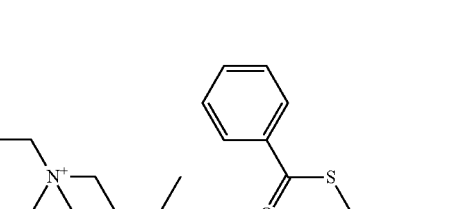
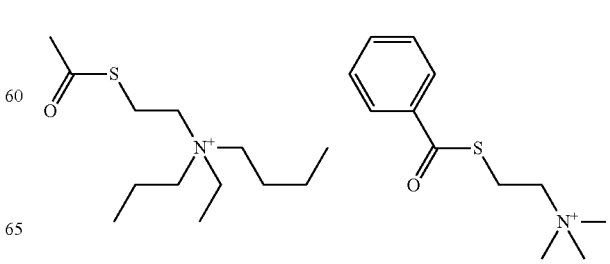

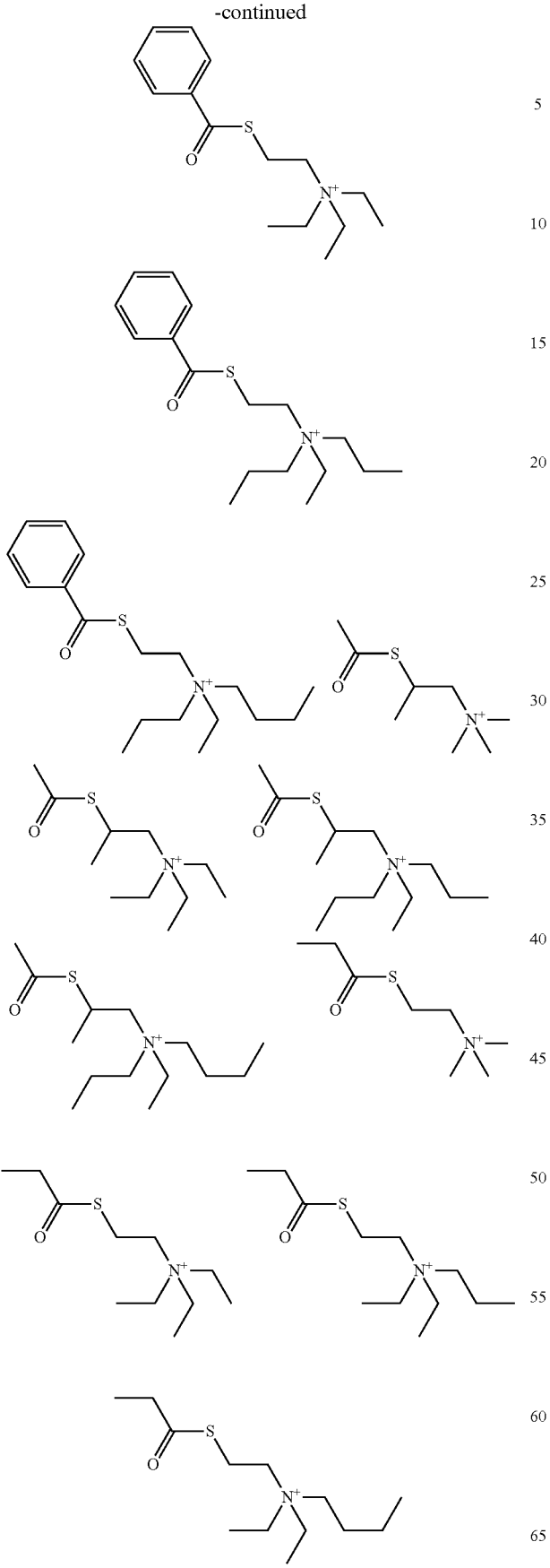
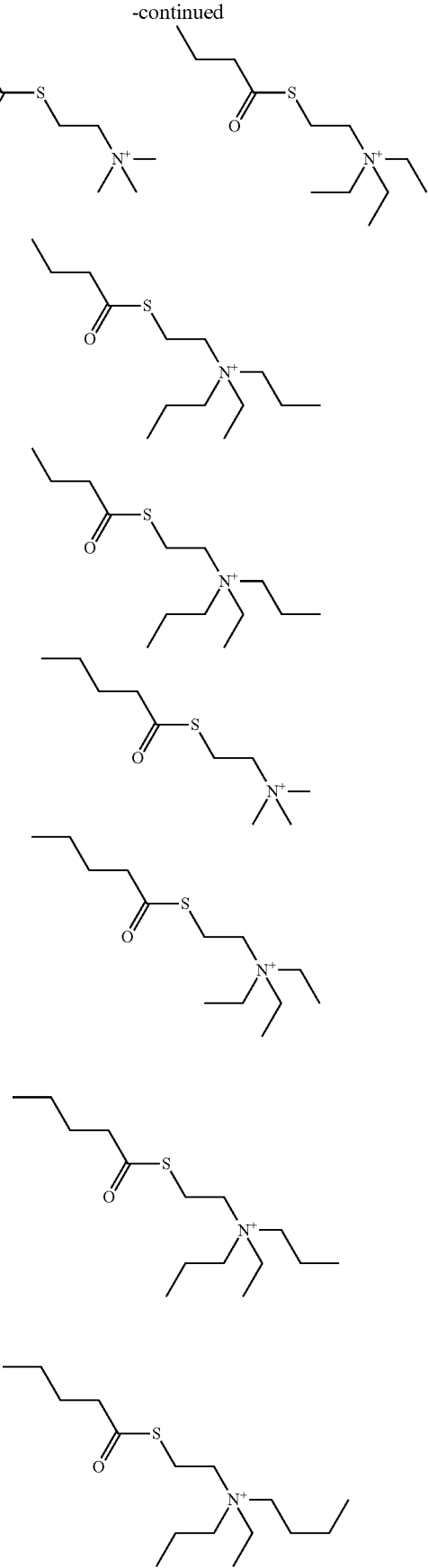

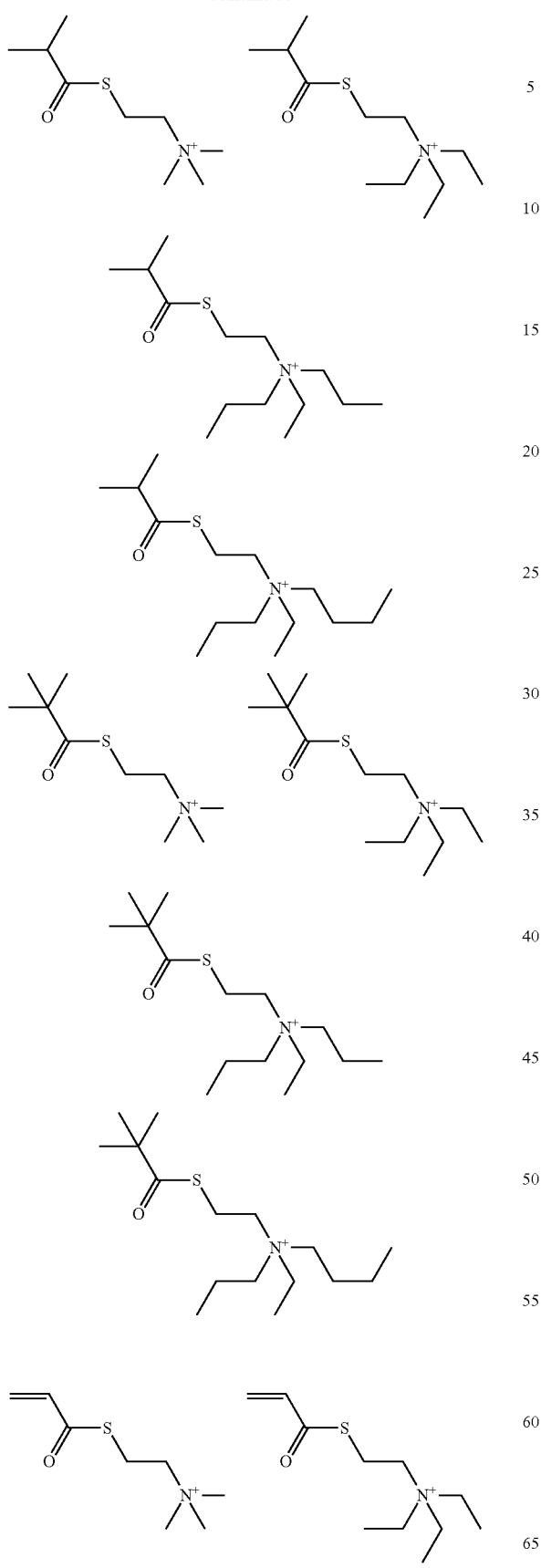
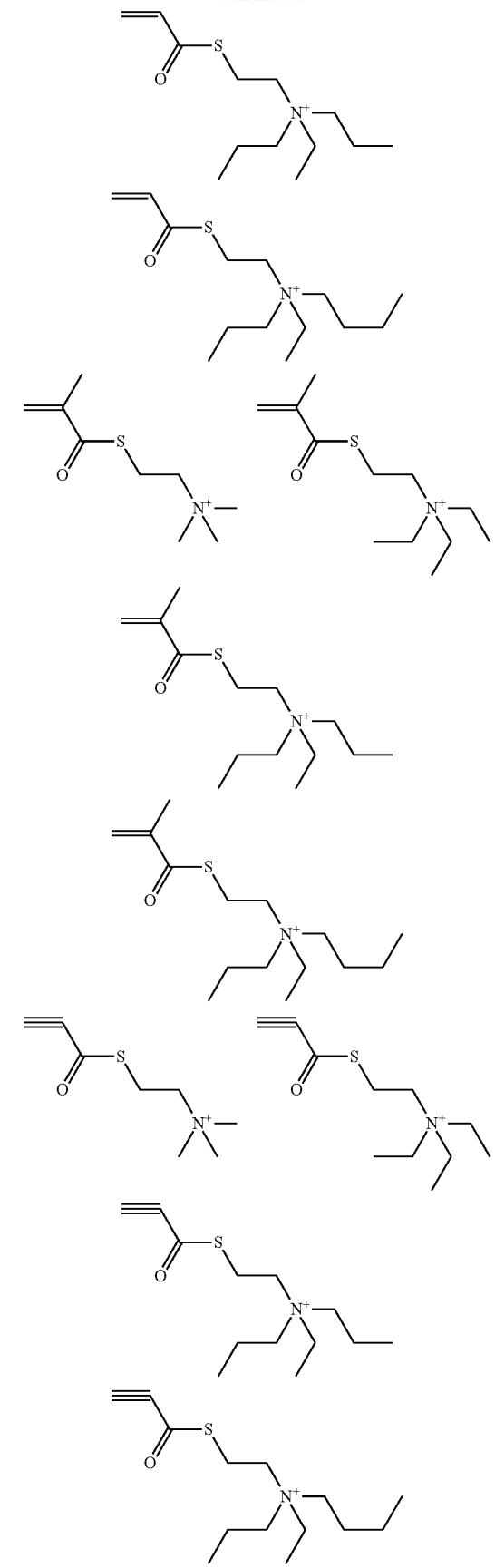

115
-continued
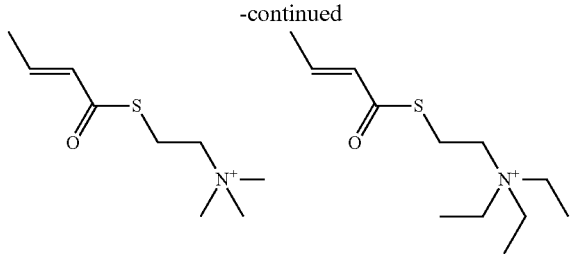
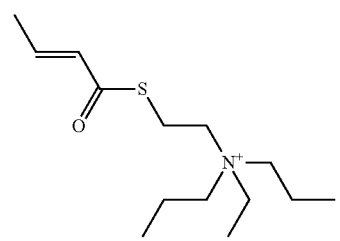
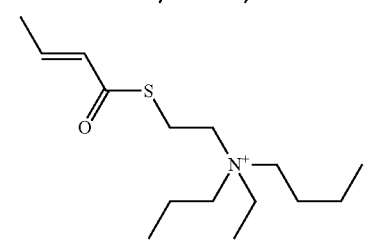
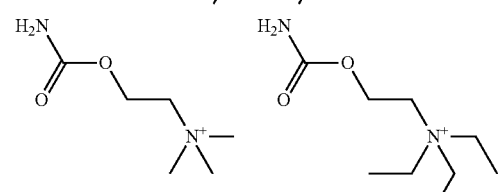
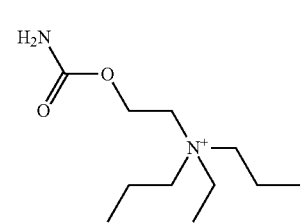
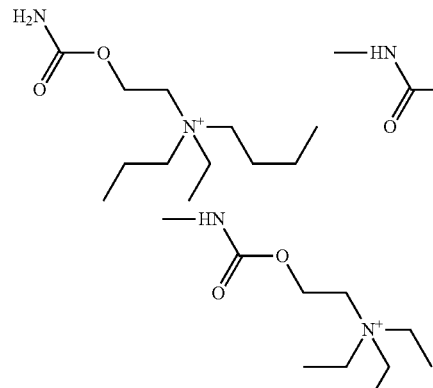
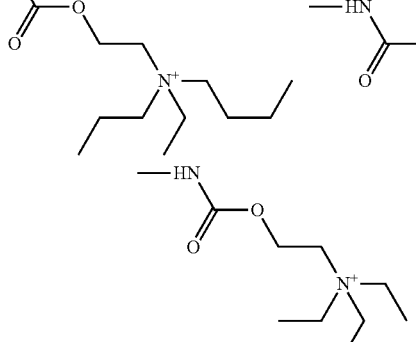
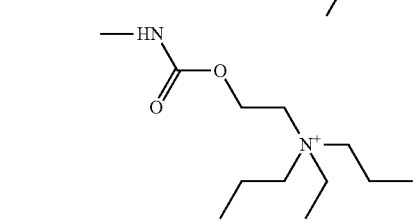
116
-continued
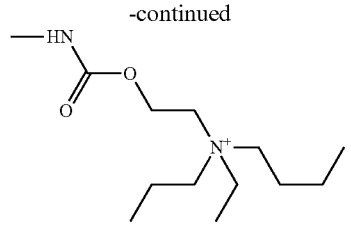
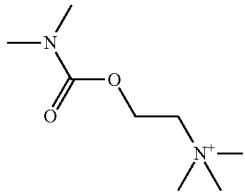
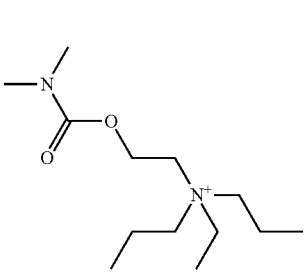
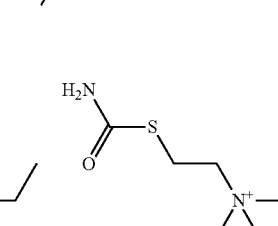
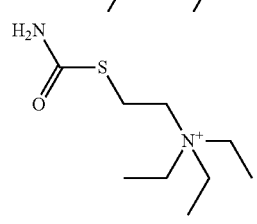
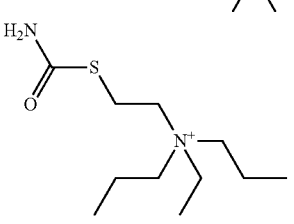
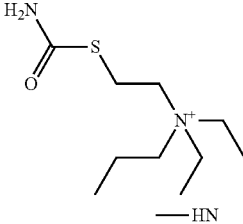
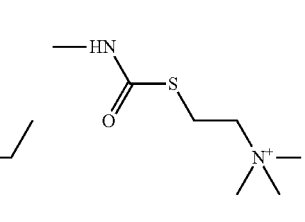
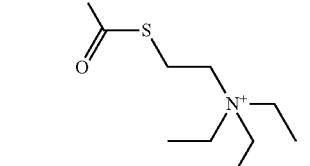
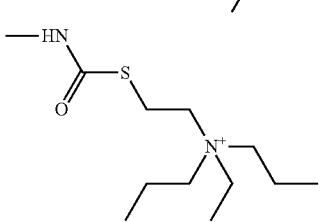
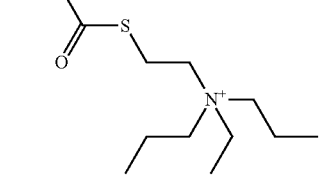

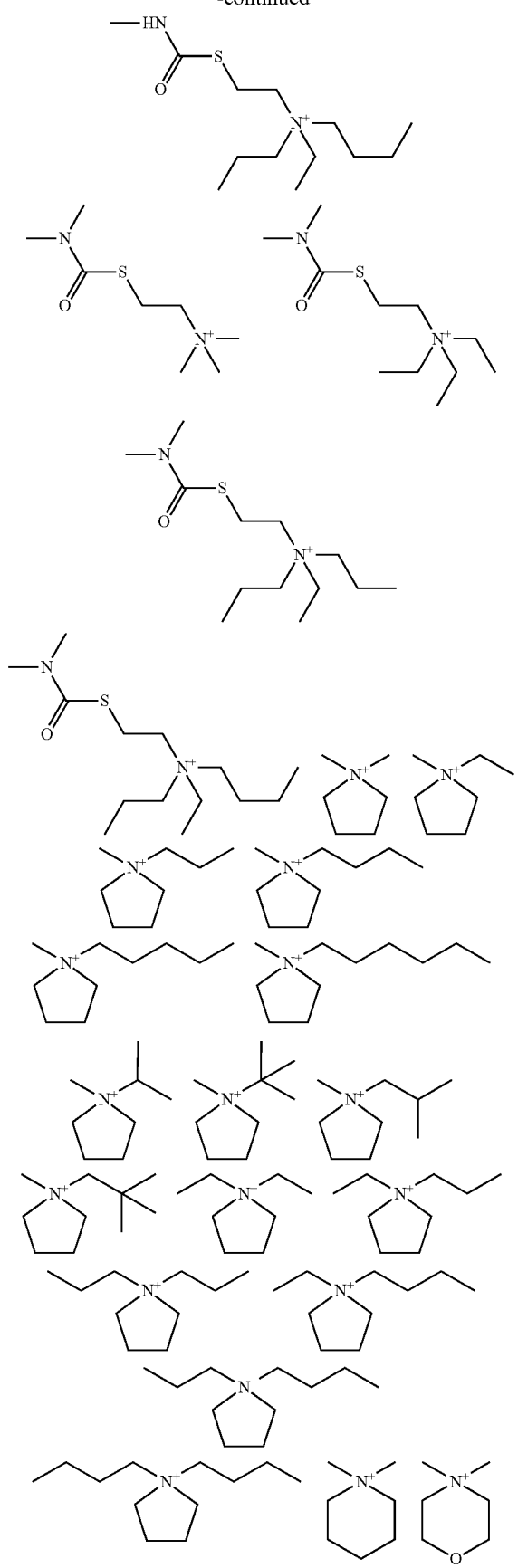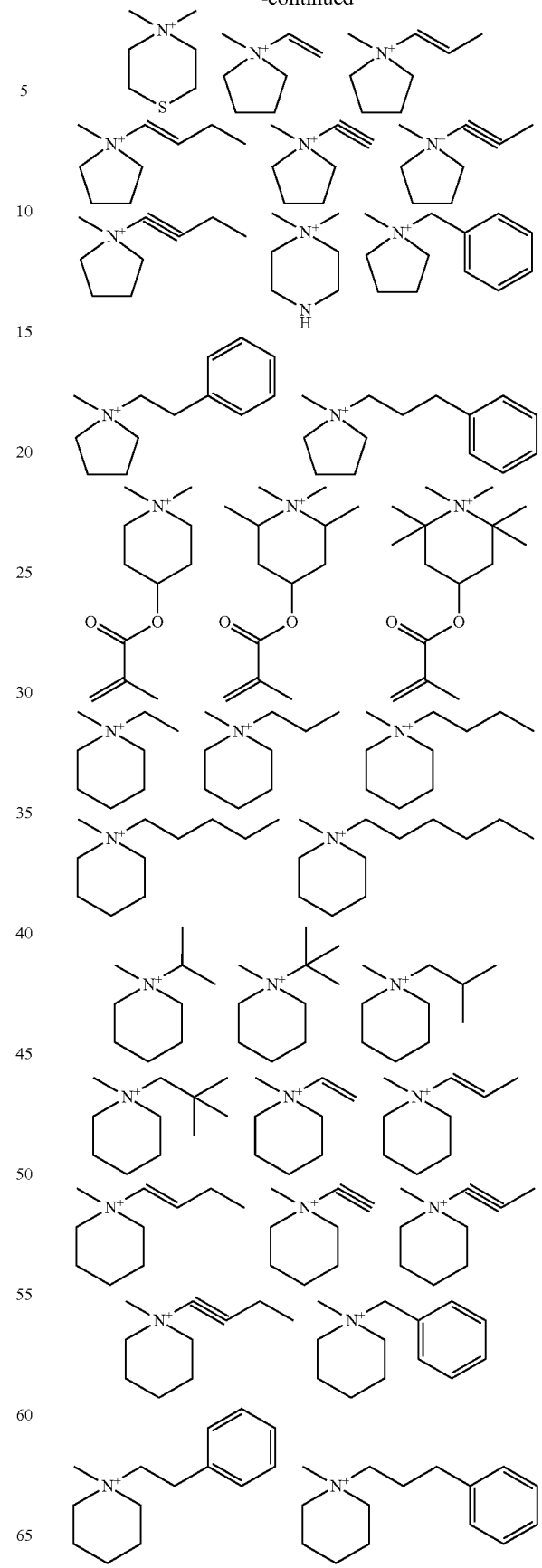

119
-continued
120
-continued
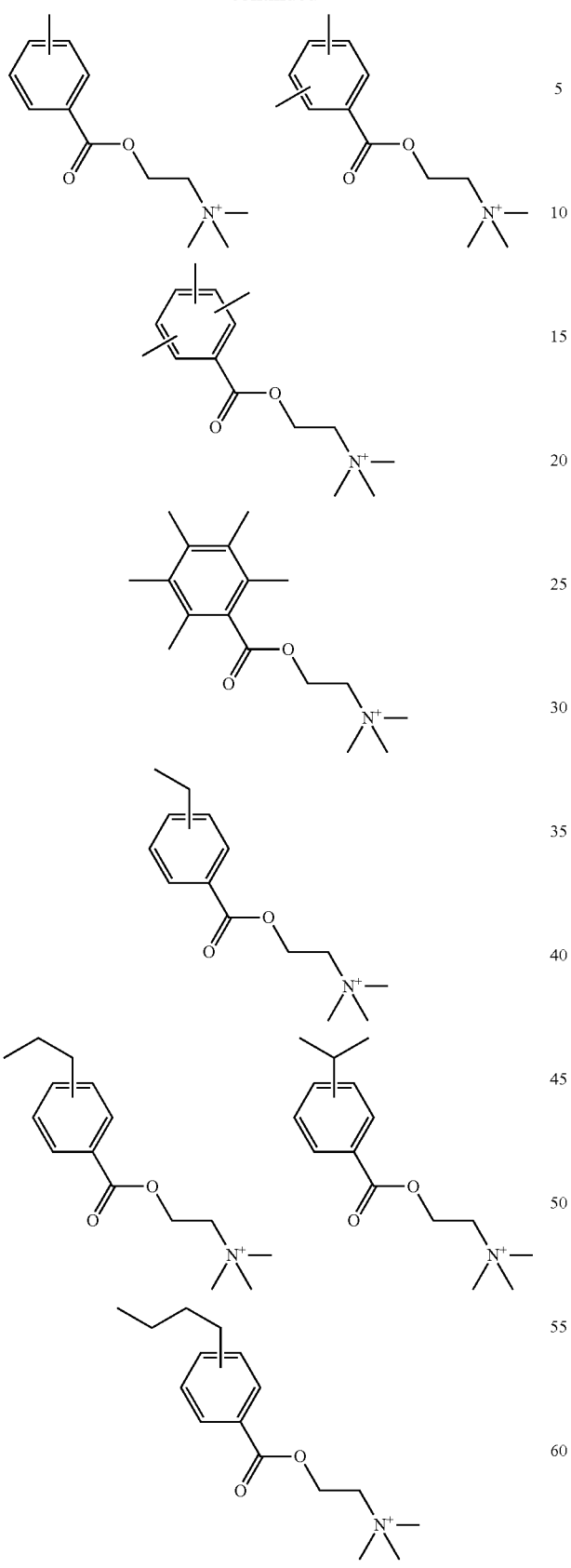
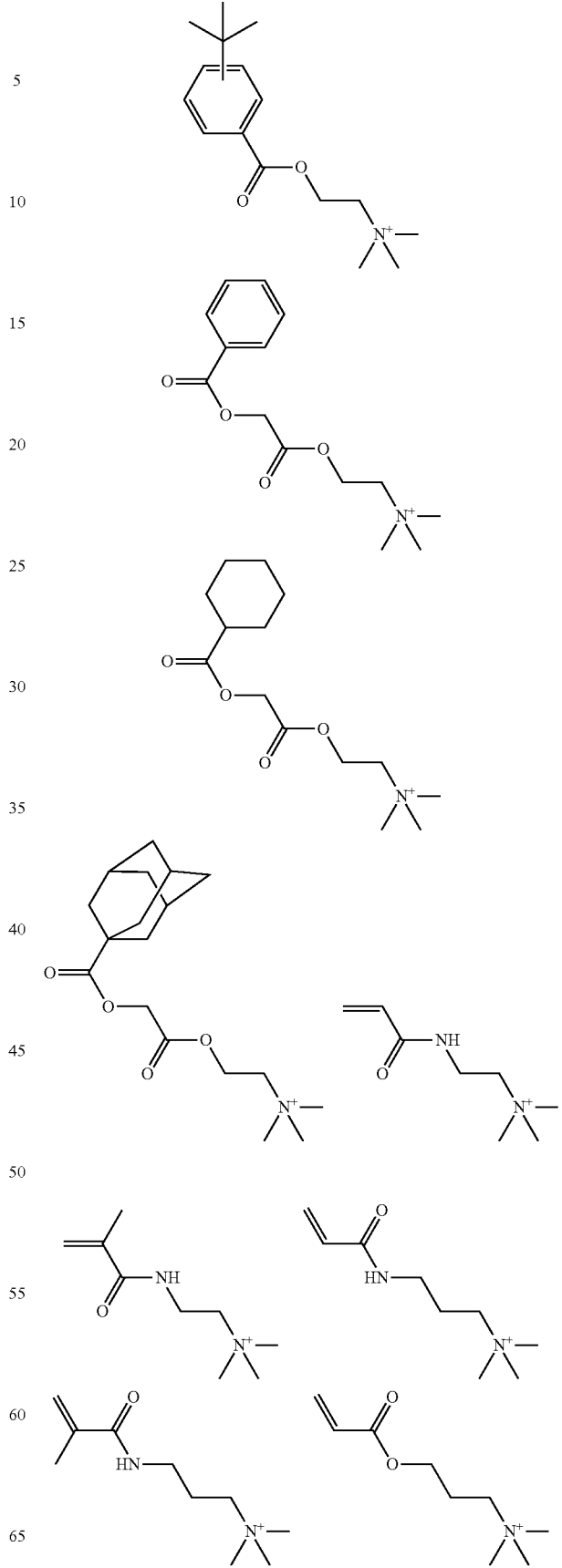

121
-continued
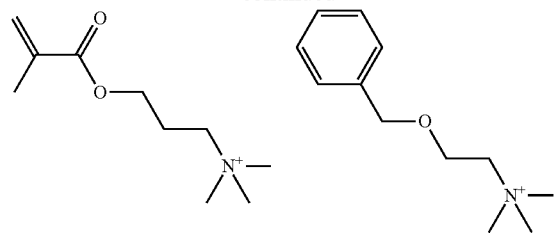
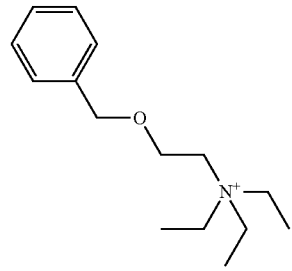
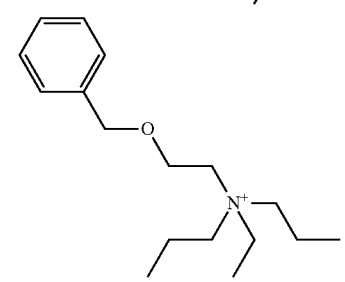
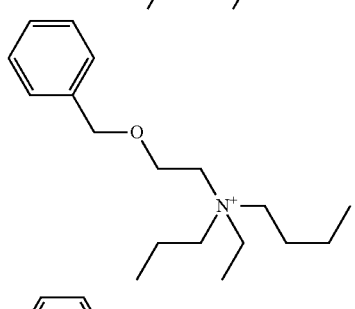
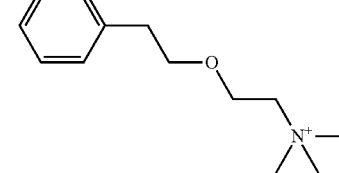
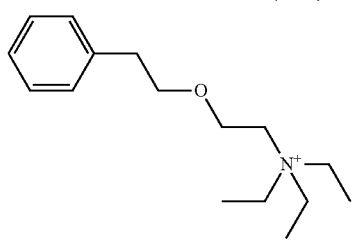
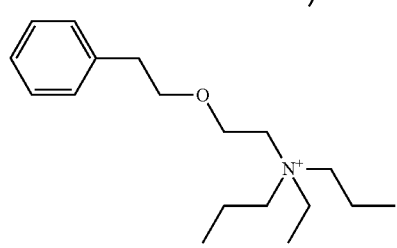
122
-continued
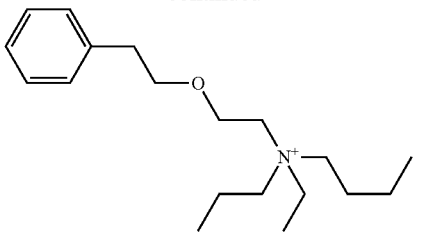
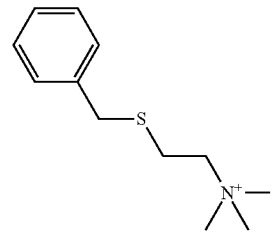
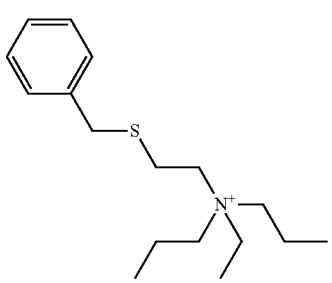
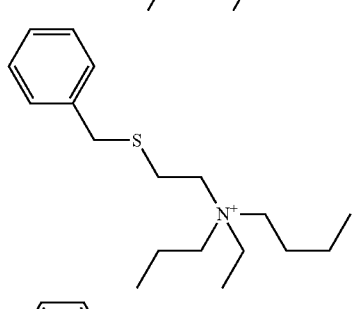
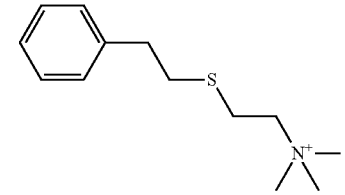
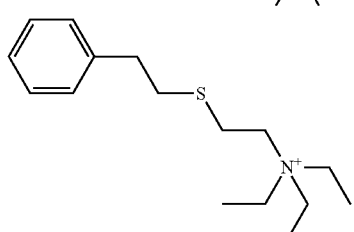
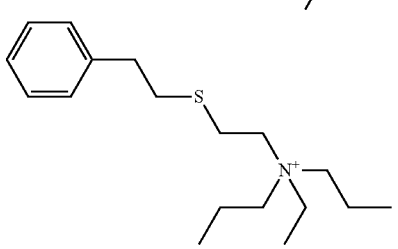

123
-continued
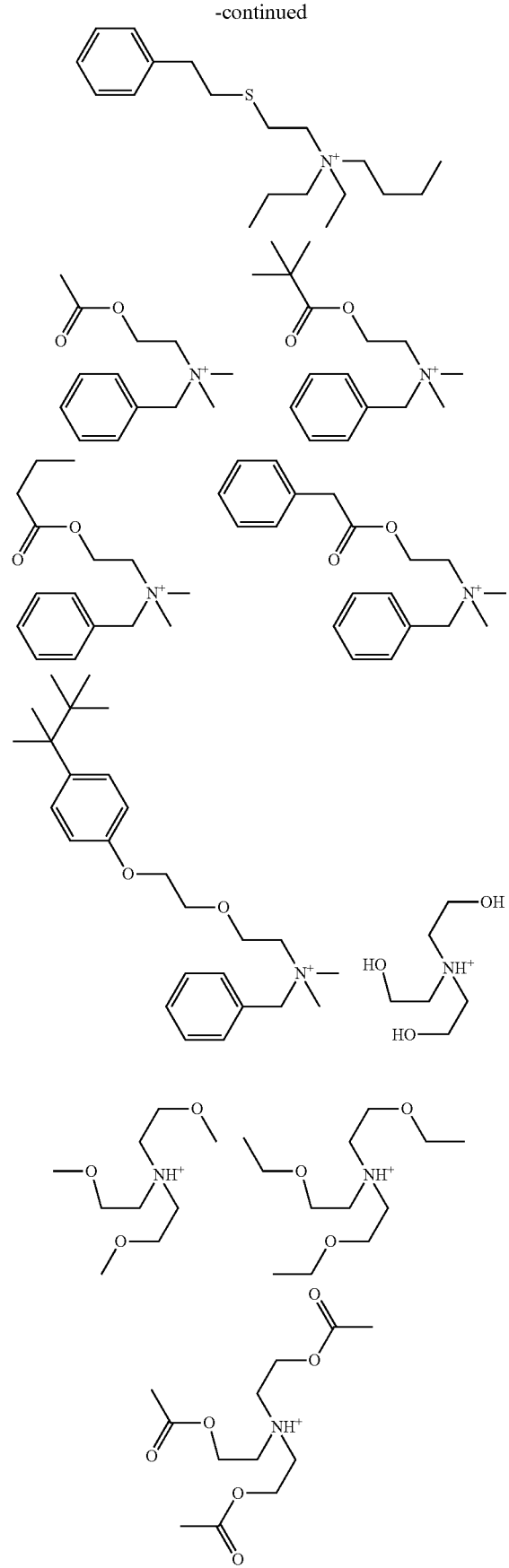
124
-continued
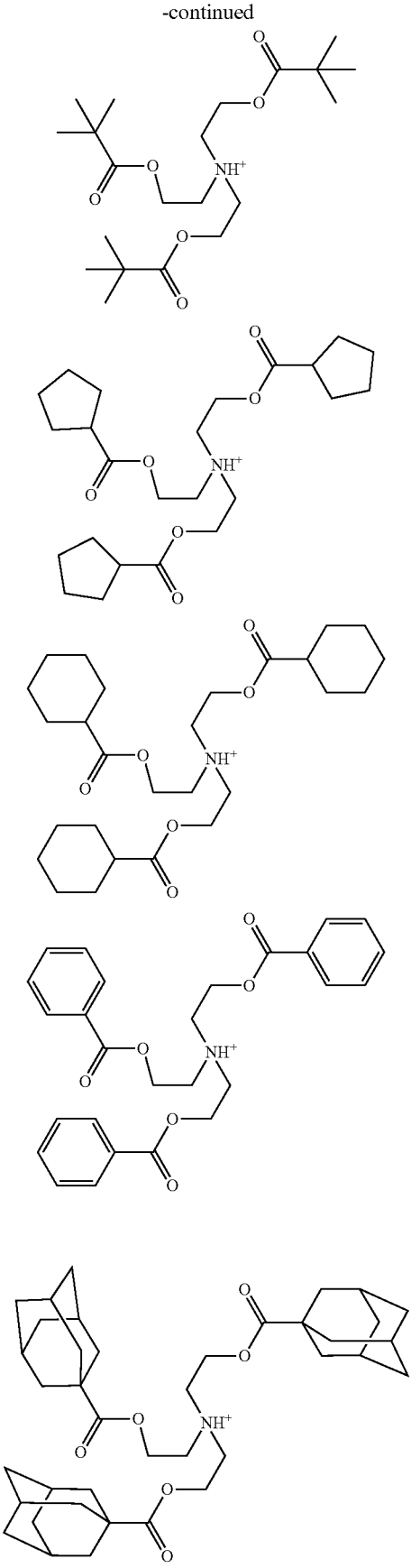

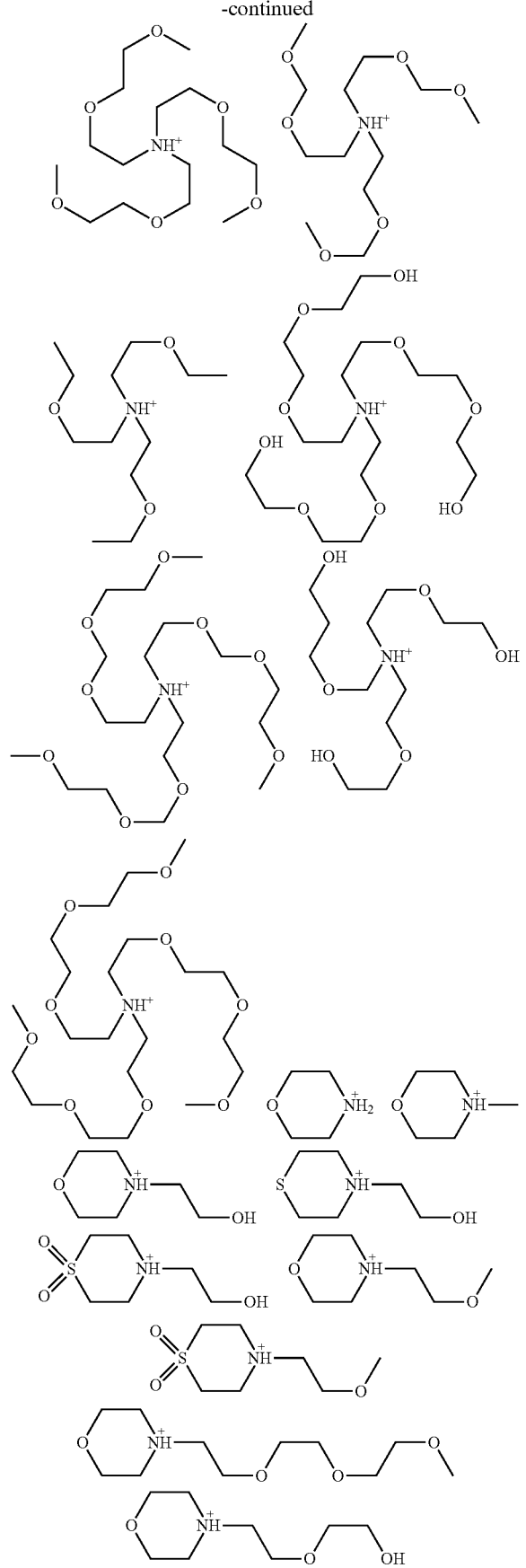
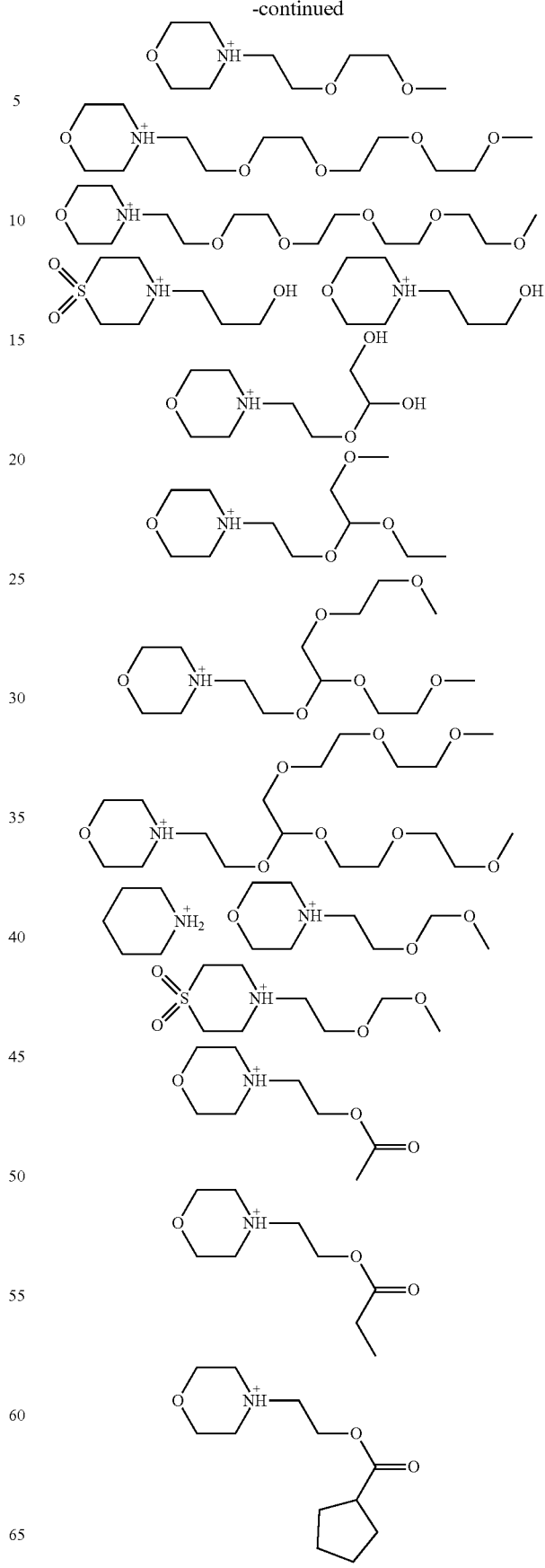

127
-continued

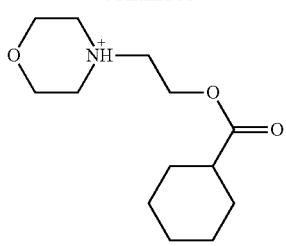

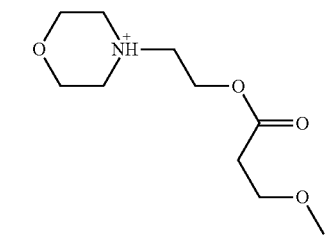

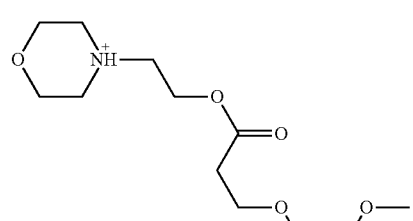

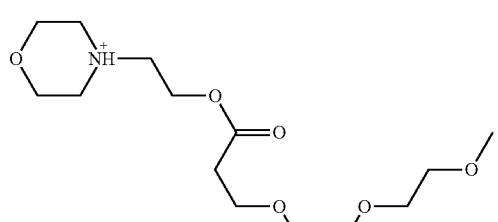

The bio-electrode composition used for the present invention preferably contains an ionic polymer that has a repeating unit (s) of an ionic monomer shown by a1 to a7, but the ionic polymer may also be copolymerized with repeating unit-b having tackiness function. The monomer for obtaining the repeating unit-b that brings tackiness is not particularly limited, and concrete examples thereof include the following.

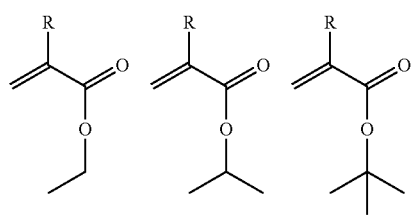

128
-continued

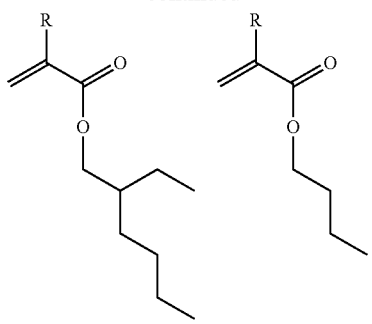

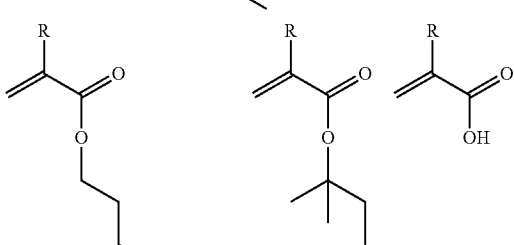

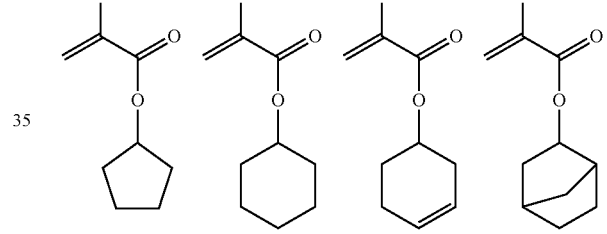

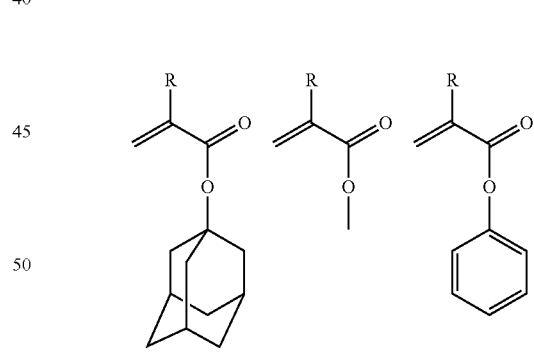

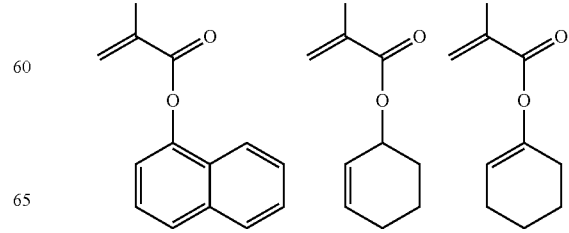

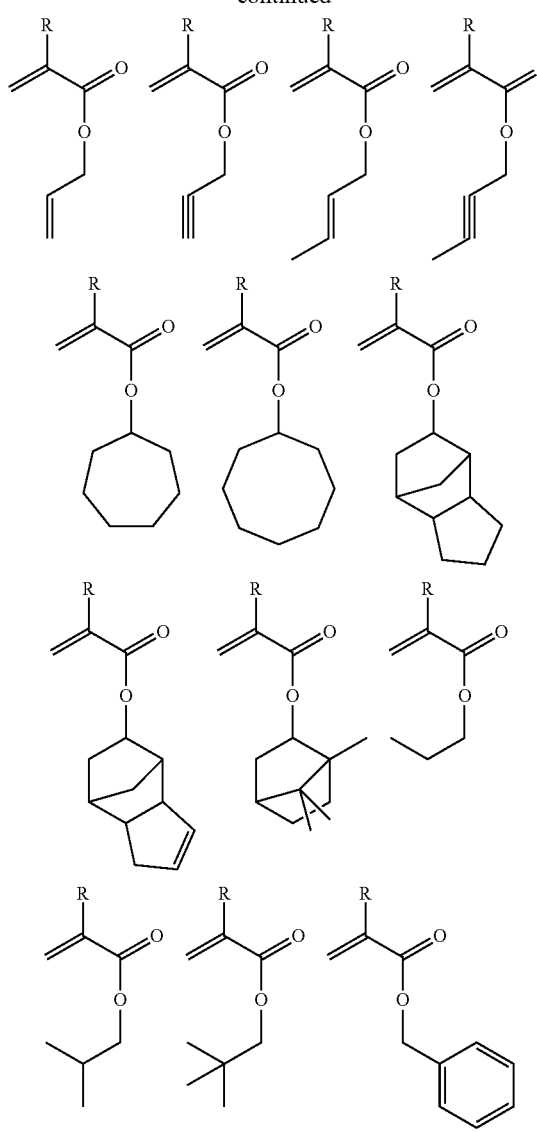
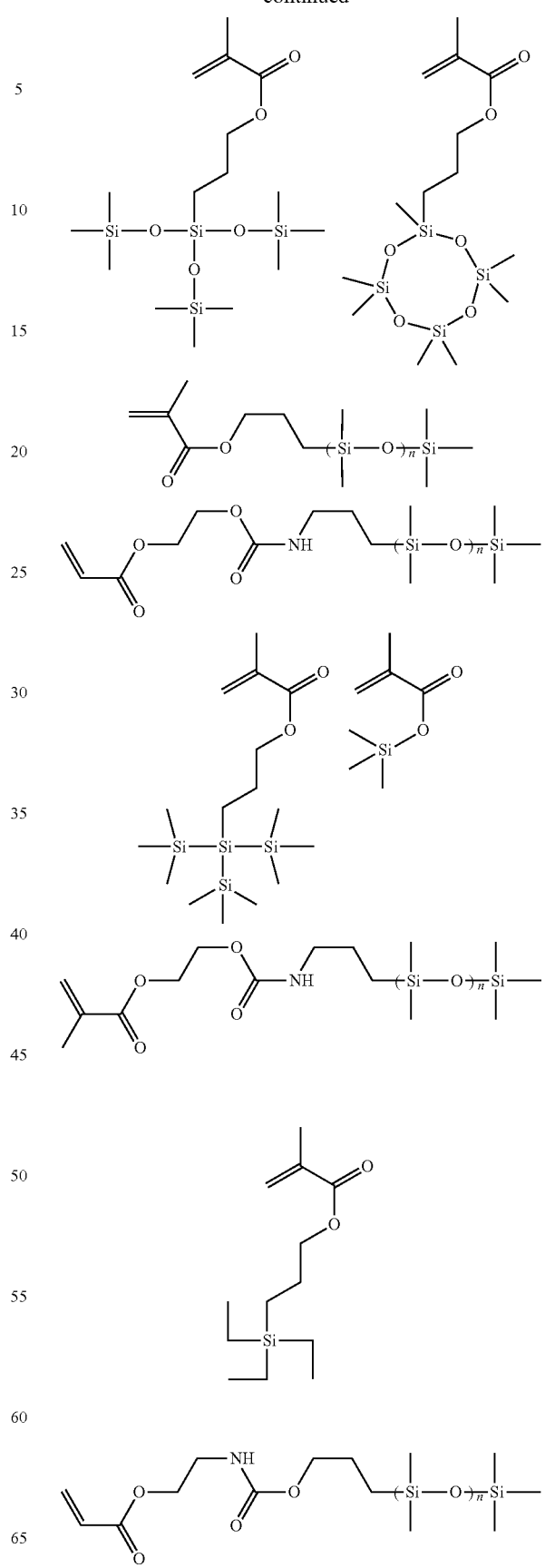
In the formulae, R represents a hydrogen atom or a methyl group.
To improve the repellency, it is also possible to copolymerize repeating unit-c, which contains a silicon. The monomer for obtaining the repeating unit-c containing a silicon is not particularly limited, and concrete examples thereof include the following.

131
-continued
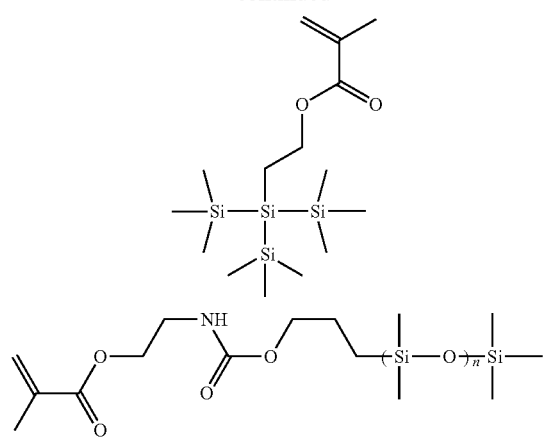
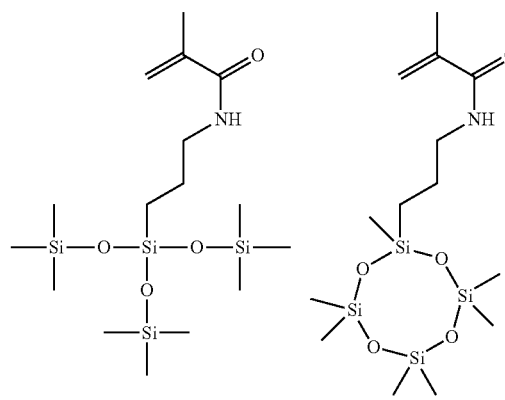
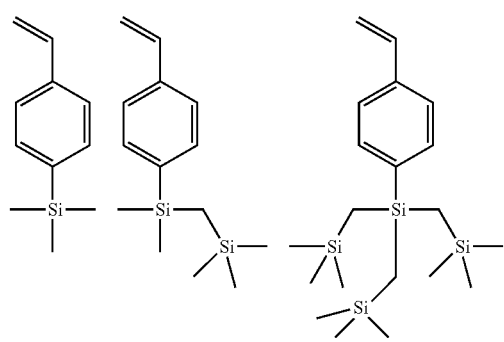
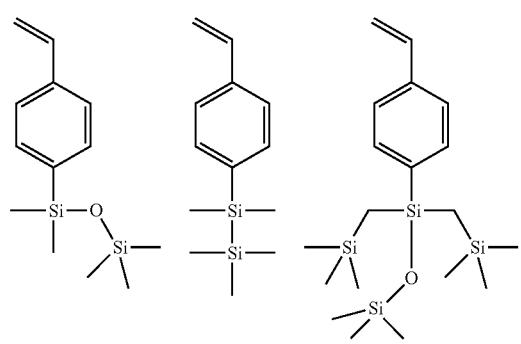
132
-continued
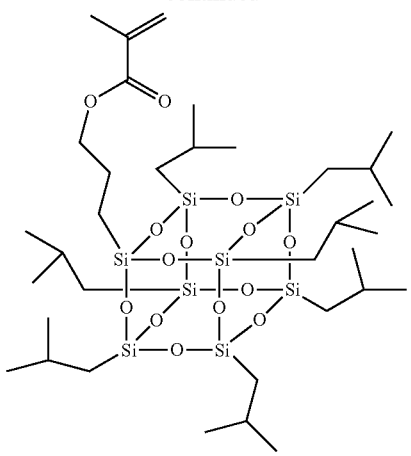
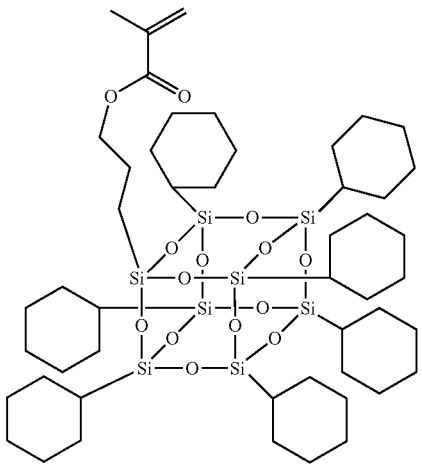
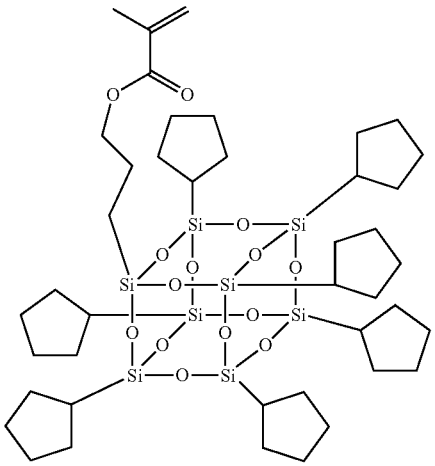
In the formulae, "n" is an integer of 0 to 100.
Additionally, it is also possible to copolymerize repeating unit-d, which has a glyme chain, to improve the electric conductivity. The monomer for obtaining the repeating unit-d having a glyme chain is not particularly limited, and concrete examples thereof include the following.

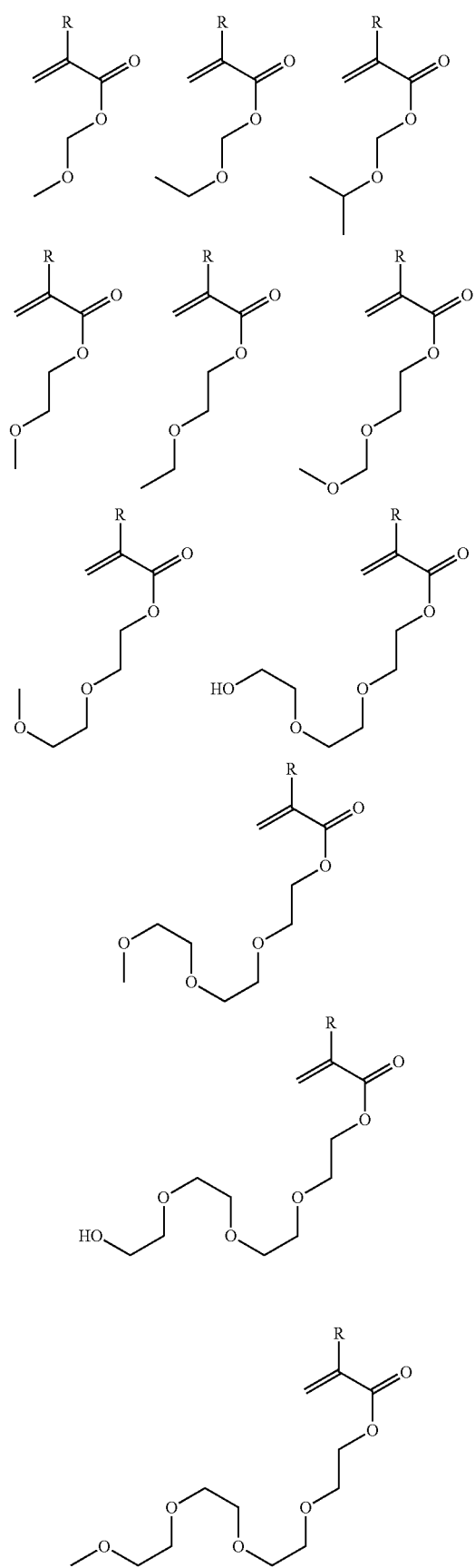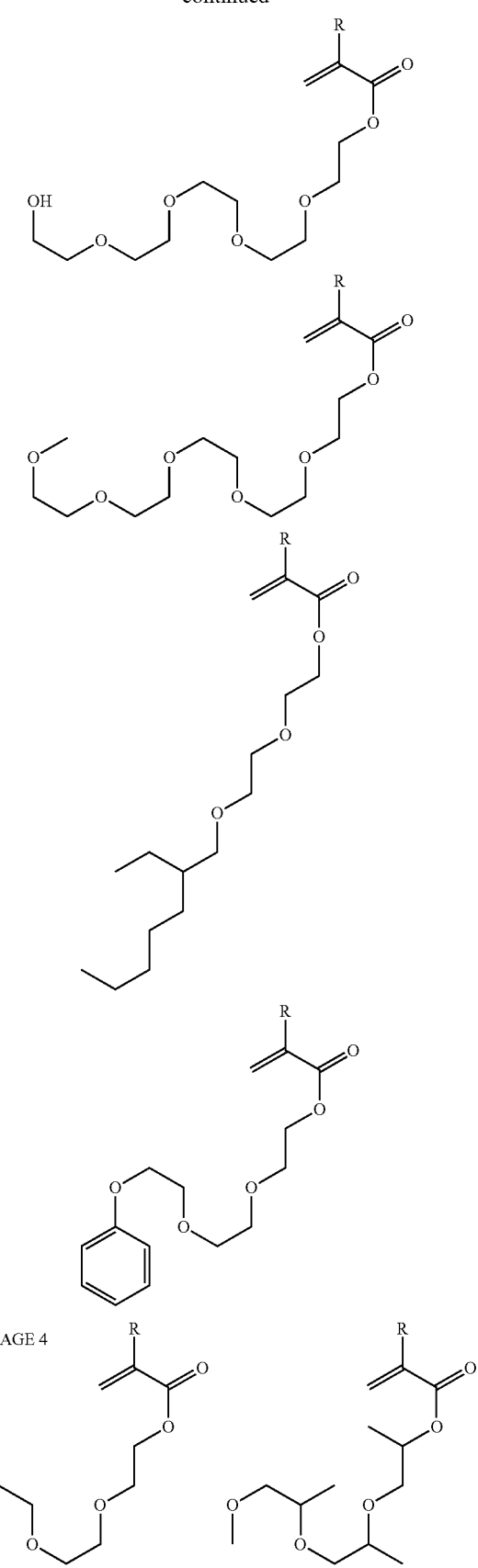

135
-continued
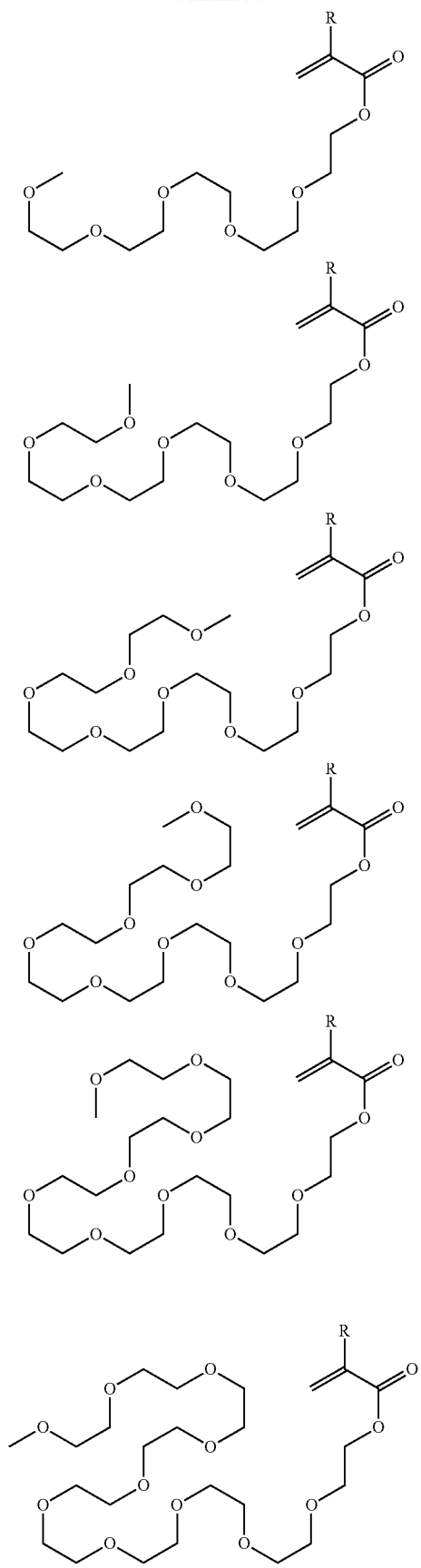
136
-continued
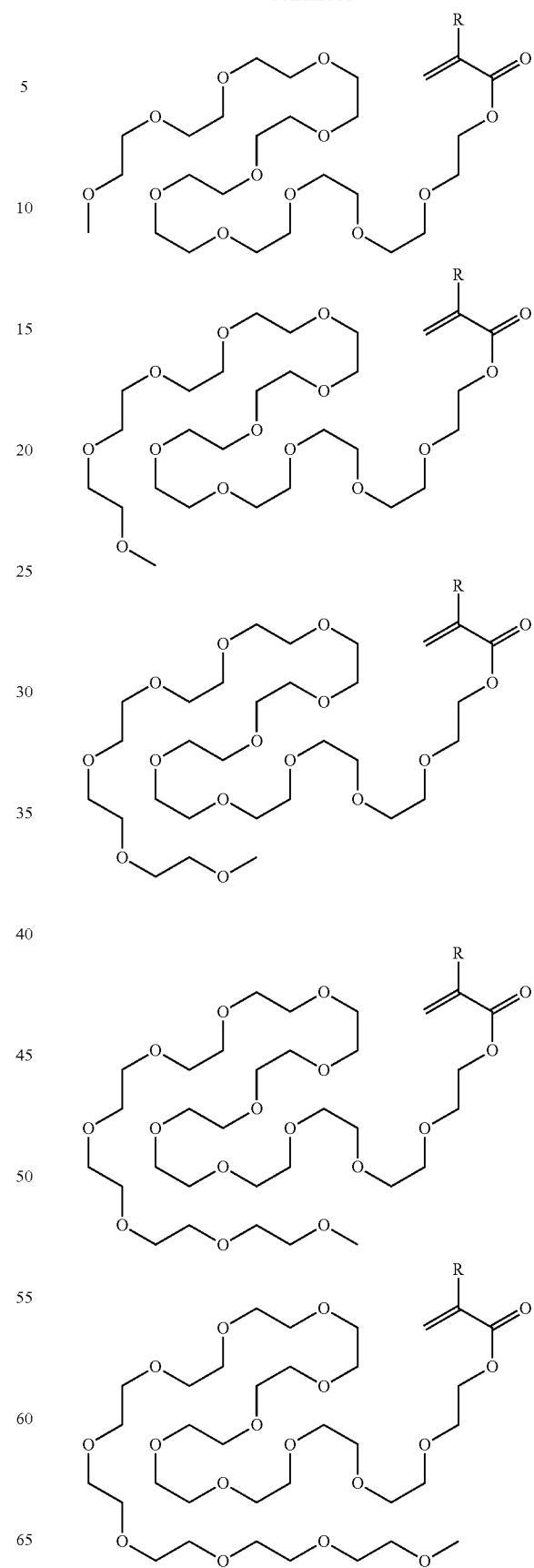

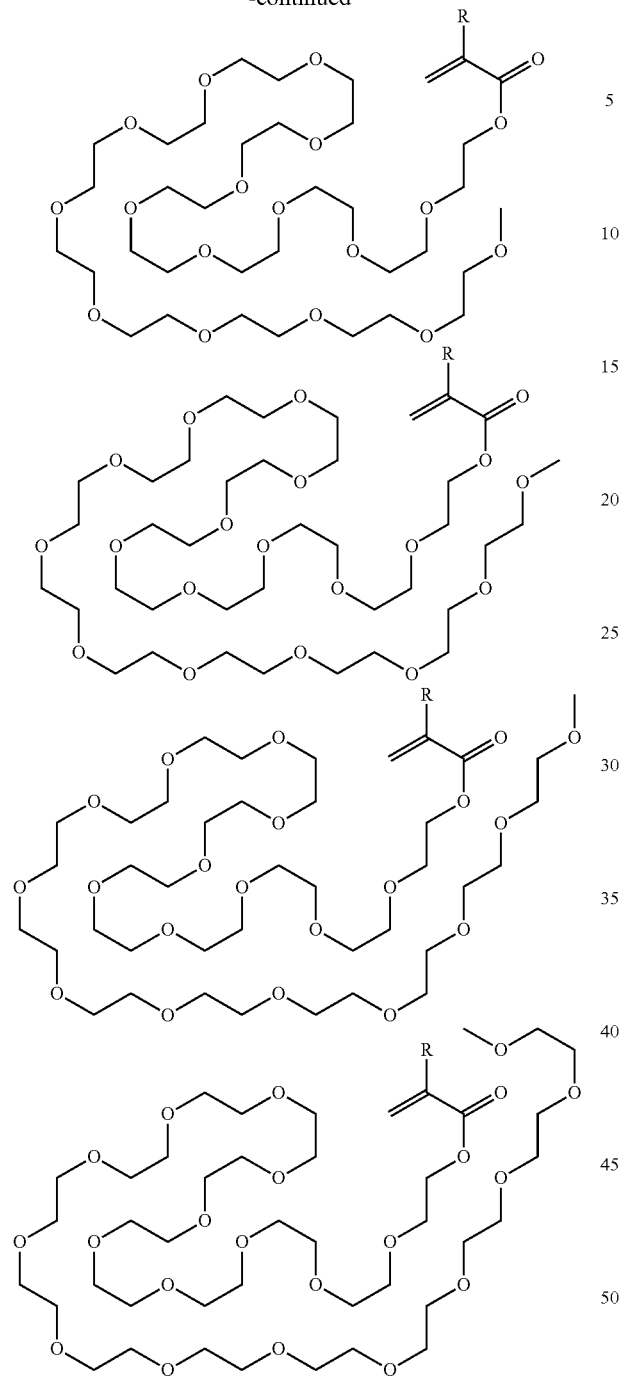

In the formulae, R represents a hydrogen atom or a methyl group.

By bonding an electro-conductive material to be added to the inventive bio-electrode composition and a urethane resin to be the base of the bio-electrode, which will be described later, the electro-conductive material and the urethane resin are integrated, thereby making it possible to prevent elution of the electro-conductive material. The electro-conductive material and the urethane resin can be bonded by the method of copolymerizing repeating unit-e, which has a hydroxy group, an oxirane group, an oxetane group, or an isocyanate group, in the urethane polymer to form the urethane resin in the presence of the electro-conductive material. The mono-mer for obtaining the repeating unit-e having a hydroxy group, an oxirane group, an oxetane group, or an isocyanate group is not particularly limited, and concrete examples thereof include the following.

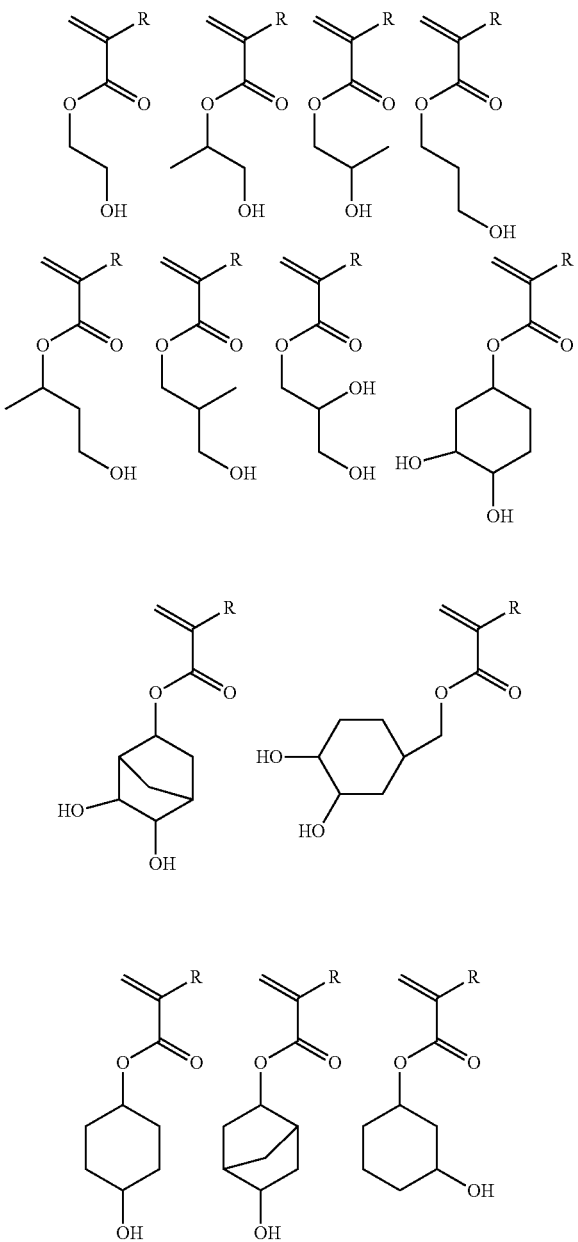

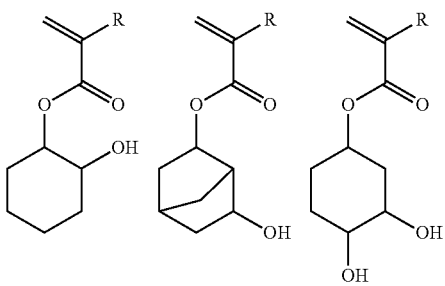

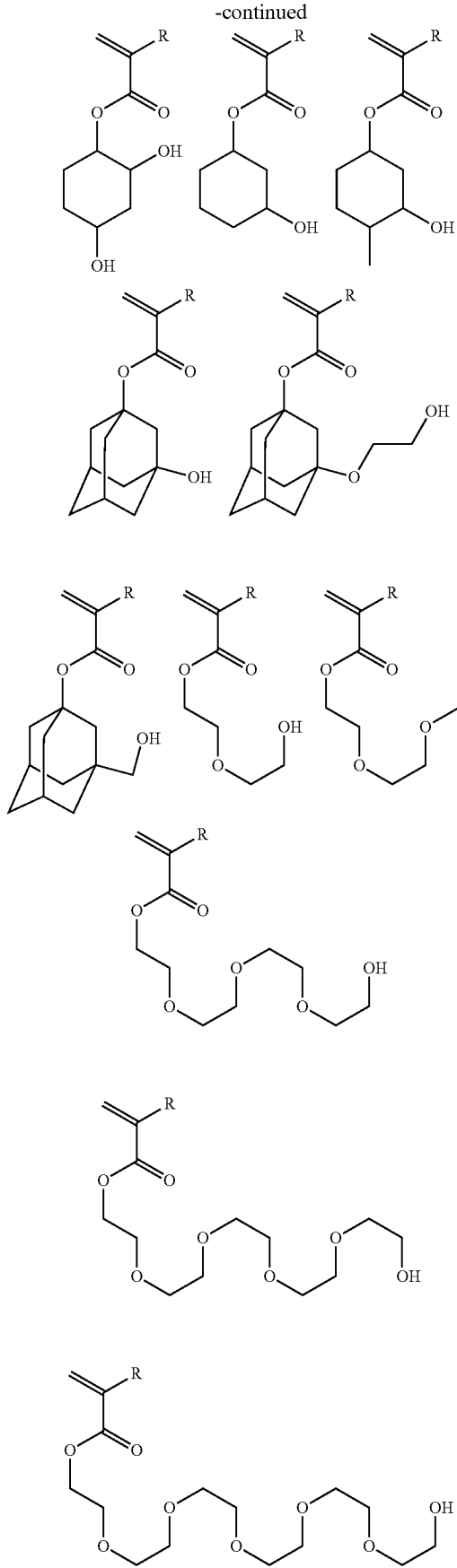
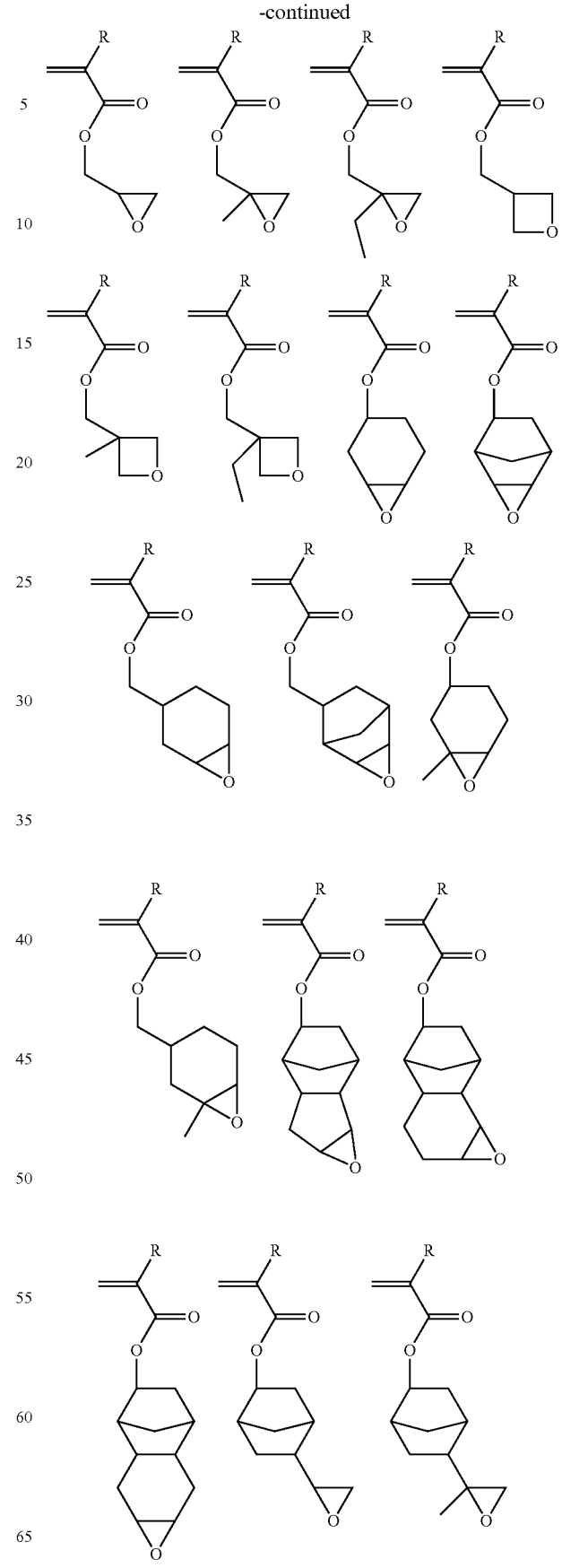

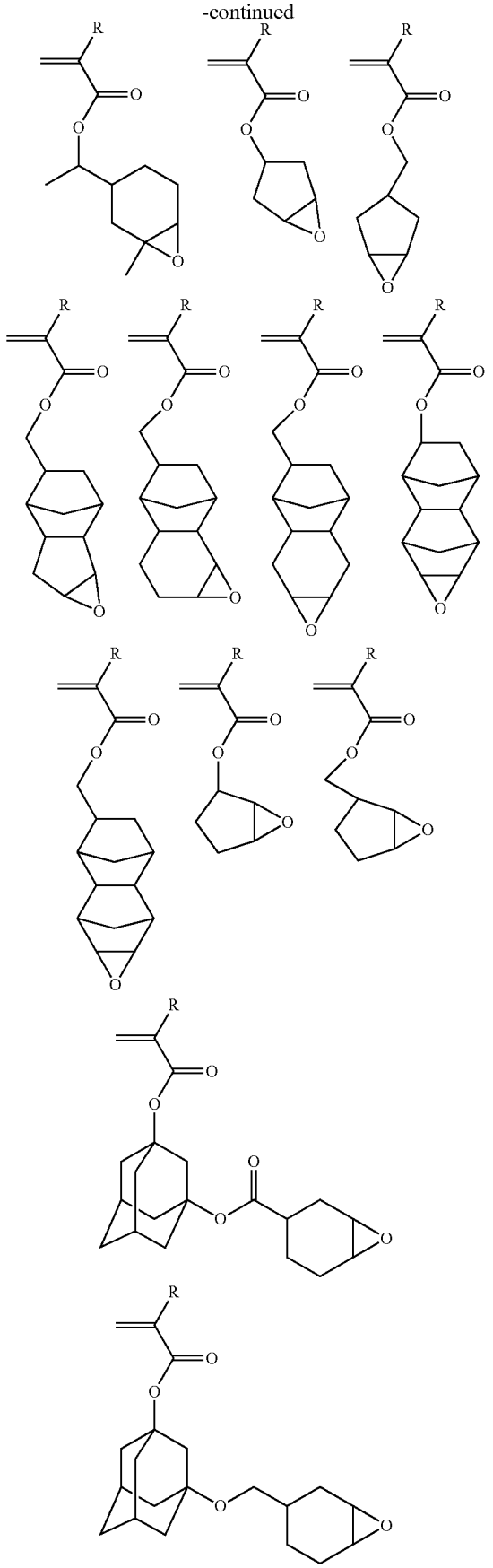
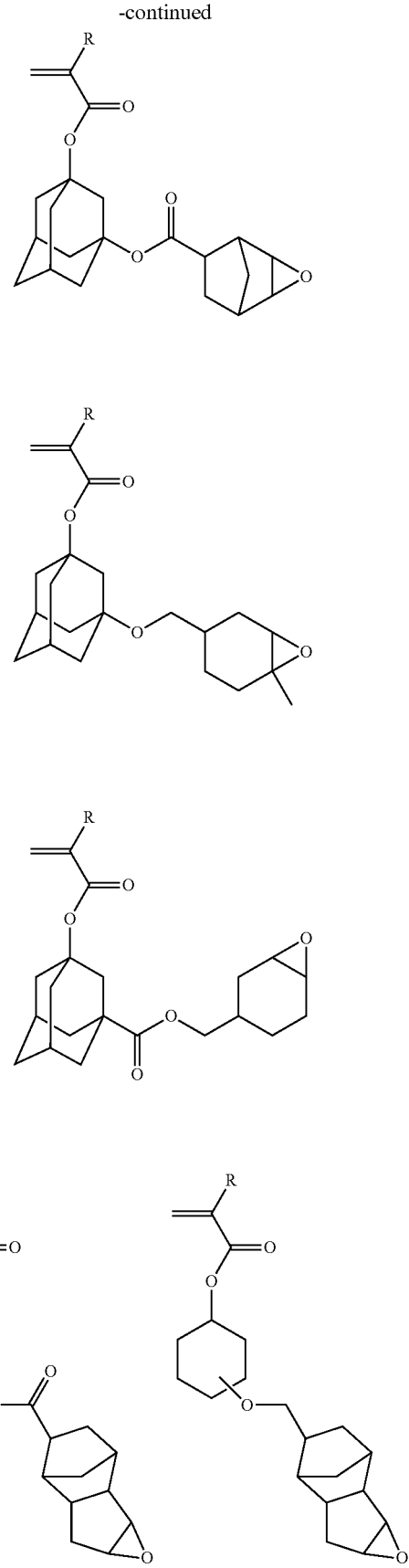

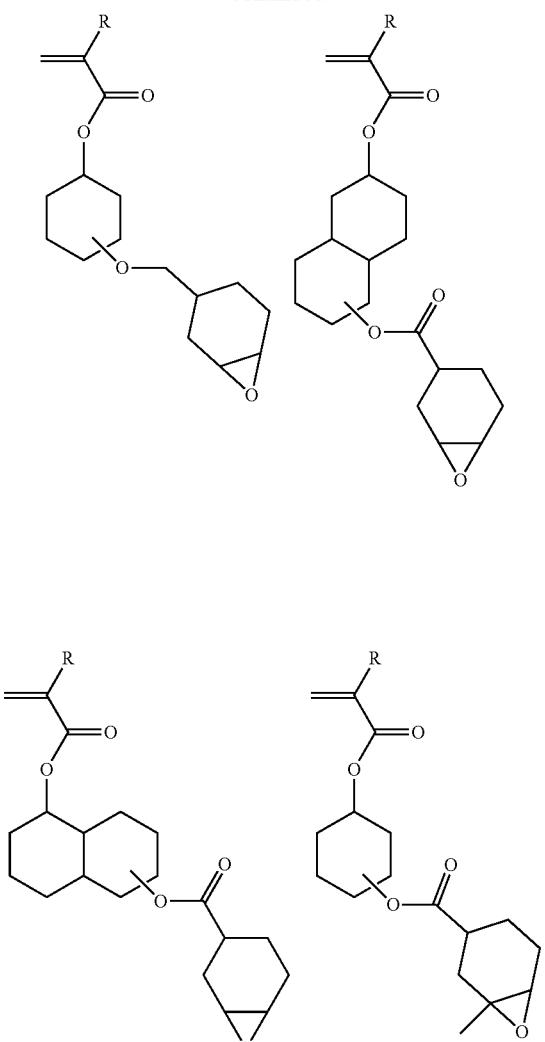
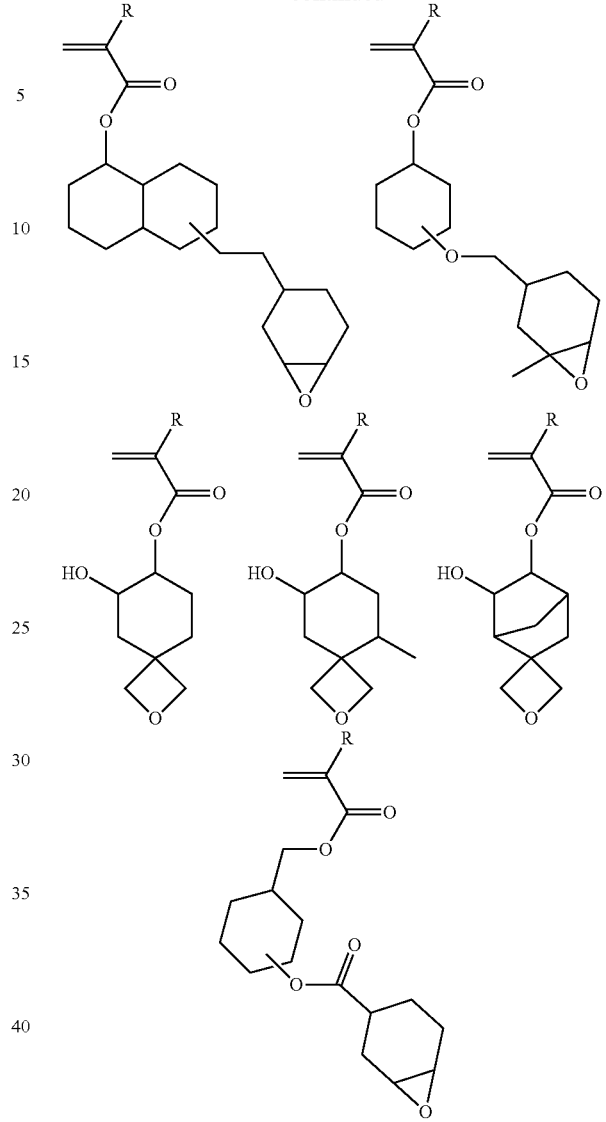
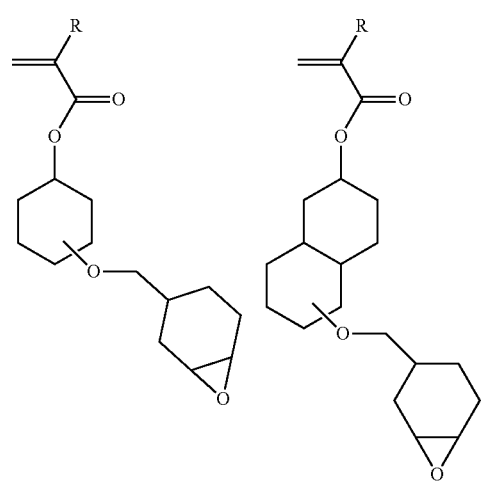

In the formulae, R represents a hydrogen atom or a methyl group.

As the method for synthesizing these polymer compounds to produce the electro-conductive material, heat polymerization can be performed, for example, on a desired monomer that contains one or more repeating units a1 to a7 among the monomers to give the repeating unit a1, a2, a3, a4, a5, a6, a7, "b", "c", "d", or "e" by adding a radical polymerization initiator in an organic solvent to give an electro-conductive material as a polymer compound of copolymer.

As the organic solvent used in the polymerization, toluene, benzene, tetrahydrofuran, diethyl ether, dioxane and so on can be exemplified. Illustrative examples of the polymerization initiator include 2,2'-azobis(isobutyronitrile) (AIBN), 2,2'-azobis(2,4-dimethylvaleronitrile), dimethyl 2,2'-azobis(2-methylpropionate), benzoyl peroxide, and lauroyl peroxide.

The temperature in the heat polymerization is preferably 50 to 80° C. The reaction time is preferably 2 to 100 hours, more preferably 5 to 20 hours.

The ratios of the repeating units a1 to a7, "b", "c", "d", and "e" are preferably $0 \leq a1 \leq 1.0$, $0 \leq a2 \leq 1.0$, $0 \leq a3 \leq 1.0$, 0≤a4≤1.0, 0≤a5≤1.0, 0≤a6≤1.0, 0≤a7≤1.0, 0≤a1+a2+a3+a4+a5+a6+a7≤1.0, 0≤b≤1.0, 0≤c≤1.0, 0≤d≤1.0, and 0≤e≤1.0; more preferably 0≤a1≤0.9, 0≤a2≤0.9, 0≤a3≤0.9, 0≤a4≤0.9, 0≤a5≤0.9, 0≤a6≤0.9, 0≤a7≤0.9, 0.1≤a1+a2+a3+a4+a5+a6+a7≤0.9, 0≤b≤0.9, 0≤c≤0.9, 0≤d≤0.8, and 0≤e≤0.5; and further preferably 0≤a1≤0.8, 0≤a2≤0.8, 0≤a3≤0.8, 0≤a4≤0.8, 0≤a5≤0.8, 0≤a6≤0.8, 0≤a7≤0.8, 0.2≤a1+a2+a3+a4+a5+a6+a7≤0.8, 0≤b≤0.8, 0≤c≤0.8, 0≤d≤0.7, and 0≤e≤0.5.

Incidentally, a1+a2+a3+a4+a5+a6+a7+b+c+d+e=1, for example, means that the total amount of repeating units a1 to a7, "b", "c", "d", and "e" is 100 mol % on the basis of the total amount of the whole repeating units in a polymer compound that contains repeating units-a1 to a7, "b", "c", "d", and "e"; and a1+a2+a3+a4+a5+a6+a7+b+c+d+e<1 means that the total amount of repeating units-a1 to a7, "b", "c", "d", and "e" is less than 100 mol % on the basis of the total amount of the whole repeating units, and another repeating unit(s) is contained other than the repeating units a1 to a7, "b", "c", "d", and "e".

The molecular weight of the polymer, as a weight average molecular weight, is preferably 500 or more, more preferably in a range of 1000 or more and 1000000 or less, further preferably in a range of 2000 or more and 500000 or less. The presence of a large amount of residual monomer, which is not incorporated into the polymer after polymerization of ionic monomers, can permeate to skin in a biocompatibility test to cause allergy. Accordingly, the amount of residual monomer have to be decreased. The amount of residual monomer is preferably 10 parts by mass or less when the total polymer is 100 parts by mass.

The amount of the ionic polymer blended as an electro-conductive material is preferably in a range of 0.1 to 300 parts by mass, more preferably 1 to 200 parts by mass on the basis of 100 parts by mass of the urethane resin. The ionic polymer blended as an electro-conductive material may be used singly or in admixture of two or more kinds.

As a method for synthesizing the salt shown by a1 to a7 in the formulae (2) when X is a cation having an ammonium structure shown by the formula (1)-5, the method described in JP 2010-113209A can be exemplified, for example. More specifically, it can be obtained by a method in which sodium fluorosulfonate containing the fluorosulfonate anion is mixed with quarternary ammonium chloride containing a cation having one or two quarternary ammonium cation structure described above in an organic solvent, for example. In this case, it is preferable to remove sodium chloride that is formed as a bi-product by washing with water.

[Resin Containing Main Chain Having Urethane Bond and Two Side Chains Each Having Silicon-Containing Group (Urethane Resin)]

The resin to be blended in the inventive bio-electrode composition is a component to hold the electro-conductive material and a conductivity improver such as carbon to improve the electric conductivity, and have to be soft as well as flexible and stretchable to be in contact with skin in accordance with the motion, and is required to have tackiness in some cases. As such a material, a resin having a urethane bond in the main chain and a silicon-containing group in each of the two side chains is used. Among them, a resin based on urethane gel (urethane gel composition) is preferably used. In order to exhibit the functions as a bio-electrode without being affected by water, repellency is also necessary. Accordingly, silicone-urethane gel is preferably used.

The urethane gel composition is exemplified by the one that can be obtained by mixing a hydroxy compound and an isocyanate compound, for example, and by adding a catalyst to promote the reaction in some cases. The urethane gel with lower hardness can be obtained by reducing the crosslinking density or totally inhibiting the crosslinking. Accordingly, it is preferable to avoid addition of a cross-linkable hydroxy group-containing compound that has three or more of hydroxy groups in one molecule as possible or to reduce the amount.

The method for forming urethane gel can be exemplified by a one shot method of mixing a hydroxy compound, an isocyanate compound, a diol compound shown by the formula (5), and an ionic polymer, followed by curing thereof by heating, etc. The one shot method has an advantage of higher productivity, but sometimes lowers the strength or stretchability due to remaining of unreacted hydroxy groups or isocyanate groups.

It is also possible to exemplify a prepolymer method in which a hydroxy compound and an isocyanate compound are previously mixed, and then a hydroxy compound, an isocyanate compound, a diol compound shown by the formula (5), and an ionic polymer are additionally mixed, followed by curing. In this case, the hydroxy groups and the isocyanate groups have sufficiently reacted, and there is a feature of lower ratio of residual isocyanate groups. When the prepolymer is prepared, the diol compound shown by the formula (5) can also be mixed not only the hydroxy compound and the isocyanate compound. In case of preparing the prepolymer, it is preferable that excess isocyanate groups has been mixed to make the terminals of prepolymer be isocyanate.

The urethane resin contained in the inventive bio-electrode composition preferably has a urethane bond in the main chain and two silicon-containing groups in the side chains branched from a carbon atom of the main chain shown by the following formula (3). This makes it possible to improve the repellency. Although urethane resin in which silicone is incorporated into the main chain lowers the strength of the film, urethane structure which has pendant silicon-containing groups entails less lowering of the strength and is usable for a bio-electrode composition favorably.

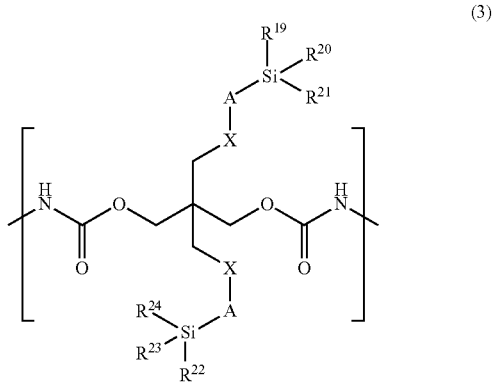

(3)

In the formula, $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —$(OSiR^{25}R^{26})_n$—$OSiR^{27}R^{28}R^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; and X represents a methylene group or an ether group.

The resin having a urethane bond in the main chain and two silicon-containing groups in the side chains branched from a carbon atom of the main chain is preferably a resin that has a structure containing a polyether main chain shown by the following formula (4). The polyurethane having a polyether main chain makes it possible to form a flexible living body electrode film and to improve the ionic conductivity.

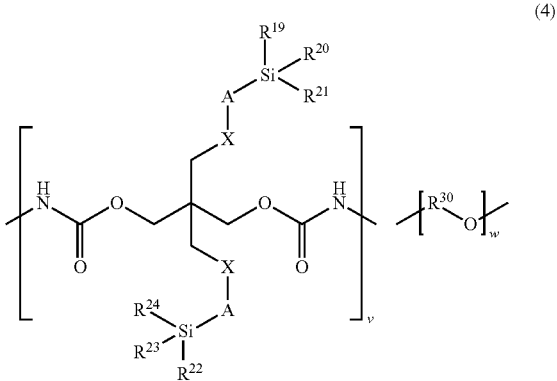

(4)

In the formula, $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —(OSiR$^{25}$R$^{26}$)$_n$—OSiR$^{27}$R$^{28}$R$^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; X represents a methylene group or an ether group; $R^{30}$ represent a linear, branched, or cyclic alkylene group having 2 to 12 carbon atoms; and "v" and "w" satisfy 0<v<1.0, 0<w<1.0, and 0<v+w≤1.0.

It is further preferable that the resin having a urethane bond in the main chain and two silicon-containing groups in the side chains branched from a carbon atom of the main chain is a reaction product of a diol compound shown by the following formula (5), a polyether compound having a hydroxy group(s) at the terminal, and a compound having an isocyanate group(s).

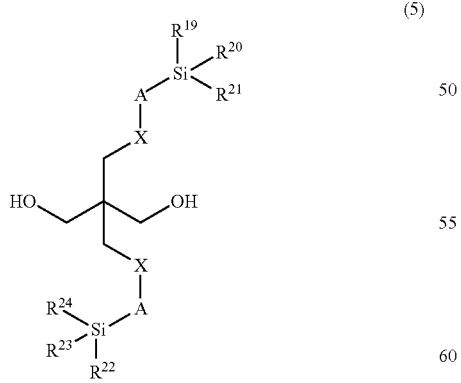

(5)

In the formula, $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —(OSiR$^{25}$R$^{26}$)$_n$—OSiR$^{27}$R$^{28}$R$^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; and X represents a methylene group or an ether group.

The diol compound having pendant silicon-containing groups shown by the following formula (5) can be obtained by reaction of a dihydroxydialkenyl compound and a short-chain silicon-containing compound having a SiH group(s) in the presence of a platinum catalyst, for example.

The diol compound shown by the formula (5) is not particularly limited, and concrete examples thereof include the following.

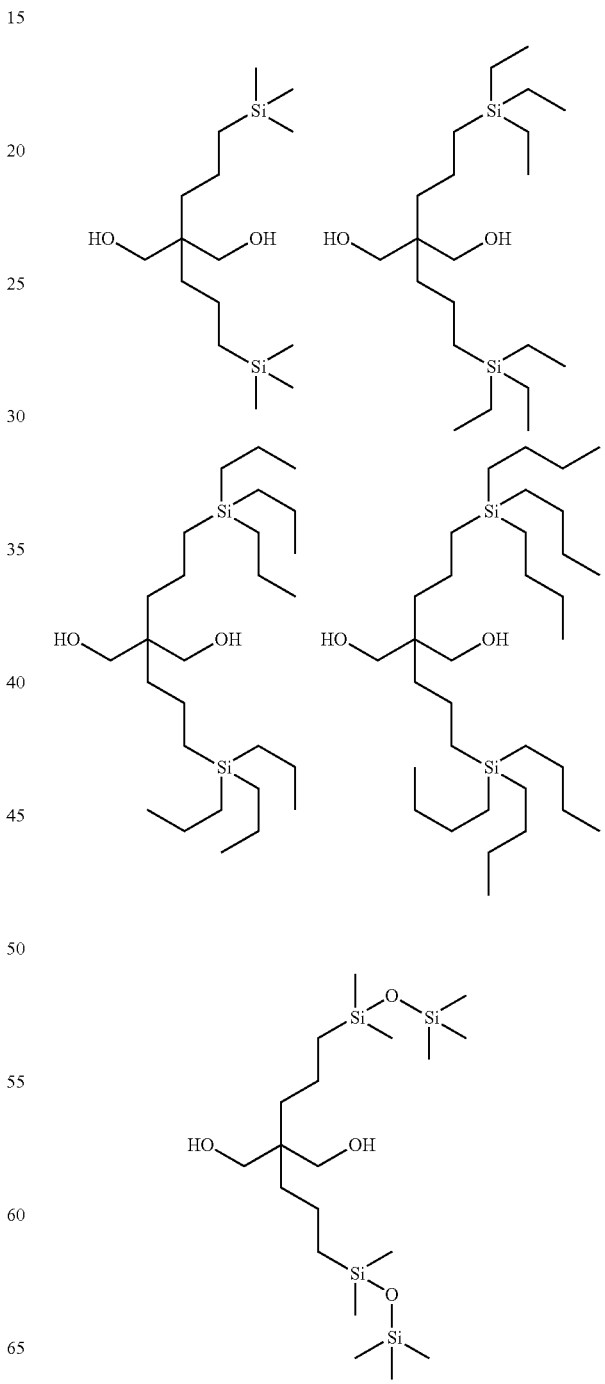

-continued
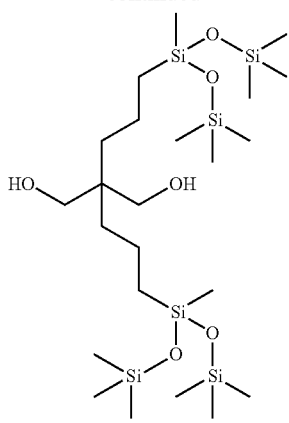
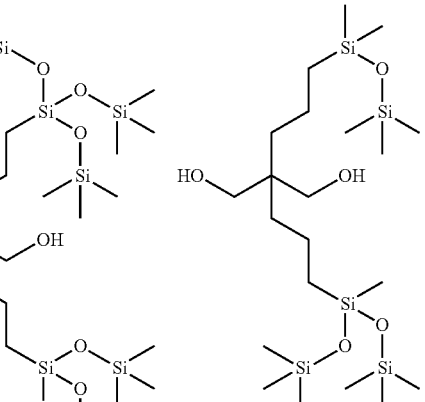
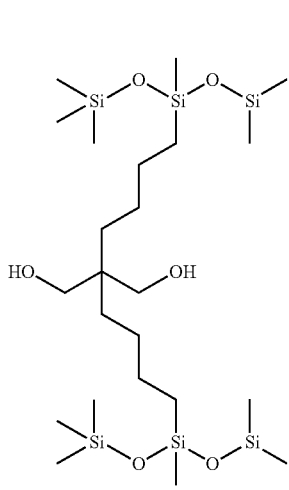
-continued
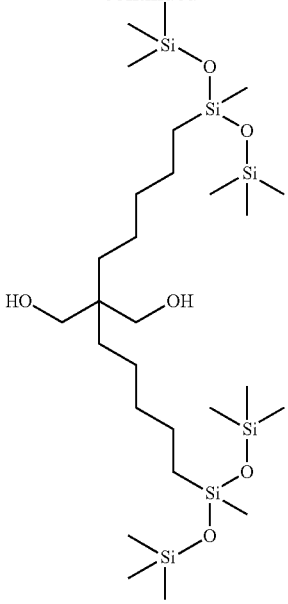
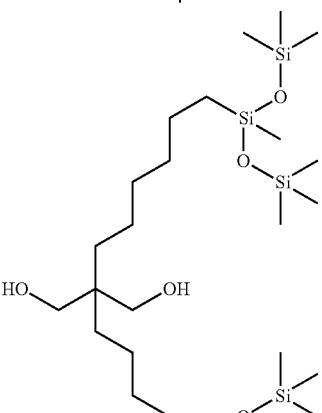

151
-continued
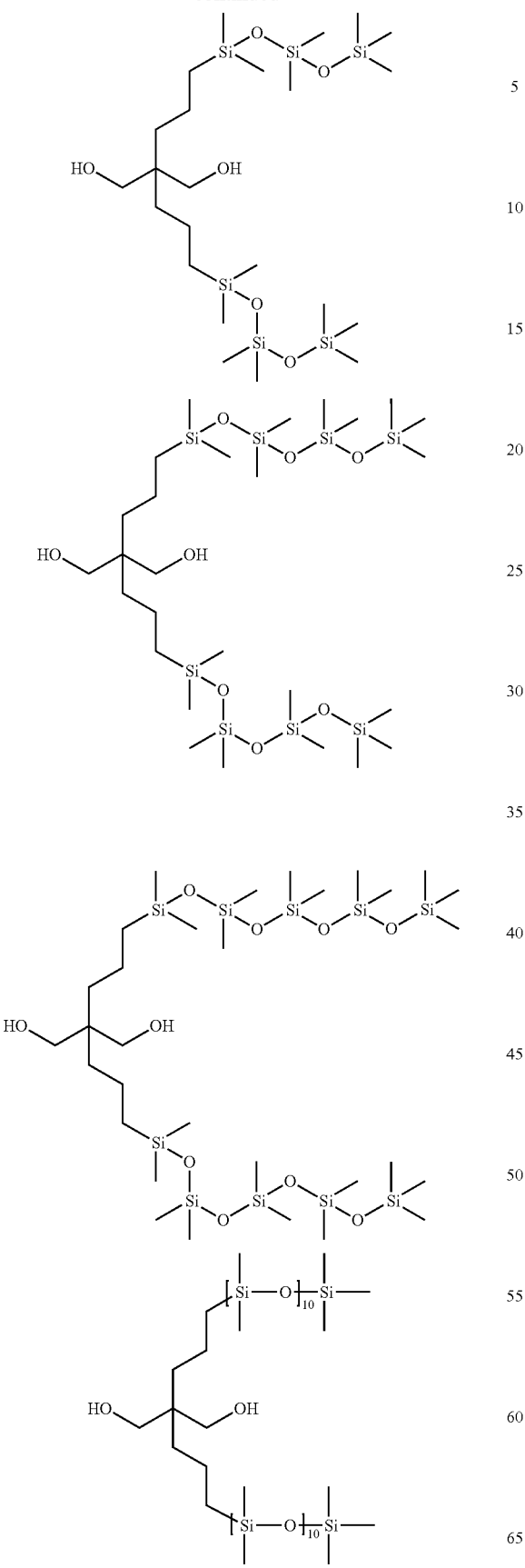
152
-continued
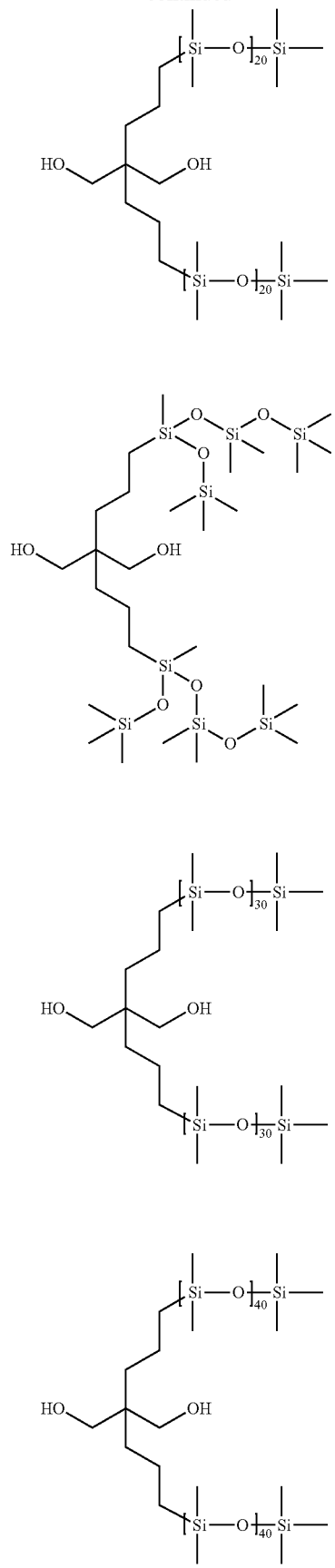

153
-continued
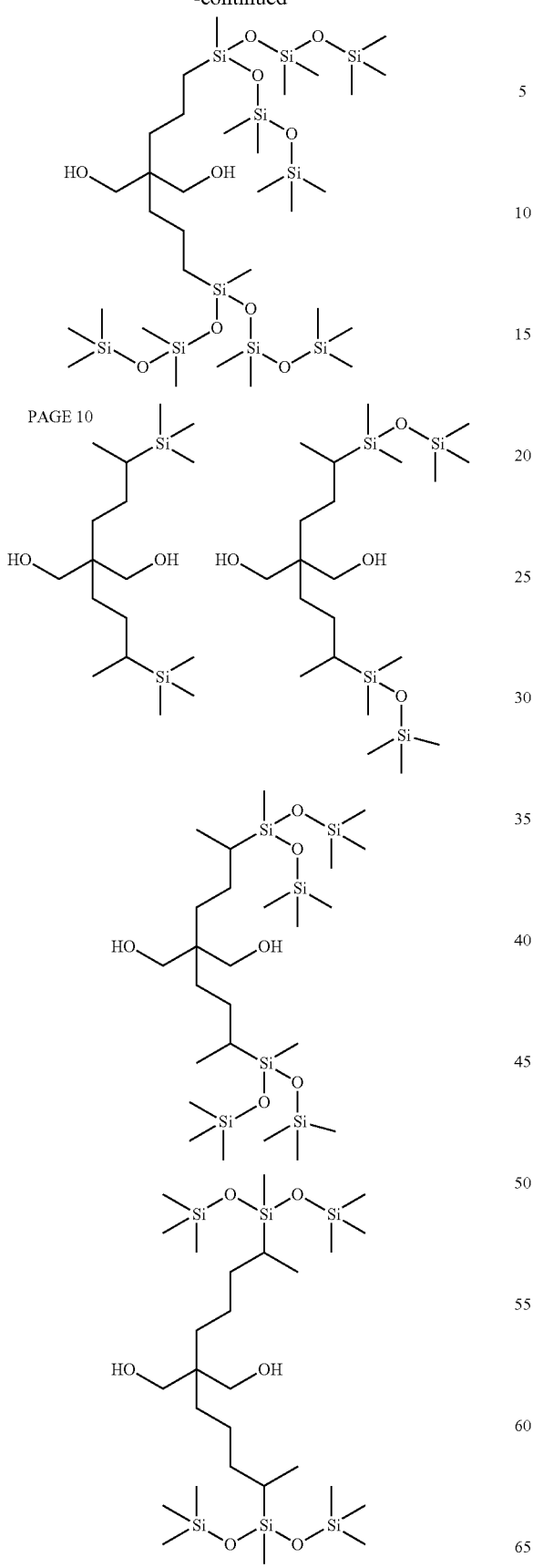
154
-continued
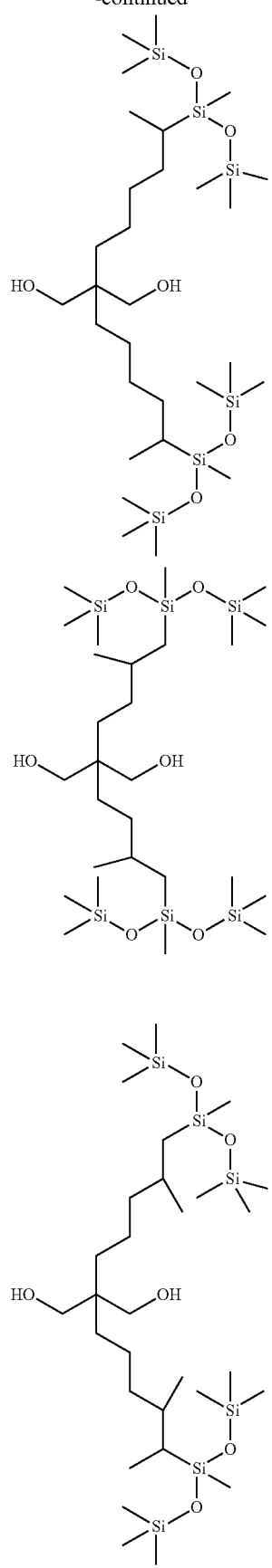

155
-continued
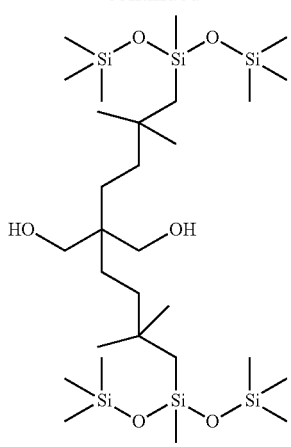
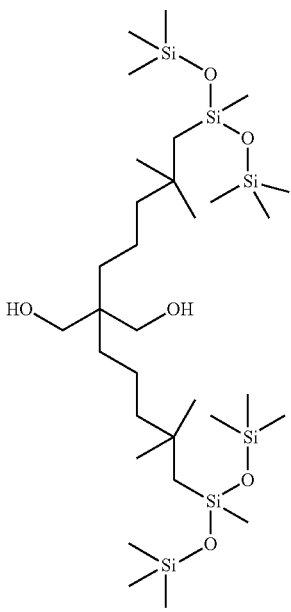
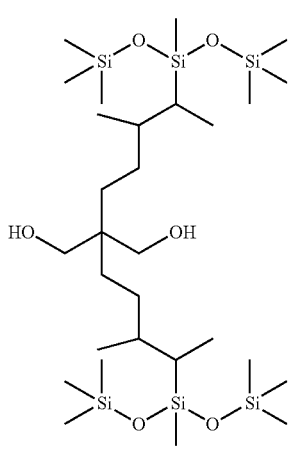
156
-continued
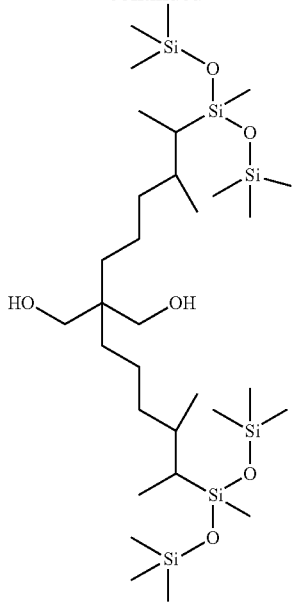
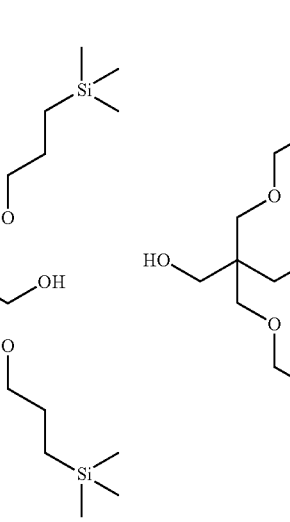
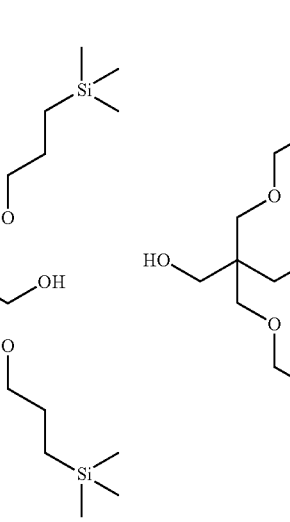
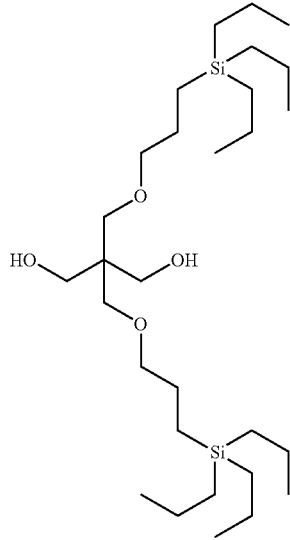

157
-continued
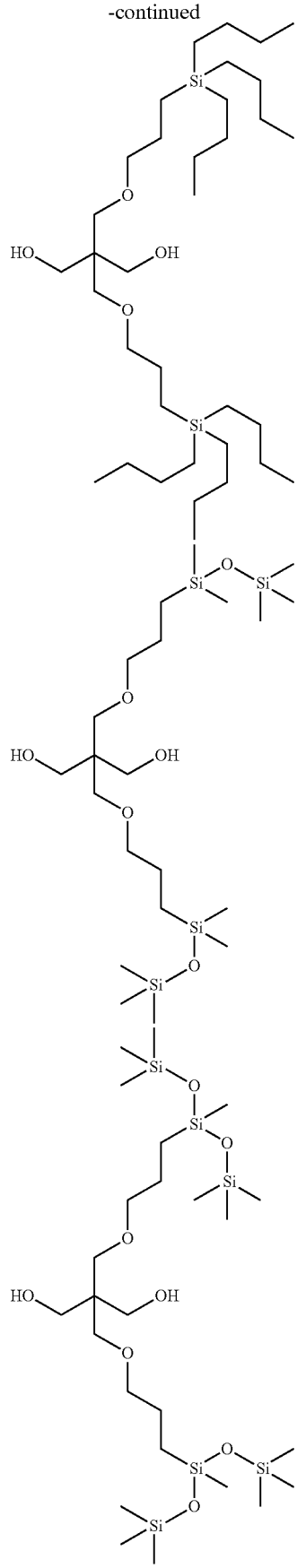
158
-continued

159
-continued
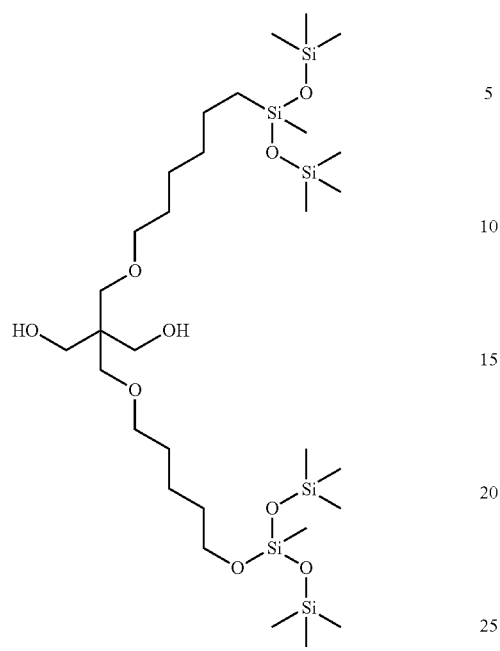
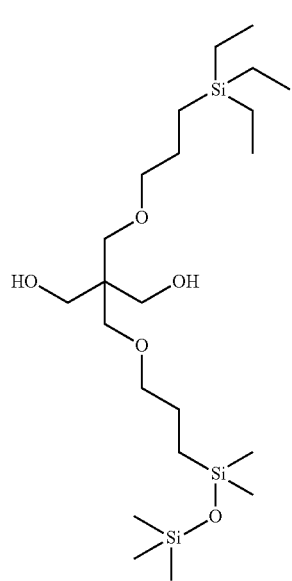
160
-continued
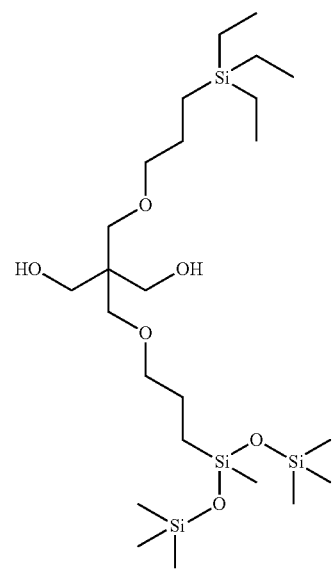
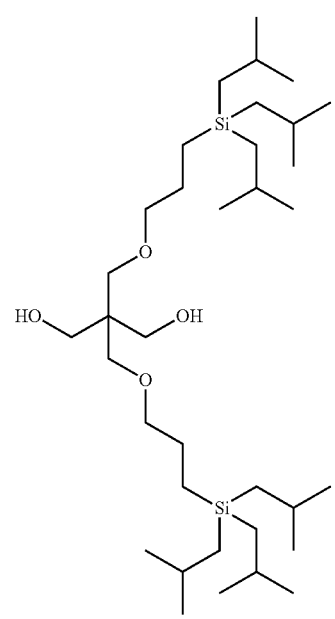

161
-continued
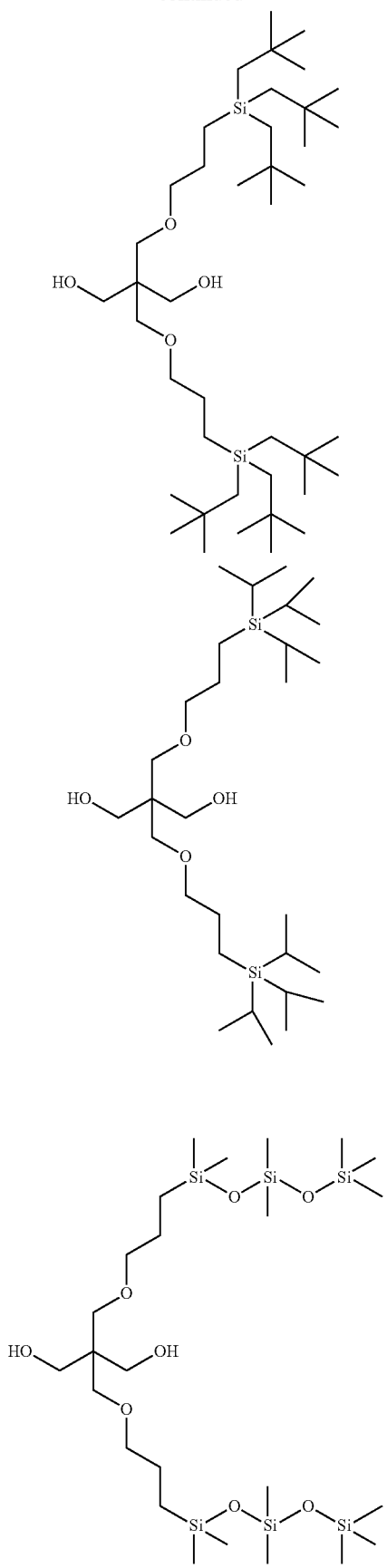
162
-continued
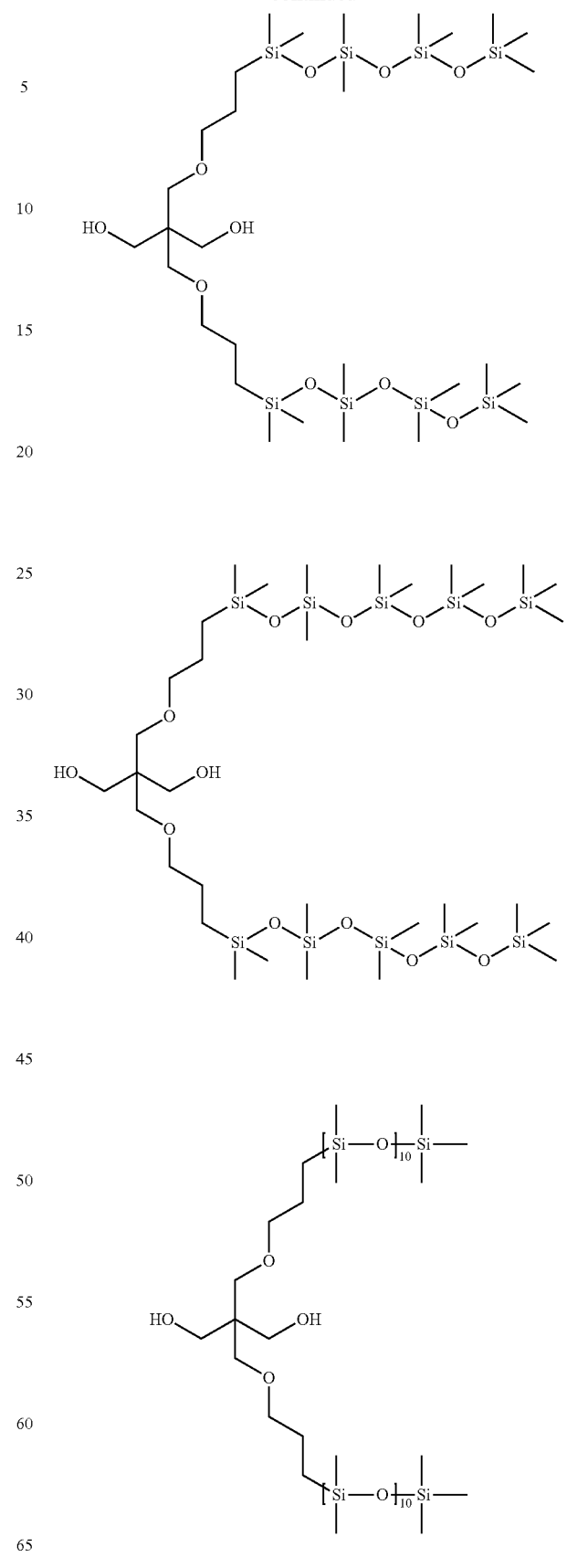

163
-continued
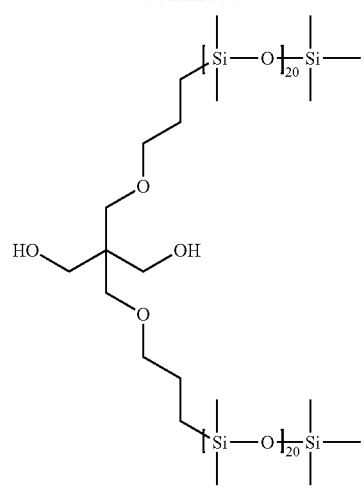
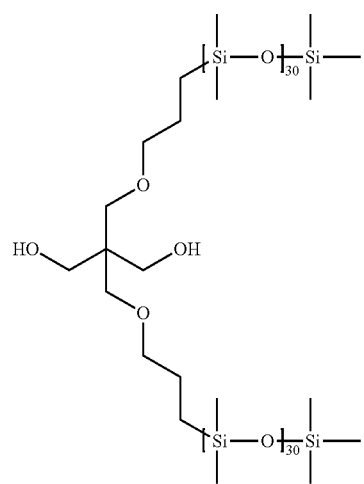
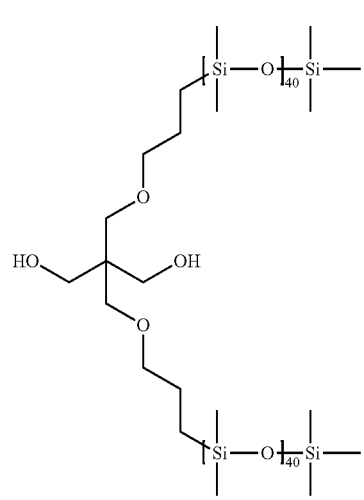
164
-continued
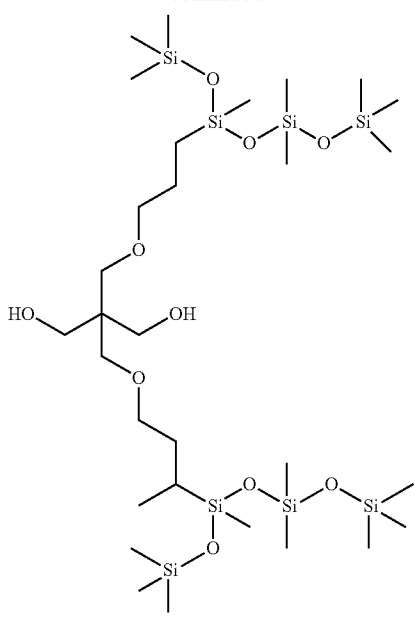
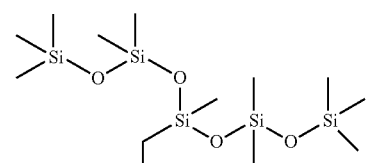

165
-continued
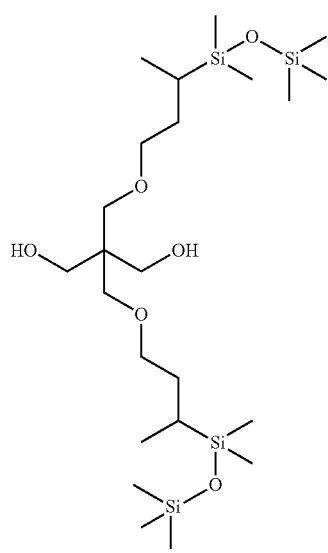
166
-continued
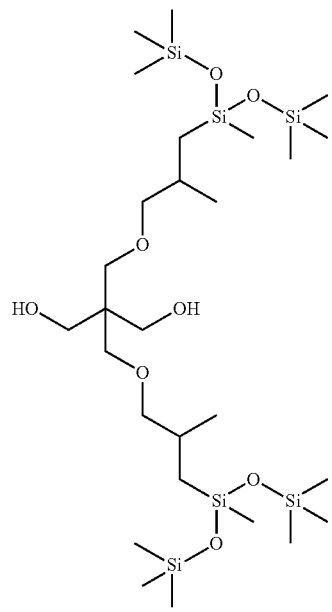
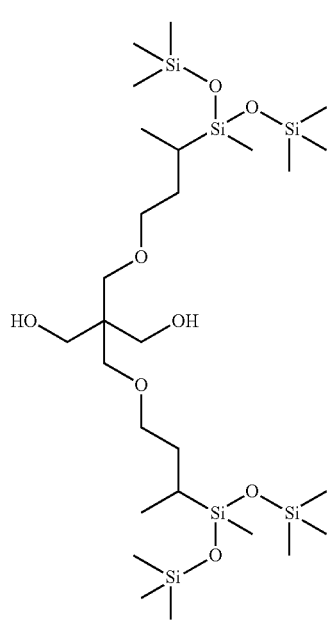
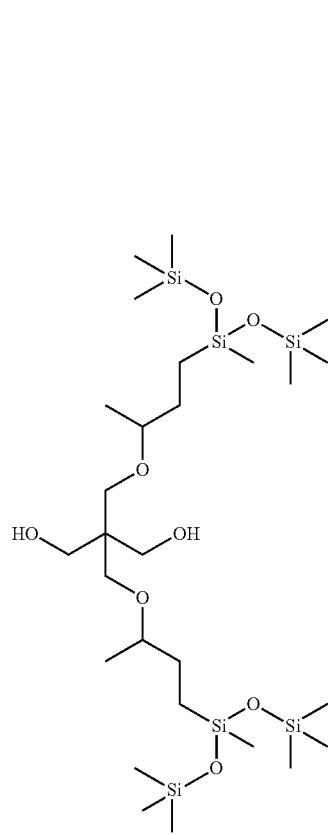

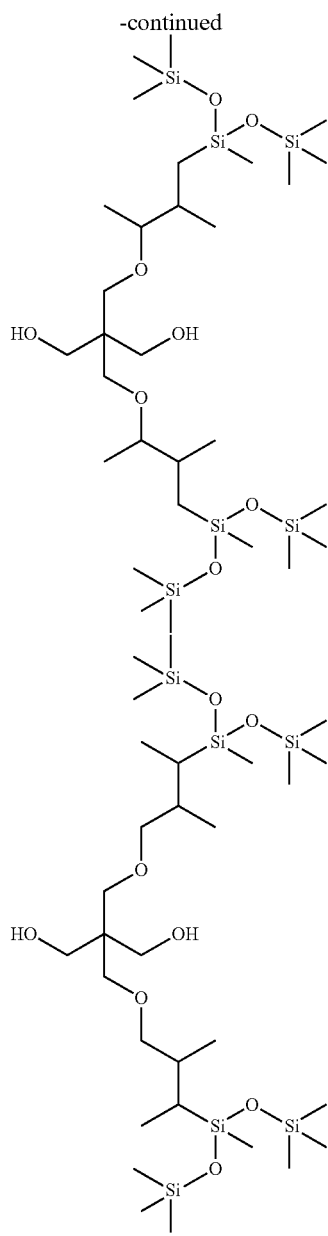

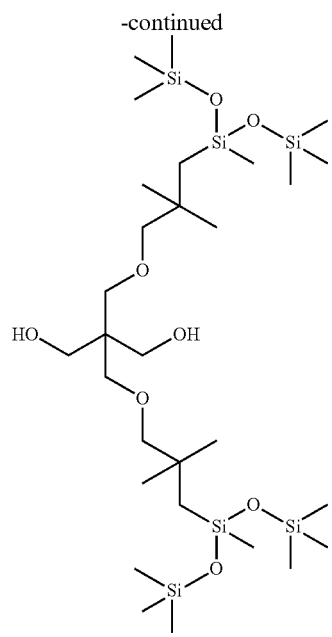

In the formulae, each number of repeating unit shows the average value.

The diol compound preferably has 1 to 20 silicon atoms in one side chain. When the number of silicon atoms is in this range, the stretchable film has improved strength. Additionally, the short-chain silicon-containing group with 1 to 20 silicon atoms is sufficient for improving the repellency.

In producing the urethane resin contained in the inventive bio-electrode composition, it is preferable to add a compound that has plurality of hydroxy groups (hydroxy compound) in addition to the diol compound described above for extending the chain length or crosslinking. The hydroxy compound preferably has a polyether structure.

The hydroxy compound is not particularly limited, and concrete examples thereof include the following.

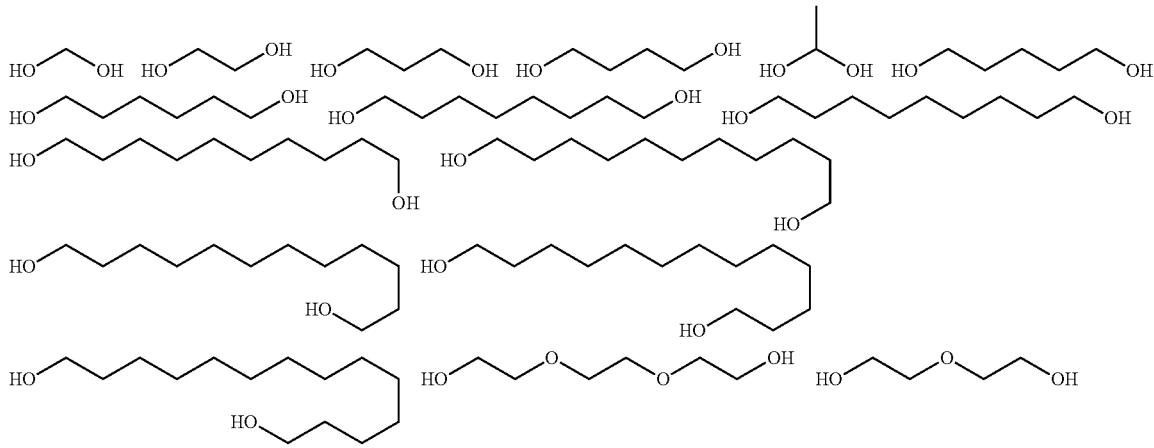

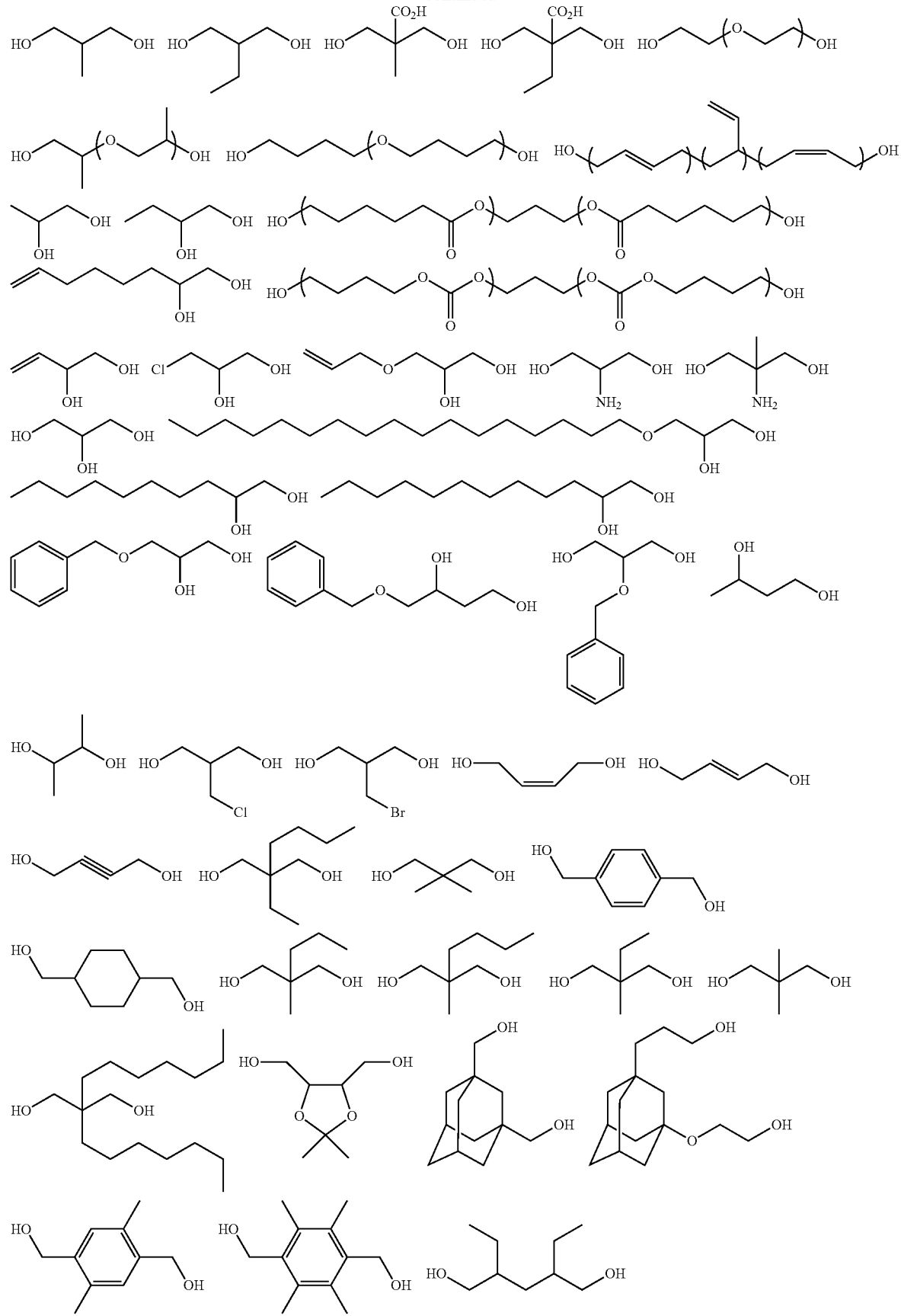

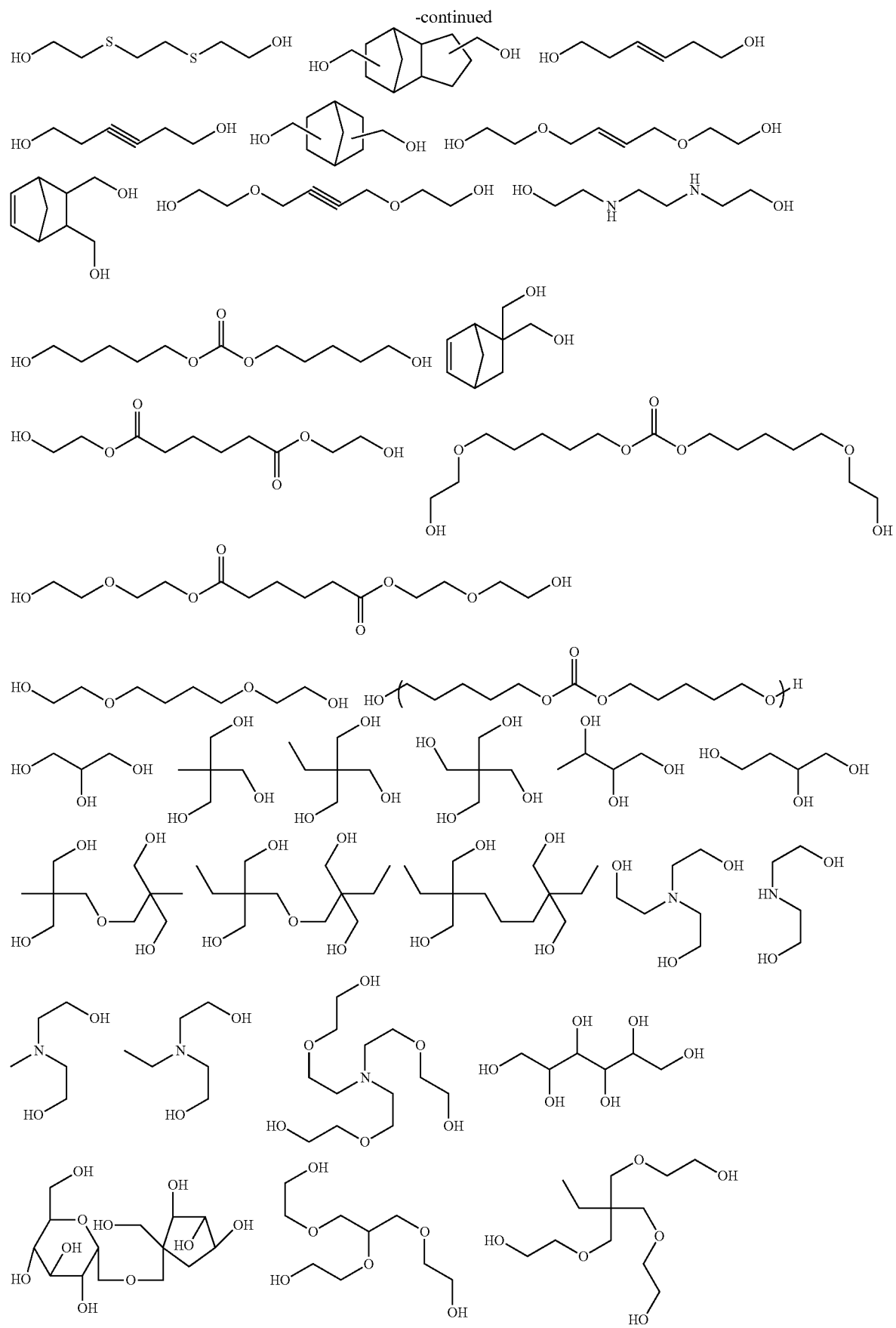

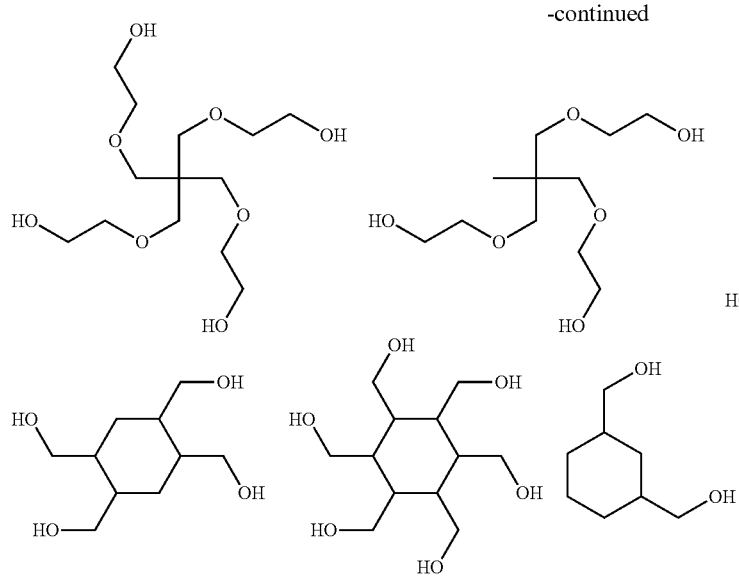
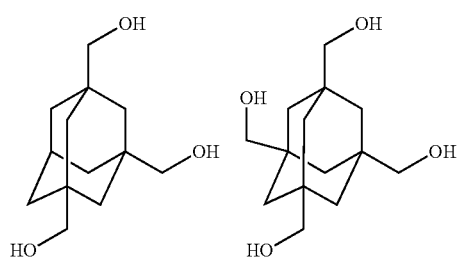
By mixing a hydroxy compound and an isocyanate compound, urethane bonds are formed to promote the reaction for curing, thereby forming a urethane resin.
The isocyanate compound to be used for the reaction with a hydroxy compound is not particularly limited, and concrete examples thereof include the following.
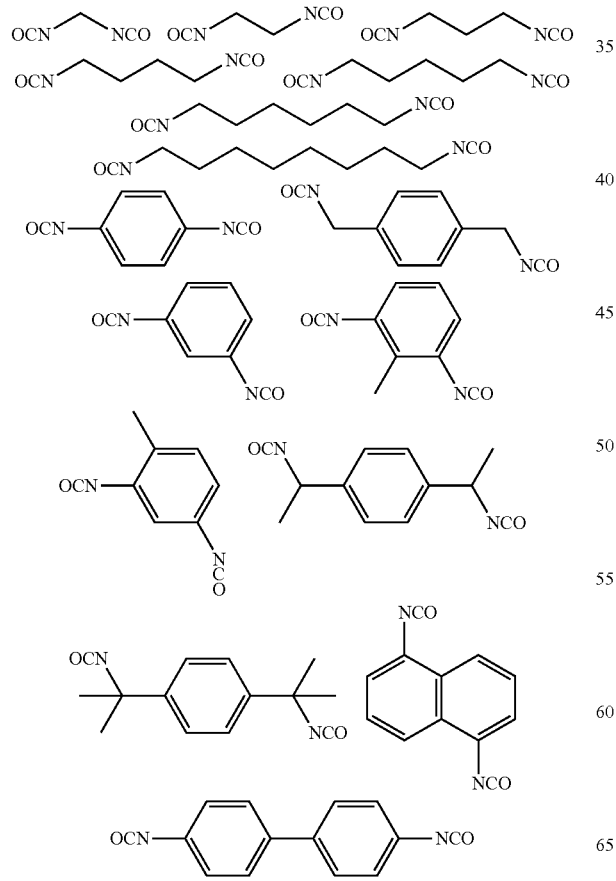
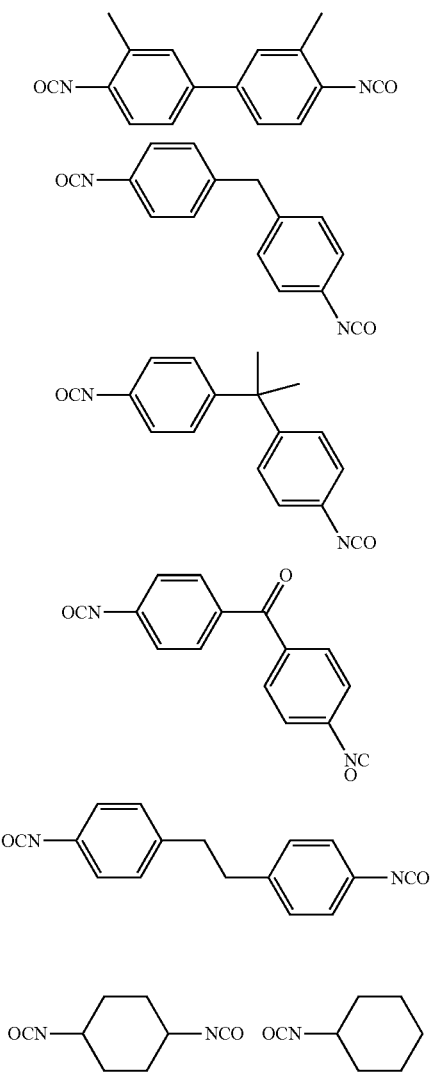

175
-continued
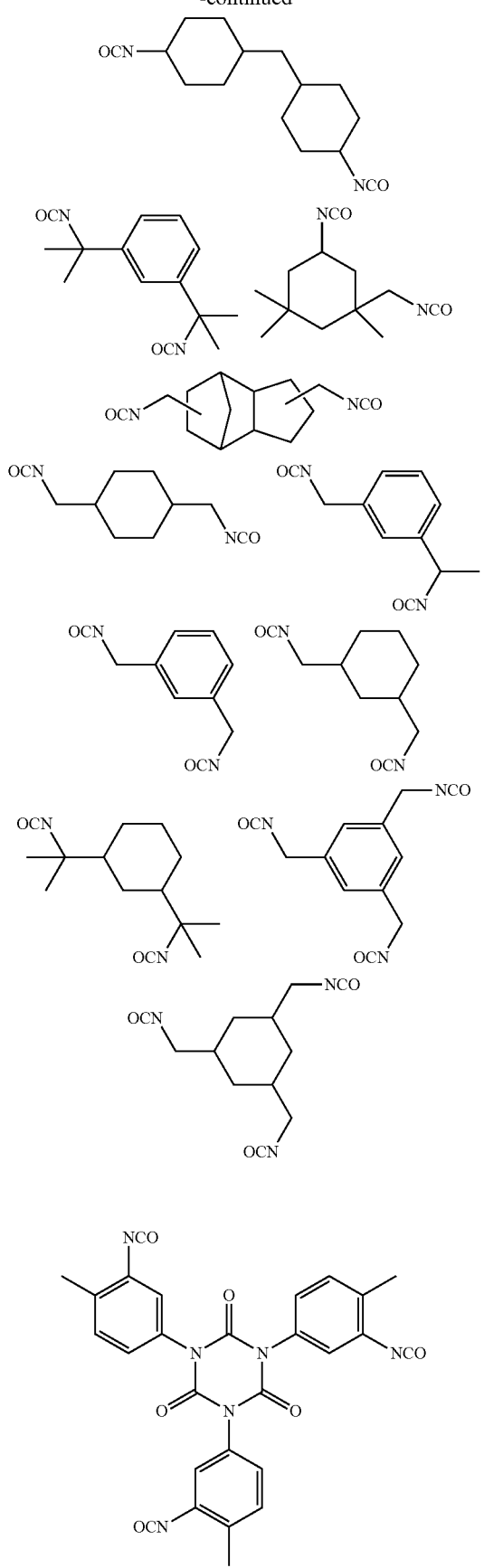
176
-continued
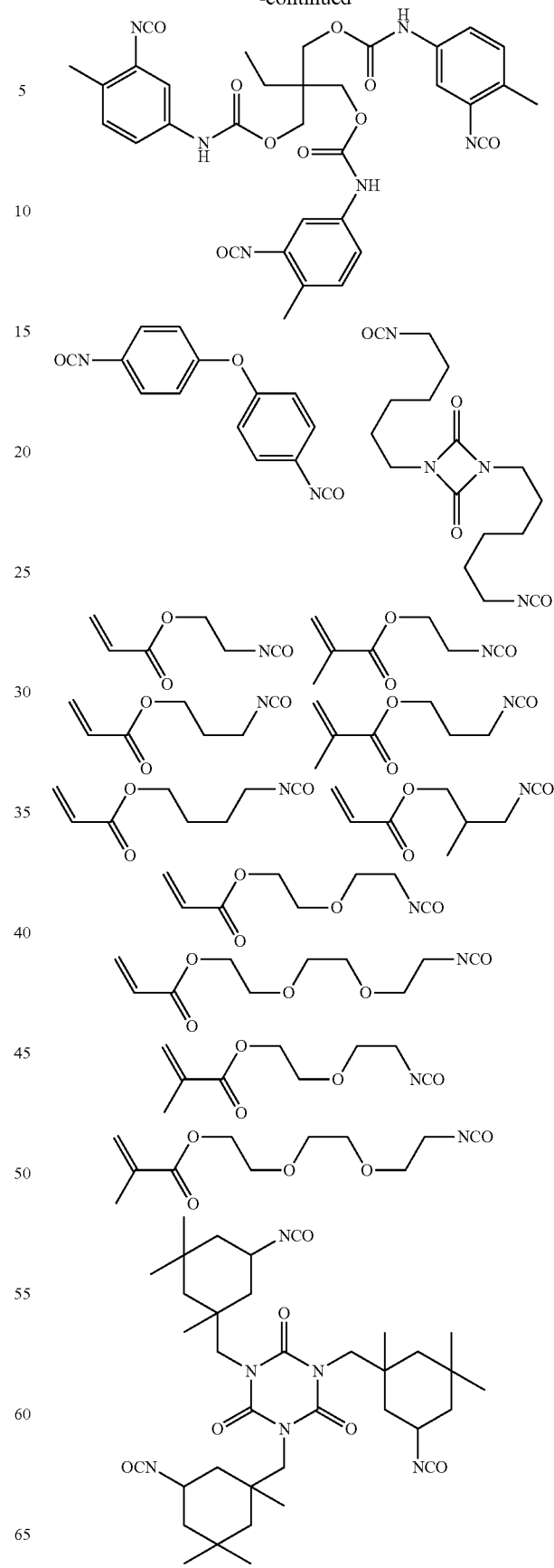

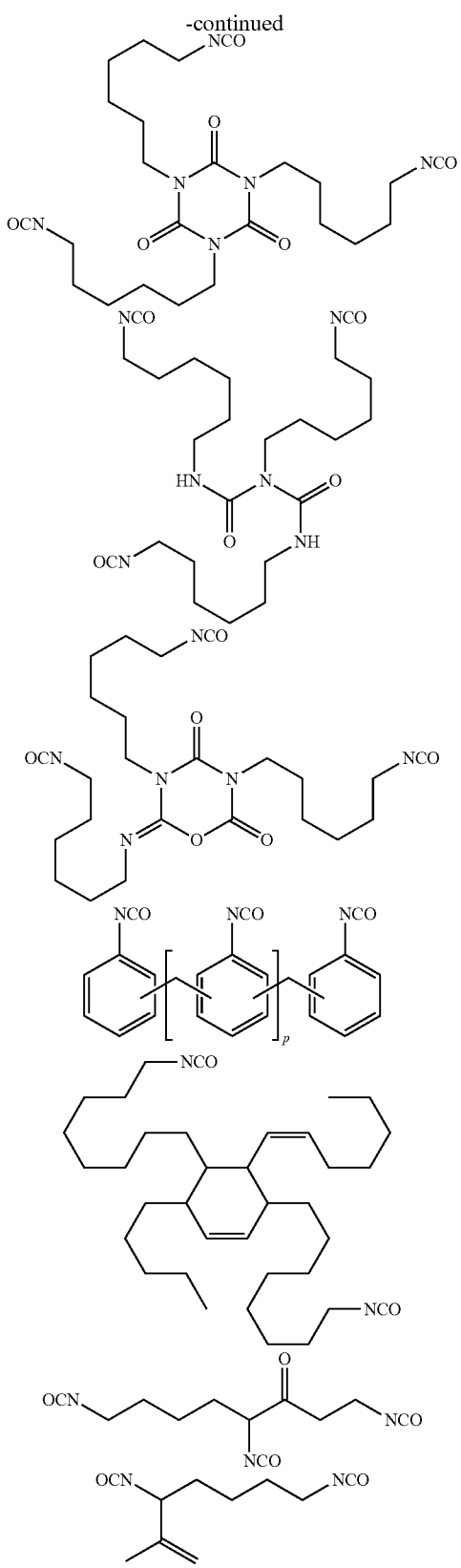

In the formulae, "p" is an integer of 1 or more.

As the isocyanate compound, it is preferable to use a compound having a blocked isocyanate group in which the isocyanate group is protected by a substituent. This facilitates to control the reaction even when the reactivity with the hydroxy group-containing compound is high. The isocyanate compound sometimes reacts with moisture in the air during the storage to cause inactivation of the isocyanate group, and requires full attention such as fully preventing moisture for the storage. In the compound having a blocked isocyanate group, however, these phenomena can be prevented.

The blocked isocyanate group is deprotected by heating to be an isocyanate group. Illustrative examples thereof include isocyanate groups substituted with alcohol, phenol, thioalcohol, imine, ketimine, amine, lactam, pyrazol, oxime, and 3-diketone.

In using a blocked isocyanate compound, a catalyst can be added to decrease the temperature for deprotecting the blocked isocyanate group. This catalyst is not particularly limited, and known examples thereof include organic tin compounds such as dibutyl tin dilaurate, bismuth salts, and zinc carboxylate such as zinc 2-ethylhexanoate and zinc acetate.

It is preferable to use zinc α,β-unsaturated carboxylate as a catalyst for dissociation of blocked isocyanate as described in JP 2012-152725A.

In the synthesis of urethane resin contained in the inventive bio-electrode composition, it is also possible to add a compound that has an amino group(s). Reaction of an isocyanate group and an amino group forms a urea bond. The moieties of urethane bond and urea bond are called hard segments, and their hydrogen bonds improve the strength. It is possible to improve the strength by introducing a urea bond(s) in addition to the urethane bond(s) not only the urethane bond(s) alone.

[Organic Solvent]

The inventive bio-electrode composition may contain organic solvent. The organic solvent is not particularly limited, and illustrative examples thereof include aromatic hydrocarbon solvent such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, 3,9-dodecadiyne, pentamethylbenzene, hexamethylbenzene, hexylbenzene, and 1,3,5-triethylbenzene; aliphatic hydrocarbon solvent such as n-heptane, isoheptane, 3-methylhexane, 2,3-dimethylpentane, 3-ethylpentane, 1,6-heptadiene, 5-methyl-1-hexyn, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-methylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, isoparaffin; ketone solvent such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvent such as 3-methoxybutanol, 3-methyl-3-methoxybutanol, 1-methoxy-2-propanol, and 1-ethoxy-2-propanol; ether solvent such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methyl cylopentyl ether, methyl cyclohexyl ether, di-n-butyl ether, di-sec-butyl ether, di-sec-pentyl ether, di-tert-amyl ether, di-n-hexyl ether, and anisole; ester solvent such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate; lactone solvent such as γ-butyrolactone.

The amount of organic solvent is preferably in a range of 10 to 50,000 parts by mass on the basis of 100 parts by mass of the resin.

[Carbon Material]

The inventive bio-electrode composition can contain a carbon material as an electric conductivity improver to further enhance the electric conductivity. The carbon material may be exemplified by carbon black and carbon nanotube, and is preferably either or both of them. The carbon nanotube may be either single layer or multilayer, and the surface may be modified with an organic group(s). The amount of carbon material is preferably in a range of 1 to 50 parts by mass on the basis of 100 parts by mass of the resin.

[Electric Conductivity Improver Other than Carbon Material]

The inventive bio-electrode composition also can contain an electric conductivity improver other than the carbon material. Illustrative examples thereof include particles of resin coated with noble metal such as gold, silver, and platinum; nanoparticles of gold, silver, and platinum; particles of metal oxide such as indium-tin oxide (ITO), indium-zinc oxide (IZO), tin oxide, and zinc oxide; as well as silver nanowire.

As described above, the inventive bio-electrode composition makes it possible to form a living body contact layer for a bio-electrode that is capable of conducting electric signals efficiently from skin to a device (i.e., excellent in electric conductivity), free from the risk of causing allergies even when it is worn on skin for a long time (i.e., excellent in biocompatibility), light in weight, manufacturable at low cost, and free from large lowering of the electric conductivity even when it is wetted with water or dried. It is possible to improve the electric conductivity still more by adding a carbon material, and to manufacture a particularly soft bio-electrode with high stretchability by combining urethane resin with flexibility and stretchability. Furthermore, it is possible to improve the stretchability and tackiness to skin by additives, and to control the stretchability and tackiness by adjusting the composition of the urethane resin and the thickness of the living body contact layer appropriately.

<Bio-Electrode>

The present invention also provides a bio-electrode comprising an electro-conductive base material and a living body contact layer formed on the electro-conductive base material; wherein the living body contact layer is a cured material of the inventive bio-electrode composition described above.

Hereinafter, the inventive bio-electrode will be specifically described by reference to the FIGS., but the present invention is not limited thereto.

FIG. 1 is a schematic sectional view showing an example of the inventive bio-electrode. The bio-electrode 1 of FIG. 1 has the electro-conductive base material 2 and the living body contact layer 3 formed on the electro-conductive base material 2. The living body contact layer 3 is a layer in which the electro-conductive material 4 and the carbon material 5 are dispersed in the urethane resin 6. Provided that, the carbon material 5 is an optional component.

Figure 2:
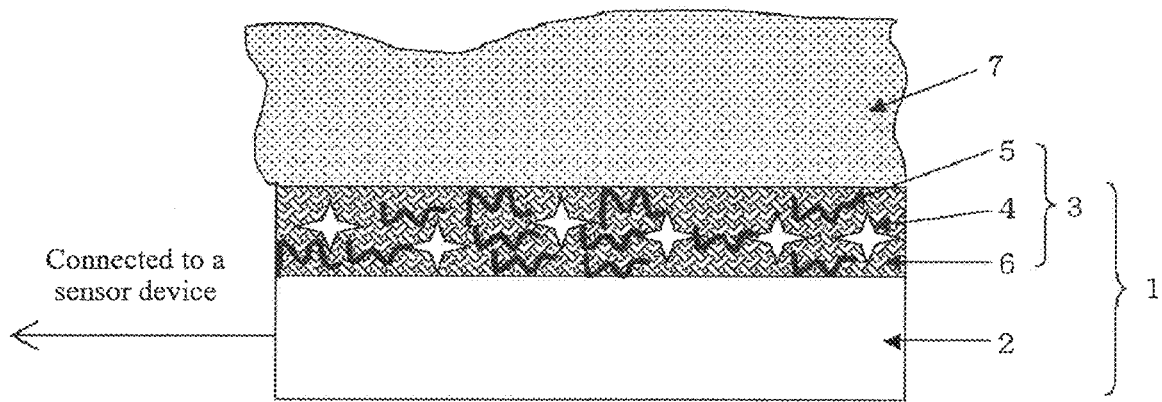
FIG. 2 is a schematic sectional view showing an example of the inventive bio-electrode worn on a living body.

When using the bio-electrode 1 of FIG. 1 like this, electric signals are picked from the living body 7 through the electro-conductive material 4 and the carbon material 5 while bringing the living body contact layer 3 (i.e., the layer in which the electro-conductive material 4 and the carbon material 5 are dispersed in the urethane resin 6) into contact with the living body 7, and then conducted to a sensor device (not shown) through the electro-conductive base material 2 as shown in FIG. 2. As described above, the inventive bio-electrode is capable of coping with both electric conductivity and biocompatibility by using the electro-conductive material described above, improving the electric conductivity further by adding electric conductivity improver such as a carbon material in accordance with needs, and obtaining electric signals from skin stably in high sensitivity because the contact area with skin is kept constant due to the tackiness thereof.

Hereinafter, each component composing the inventive bio-electrode will be more specifically described.

[Electro-Conductive Base Material]

The inventive bio-electrode comprises an electro-conductive base material. This electro-conductive base material is usually connected electrically with a sensor device and so on, and conduct electrical signals picked from a living body through the living body contact layer to the sensor device and so on.

As the electro-conductive base material, any electro-conductive material can be used without being limited to particular ones. However, it is preferable to comprise one or more species selected from gold, silver, silver chloride, platinum, aluminum, magnesium, tin, tungsten, iron, copper, nickel, stainless steel, chromium, titanium, and carbon, for example.

The electro-conductive base material may be a hard electro-conductive substrate, an electro-conductive film having flexibility, a cloth with the surface being coated with electro-conductive paste, and a cloth into which electro-conductive polymer is kneaded without being limited to particular substrates. The electro-conductive substrate may be flat, uneven, or mesh-form of woven metal wires, which can be appropriately selected in accordance with the use of the bio-electrode.

[Living Body Contact Layer]

The inventive bio-electrode comprises a living body contact layer formed on the electro-conductive base material. This living body contact layer is a part to be actually in contact with a living body when using the bio-electrode, and is a urethane resin that has electric conductivity and repellency. The living body contact layer is a cured material of the inventive bio-electrode composition described above, that is to say, a resin layer that contains the resin and the electro-conductive material (salt) described above, together with additives such as a carbon material in accordance with needs, with the resin containing a main chain having a urethane bond and two side chains each having a silicon-containing group.

The living body contact layer of the bio-electrode preferably has a thickness of 1 µm or more and 5 mm or less, more preferably 2 µm or more and 3 mm or less. As the living body contact layer is thinner, the tackiness lowers, but the flexibility is improved, and the weight decreases to improve the compatibility with skin. The thickness of the living body contact layer can be selected based on the balance of flexibility, tackiness, and texture.

The inventive bio-electrode may be provided with a tacky film separately on the living body contact layer as previous bio-electrodes (e.g., the bio-electrode described in JP 2004-033468A) in order to prevent peeling off of the bio-electrode from a living body during the use. When the tacky film is prepared separately, the tacky film may be formed by using a raw material for the tacky film such as an acrylic type, a urethane type, and a silicone type. Particularly, the silicone type is suitable because of the high transparency of oxygen, which enables breathing through the skin while pasting the same, the high water repellency, which decreases lowering of tackiness due to perspiration, and the low irritation to skin. It is to be noted that the inventive bio-electrode does not necessarily require the tacky film that is prepared separately described above, because peeling off from a living body can be prevented by adding tackifier to the bio-electrode composition or using a resin having good tackiness to a living body.

When the inventive bio-electrode is used as a wearable device, the components such as wiring between the bio-electrode and a sensor device may be any material without being limited to particular ones. For example, it is possible to apply the ones described in JP 2004-033468A.

As described above, the inventive bio-electrode is capable of conducting electric signals efficiently from skin to a device (i.e., excellent in electric conductivity), free from the risk of causing allergies even when it is worn on skin for a long time (i.e., excellent in biocompatibility), light in weight, manufacturable at low cost, and free from large lowering of the electric conductivity even when it is wetted with water or dried, because the living body contact layer is formed from a cured material of the inventive bio-electrode composition described above. It is possible to improve the electric conductivity still more by adding a carbon material, and to manufacture a highly stretchable bio-electrode that is always in contact with skin by combining a urethane resin that has flexibility and stretchability. This urethane resin, having silicon-containing groups in the side chains, has higher repellency to repel perspiration or water to exclude the influences thereof, together with higher biocompatibility. Additionally, this urethane resin has improved strength since it has a urethane main chain, exhibits higher ionic conductivity since it also has a polyether main chain, and functions as a highly sensitive bio-electrode thereby. It is also possible to improve the stretchability and tackiness to skin by additives, and to control the stretchability and tackiness by adjusting the composition of the resin and the thickness of the living body contact layer appropriately. Accordingly, the inventive bio-electrode described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, comprising: applying the inventive bio-electrode composition described above onto the electro-conductive base material; and curing the bio-electrode composition; thereby forming the living body contact layer.

Incidentally, the electro-conductive base material, the bio-electrode composition, etc. used for the inventive method for manufacturing a bio-electrode are the same as those in the inventive bio-electrode described above.

As an example of a method for manufacturing a bio-electrode of the present invention, it is preferable to produce a living body contact layer based on a urethane resin by mixing a silicone-pendant diol compound, a hydroxy group-containing compound, an ionic polymer, an electric conductivity improver, etc., followed by mixing an isocyanate compound. Since the curing reaction occurs when the isocyanate compound is mixed, it is preferable to mix the isocyanate compound at the end. The living body contact layer is preferable not to have openings due to foaming. Accordingly, it is preferable that the molar amounts of the isocyanate groups and the hydroxy groups be the same or the hydroxy groups be excess.

The bio-electrode composition can be made from a material in which a hydroxy group-containing compound, an isocyanate compound, an ionic polymer, and an electric conductivity improver are mixed with a silicone-pendant diol compound, for example. In this case, the hydroxy group-containing compound and the isocyanate compound may be mixed at one time or may be mixed in stages.

As the method for applying the inventive bio-electrode composition onto the electro-conductive base material, any method can be used without being limited to particular ones; and, for example, dip coating, spray coating, spin coating, roll coating, flow coating, doctor coating, screen printing, flexographic printing, gravure printing, and inkjet printing are suitable.

The method for curing the bio-electrode composition can be appropriately selected based on a kind of resin used for the bio-electrode composition without being limited to particular methods. For example, the resin is preferably cured by either or both of heat and light. The foregoing bio-electrode composition can also be cured by adding a catalyst to generate acid or base, which causes a crosslinking reaction.

In case of heating, the temperature may be appropriately selected based on a kind of resin used for the bio-electrode composition without being limited to particular temperature. For example, it is preferable to be about 50 to 250° C., but it is also possible to cure by leaving the composition at room temperature for a long time.

When the heating and light irradiation are combined, it is possible to perform the heating and the light irradiation simultaneously, to perform the heating after the light irradiation, or to perform the light irradiation after the heating. It is also possible to perform air-drying to evaporate solvent before heating the coating film.

As described above, the inventive method for manufacturing a bio-electrode makes it possible to manufacture the inventive bio-electrode easily and at low cost, which is excellent in electric conductivity and biocompatibility, light in weight, and free from large lowering of the electric conductivity even when it is wetted with water or dried.

EXAMPLES

Hereinafter, the present invention will be specifically described by showing Examples and Comparative Examples, but the present invention is not limited to the following Examples.

Ionic polymers-1 to 12 blended to solutions of bio-electrode composition as an electro-conductive material were synthesized as follows. Each 30 mass % monomer solution in PGMEA was introduced into a reaction vessel and mixed. The reaction vessel was cooled to −70° C. under a nitrogen atmosphere, and subjected to vacuum degassing and nitrogen blowing repeated for three times. After raising the temperature to room temperature, azobis(isobutyronitrile) (AIBN) was added thereto as a polymerization initiator in an amount of 0.01 mole per 1 mole of the whole monomers, this was warmed to a temperature of 60° C. and then allowed to react for 15 hours. The composition of obtained polymer was determined by $^1$H-NMR after drying the solvent, and the Mw and Mw/Mn were determined by gel permeation chromatography (GPC) using tetrahydrofuran (THF) as a solvent.

The following are Ionic polymers-1 to 12 and Comparative Ammonium salts-1 to 2 each blended to the bio-electrode composition solution as an electro-conductive material.

Ionic Polymer-1
Mw=20,900
Mw/Mn=2.21

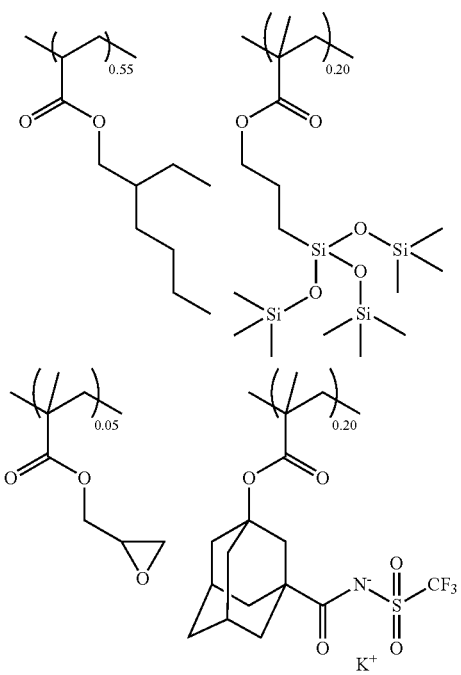

Ionic Polymer-2
Mw=23,100
Mw/Mn=2.01

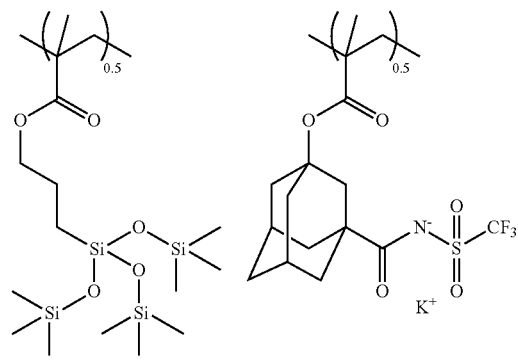

Ionic Polymer-3
Mw=27,400
Mw/Mn=1.94

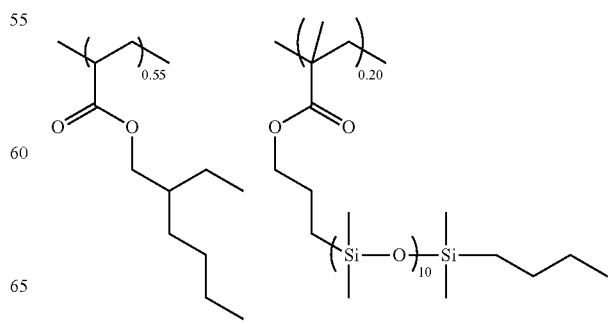

-continued
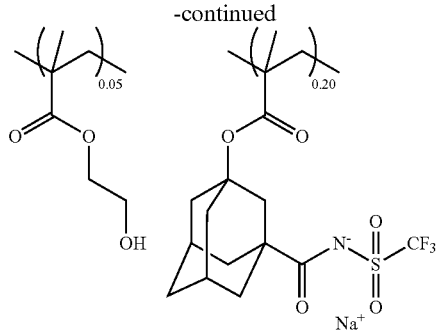
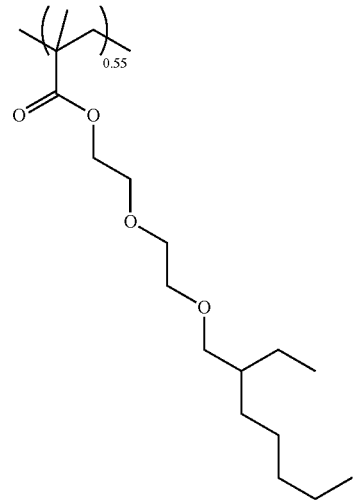
The number of repeating siloxane unit in the formula shows the average value.
Ionic Polymer-4
Mw=30,600
Mw/Mn=1.88
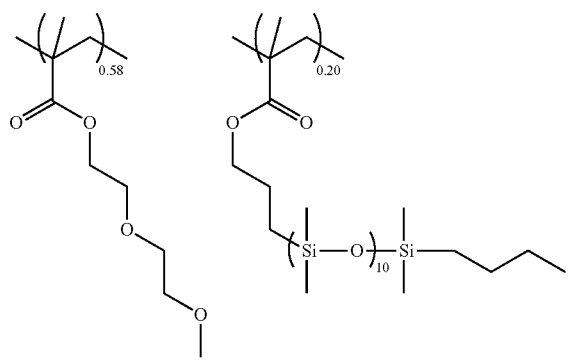
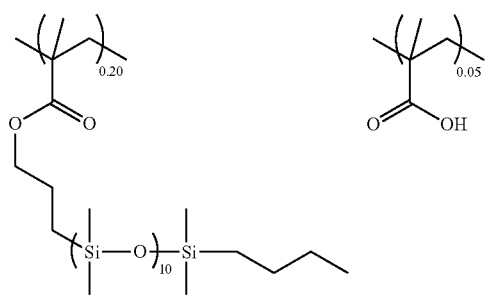
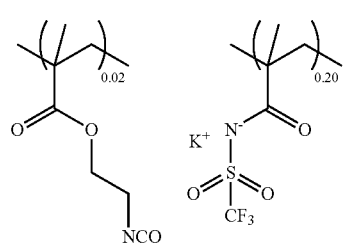
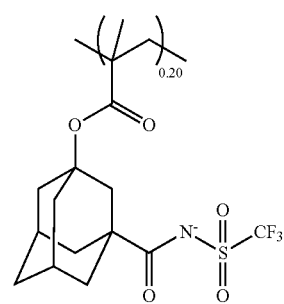
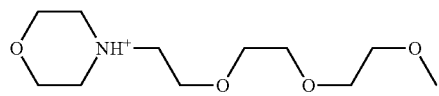
The number of repeating siloxane unit in the formula shows the average value.
Ionic Polymer-5
Mw=26,600
Mw/Mn=1.86
The number of repeating siloxane unit in the formula shows the average value.
Ionic Polymer-6
Mw=21,900
Mw/Mn=2.10

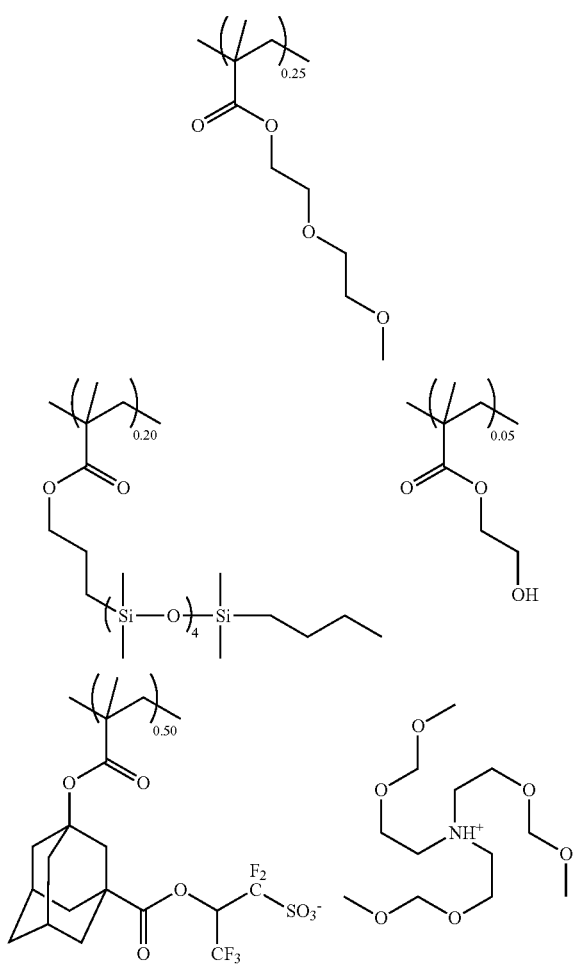
The number of repeating siloxane unit in the formula shows the average value.
Ionic Polymer-7
Mw=35,700
Mw/Mn=2.33
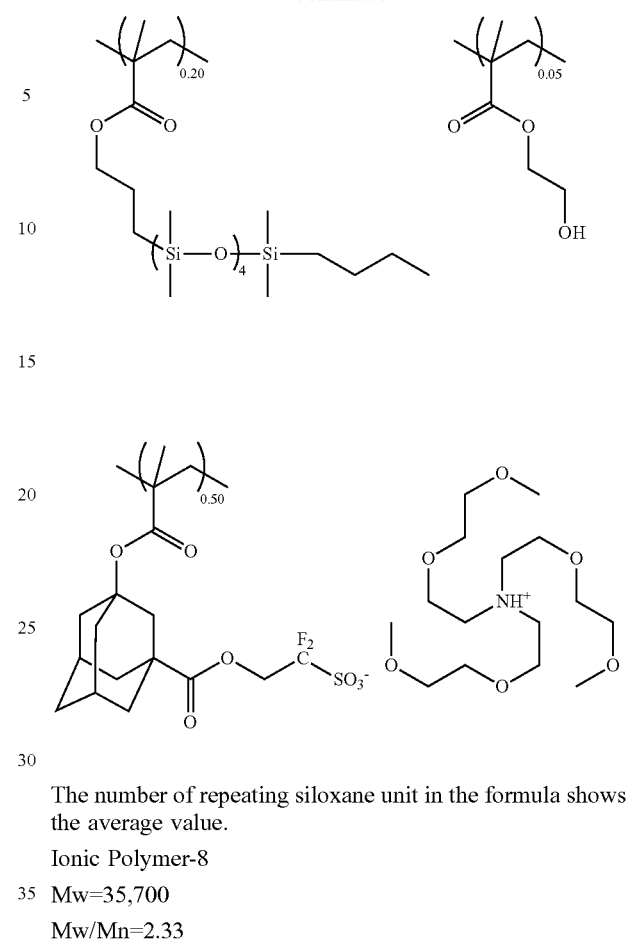
The number of repeating siloxane unit in the formula shows the average value.
Ionic Polymer-8
Mw=35,700
Mw/Mn=2.33
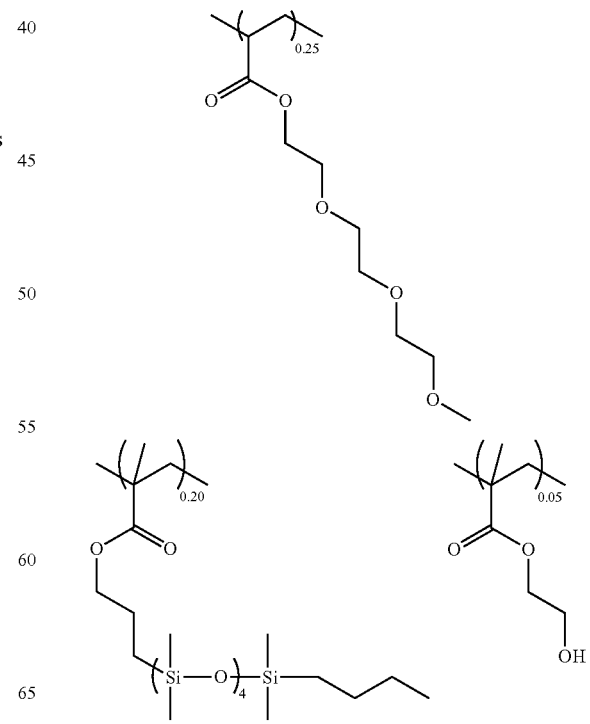

-continued
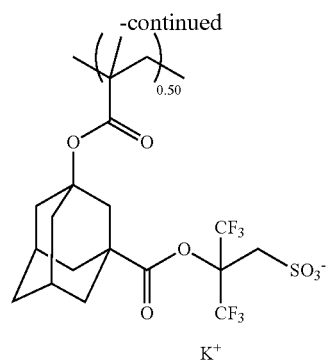
The number of repeating siloxane unit in the formula shows the average value.
Ionic Polymer-9
Mw=33,100
Mw/Mn=2.02
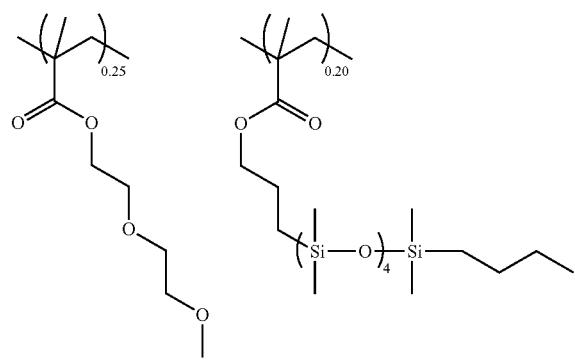
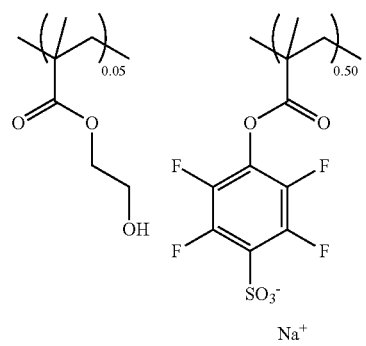
The number of repeating siloxane unit in the formula shows the average value.
Ionic Polymer-10
Mw=21,500
Mw/Mn=1.96
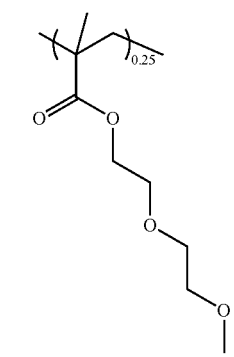
The number of repeating siloxane unit in the formula shows the average value.
Ionic Polymer-11
Mw=24,500
Mw/Mn=1.91
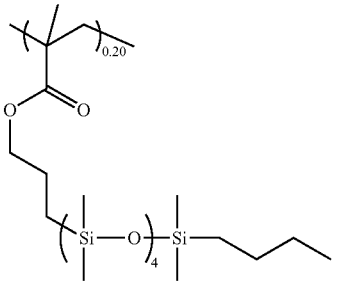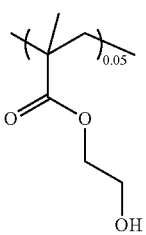

191

-continued

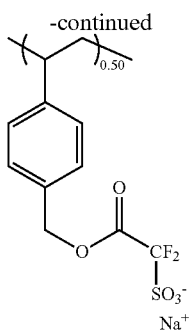

The number of repeating siloxane unit in the formula shows the average value.
Ionic Polymer-12
Mw=16,300
Mw/Mn=1.75

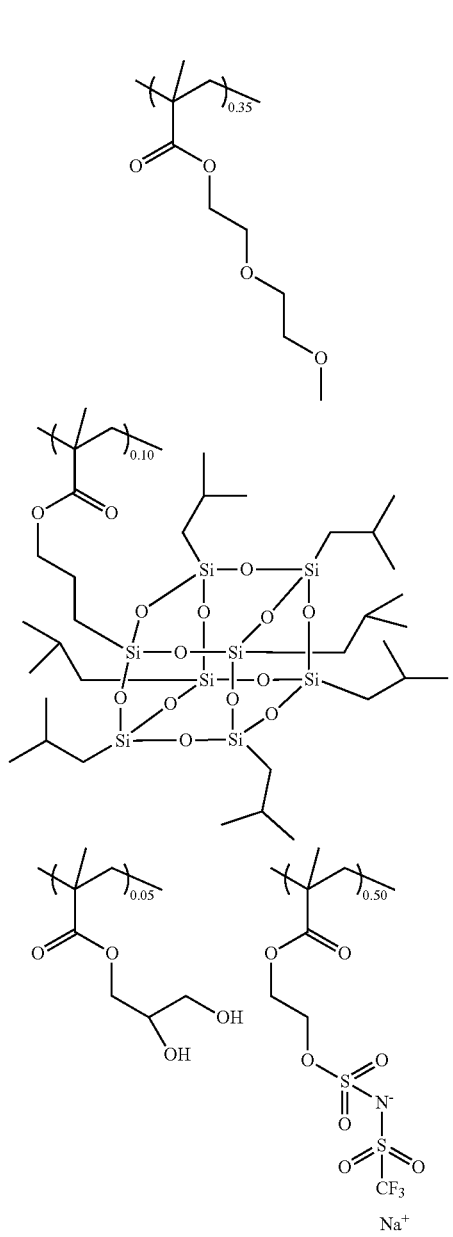

192

Comparative Ammonium Salts-1 and 2

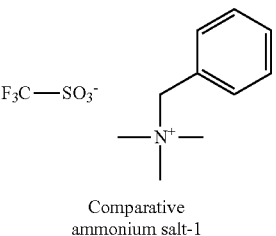

Comparative ammonium salt-1

Comparative ammonium salt-2

The following are Silicon-containing compounds-1 to 8 each blended to the bio-electrode composition as a raw material of the resin containing a main chain having a urethane bond and two side chains each having a silicon-containing group.

Silicon-containing compound-8

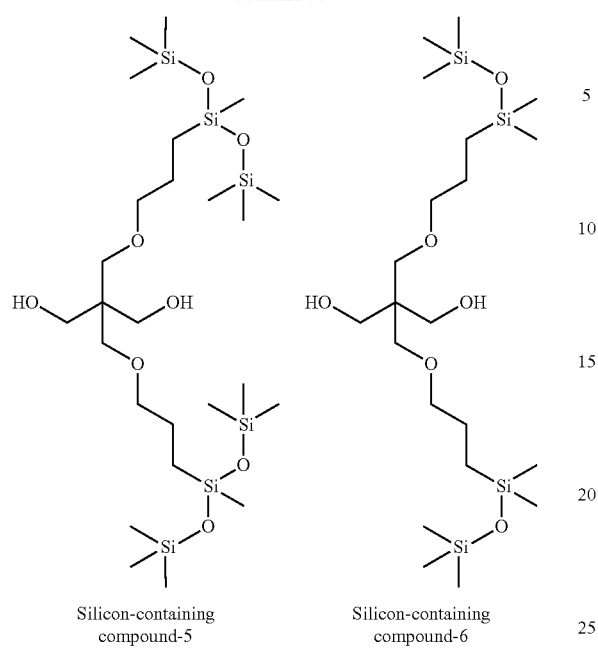
Silicon-containing compound-5
Silicon-containing compound-6
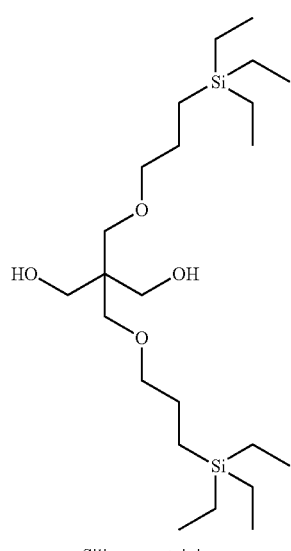
Silicon-containing compound-7
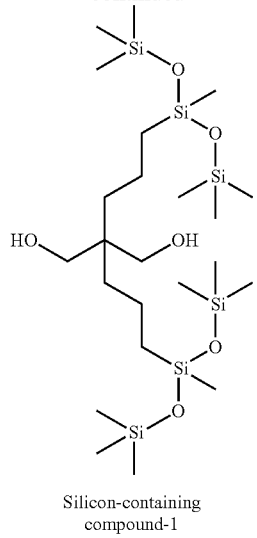
Silicon-containing compound-1
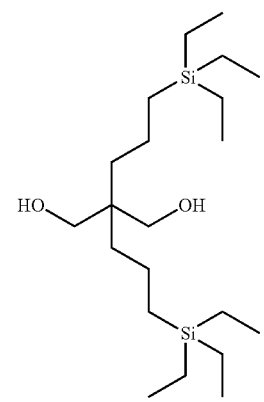
Silicon-containing compound-3
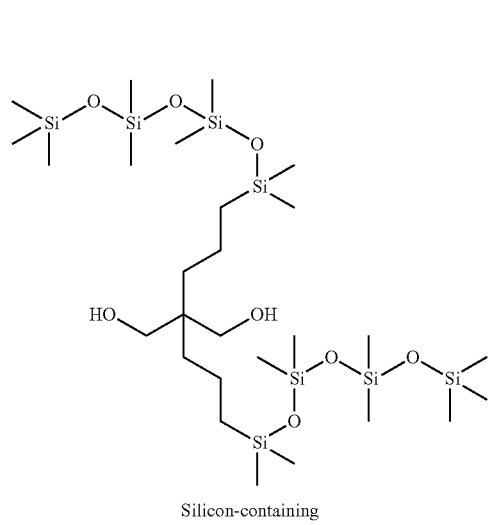
Silicon-containing compound-4
The following are Hydroxy compounds-1 to 7 each blended to the bio-electrode composition.

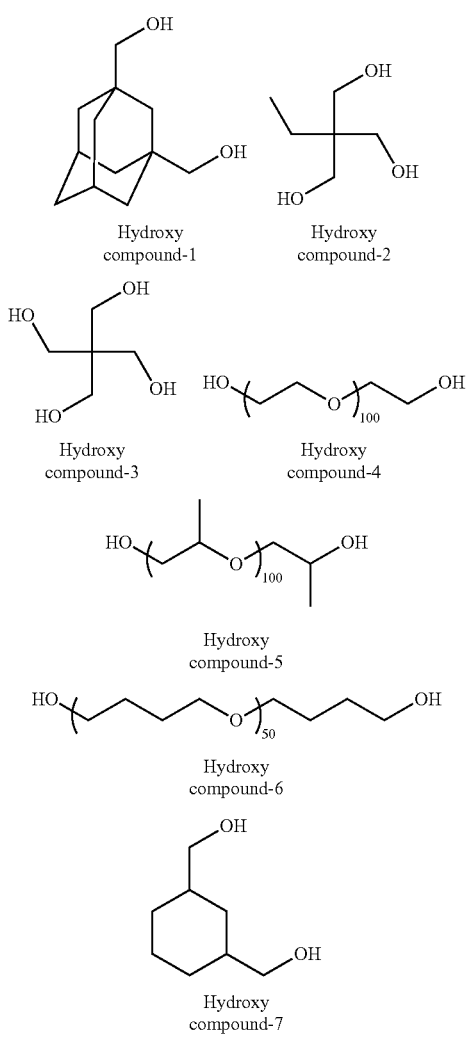

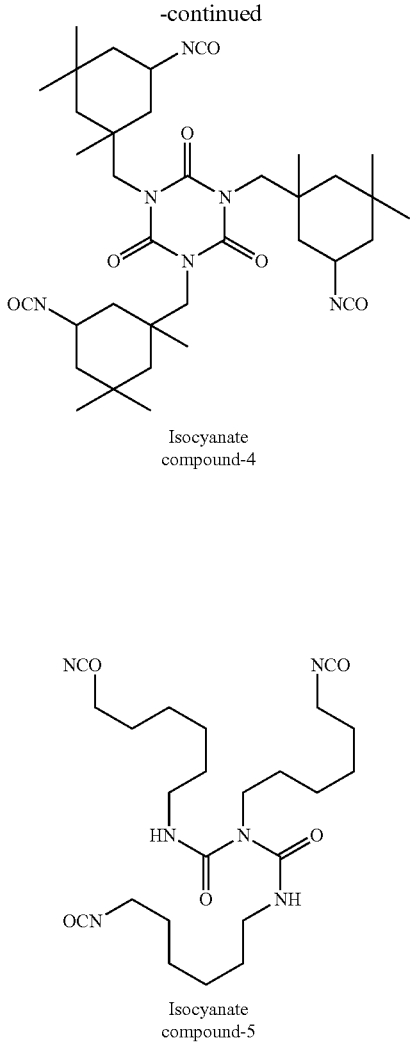

The numbers of repeating unit in the formulae show the average values.

The following are Isocyanate compounds-1 to 5 each blended to the bio-electrode composition.

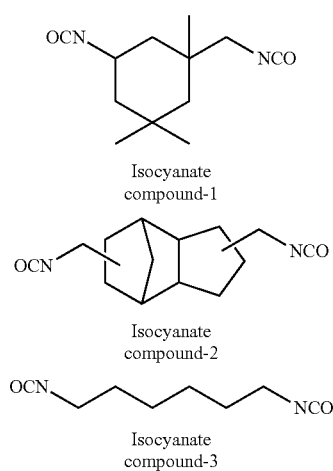

The following are electric conductivity improvers (carbon black, carbon nanotube, Au-coated particle, and Ag-coated particle) blended to the bio-electrode composition solution as an additive.

Carbon black: DENKA BLACK HS-100 manufactured by Denka Co., Ltd.

Multilayer carbon nanotube: carbon nanotube having a diameter of 0.7 to 1.1 nm and a length of 300 to 2,300 nm manufactured by Sigma-Aldrich Co. LLC.

Au-coated particle: Micropearl AU (the diameter of 3 m) manufactured by SEKISUI CHEMICAL CO. LTD.

Ag-coated particle: Ag-coated powder (the diameter of 30 μm) manufactured by Mitsubishi Materials Electronic Chemicals Co., Ltd.

Examples 1 to 15, Comparative Examples 1 to 3

On the basis of each composition described in Table 1, the ionic polymer, the hydroxy compound(s), and the additive (electric conductivity improver) were mixed and degassed, and the isocyanate compound(s) was mixed thereto at the end to prepare each bio-electrode composition solution (Bio-electrode solutions-1 to 15, Comparative bio-electrode solutions-1 to 3).

TABLE 1

| Bio-electrode solution | Electroconductive material (parts by mass) | Hydroxy compounds (parts by mass) | Isocyanate compound (parts by mass) | Additive (parts by mass) |
|---|---|---|---|---|
| Bio-electrode solution-1 | Ionic polymer-1 (4) | Silicon-containing compound-1 (3) Hydroxy compound-1 (5) Hydroxy compound-2 (2) Hydroxy compound-4 (10) | Isocyanate compound-1 (11) | Carbon black (2) |
| Bio-electrode solution-2 | Ionic polymer-2 (6) | Silicon-containing compound-2 (5) Hydroxy compound-3 (1) Hydroxy compound-5 (15) | Isocyanate compound-2 (7) | Carbon black (3) |
| Bio-electrode solution-3 | Ionic polymer-3 (5) | Silicon-containing compound-3 (4) Hydroxy compound-3 (1) Hydroxy compound-6 (20) | Isocyanate compound-3 (4) | Carbon black (2) |
| Bio-electrode solution-4 | Ionic polymer-4 (5) | Silicon-containing compound-4 (5) Hydroxy compound-7 (5) Hydroxy compound-3 (1) Hydroxy compound-4 (15) | Isocyanate compound-3 (9) | Carbon black (2) |
| Bio-electrode solution-5 | Ionic polymer-5 (5) | Silicon-containing compound-5 (3) Hydroxy compound-7 (5) Hydroxy compound-3 (1) Hydroxy compound-4 (15) | Isocyanate compound-3 (9) | Carbon black (2) |
| Bio-electrode solution-6 | Ionic polymer-6 (5) | Silicon-containing compound-6 (3) Hydroxy compound-7 (5) Hydroxy compound-3 (1) Hydroxy compound-4 (15) | Isocyanate compound-3 (9) | Carbon black (2) |
| Bio-electrode solution-7 | Ionic polymer-7 (5) | Silicon-containing compound-7 (3) Hydroxy compound-7 (5) Hydroxy compound-3 (1) Hydroxy compound-4 (15) | Isocyanate compound-3 (9) | Carbon black (2) |
| Bio-electrode solution-8 | Ionic polymer-8 (5) | Silicon-containing compound-8 (3) Hydroxy compound-7 (5) Hydroxy compound-3 (1) Hydroxy compound-4 (15) | Isocyanate compound-3 (9) | Carbon black (2) |
| Bio-electrode solution-9 | Ionic polymer-6 (6) | Silicon-containing compound-1 (5) Hydroxy compound-4 (18) | Isocyanate compound-4 (1) Isocyanate compound-3 (2) | Carbon black (2) |
| Bio-electrode solution-10 | Ionic polymer-7 (6) | Silicon-containing compound-1 (5) Hydroxy compound-4 (18) | Isocyanate compound-4 (1) Isocyanate compound-3 (2) | Carbon black (2) |
| Bio-electrode solution-11 | Ionic polymer-8 (6) | Silicon-containing compound-1 (5) Hydroxy compound-4 (18) | Isocyanate compound-4 (1) Isocyanate compound-3 (2) | Carbon black (2) |
| Bio-electrode solution-12 | Ionic polymer-9 (6) | Silicon-containing compound-1 (5) Hydroxy compound-4 (18) | Isocyanate compound-4 (1) Isocyanate compound-3 (2) | Multilayer carbon nanotube (2) |
| Bio-electrode solution-13 | Ionic polymer-10 (6) | Silicon-containing compound-1 (5) Hydroxy compound-4 (18) | Isocyanate compound-4 (1) Isocyanate compound-3 (2) | Ag-coated particle (6) |
| Bio-electrode solution-14 | Ionic polymer-11 (8) | Silicon-containing compound-1 (5) Hydroxy compound-4 (18) | Isocyanate compound-4 (1) Isocyanate compound-3 (2) | Au-coated particle (6) |
| Bio-electrode solution-15 | Ionic polymer-12 (2) | Silicon-containing compound-1 (5) Hydroxy compound-4 (18) | Isocyanate compound-5 (1) Isocyanate compound-3 (2) | Carbon black (2) |
| Comparative bio-electrode solution-1 | Comparative ammonium salt-1 (2) | Silicon-containing compound-1 (5) Hydroxy compound-4 (18) | Isocyanate compound-4 (1) Isocyanate compound-3 (2) | Carbon black (2) |
| Comparative bio-electrode solution-2 | Comparative ammonium salt-2 (2) | Silicon-containing compound-1 (5) Hydroxy compound-4 (18) | Isocyanate compound-4 (1) Isocyanate compound-3 (2) | Carbon black (2) |
| Comparative bio-electrode solution-3 | Ionic polymer-1 (4) | Hydroxy compound-1 (5) Hydroxy compound-2 (2) Hydroxy compound-4 (10) | Isocyanate compound-1 (10) | Carbon black (2) |

(Evaluation of Electric Conductivity)

Figure 3A:
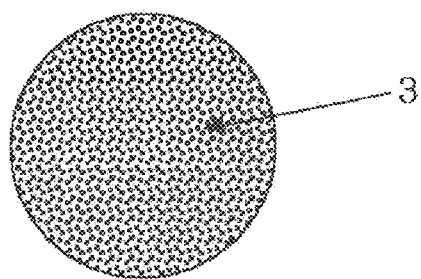
FIG. 3(a) is a schematic view of the bio-electrode produced in Examples of the present invention viewed from the living body contact layer side.
Figure 3B:
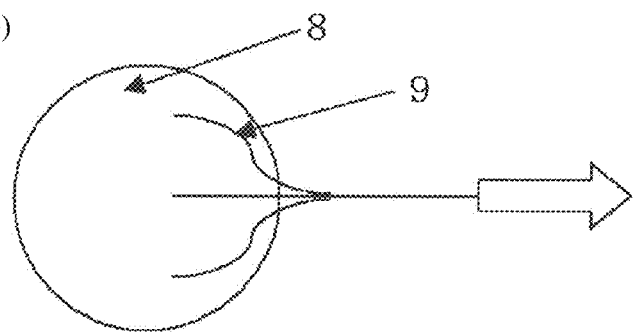
FIG. 3(b) is a schematic view of the bio-electrode produced in Examples of the present invention viewed from the electro-conductive base material side.
Figure 4:
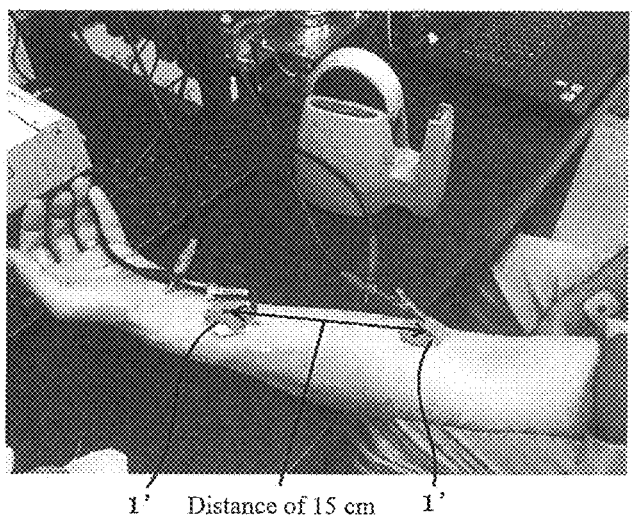
FIG. 4 is a photograph of a scene of measuring impedance on the surface of skin by using the bio-electrode produced in Examples of the present invention.

Each bio-electrode solution was applied onto an aluminum disk having a diameter of 3 cm and a thickness of 0.2 mm by using an applicator. This was baked at 100° C. for 60 minutes under a nitrogen atmosphere by using an oven to be cured, thereby producing four pieces of bio-electrodes for each bio-electrode composition solution. Thus obtained bio-electrode was provided with the living body contact layer 3 at one side and provided with the aluminum disk 8 at the other side as an electro-conductive base material as shown in FIGS. 3(*a*) and (*b*). Then, the copper wiring 9 was pasted on the surface of the aluminum disk 8 with self-adhesive tape at the side that had not been coated with the living body contact layer to form a lead-out electrode, which was connected to an impedance measurement apparatus as shown in FIG. 3 (*b*). Two pieces of the bio-electrodes 1' were pasted on a human arm at a distance of 15 cm from each other such that the side of each living body contact layer was in contact with the skin as shown in FIG. 4. The initial impedance was measured while altering the frequency by using an AC impedance measurement apparatus SI1260 manufactured by Solartron. Then, the remained two pieces of the bio-electrodes were immersed in pure water for 1 hour, and used for measuring the impedance on skin by the same method described above immediately after the immersion. Each impedance at the frequency of 1,000 Hz is shown in Table 2.

(Measurement of Thickness and Contact Angle of Living Body Contact Layer)

On each bio-electrode produced in the evaluation test of electric conductivity described above, the thickness of the living body contact layer was measured by using a micrometer. The contact angle with water of the surface of each living body contact layer was measured by using a contact angle meter. The results are shown in Table 2.

TABLE 2

| Example | Bio-electrode solution | Thickness of resin (μm) | Contact angle (°) | Initial impedance (Ω) | Impedance after water immersion (Ω) |
|---|---|---|---|---|---|
| Example 1 | Bio-electrode solution-1 | 520 | 103 | $3.8E^4$ | $3.5E^4$ |
| Example 2 | Bio-electrode solution-2 | 510 | 104 | $5.5E^4$ | $6.0E^4$ |
| Example 3 | Bio-electrode solution-3 | 470 | 98 | $1.2E^4$ | $1.3E^4$ |
| Example 4 | Bio-electrode solution-4 | 460 | 103 | $8.8E^3$ | $8.5E^3$ |
| Example 5 | Bio-electrode solution-5 | 440 | 102 | $8.6E^4$ | $7.5E^4$ |
| Example 6 | Bio-electrode solution-6 | 490 | 103 | $6.5E^4$ | $7.1E^4$ |
| Example 7 | Bio-electrode solution-7 | 510 | 98 | $5.5E^4$ | $5.3E^4$ |
| Example 8 | Bio-electrode solution-8 | 500 | 103 | $6.0E^3$ | $7.1E^3$ |
| Example 9 | Bio-electrode solution-9 | 530 | 102 | $7.2E^4$ | $7.1E^4$ |
| Example 10 | Bio-electrode solution-10 | 510 | 104 | $6.2E^4$ | $7.3E^4$ |
| Example 11 | Bio-electrode solution-11 | 530 | 103 | $6.4E^4$ | $5.9E^4$ |
| Example 12 | Bio-electrode solution-12 | 520 | 103 | $2.2E^3$ | $2.5E^3$ |
| Example 13 | Bio-electrode solution-13 | 710 | 104 | $9.2E^4$ | $9.3E^4$ |
| Example 14 | Bio-electrode solution-14 | 700 | 103 | $9.4E^4$ | $9.9E^4$ |
| Example 15 | Bio-electrode solution-15 | 480 | 103 | $7.2E^4$ | $7.5E^4$ |
| Comparative Example 1 | Comparative bio-electrode solution-1 | 510 | 103 | $5.2E^4$ | $8.3E^6$ |
| Comparative Example 2 | Comparative bio-electrode solution-2 | 520 | 103 | $6.2E^4$ | $8.9E^6$ |
| Comparative Example 3 | Comparative bio-electrode solution-3 | 520 | 70 | $5.1E^4$ | $2.3E^3$ |

As shown in Table 2, each of Examples 1 to 15, in which the inventive living body contact layer was formed, exhibited higher contact angle with water and lower initial impedance, without causing large increase of impedance by an order of magnitude after the water immersion and drying. That is, Examples 1 to 15 each gave a bio-electrode with higher initial electric conductivity without causing large change of the electric conductivity when it was wetted with water or dried.

On the other hand, each of Comparative Examples 1 and 2, in which the living body contact layer was formed using a bio-electrode solution containing a previous salt, caused large increase of the impedance such that the order of magnitude was changed after water immersion and drying although the initial impedance was low. That is, each of Comparative Examples 1 and 2 only gave a bio-electrode in which the electric conductivity largely lowered when it was wetted with water or dried although the initial electric conductivity was high. Comparative Example 3, in which silicone-pendant urethane was not contained whereas an ionic polymer was contained, exhibited lower contact angle with water, that is, higher hydrophilicity. As a result, the bio-electrode was soaked with water after water immersion to lower the impedance, causing a result that the impedance was changed due to an influence of water.

As described above, it was revealed that the bio-electrode, with the living body contact layer being formed by using the inventive bio-electrode composition, was excellent in electric conductivity, biocompatibility, and adhesion properties to an electro-conductive base material; excellent in holding the electro-conductive materials such as an ionic polymer and carbon black to prevent large lowering of electric conductivity even when it was wetted with water and dried; light in weight, and manufacturable at low cost.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:
1. A bio-electrode composition comprising:
a resin containing a main chain having a urethane moiety and two side chains each having a silicon-containing group; and
an electro-conductive material,
wherein the electro-conductive material is a polymer compound having one or more fragments selected from the group consisting of fluorosulfonic acid salts shown by the following formulae (1)-1 and (1)-2, sulfonimide salts shown by the following formula (1)-3, and sulfonamide salts shown by the following formula (1)-4,

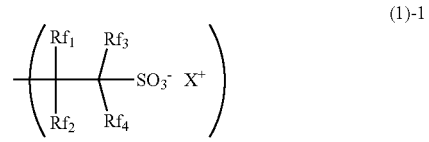

(1)-1

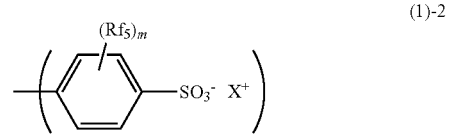

(1)-2

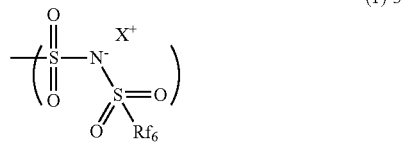

(1)-3

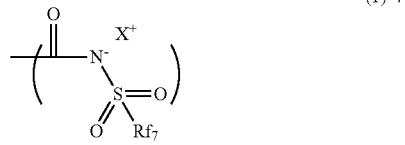

(1)-4 wherein $Rf_1$ and $Rf_2$ each represent a hydrogen atom, a fluorine atom, a trifluoromethyl group, or an oxygen atom, provided that when $Rf_1$ represents an oxygen atom, $Rf_2$ also represents an oxygen atom to form a carbonyl group together with a carbon atom bonded therewith; $Rf_3$ and $Rf_4$ each represent a hydrogen atom, a fluorine atom, or a trifluoromethyl group; provided that one or more fluorine atoms are contained in $Rf_1$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; $X^+$ represents a sodium ion, a potassium ion, or a cation having an ammonium ion structure shown by the following formula (1)-5; and "m" is an integer of 1 to 4,

(1)-5 wherein $R^1$ to $R^4$ each represent a hydrogen atom, a linear, branched, or cyclic alkyl group having 1 to 20 carbon atoms, an alkenyl group having 2 to 14 carbon atoms, or an alkynyl group having 2 to 5 carbon atoms, optionally having an ether group, an ester group, a carbonyl group, a sulfonyl group, a cyano group, an amino group, a nitro group, hydroxy group, a sulfur atom except in the sulfonyl group, or a halogen atom, and optionally bonded to each other to form a ring.

2. The bio-electrode composition according to claim 1, wherein the one or more fragments are present in one or more repeating units selected from repeating units a1 to a7 shown by the following formulae (2),

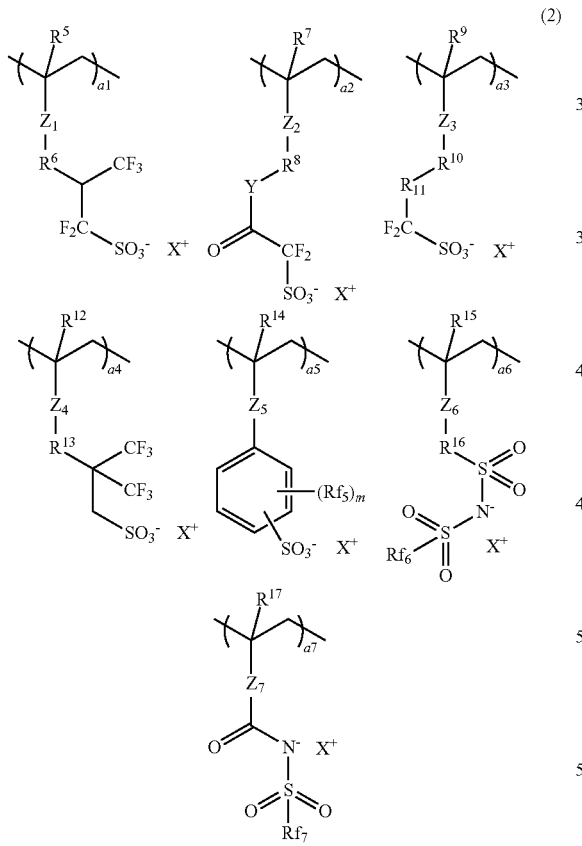

(2)

wherein $R^5$, $R^7$, $R^9$, $R^{12}$, $R^{14}$, $R^{15}$, and $R^{17}$ each independently represent a hydrogen atom or a methyl group; $R^6$, $R^8$, $R^{10}$, $R^{13}$ and $R^{16}$ each independently represent any of a single bond, an ester group, or a linear, branched, or cyclic hydrocarbon group having 1 to 13 carbon atoms optionally having either or both of an ether group and an ester group; $R^{11}$ represents a linear or branched alkylene group having 1 to 4 carbon atoms, and one or two of the hydrogen atoms in $R^{11}$ are optionally substituted with a fluorine atom; $Z_1$, $Z_2$, $Z_3$, $Z_4$, and $Z_6$ each independently represent any of a single bond, a phenylene group, a naphthylene group, an ether group, an ester group, or an amide group; $Z_5$ represents any of a single bond, an ether group, or an ester group; $Z_7$ represents a single bond, an arylene group having 6 to 12 carbon atoms, or —C(=O)—O—$Z^8$—; and $Z^8$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $Z^8$; Y represents an oxygen atom or an —$NR^{18}$— group; $R^{18}$ represents a hydrogen atom, or a linear or branched alkyl group having 1 to 4 carbon atoms, optionally bonded to $R^8$ to form a ring; "m" is an integer of 1 to 4; a1, a2, a3, a4, a5, a6, and a7 satisfy 0≤a1≤1.0, 0≤a2≤1.0, 0≤a3≤1.0, 0<a4<1.0, 0<a5<1.0, 0≤a6≤1.0, 0≤a7≤1.0, and 0<a1+a2+a3+a4+a5+a6+a7≤1.0; and $Rf_5$, $Rf_6$, $Rf_7$, and $X^+$ have the same meanings as defined above.

3. The bio-electrode composition according to claim 1, wherein the electro-conductive material is a polymer compound having a repeating unit containing a sulfonamide salt shown by the formula (1)-4.

4. The bio-electrode composition according to claim 1, wherein the resin containing a main chain having a urethane moiety and two side chains each having a silicon-containing group has a structure shown by the following formula (3),

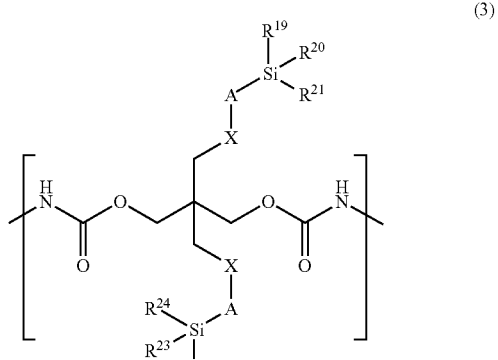

(3)

wherein $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —$(OSiR^{25}R^{26})_n$—$OSiR^{27}R^{28}R^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; and X represents a methylene group or an ether group.

5. The bio-electrode composition according to claim 2, wherein the resin containing a main chain having a urethane moiety and two side chains each having a silicon-containing group has a structure shown by the following formula (3), (3)

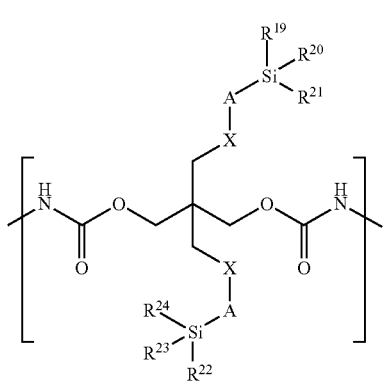

wherein $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —$(OSiR^{25}R^{26})_n$—$OSiR^{27}R^{28}R^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; and X represents a methylene group or an ether group.

6. The bio-electrode composition according to claim 3, wherein the resin containing a main chain having a urethane moiety and two side chains each having a silicon-containing group has a structure shown by the following formula (3), (3)

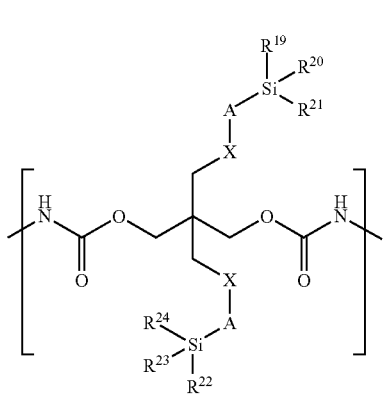

wherein $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —$(OSiR^{25}R^{26})_n$—$OSiR^{27}R^{28}R^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; and X represents a methylene group or an ether group.

7. The bio-electrode composition according to claim 1, wherein the resin containing a main chain having a urethane moiety and two side chains each having a silicon-containing group has a structure containing a polyether main chain shown by the following formula (4), (4)

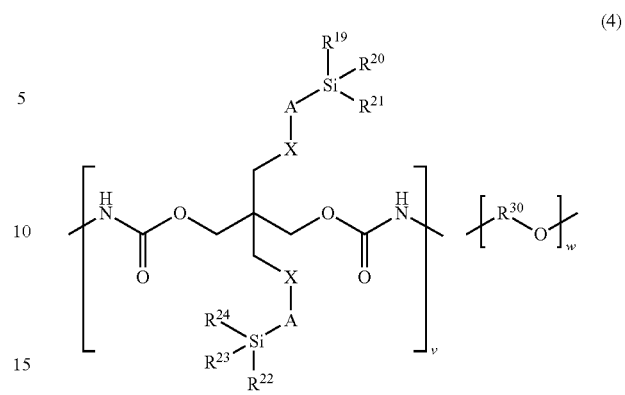

wherein $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —$(OSiR^{25}R^{26})_n$—$OSiR^{27}R^{28}R^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; X represents a methylene group or an ether group; $R^{30}$ represent a linear, branched, or cyclic alkylene group having 2 to 12 carbon atoms; and "v" and "w" satisfy $0<v<1.0$, $0<w<1.0$, and $0<v+w\leq1.0$.

8. The bio-electrode composition according to claim 2, wherein the resin containing a main chain having a urethane moiety and two side chains each having a silicon-containing group has a structure containing a polyether main chain shown by the following formula (4), (4)

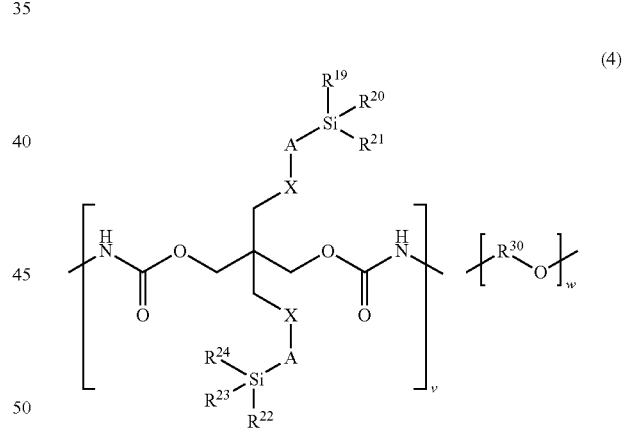

wherein $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —$(OSiR^{25}R^{26})_n$—$OSiR^{27}R^{28}R^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; X represents a methylene group or an ether group; $R^{30}$ represent a linear, branched, or cyclic alkylene group having 2 to 12 carbon atoms; and "v" and "w" satisfy $0<v<1.0$, $0<w<1.0$, and $0<v+w\leq1.0$.

9. The bio-electrode composition according to claim 3, wherein the resin containing a main chain having a urethane moiety and two side chains each having a silicon-containing group has a structure containing a polyether main chain shown by the following formula (4),

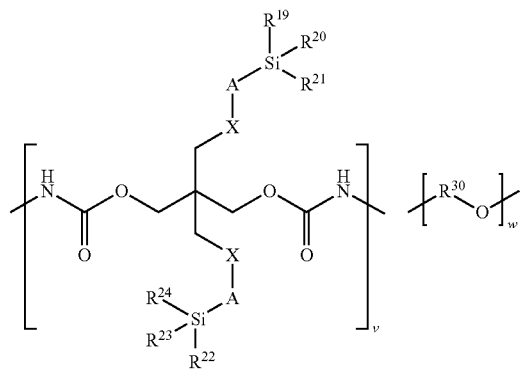

(4)

wherein $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —$(OSiR^{25}R^{26})_n$—$OSiR^{27}R^{28}R^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; X represents a methylene group or an ether group; $R^{30}$ represent a linear, branched, or cyclic alkylene group having 2 to 12 carbon atoms; and "v" and "w" satisfy 0<v<1.0, 0<w<1.0, and 0<v+w≤1.0.

10. The bio-electrode composition according to claim 1, wherein the resin containing a main chain having a urethane moiety and two side chains each having a silicon-containing group is a reaction product of a diol compound shown by the following formula (5), a polyether compound having a hydroxy group at the terminal, and a compound having an isocyanate group,

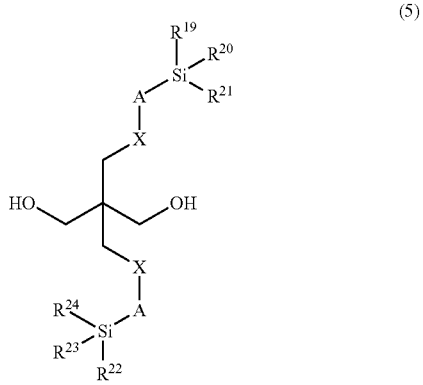

(5)

wherein $R^{19}$, $R^{20}$, $R^{21}$, $R^{22}$, $R^{23}$, and $R^{24}$ each represent a linear, branched, or cyclic alkyl group having 1 to 6 carbon atoms, a phenyl group, a 3,3,3-trifluoropropyl group, or a group shown by —$(OSiR^{25}R^{26})_n$—$OSiR^{27}R^{28}R^{29}$; $R^{25}$, $R^{26}$, $R^{27}$, $R^{28}$, and $R^{29}$ have the same meanings as $R^{19}$ to $R^{24}$; "n" is a number in a range of 0 to 100; "A" represents a linear or branched alkylene group having 1 to 4 carbon atoms; and X represents a methylene group or an ether group.

11. The bio-electrode composition according to claim 1, further comprising an organic solvent.

12. The bio-electrode composition according to claim 1, further comprising a carbon material.

13. The bio-electrode composition according to claim 12, wherein the carbon material is either or both of carbon black and carbon nanotube.

14. A bio-electrode comprising an electro-conductive base material and a living body contact layer formed on the electro-conductive base material;
wherein the living body contact layer is a cured material of the bio-electrode composition according to claim 1.

15. The bio-electrode according to claim 14, wherein the electro-conductive base material comprises one or more species selected from gold, silver, silver chloride, platinum, aluminum, magnesium, tin, tungsten, iron, copper, nickel, stainless steel, chromium, titanium, and carbon.

16. A method for manufacturing a bio-electrode having an electro-conductive base material and a living body contact layer formed on the electro-conductive base material, comprising:
applying the bio-electrode composition according to claim 1 onto the electro-conductive base material; and curing the bio-electrode composition; thereby forming the living body contact layer.

17. The method for manufacturing a bio-electrode according to claim 16, wherein the electro-conductive base material comprises one or more species selected from gold, silver, silver chloride, platinum, aluminum, magnesium, tin, tungsten, iron, copper, nickel, stainless steel, chromium, titanium, and carbon.

* * * * *